US012516357B1

(12) United States Patent
Raetz

(10) Patent No.: US 12,516,357 B1
(45) Date of Patent: Jan. 6, 2026

(54) MODIFIED HOST CELLS FOR HIGH EFFICIENCY PRODUCTION OF VANILLIN

(71) Applicant: AMYRIS, INC., Emeryville, CA (US)

(72) Inventor: Lauren Raetz, Emeryville, CA (US)

(73) Assignee: AMYRIS, INC., Emeryville, CA (US)

( * ) Notice: Subject to any disclaimer, the term of this patent is extended or adjusted under 35 U.S.C. 154(b) by 1050 days.

(21) Appl. No.: 16/945,559

(22) Filed: Jul. 31, 2020

Related U.S. Application Data

(60) Provisional application No. 62/881,869, filed on Aug. 1, 2019.

(51) Int. Cl.

| | |
|---|---|
| ***C12P 7/26*** | (2006.01) |
| ***C12N 1/18*** | (2006.01) |
| ***C12N 15/52*** | (2006.01) |
| ***C12P 19/46*** | (2006.01) |
| ***C12R 1/865*** | (2006.01) |

(52) U.S. Cl.

CPC ................ *C12P 7/26* (2013.01); *C12N 15/52* (2013.01); *C12P 19/46* (2013.01); *C12N 1/185* (2021.05); *C12R 2001/865* (2021.05); *C12Y 105/0102* (2013.01); *C12Y 201/01014* (2013.01); *C12Y 201/02001* (2013.01); *C12Y 204/01126* (2013.01); *C12Y 205/01006* (2013.01); *C12Y 205/01054* (2013.01); *C12Y 207/08007* (2013.01); *C12Y 303/01001* (2013.01); *C12Y 402/0101* (2013.01); *C12Y 402/01118* (2013.01); *C12Y 402/03004* (2013.01)

(58) Field of Classification Search

None

See application file for complete search history.

(56) References Cited

U.S. PATENT DOCUMENTS 11,053,519 B2 7/2021 Mijts et al.

FOREIGN PATENT DOCUMENTS

| | | | |
|---|---|---|---|
| EP | 2 957 629 | A1 | 12/2015 |
| WO | WO 2015/009558 | A1 | 1/2015 |

OTHER PUBLICATIONS

Jouhten ("Yeast metabolic chassis designs for diverse biotechnological products" Scientific Reports, 6, Article No. 29694, 2016 pp. 1-9, Supplementary Information Table Attached) (Year: 2016).*

McNeil ("Cloning and Molecular Characterization of Three Genes, Including Two Genes Encoding Serine Hydroxyl methyltransferase, Whose inactivation is required to render Yeast Auxotrophic for Glycine" The Journal of Biological Chemistry, vol. 269. No. 12, 9155-9165, 1994) (Year: 1994).*

Thomas ("SAM1, the Structural Gene for on of the S-Adenosylmethionine Synthetases in Saccharomyces cerevisiae", The Journal of Biological Chemistry, vol. 262, No. 34, 1987, 16704-16709 (Year: 1987).*

Chan ("Regulation of S-Adenosylmethionine Levels in *Saccharomyces cerevisiae*", The Journal of Biological Chemistry, vol. 278, No. 44, 2003, 43051-43059). (Year: 2003).*

International Search Report and Written Opinion of PCT/US2020/044613 dated Nov. 19, 2020; 16 pages.

Averesch et al., "Metabolic Engineering of the Shikimate Pathway for Production of Aromatics and Derived Compounds-Present and Future Strain Construction Strategies", Frontiers In Bioengineering and Biotechnology, vol. 6, No. 32, Mar. 26, 2018.

Di Gioia et al., "Metabolic engineering of Pseudomonas fluorescens for the production of vanillin from ferulic acid", Journal of Biotechnology, vol. 156, No. 4, Aug. 22, 2011, pp. 309-316, XP055175458.

Fleige et al., "Metabolic Engineering of the Actinomycete Amycolatopsis sp. Strain ATCC 39116 towards Enhanced Production of Natural Vanillin", Applied And Environmental Microbiology, vol. 82, No. 11, Apr. 1, 2016, pp. 3410-3419.

Garcia-Bofill et al., "Enzymatic synthesis of vanillin catalysed by an eugenol oxidase", Applied Catalysis A: General, Elsevier, Amsterdam, NL, vol. 582, Jul. 25, 2019, DOI:10.1128/AeM.02681-08.

Hansen et al., "De Novo Biosynthesis of Vanillin in Fission Yeast (Schizosaccharomyces pombe) and Baker's Yeast (*Saccharomyces cerevisiae*)", Applied And Environmental Microbiology, American Society for Microbiology, US, vol. 75, No. 9, May 2009, pp. 2765-2774, XP002666446.

R. Plaggenborg et al., "Functional analyses of genes involved in the metabolism of ferulic acid in Pseudomonas putida KT2440", Applied Microbiology And Biotechnology, vol. 61, No. 5-6, Mar. 27, 2003, pp. 528-535, DOI: 10.1007/s00253-003-1260-4.

Sainsbury et al., "Breaking Down Lignin to High-Value Chemicals: The Conversion of Lignocellulose to Vanillin in a Gene Deletion Mutant of Rhodococcus jostii RHA1", Acs Chemical Biology, vol. 8, No. 10, Jul. 30, 2013, pp. 2151-2156, XP055744491.

Zhou et al., "Production of fatty acid-derived oleochemicals and biofuels by synthetic yeast cell factories", Nature Communications, vol. 7, No. 1, May 25, 2016, DOI: 10.1038/ncomms11709lwww.nature.com/naturecommunications.

* cited by examiner

*Primary Examiner* — Robert J Yamasaki

*Assistant Examiner* — Charles Zoltan Constant

(74) *Attorney, Agent, or Firm* — Squire Patton Boggs (US) LLP

(57) ABSTRACT

Provided herein are genetically modified host cells, compositions, and methods for improved production of vanillin and/or glucovanillin. The host cells, compositions, and methods described herein provide an efficient route for the heterologous production of vanillin and/or glucovanillin and any compound that can be synthesized or biosynthesized from either or both.

39 Claims, 5 Drawing Sheets

Specification includes a Sequence Listing.

SEQUENCE LISTING

<160> NUMBER OF SEQ ID NOS: 24

<210> SEQ ID NO 1
<211> LENGTH: 8262
<212> TYPE: DNA
<213> ORGANISM: Artificial Sequence
<220> FEATURE:
<223> OTHER INFORMATION: Synthetic: MS106908 sequence

<400> SEQUENCE: 1
gacggcacgg ccacgcgttt aaaccgcccc atggcaaaga atgctttcca tgacgatcat 60
cgtagtgccc aattgggtgc ctctatgatg ggtatggctt gggcaagtgt ctttttatgt 120
atcgtggaat ttatcctgct ggtcttctgg tctgttaggg caaggttggc ctctacttac 180
tccatcgaca attcaagata cagaacctcc tccagatgga atcccttcca tagagagaag 240
gagcaagcaa ctgacccaat attgactgcc actggacctg aagacatgca acaaagtgca 300
agcatagtgg ggccttcttc caatgctaat ccggtcactg ccactgctgc tacggaaaac 360
caacctaaag gtattaactt cttcactata agaaaatcac acgagcgccc ggacgatgtc 420
tctgtttaaa tggcgcaagt tttccgcttt gtaatatata tttatacccc tttcttctct 480
cccctgcaat ataatagttt cgctcgtcca acgccggcgg acctagttaa ttaatagtct 540
tggatgtaat tcttattgtt atactgaata cgctaaaacc actcacaaca agtatggagt 600
atattgtgtc tctttatata ctgagtactt atgcaatatg cgctcactca ggatgaaatg 660
tacacagccg aaagtatatt gaaagctgcc tctgtggaaa cttctatcta atgttgtctc 720
cagatgtaga ctatgaggcc tgaagaagtc tttaaacacc tgttggagag tataaggaga 780
ctgctacaac aacgtcttcc ccacaaaaat tatgtggagg ccggtatgat acctgcacaa 840
acgttaagtt acacatgaaa aagagactga cataactttg atctctgaaa atatgttttc 900
ccctgagtag cttcactgct tggataccaa tacgaataga ccttggctat agtaagttgc 960
atctgtaccg tagagattct tgcaacctcg cttaaactct cgcttttata taatatttct 1020
ccttattgcg cgcttcgttg aaaatttcgc taaacacggg gtttaagttt aagtttacag 1080
gatttatccg gaagttttcg cggaccccac acaattaaga attggctcga agagtgataa 1140
cgcatacttt tcttttcttt tttcagttcc tagcgtacct aacgtaggta acatgatttg 1200
gatcgtggga tgatacaaac aacgtaagat gagtagttcc ttcctcaatt cttctttcag 1260
catcattttc ttgaggcgct ctgggcaagg tataaaaagt tccattaata cgtctctaaa 1320
aaattaaacc atctatctct taagcagttt ttttgataat ctcaaatgta catcaacctc 1380
ccgcgacctc caaaatcgaa ctaccttcac aatgcagatt ttcgtcaaga ctttgaccgg 1440
taaaaccata acattggaag ttgaatcttc cgataccatc gacaacgtta agtcgaaaat 1500
tcaagacaag gaaggtatcc ctccagatca acaaagattg atctttgccg gtaagcagct 1560
agaagacggt agaacgctgt ctgattacaa cattcagaag gagtccacct tacatcttgt 1620

-continued

```
gctaaggcta agaggtggta ggcacggatc cggcatcatg gttcgaccat tgaactgcat   1680
cgtcgccgtg tcccaaaata tggggattgg caagaacgga gacctaccct ggcctccgct   1740
caggaacgag ttcaagtact tccaaagaat gaccacaacc tcttcagtgg aaggtaaaca   1800
gaatctggtg attatgggta ggaaaacctg gttctccatt cctgagaaga atcgactttt   1860
aaaggacaga attaatatag ttctcagtag agaactcaaa gaaccaccac gaggagctca   1920
ttttcttgcc aaaagtttgg atgatgcctt aagacttatt gaacaaccgg aattggcaag   1980
taaagtagac atggtttgga tagtcggagg cagttctgtt taccaggaag ccatgaatca   2040
accaggccac ctcagactct ttgtgacaag gatcatgcag gaatttgaaa gtgacacgtt   2100
tttcccagaa attgatttgg ggaaatataa acttctccca gaatacccag gcgtcctctc   2160
tgaggtccag gaggaaaaag gcatcaagta taagtttgaa gtctacgaga agaaagacgg   2220
taccgaacaa aagcttattt ctgaagaaga cttgggagct ggtgcaggcg ctggagcggg   2280
tgccatggac tacaacaaga gatcttcggt ctcaaccgtg cctaatgcag ctcccataag   2340
agtcggattc gtcggtctca acgcagccaa aggatgggca atcaagacac attaccccgc   2400
catactgcaa ctatcgtcac aatttcaaat cactgcctta tacagtccaa aaattgagac   2460
ttctattgcc accatccagc gtctaaaatt gagtagtgcc actgcttttc ccactttaga   2520
gtcatttgca tcatcttcca ctatagatat gatagtgcta gctatccaag tggccagtca   2580
ttatgacgtt gttatgcctc tcttggaatt ctccaaaaat aatccgaacc tcaagtatct   2640
tttcgtagaa tgggcccttg catgttcact agatcaagcc gaatccattt ataaggctgc   2700
tgctgaacgt ggggttcaaa ccatcatctc tttacaaggt cgtaaatcac catatatttt   2760
gagagcaaaa gaattaatat ctcaaggcta tatcggcgac attaattcta tcgagattgc   2820
tggaaatggc ggttggtacg gctacgaaag gcctgttaaa tcaccaaaat acatctatga   2880
aatcgggaac ggtgtagatc tggtaaccac aacatttggt cacacaatcg atattttaca   2940
atacatgaca agttcgtact tttccaggat aaatgcaacg gttttcaata atattccaga   3000
gcaagagctg atagatgagc gtggtaaccg attgggccag cgagtcccaa agacagtacc   3060
ggatcatctt ttataccaag gcacattgtt aaatggcaat gttccagtgt catgcagttt   3120
caaaggtggc aaacctacca aaaaatttac caaaaatttg gtcattgata ttcacggtac   3180
caagggagat ttgaaacttg aaggcgacgc cggattcgca gaaatttcaa atctggtcct   3240
ttactacagt ggaactagag caaacgactt cccgctagct aatggacaac aagctccttt   3300
agacccgggg tatgatgcag gtaaagaaat catgaaagta tatcatttac gaaattataa   3360
tgccattgtc ggtaatattc atcgactgta tcaatctatc tctgacttcc acttcaatac   3420
aaagaaaatt cctgaattac cctcacaatt tgtaatgcaa ggtttcgatt tcgaaggctt   3480
tcccaccttg atggatgctc tgatattaca caggttaatc gagagcgttt ataaaagtaa   3540
catgatgggc tccacattaa acgttagcaa tatctcgcat tatagtttat aaaagcatct   3600
tgccctgtgc ttggcccccca gtgcagcgaa cgttataaaa acgaatactg agtatatatc   3660
tatgtaaaac aaccatatca tttcttgttc tgaactttgt ttacctaact agttttaaat   3720
ttcccttttt cgtgcatgcg ggtgttctta tttattagca tactacattt gaaatatcaa   3780
atttccttag tagaaaagtg agagaaggtg cactgacaca aaaaataaaa tccccgcgtg   3840
cttggccggc cgtaagatta ttacttgcta taagtgcgtg cctgatgaac aggatattgc   3900
ggtcaataat gctgatggtt cattagactt cagcaaagcc gatgccaaaa taagccaata   3960
```

cgatctcaac gctattgaag cggcttgcca gctaaagcaa caggcagcag aggcgcaggt 4020
gacagcctta agtgtgggcg gtaaagccct gaccaacgcc aaagggcgta aagatgtgct 4080
atcgcgcggc ccggatgaac tgattgtggt gattgatgac cagttcgagc aggcactgcc 4140
gcaacaaacg gcgagcgcac tggctgcagc cgcccagaaa gcaggctttg atctgatcct 4200
ctgtggcgat ggttcttccg acctttatgc ccagcaggtt ggtctgctgg tgggcgaaat 4260
cctcaatatt ccggcagtta acggcgtcag caaaattatc tccctgacgg cagataccct 4320
caccgttgag cgcgaactgg aagatgaaac cgaaacctta agcattccgc tgcctgcggt 4380
tgttgctgtt tccactgata tcaactcccc acaaattcct tcgatgaaag ccattctcgg 4440
cgcggcgaaa aagcccgtcc aggtatggtc ggcggcggat attggtttta acgcagaggc 4500
agcctggtca gaacaacagg ttgccgcgcc gaaacagcgc gaacgtcagc gcaacggccg 4560
gccaagcacg cggggattga gcgaagcttc tgaataagcc ctcgtaatat attttcatga 4620
agaatttagg tccaaaaaaa agatgggcat taattctagt catttaaaaa attctataga 4680
tcagaggtta catggccaag attgaaactt agaggagtat agttacataa aagaaggcaa 4740
aacgatgtat aaatgaaaga aattgagatg gtgcacgatg cacagttgaa gtgaacttgc 4800
ggggtttttc agtatctacg attcatttta ctcttttttt gggtttggtg gggtatcttc 4860
atcatcgaat agatagttat atacatcatc cattgtagtg gtattaaaca tccctgtagt 4920
gattccaaac gcgttatacg cagtttggtc cgtccaacca ggtgacagtg gttttgaatt 4980
attaccatca tcaattttac tagccgtgat ttcattattc atgaagttat catgaacgtt 5040
agaggaggca attggttgtg aaagcgcttg agaatttgtt tgagttgtta tgaggttcgg 5100
accgttgcta ctgttagtga aagtgaagga caatgagcta tcagcaatat tcccactttg 5160
attaaaattg gcgccaccaa acaaagcaga cggggtcagt ggcactaatg attgcagctg 5220
ttgctgttgc cctagaaaag gcgtgactga gcgatgcgaa ggtgtgcttc ttggtattgt 5280
cactggagag ttacgagagg gtggacggtt agataacagc ttgactagat cactgaaact 5340
tgctcctgat ttcaatggca caggtgaagg ccctactgag ccaggagaaa catatttaac 5400
actgatattg ttgacatttt cctccggaag agtagggtat tgggcgatag ttgcagaacc 5460
gacaatattt ttaatggcgc taccattact attgttataa ctgatatgcg gtaatgggat 5520
tgcacactgt gataacagaa acggcgcaca tacctcttcc agtacttgaa tgtatttttc 5580
acaagtctgg attttaaaag tggccagttt ttttaatagc atcagaacag tgttaatttg 5640
ttgtaataat tgtgcggtct cgttattctc agcattcgat tttgagtttg agagtagagt 5700
ctttatgggt actaggactg cattgaacaa gtaataagaa caattccagg caaaatatgg 5760
ggtgacatta tgattgtcca tatagctact tacagacata acagttcttt gtgctgcatc 5820
gcttaacatg atggagcatc gtttaacttc ataactttga tgatcatttt gatcctgttc 5880
tagttgtgac tttttctggg taaaattagt gaaaaaatct cttaatacat aaatgataag 5940
agacaactgt ttccacttca gttcgaatct tgtaaaggat agccaagggt gttccttcaa 6000
caaattggtt agagcggtgg tggaaatatc catttgtaaa aactttggtg cctgtctcga 6060
aacctcctca atctcattac aaatcatcaa gcattttttt gcacatatag gactttttc 6120 tgcagttact gttttgtcta gttcatagat ttttgtgaaa acttgtaaga gccttgctgt 6180
ttcaatgatg ccatgatata tggtgggacc tgttgtggta cgctgcacat cgtcgacaga 6240
agaagggaag gagattgtat tctgagaaag ctggatggat cgaccataaa gcagggacaa 6300
ttggatctcc caagagtaga cagaccacca aattcggcgt ctttgttcca gaatgctgct 6360
atcactgaag gacgagggga ggtccctatt caagcccaat gatatggcca ttcttatgga 6420
aaagctgtga aaattatagc tagtatttgt tttctgcctc cactgtgtat atcgcgacag 6480
aagatgtagg gctgtcacca aaattatgga acctgactcg aagaccttgc tcgtcaaatg 6540
agatttagca ttttgatagt aaaaaacatc tatatcagta gattcccct ctatacacca 6600 ggctccaatg gctaatatgc agttaaaaag gatttgccat tgatccttcg acgcgatttc 6660
aatctggtta ttatacaaca tcattagcgt cggtgagtgc acgatagggc agtaggggtg 6720
aaaattattg agataacttt gaagtaaacg ggatgttgtg gatctagaag ccaacgtgta 6780
tctatccgta atcatggtcg ggagcctgtt aacgttagag ttcgtgtaat tttccggttt 6840
aaagccaata gatcgaagaa tacataagag agaaccgtcg ccaaagaacc cattattgtt 6900
ggggtccgtt ttcaggaagg gcaagccatc cgacatgtca tcctcttcag accaatcaaa 6960
tccatgaaga gcatccctgg gcataaaatc caacggaatt gtggagttat catgatgagc 7020
tgccgagtca atcgatacag tcaactgtct ttgacctttg ttactactct cttccgatga 7080
tgatgtcgca cttattctat gctgtctcaa tgttagaggc atatcagtct ccactgaagc 7140
caatctatct gtgacggcat ctttattcac attatcttgt acaaataatc ctgttaacaa 7200
tgcttttata tcctgtaaag aatccatttt caaaatcatg tcaaggtctt ctcgaggaaa 7260
aatcagtaga aatagctgtt ccagtctttc tagccttgat tccacttctg tcagatgtgc 7320
cctagtcagc ggagaccttt tggttttggg agagtagcga cactcccagt tgttcttcag 7380
acacttggcg cacttcggtt tttctttgga gcacttgagc tttttaagtc ggcaaatatc 7440
gcatgcttgt tcgatagaag acagtagctt catctttcag gaggcttgct tctctgtcct 7500
ctcttaaaat gatggcgtgc attacgtaga cacaatctgg agatgaagct gaaaatctgg 7560
atccggaagg atgacggaaa aaatagctca taaaacagaa aaaggcccga agtaacaata 7620
ggaaaaatta attgcactaa acaaagaaaa cgatattatg gtgattaaac tgatacagaa 7680
ttatgtaaat actttgaaat tatagaaggt ttgtagaata aaaaaaatac tgggcgaatg 7740
ctgaggtccg ccggcgttgg acgagcggct acgtataact gtcaaaactt tgcagcagcg 7800
ggcatccttc catcatagct tcaaacatat tagcgttcct gatcttcata cccgtgctca 7860
aaatgatcaa acaaactgtt attgccaaga aataaacgca aggctgcctt caaaaactga 7920
tccattagat cctcatatca agcttcctca tagaacgccc aattacaata agcatgtttt 7980
gctgttatca ccgggtgata ggtttgctca accatggaag gtagcatgga atcataattt 8040
ggatactaat acaaatcggc catataatgc cattagtaaa ttgcgctccc atttaggtgg 8100
ttctccagga atactaataa atgcggtgca tttgcaaaat gaatttattc caaggccaaa 8160
acaacacgat gaatggcttt attttttgt tattcctgac atgaagcttt atgtaattaa 8220
ggaaacggac atcgggcggt ttaaacgcgt ggccgtgccg tc 8262

<210> SEQ ID NO 2
<211> LENGTH: 920
<212> TYPE: DNA
<213> ORGANISM: Saccharomyces cerevisiae
<220> FEATURE:
<221> NAME/KEY: misc_feature
<223> OTHER INFORMATION: MS73609 sequence

<400> SEQUENCE: 2
gacggcacgg ccacgcgttt aaaccgccct gtgacacaat ttgtgtctct actgtgtgaa 60
cttccattgc tgactaaaga ttccccgctc cgcttatatg tccggtccgt ccttgaccga 120

-continued

```
agatcacatt gccaattttt cacatctgga agcgatacga caatatagga gaaaaagaaa    180

agtgaaaggc aaaaaagcac caacagttct cgaggtgaag tgccgtcaat cttctgtata    240

aattcggcca attcaatcta atttaataga tttgcgacag actttcacat ccacattcga    300

ggaagaaatt caacacaaca acaagaaaag ccaaaatccg ctcgtccaac gccggcggac    360

ctgttgtcaa gctcttgata aatgtagctc ctttcttttt aactgctcca tgttttgggt    420

ctgtatatag gagtgctgtt ttaatcgata taggttacat ttgaaacttt tttttatgat    480

tataaggtac tatttaaata tttacaactc gtacagttct cttttgtttt ttctcttttt    540

ctccttgcta agcaccttta aggtgaaaag aaacacatat caatacacta acaaaaaagg    600

tgcacgttca tagggtatcg gacaataact atattactaa gctaccaaag caatagcgcc    660

aataacaaaa gctttcatgt taatgttcag ggatgcaccg gtatttcctt ttgccgtgct    720

gacagtatat gttgtgcttt gtttagcgga tgaggatgtt ccatgaatcg ctgccgtagg    780

tttggtggta gatctgttta ccttttcagt ggatgaactt agttgtgatg ttaatagcga    840

cttttggctc gagacaatta tcgtttcaag ggtagtttca cccctcccga tccggtgttt    900

aaaccccagc gcctggcggg                                                920


<210> SEQ ID NO 3
<211> LENGTH: 1069
<212> TYPE: DNA
<213> ORGANISM: Saccharomyces cerevisiae
<220> FEATURE:
<221> NAME/KEY: misc_feature
<223> OTHER INFORMATION: MS120584 sequence

<400> SEQUENCE: 3

gacggcacgg ccacgcgttt aaaccgccat taccgcgtga actatgtcat atttgcgatt     60

ttaggtacaa taaatattat cattattata ttatgtttgc atgtaggttc tacaaataca    120

ttgttgtacg ctatagtttc ctttcaaaac tagaaagaat tcgtaacaaa ataatctcca    180

atattttata gcaccttatt aatatcaatg ctgcaatacc ttctcatttc aacaattggc    240

cctcacctct tttgtacaaa aaacgtcgcc attgataaaa taagtaagaa gcatataatt    300

ggaatgtcca ttacgtaaaa gaaaaaaaat catgtgtaca tattacgtaa tagaatacgg    360

aattttctcg cggaagtaga tcttccgtgg aaaaaaagga aaaagtccga tcaatattga    420

aaaagggatc cttagtttcc caactatata aggaggaaaa gtctatctct gtagcgttga    480

tataacgtgt acgattttca aacaaacaga tagcagtatc acacgcccgt aaatacttta    540

aatgaaaata gataatattt atatatatta acgttattac aattattttt tatcatctgg    600

tacatctctg cgtatttttc tcttctatat acagcttaat atgtcgaaaa cgcgaagcaa    660

gaaagaaaag aaaattgacg aaaaaacaat agagaaacgt tcagataagc atttatcttt    720

gcaacacatc acaagaaaag ctgtgcacaa tgaccggagc agcaactgca gcagaaaact    780

ctgccacaca gttagaattc tatagaaaag ctttgaattt caacgttatt gggagatacg    840

atccaaaaat aaagcaactg ctttttcaca caccacatgc gtcactgtat aaatgggact    900

tcaagaagga cgaatggaat aaactagaat atcaaggtgt tttggccata tatttgagag    960

acgtctcgca aaatacaaat cttctacccg tctccccaca agaagtagat atttttgatt   1020

cgcaaaatgg tagtaataac acggtgttta aaccccagcg cctggcggg               1069


<210> SEQ ID NO 4
<211> LENGTH: 1048
```

<212> TYPE: DNA
<213> ORGANISM: Saccharomyces cerevisiae
<220> FEATURE:
<221> NAME/KEY: misc_feature
<223> OTHER INFORMATION: MS120568 sequence

<400> SEQUENCE: 4
gacggcacgg ccacgcgttt aaaccgccca agactcgttg ggtcaatata caccacaaaa 60
aaaggtacac acgaatggtt taaccctttc ggttccttct gtaaatcgaa aaatgccctt 120
tatacagcgg gttggtctcc catcaaagtt gagaagcgat tagaaattag gttacctaat 180
gaatccataa ataaatggaa aacgctattt tgttcgaacg atggaataaa aatatgaacg 240
ggtgtcattg aaattcggtg tattttttga tcgggcctga tctggctcgg gtttggcaca 300
atttggcttg gttagttcgg caaagcttat ttaaagaacc tttttggata gccaattgag 360
agacttgaaa tagaaagatc gtaagtattt ttatgaacgc aaaatcaatc ttggtagccc 420
agttagtttc tcttcactaa ttccggagaa caaaaacata tcatacgatt gtgtgagatt 480
caacaaaaat cgatcagaaa ttttttttga acagaatagt caattaagct ttcgagaaaa 540
actttctttt aacccctcta atctaaatat aaacatatag cttatagaaa tgaatgaata 600
ttttaaatag ttacggatac aaagagttca ttatagtgcg ggcagttagt acggtatcga 660
tttatcattg gagatctgca gtgttacaga agcactgctc accagttgtc tacggaagga 720
cgttgagata gttttaccac gtttgagcta aaagtttcta ccacaagagc ctttatttgc 780
acatggcagt gaatgcatga ttaaggatat gaagaagaaa ggaataacta ggaataaatt 840
ttatttagag agggtatgat gaaaggagag cctcgttatt tatgacctgc atttttatca 900
gcatcttctt tccagctccc gctaaacatg tgctttacaa aagccatttt gtcgtcacta 960
gactgggcgc ccatctgccc cacatctggt gaaaaacttg ttattggtag aaccatcaca 1020
cggtgtttaa accccagcgc ctggcggg 1048

<210> SEQ ID NO 5
<211> LENGTH: 9085
<212> TYPE: DNA
<213> ORGANISM: Artificial Sequence
<220> FEATURE:
<223> OTHER INFORMATION: Synthetic: MS133489 sequence

<400> SEQUENCE: 5
gacggcacgg ccacgcgttt aaaccgcccg aacaagctta tccctattac agaattccaa 60
ggaggaaatc attcaacttg aaagtaaatg gatgtctatg caatctgtta aaacaactgc 120
cctacccctt caagagacta cgaatacatc atcgacctta acttctctga cgtccagcat 180
aattcccaag agtataccta taatcacgaa aggtgaagtc gccactaaac cagcatctta 240
ctgaattatt ttcaacagaa cacatcgcat ccaactgaac aaactgttac cgctgttgat 300
accaaggaac attcagtgaa cgtagggaag aacgaacatt ctccatattt ttgcatacta 360
gatacaaggg ggaagaatgc aattatttca caaaccgaaa gaaaaagaat cacaagctat 420
gtttgctatt atcaattttt cttatgatta atttaacata aattatggcc tttttcattc 480
cggctgcgct tgttctccaa tttttttttt ttttttgaga aaactttcgc tcgtccaacg 540
ccggcggacc ttcacatgta gggaccgaat tgtttacaag ttctctgtac caccatggag 600
acatcaaaga ttgaaaatct atggaaagat atggacggta gcaacaagaa tatagcacga 660
gccgcgaagt tcatttcgtt acttttgata tcgctcacaa ctattgcgaa gcgcttcagt 720
gaaaaaatca taaggaaaag ttgtaaatat tattggtagt attcgtttgg taaagtagag 780

-continued

```
ggggtaattt ttccccttta ttttgttcat acattcttaa attgctttgc ctctcctttt    840
ggaaagctat acttcggagc actgttgagc gaaggctcat tagatatatt ttctgtcatt    900
ttccttaacc caaaaataag ggaaagggtc caaaaagcgc tcggacaact gttgaccgtg    960
atccgaagga ctggctatac agtgttcaca aaatagccaa gctgaaaata atgtgtagct   1020
atgttcagtt agtttggcta gcaaagatat aaaagcaggt cggaaatatt tatgggcatt   1080
attatgcaga gcatcaacat gataaaaaaa aacagttgaa tattccctca aaaatgccca   1140
gtaaattggc tataacttcc atgtccttgg gcaggtgtta tgcaggccat tctttcacaa   1200
ctaagttaga catggctagg aaatatggtt accagggttt ggagttgttt catgaggact   1260
tagccgatgt cgcatacagg ttgtcaggtg aaacacctag tccatgcggt cccagtccag   1320
ctgctcaatt atcagccgct agacagatat tgaggatgtg ccaggttaga aacatcgaaa   1380
tagtgtgctt gcaacccttt tcacaatatg atggtttatt ggatagagag gagcacgaga   1440
ggaggttgga gcaattagag ttttggattg aattggccca cgagttggat actgacatca   1500
ttcaaattcc agccaatttc ttgcccgccg aagaagtcac agaagatatt tcattaattg   1560
tgagtgactt acaggaagtt gccgatatgg gtttacaggc aaaccctcca ataaggtttg   1620
tatatgaggc attatgctgg tccactagag ttgacacttg ggagaggtct tgggaagttg   1680
tccaaagagt aaatagacct aactttggcg tttgcttaga cacttttaac atcgcaggta   1740
gagtttatgc tgaccccaca gttgcctcag gcagaacacc aaacgctgaa gaagcaatta   1800
gaaagtcaat tgccaggttg gtcgaaaggg tcgatgtatc taaagtcttc tacgttcaag   1860
tagtggacgc cgaaaagtta aagaaaccat tagttcccgg tcatagattc tatgaccctg   1920
agcaaccagc cagaatgtca tggtcaagaa attgtaggtt gttctacggc gaaaaagaca   1980
gaggcgctta cttacctgtt aaagaaatcg cttgggcttt tttcaatgga ttgggcttcg   2040
aaggttgggt gtccttggaa ttatttaaca gaagaatgtc agatactgga tttggagttc   2100
cagaggagtt agctaggaga ggcgccgtat catgggccaa attagttaga gatatgaaaa   2160
tcacagtgga ttctccaact caacaacaag ctacacagca gcctattaga atgttgtcct   2220
tatctgcagc cttataaaag gcggccgctg gcgagggaga tgatccgctc taaccgaaaa   2280
ggaaggagtt agacaacctg aagtctaggt ccctatttat ttttttatag ttatgttagt   2340
attaagaacg ttatttatat ttcaaatttt tctttttttt ctgtacagac gcgtgtacgc   2400
atgtaacatt atactgaaaa ccttgcttga gaaggttttg ggacgctcga agcaacctgc   2460
aggccgcgag cgccgatcgg gtagtggagc ccgtttgggc tcagcgcgag gtaacaaaaa   2520
aaaatttcaa atgttggcca aaaaaaacgt caattattcc tatgtacgag gtctaaatat   2580
aaaaacatat ctattatatt ctgacgtatt tatattctat tgttctttcc tatcactggc   2640
ctacaaaaaa aaagagaagc atactcaacg cgatcgccga cgccgccgat ttaggccact   2700
cttgctgtca attggccatt caaatcctga tgaatttctc tcaacaatgc gtcggtcatt   2760
tcccatgaaa tacatgcgtc tgtaacagac acgccatact tcatttctga tcttggctgt   2820
tcggatgatt ggttaccctc atgaatattt gattcgatca tcaaaccgat gatagatctg   2880
tttccatctt ttatctgtgc aactacagat tcagcgacgg cgggttgtct cctgtaatcc   2940
ttattagagt taccgtgaga acagtcgacc atcaaggaag gtcttaaacc tgcttgttcc   3000
atttcctttt cgcactgtgc cacgtcggca ggtgaatagt ttggggcctt accacccctc   3060
aatattacat gaccatctgg gttaccctga gtttgtaata atgcgacctg accagcttga   3120
```

-continued

```
ttgataccga caaatctatg tggttgagct gcggccctca tggcatttat ggcagttgcc   3180
aatgaaccgt ctgtgccgtt tttgaagcca actggcatac tcaaaccaga tgccatttct   3240
ctgtgagttt gtgattcggt ggttctagca cctattgcag accaggagaa taaatcgccc   3300
aaatattgag gactgtttaa atccaaggct tcggtagcta aaggcaaacc catatttact   3360
aattccaaca acaatttcct tgcgatttgc aaaccagctt ccacatcaaa agatccatcc   3420
atatgtgggt cgttaatcaa tcccttccaa cctacagtgg tccttggctt ttcaaaataa   3480
accctcataa ccaaatacaa ggagtcggag acttcagctg ccaaggcctt aaatcttctt   3540
gcgtattcca atgctgtttc aggatcgtgg atactacatg ggccacatac aaccaataac   3600
cttggatctc taccggctat aatatcagaa atactctttc ttgaatcggc tatctgagcc   3660
tcttgttgca aagataaggg aaaggcagct tttaattgct caggtgtcat caaaacctgt   3720
tcatctgtta tatgtacgtt atttaaggca tctttctgca ttgtaaagtt agttggttgc   3780
gcgacttcgg gtggggtatg ttaatcttgt gtttacttaa ctattgctat tcttgatgat   3840
aattgaataa ggtgcataat gaagagcaat tcacaacacc aaatttcaa tccaattact    3900
gattgtttat atatgtctac aaaactaatc ctatctccac attttagcct gcgaaatgtt   3960
tgttttttaa acaatagctc tccagaacat tgtataattt aagaatatgt gcacagttaa   4020
ctttctagca ggagtataat gccatttgct ccccatcttg agatgggaag ggcttaacta   4080
atctcggttc ggagtgatcc gccccgatac tgccttctgc cttaatatcg tccaaggcac   4140
atggacccct gaacggcgca gatatctccg cacggacgaa agaccgccgg tgccttcctg   4200
aggcaaccgc ccctttcgaa tatagatcac gtgacccatt tttagctact aatagaaaaa   4260
gaaattgcaa cctacttaag ccattccgga aggaagcttt ccgaatcccc gcgtgcttgg   4320
ccggccgtga tcatctaccc atgccgaaat tcgggccgtt ggccggattg cgcgttgtct   4380
tctccggtat cgaaatcgcc ggaccgtttg ccgggcaaat gttcgcagaa tggggcgcgg   4440
aagttatctg gatcgagaac gtcgcctggg ccgacaccat tcgcgttcaa ccgaactacc   4500
cgcaactctc ccgccgcaat ttgcacgcgc tgtcgttaaa tattttcaaa gatgaaggcc   4560
gcgaagcgtt tctgaaatta atggaaacca ccgatatctt catcgaagcc agtaaaggtc   4620
cggcctttgc ccgtcgtggc attaccgatg aagtactgtg gcagcacaac ccgaaactgg   4680
ttatcgctca cctgtccggt tttggtcagt acggcaccga ggagtacacc aatcttccgg   4740
cctataacac tatcgcccag gcctttagtg gttacctgat tcagaacggt gatgttgacc   4800
agccaatgcc tgccttcccg tataccgccg attacttttc tggcctgacc gccaccacgg   4860
cggcgctggc agcactgcat aaagtgcgtg aaaccggtaa aggcgaaagt atcgacatcg   4920
ccatgtatga agtgatgctg cgtatgggcc agtacttcat gatggattac ttcaacggcg   4980
gcgaaatgtg cccgcgcatg agcaaaggta aagatcccta ctacgccgac ggccggccaa   5040
gcacgcgggg attcggaaag cttccttccg gaatggctta agtaggttgc aatttctttt   5100
tctattagta gctaaaaatg ggtcacgtga tctatattcg aaaggggcgg ttgcctcagg   5160
aaggcaccgg cggtctttcg tccgtgcgga gatatctgcg ccgttcaggg gtccatgtgc   5220
cttggacgat attaaggcag aaggcagtat cggggcggat cactccgaac cgagattagt   5280
taagcccttc ccatctcaag atggggagca aatggcatta tactcctgct agaaagttaa   5340
ctgtgcacat attcttaaat tatacaatgt tctggagagc tattgtttaa aaaacaaaca   5400
tttcgcaggc taaaatgtgg agataggatt agttttgtag acatatataa acaatcagta   5460
attggattga aaatttggtg ttgtgaattg ctcttcatta tgcaccttat tcaattatca   5520
```

-continued

```
tcaagaatag caatagttaa gtaaacacaa gattaacata ccccacccga agtcgcgcaa   5580
ccaactaact ttacaatgga aagaattgtt gtaacattgg gtgaaaggtc ttatccaatc   5640
actattgcat ctggtttatt taacgaacca gccagttttt taccattgaa atccggtgag   5700
caagtgatgt tagtcactaa cgaaacatta gctcccttgt atttagacaa ggtaaggggt   5760
gttttggaac aagcaggcgt aaacgtcgat tctgtgatat taccagacgg tgaacaatac   5820
aaaagtttgg cagttttaga tactgtattc actgccttat tacagaaacc acatggtaga   5880
gatactacat tggttgcctt aggaggcgga gttgtcggcg atttaacagg tttcgctgcc   5940
gcatcatatc agagaggtgt tagattcatt caggtcccaa ctactttgtt atcccaagta   6000
gactcatcag ttggaggaaa gactgctgtc aatcatcctt taggaaagaa catgattggt   6060
gccttctacc agccagcatc agtcgttgtt gatttagatt gtttgaagac attacctcca   6120
agagagttgg caagtggttt ggcagaagta ataaaatatg gtatcatatt ggatggtgca   6180
ttttttaatt ggttggaaga aaatttagat gcattattga ggttagacgg tcctgctatg   6240
gcttattgta ttagaaggtg ttgtgaatta aaggctgagg ttgtagcagc cgacgagaga   6300
gaaactggtt taagagcttt gttgaactta ggtcatacat ttggtcatgc tatcgaagct   6360
gaaatgggtt acggtaattg gttgcatggt gaagccgttg cagccggtat ggttatggct   6420
gccaggacat ctgaaagatt gggtcaattc agttctgcag aaacacaaag gataataacc   6480
ttattgaaaa gggcaggttt acctgtgaat ggtcctagag agatgagtgc tcaagcttat   6540
ttgccccaca tgttgagaga taagaaggtt ttagcaggtg aaatgaggtt aattttgccc   6600
ttagcaattg gaaaaagtga agtcagatcc ggtgtttcac atgaattagt attgaacgcc   6660
atagctgatt gccaatcagc ctaaatcggc ggcgtcggcg atcgcgttaa gggaaccttt   6720
tacaacaaat atttgaaaaa ttacctccat tattatacct tctctttatg taattgttag   6780
ttcgaaaatt ttttcttcat taatataatc aacttctaaa actttctaaa aacgttctct   6840
ttttcgagat tagtgcttct tcccaatccg taagaaatgt ttcctttctt gacaaatcgg   6900
cgctcgcggc ctgcaggtta aacttaaaat acgctgaacc cgaacataga aatatcgaat   6960
gggaaaaaaa aactgcataa aggcattaaa agaggagcga attttttttt aataaaaatc   7020
ttaataatca ttaaaagata aataatagtc tatatatacg tatataaata aaaaatattc   7080
aaaaaataaa ataaactatt attttagcgt aaaggatggg gaaagagaaa agaaaaaaat   7140
tgatctatcg atttcaattc aattcaatat ctccctcgcc agcggccgcc ttttatgctt   7200
ggtgtaatat ggtcaaaact gttctcaaat catttactga gatctgtcct ggagcagaag   7260
ctttttttgac agcaccaaat gtagcagcag atccgaacac ttcaccagct aatctagaaa   7320
tcacaccggt ttttgccata gacatagtta tgataggtct atcagcgtat tgttcttgca   7380
tttccaatgt ggcagctaac aatgttaaga catcagaggt agactgtggc attaaagcaa   7440
ttttgggtat atcagcatca aaggattgca tttttcttaa tctggctatg atttcctctg   7500
cttctggggt cttgtggaaa tcatgattag acataactac cttaacatcg tgagcgtgag   7560
cgtaagctac agtttcctta acctggtcat caccagtaaa caactccaaa tctatcatat   7620
ccactaaacc actatcaata gcagctctgt tcaaagcaat gtaggcttcg gtactaattg   7680
cttgttcacc accttcctta gctgatctga aagtgaacaa taatggtttt tcaggcatag   7740
tctctcttaa tatctttgct gcagccatta ctgattcgac atttgacaag tctgcatagt   7800
gatccactct ccattctaat atgtcaaaat ctgcttctct ataagctaag gcctcactct   7860
```

```
ttacagaggc tatgtcttta gccattaaac taacaattat tttaggggct cctgttccaa   7920
taaccaaatc tttcactgta actgtcttca tttttgaggg aatattcaac tgtttttttt   7980
tatcatgttg atgctctgca taataatgcc cataaatatt tccgacctgc ttttatatct   8040
ttgctagcca aactaactga acatagctac acattatttt cagcttggct attttgtgaa   8100
cactgtatag ccagtccttc ggatcacggt caacagttgt ccgagcgctt tttggaccct   8160
ttcccttatt tttgggttaa ggaaaatgac agaaaatata tctaatgagc cttcgctcaa   8220
cagtgctccg aagtatagct ttccaaaagg agaggcaaag caatttaaga atgtatgaac   8280
aaaataaagg ggaaaaatta ccccctctac tttaccaaac gaatactacc aataatattt   8340
acaacttttc cttatgattt tttcactgaa gcgcttcgca atagttgtga gcgatatcaa   8400
aagtaacgaa atgaacttcg cggctcgtgc tatattcttg ttgctaccgt ccatatcttt   8460
ccatagattt tcaatctttg atgtctccat ggtggtacag agaacttgta aacaattcgg   8520
tccctacatg tgaaggtccg ccggcgttgg acgagcggca tagtaaaaaa atagatgcag   8580
aatttactca cctcaaggag gggcaaagta ataagaaaag ttaccatagg ctagttgaat   8640
gtccaagatc gtaaagaatg aagaaaaaag gagtaaaaag tatgaataag ataaatgaaa   8700
atataaaaat aaaaaccaac taatacatga agaaaaaaaa gcagacaaaa acattttatg   8760
gacctgatgc aatctagtag tccatagaat aatcaccact agaaaattct tcctcttcat   8820
tactaccgtt tgccattata ggaatatgat ttgctgcagg attctgcgga ggtattatat   8880
agggcactgg cggcacctgt ggaataaacc caaatgatgg gaacattggc atcatccagt   8940
tagcgttatt ttggtttgca cttattaagt tgtaactgtt cacgggcttt gtgttggtat   9000
tagggtactg cagtggtatg aaataatttt ccctcgagac ttgctgttgc gattggtggc   9060
ggtttaaacg cgtggccgtg ccgtc                                         9085
```

<210> SEQ ID NO 6
<211> LENGTH: 10078
<212> TYPE: DNA
<213> ORGANISM: Artificial Sequence
<220> FEATURE:
<223> OTHER INFORMATION: Synthetic: MS134781 sequence

<400> SEQUENCE: 6

```
gacggcacgg ccacgcgttt aaaccgcctg catacttcaa gttcagggtt ggacctgcca     60
atgaaaattt tagatatgtt tggctcaggt cttcctgtta ttgcaatgaa ctatccagtg    120
cttgacgaat tagtacaaca caatgtaaat gggttaaaat ttgttgatag aagggagctt    180
catgaatctc tgatttttgc tatgaaagat gctgatttat accaaaaatt gaagaaaaat    240
gtaacgcagg aagctgagaa cagatggcaa tcaaattggg aacgaacaat gagagatttg    300
aagctaattc attgagtcaa tggtaactca gcctttcttt tttgaaaatt actattttcg    360
actctttttt tatacagtta catagtacta cctctaatac acattcatga ttaacaatgt    420
ttcaaacaat ataaagtccc gataacgacc ttttgaagtg gtgacgttac cgctcttcgt    480
tgacaagatt caagagggct gtcagaataa cagctatcat ggtggaacgc tcgtccaacg    540
ccggcggacc taaacttaaa atacgctgaa cccgaacata gaaatatcga atgggaaaaa    600
aaaactgcat aaaggcatta aaagaggagc gaattttttt ttaataaaaa tcttaataat    660
cattaaaaga taaataatag tctatatata cgtatataaa taaaaaatat tcaaaaaata    720
aaataaacta ttattttagc gtaaaggatg gggaaagaga aaagaaaaaa attgatctat    780
cgatttcaat tcaattcaat atccccgcgt gcttggccgg ccgttacaag atggtcctcg    840
```

-continued

```
gaggtcacaa ttatcacctc tccgcattca caatcacagt gtattatctc tatgaataaa    900
aaagttgaaa attctaaaaa aaaaacagaa atatatatta atctaagtta gtattataaa    960
tcgattaagt gacggcggta gcagcgataa cgtaaccatc tcttaaaacc cacttaccgg   1020
agataaatgg aactggagtt ggtctaacca ataagtagga gacgaaggta ccatcgtctc   1080
ttaaatcaat ctcggcttgt tcgaaaccca accaacgatg ggtcaaagga aaccaggctt   1140
tgtaagtggc ttctttagca caaaacaaca atctgtcagc acagtgaaca ccttgttcct   1200
ctaaacgttt caattgtggg atttcaccaa ctctagcgat agaacccaag acatcctttg   1260
gcaatggttc agctggttcg gcgtccaaac ccatagatct gactaataat cttggagcga   1320
caacagcagc tctgaaacca tcggtgtggg tcaaagaacc agaaacggaa gaaggccata   1380
aaggcatacc tctttcacct ctcaaaattg gatcaccaga gtctctaccc aaggcttgca   1440
aggcttggtg ggcacaccat ctagcgtcac caaattcggc ctttctgatg tcgacggaat   1500
gagcgaccaa ggctttttcc aatggatgca attggtggaa gtggtccaag ttgacagcgt   1560
caccagtttt gataaaagaa aacttagcgg agtttggaaa caaagattcg tccaacattg   1620
taaagttagt tggttgcgcg acttcgggtg gggttacttt tttttggat ggacgcaaag   1680
aagtttaata atcatattac atggcaatac caccatatac atatccatat ctaatcttac   1740
ttatatgttg tggaaatgta aagagcccca ttatcttagc ctaaaaaaac cttctctttg   1800
gaactttcag taatacgctt aactgctcat tgctatattg aagtacggat tagaagccgc   1860
cgagcgggcg acagccctcc gacggaagac tctcctccgt gcgtcctggt cttcaccggt   1920
cgcgttcctg aaacgcagat gtgcctcgcg ccgcactgct ccgaacaata aagattctac   1980
aatactagct tttatggtta tgaagaggaa aaattggcag taacctggcc ccacaaacct   2040
tcaaatcaac gaatcaaatt aacaaccata ggataataat gcgattagtt ttttagcctt   2100
atttctgggg taattaatca gcgaagcgat gatttttgat ctattaacag atatataaat   2160
gcaaaagctg cataaccact ttaactaata ctttcaacat tttcggtttg tattacttct   2220
tattcaaatg tcataaaagt atcaacaaaa aattgttaat atacctctat acttacctcc   2280
cgcgacctcc aaaatcgaac taccttcaca atggctgttg actctccaga cgaaagattg   2340
caaagaagaa ttgctcaatt attcgctgag gacgaacaag tcaaggccgc tagaccattg   2400
gaagctgttt ctgctgccgt ttctgctcca ggtatgagat tagcccaaat cgctgccact   2460
gtcatggctg gttatgctga tagaccagct gctggtcaaa gagctttcga attaaacacc   2520
gacgacgcta ccggtagaac ctctttacgt ttgttaccta gattcgaaac tattacctac   2580
cgtgaattat ggcaaagagt cggtgaagtt gctgctgctt ggcaccatga tccagaaaac   2640
ccattgcgtg ccggtgactt cgttgctttg ttaggtttca cctctattga ctacgccact   2700
ttggacttgg ccgatatcca tttgggtgcc gttactgtcc cattacaagc ttccgctgct   2760
gtttcccaat taattgctat tttgactgag acctctccac gtttattagc ttctactcca   2820
gaacacttag atgctgctgt tgaatgctta ttggccggta ccacccccaga aagattggtc   2880
gttttcgatt atcatccaga agatgatgat caaagagctg ctttcgaatc tgctagaaga   2940
agattagctg atgctggttc tttggttatc gttgaaacct tggacgctgt cagagccaga   3000
ggtagagatt tgccagccgc cccattgttc gttccagaca ctgatgacga cccattagct   3060
ttgttaattt acacttctgg ttctaccggt actccaaagg gtgctatgta caccaacaga   3120
ttagctgcta ccatgtggca aggtaactcc atgttacaag gtaattctca aagagtcggt   3180
```

-continued

```
attaacttga attacatgcc aatgtcccac attgctggta gaatttcttt gtttggtgtc   3240
ttagccagag gtggtactgc ttatttcgcc gccaagtccg atatgtctac cttgttcgaa   3300
gatattggtt tggttagacc tactgaaatt ttcttcgtcc caagagtttg cgatatggtc   3360
ttccaaagat accaatctga attagacaga agatctgttg ctggtgctga cttagacacc   3420
ttggatcgtg aggttaaagc tgatttgaga caaaactact tgggtggtcg tttcttggtt   3480
gctgttgtcg gttctgctcc attggccgct gaaatgaaga ctttcatgga atctgttttg   3540
gatttgcctt tgcatgacgg ttacggttcc accgaagctg gtgcttccgt cttgttggac   3600
aaccaaattc aaagaccacc agttttggac tacaagttgg ttgatgtccc tgagttaggt   3660
tacttcagaa ctgacagacc tcacccaaga ggtgagttat tgttgaaggc cgaaactact   3720
atccctggtt actacaaaag acctgaagtt accgccgaaa ttttcgacga agatggtttt   3780
tacaagactg gtgatattgt tgctgaatta gaacacgaca gattggttta tgttgatcgt   3840
agaaacaatg tcttgaagtt gtctcaaggt gaattcgtca ctgttgctca cttggaagct   3900
gtttttgctt cttccccatt aatcagacaa atcttcatct atggttcctc cgaaagatcc   3960
tacttgttgg ctgttattgt cccaactgat gatgctttga gaggtagaga tactgctact   4020
ttgaagtctg ctttagctga atctatccaa agaattgcta aggatgctaa cttgcaacct   4080
tacgaaattc caagagattt cttgattgaa actgaaccat tcactatcgc taacggttta   4140
ttgtccggta ttgccaagtt gttgcgtcct aacttgaagg aaagatacgg tgcccaattg   4200
gaacaaatgt acaccgactt ggctactggt caagctgacg agttattggc cttgagaaga   4260
gaagctgctg atttaccagt tttggaaacc gtttctagag ctgccaaggc catgttaggt   4320
gttgcttccg ctgacatgag accagacgcc cactttaccg acttgggtgg tgattccttg   4380
tctgctttat ccttttccaa cttgttgcac gaaatttttg gtgtcgaagt cccagttggt   4440
gttgtcgtct ccccagctaa cgaattgaga gacttagcca attacatcga agctgaacgt   4500
aactctggtg ctaagagacc aaccttcacc tccgttcatg gtggtggttc cgagattaga   4560
gctgccgact taaccttgga taagttcatt gatgctagaa ctttagctgc cgctgactcc   4620
attccacacg ctcctgtccc agctcaaact gttttgttga ccggtgctaa cggttatttg   4680
ggtagattct tatgtttgga atggttggaa agattggata agaccggtgg taccttgatc   4740
tgcgttgttc gtggttccga tgccgccgct gccagaaaga gattggactc cgctttcgac   4800
tccggtgatc caggtttgtt ggaacactat caacaattgg ccgctcgtac cttggaagtt   4860
ttggctggtg acattggtga cccaaacttg ggtttggacg atgctacttg gcaacgttta   4920
gctgaaaccg tcgatttgat tgttcaccca gccgctttgg tcaaccacgt tttaccatat   4980
acccaattat tcggtccaaa cgttgttggt actgctgaaa ttgttcgttt agctatcact   5040
gctagaagaa agccagttac ttatttatcc accgttggtg ttgctgatca agttgaccca   5100
gctgaatacc aagaagactc tgatgtcaga gaaatgtccg ccgtccgtgt tgttagagaa   5160
tcctatgcta acggttatgg taactctaag tgggctggtg aagttttgtt gagagaagct   5220
catgatttgt gcggtttgcc agtcgctgtc ttccgttctg acatgatctt ggctcactcc   5280
agatacgctg gtcaattaaa cgttcaagat gttttcaccc gtttgatctt gtccttggtt   5340
gccactggta tcgctccata ctccttctac agaactgacg ccgacggtaa cagacaaaga   5400
gctcattacg atggtttgcc agctgacttc actgctgctg ctattaccgc tttgggtatt   5460
caagctaccg aaggtttccg tacttacgat gttttgaacc catacgacga tggtatttct   5520
ttggatgaat tcgttgactg gttagttgaa tctggtcatc caatccaaag aatcaccgac   5580
```

tactctgatt ggttccacag atttgaaact gccatcagag ctttgccaga aaagcaaaga 5640
caagcttctg tcttaccatt gttggatgcc tacagaaacc catgtcctgc tgtccgtggt 5700
gctatcttgc cagctaagga atttcaagcc gctgtccaaa ctgctaagat cggtccagaa 5760
caagacatcc cacatttgtc cgccccattg attgacaagt acgtttctga tttggaattg 5820
ttgcaattat tgtaaaacct gcaggccgcg agcgccgata agggaacctt ttacaacaaa 5880
tatttgaaaa attacctcca ttattatacc ttctctttat gtaattgtta gttcgaaaat 5940
tttttcttca ttaatataat caacttctaa aactttctaa aaacgttctc tttttcgaga 6000
ttagtgcttc ttcccaatcc gtaagaaatg tttcctttct tgacaaaacg cgatcgccga 6060
cgccgccgat aagattatta cttgctataa gtgcgtgcct gatgaacagg atattgcggt 6120
caataatgct gatggttcat tagacttcag caaagccgat gccaaaataa gccaatacga 6180
tctcaacgct attgaagcgg cttgccagct aaagcaacag gcagcagagg cgcaggtgac 6240
agccttaagt gtgggcggta aagccctgac caacgccaaa gggcgtaaag atgtgctatc 6300
gcgcggcccg gatgaactga ttgtggtgat tgatgaccag ttcgagcagg cactgccgca 6360
acaaacggcg agcgcactgg ctgcagccgc ccagaaagca ggctttgatc tgatcctctg 6420
tggcgatggt tcttccgacc tttatgccca gcaggttggt ctgctggtgg gcgaaatcct 6480
caatattccg gcagttaacg gcgtcagcaa aattatctcc ctgacggcag ataccctcac 6540
cgttgagcgc gaactggaag atgaaaccga aaccttaagc attccgctgc ctgcggttgt 6600
tgctgtttcc actgatatca actccccaca aattccttcg atgaaagcca ttctcggcgc 6660
ggcgaaaaag cccgtccagg tatggtcggc ggcggatatt ggttttaacg cagaggcagc 6720
ctggtcagaa caacaggttg ccgcgccgaa acagcgcgaa cgtcagcgca atcggcggcg 6780
tcggcgatcg cgttgcttcg agcgtcccaa aaccttctca agcaaggttt tcagtataat 6840
gttacatgcg tacacgcgtc tgtacagaaa aaaaagaaaa atttgaaata taaataacgt 6900
tcttaatact aacataacta taaaaaaata aatagggacc tagacttcag gttgtctaac 6960
tccttccttt tcggttagag cggatcatcg gcgctcgcgg cctgcaggtt ttagacgaca 7020
cgtctgcaca aggtaatacc gtcggcgatt ggtaattgaa ctggttcgac tctggcgtcg 7080
gcagcaatca tggcattgaa accacgaatg gagtctctct tctttctgtc ttcttcggtc 7140
aatggagtgt catctggcat ggagacggta ccaccccata aggtattgtc gtaagccaaa 7200
acaccaccaa ctctaaccaa tctcaacaat tgttcgtggt aggaaccgta gttgtactta 7260
tcggcatcaa cgaaagcgaa atcaaaagaa ccttcgtctt catcagcaat caatttgtcc 7320
aaaattggac cagcaggacc ttcacggaaa tcaaccttat gggcaacacc ggccttctta 7380
ataactggca aacccaagtc aaagtattca cgggaaacgt caatagcaat gattctacca 7440
tcgtctggga tagctaaggc agtagtcaag acggaacaac cagtgtagac accgacttcg 7500
atggttctct tagcacccat aacctttaac aacaaggaca ataacaaacc ttcatctggt 7560
ggagaagaca tgaaaccgaa gatatgttcg gaagtgattt gtctcaattc tctcataaat 7620
tcgttctctc ttggatagac catagtcttc aacatataat cgtataaagc atcggatttc 7680
aataaagtct tggtagtttc ggaggagtga acttctctaa cctcaccggc agaaccatta 7740
cttgccatat ccattgtgaa ggtagttcga ttttggaggt cgcgggaggt aagtatagag 7800
gtatattaac aatttttttgt tgatactttt atgacatttg aataagaagt aatacaaacc 7860
gaaaatgttg aaagtattag ttaaagtggt tatgcagctt ttgcatttat atatctgtta 7920

```
atagatcaaa aatcatcgct tcgctgatta attaccccag aaataaggct aaaaaactaa   7980
tcgcattatt atcctatggt tgttaatttg attcgttgat ttgaaggttt gtggggccag   8040
gttactgcca atttttcctc ttcataacca taaaagctag tattgtagaa tctttattgt   8100
tcggagcagt gcggcgcgag gcacatctgc gtttcaggaa cgcgaccggt gaagaccagg   8160
acgcacggag gagagtcttc cgtcggaggg ctgtcgcccg ctcggcggct tctaatccgt   8220
acttcaatat agcaatgagc agttaagcgt attactgaaa gttccaaaga gaaggttttt   8280
ttaggctaag ataatggggc tctttacatt tccacaacat ataagtaaga ttagatatgg   8340
atatgtatat ggtggtattg ccatgtaata tgattattaa acttctttgc gtccatccaa   8400
aaaaaaagta accccacccg aagtcgcgca accaactaac tttacaatgg gtgcagccac   8460
tactagaaga ccatttgatg gtagaagacg tagatcctcc tggcgtccag aatccccagc   8520
cagaggtgcc gtcggtatcc actctgctag aaaggttgct caaggtgcta gatccactgc   8580
tatggctgct gatggtgaag ttaagaacat tcatactaac gactctacta aaactttatt   8640
aaaaaatgaa gctttgtacg aatacatgtt aaacactatg gtttatccaa gagaaaacga   8700
acacttaaga gaattaagac acattaccga acaacacgct tacggtttta tgttgtctcc   8760
tccagacgaa gaacaattgt tgtccttatt gttaaaggtt atgggtgctc gtaacactat   8820
tgaagtcggt gttttcaccg gtggttctgt tttggccgct gccttggcta ttccagatga   8880
tggtcgtatt gtcgctattg acgtttctag agagtattat gacttgggta gaccagtcat   8940
tgaaaaagcc ggtgttgccc acaaagttga cttcagagaa ggtccagctt tgggtcattt   9000
ggacgcctta ttggctgatg aaggtaacgc cggtgctttt gatttgcttt tcgtcgatgc   9060
tgacaagggt aactatggta attatcacga acaattgttg agattggtta gagtcggtgg   9120
tgttattgct tacgataaca ctttgtgggg tggttctgtt gctatgccag atgacgcccc   9180
attaactgaa aaggatagag aagttcgtga agctattaga gcctttaacg ctagaattgc   9240
tgctgatact agagtcgaag ctgttcaatt accagtcgct gatggtatca ccttgtgtag   9300
aagagtcgtc taaacggccg gccaagcacg cggggatgag tatgcttctc tttttttttg   9360
taggccagtg ataggaaaga acaatagaat ataaatacgt cagaatataa tagatatgtt   9420
tttatattta gacctcgtac ataggaataa ttgacgtttt ttttggccaa catttgaaat   9480
tttttttgt tacctcgcgc tgagcccaaa cgggctccac tacccgaggt ccgccggcgt   9540
tggacgagcg aagatggcaa atagccttgt caaatttcct acggaatgtt attttcatta   9600
cgtccttctt tttcaatgta cttattcata aatgggacac tatcttgttg caaaaggtac   9660
tttgtatttt ggtattaaca tctcgcctat ttttcataca gaaacactac ttatcgctat   9720
ctatttgatg tggtattgct tggccatgag gataccttga gctacgtttt gaacacgtgc   9780
atccaacttg tagccttgtt gatccaactt aaccatttca tcaggaaact tgtgcaactc   9840
aacgctaaag cattcgataa attcattatc ttccaattga gtaactggtt tttggttttc   9900
aggtaaactc atatcaactt cgacagtaac cagacagagg ttggtgtttg tgaaaccagg   9960
atcgttaaaa actgttgggc ttttagaaat tattttacca ctgtaaccag tctcttcttt  10020
taattctctt aaggcagcag tgtcaatatc ggcggtttaa acgcgtggcc gtgccgtc    10078
```

<210> SEQ ID NO 7
<211> LENGTH: 3658
<212> TYPE: DNA
<213> ORGANISM: Artificial Sequence
<220> FEATURE:
<223> OTHER INFORMATION: Synthetic: MS130477 sequence

<400> SEQUENCE: 7

```
gacggcacgg ccacgcgttt aaaccgccaa aaactcacaa gaagttcggt gtccttattt     60
gcgatgggaa ttgctaatat catatcacca caaatatgga gagagaagga ctctcctcgc    120
tttttacctg cctggattgt tcaaatcgtt ttatcattct ctcttgcacc agccattttg    180
ttactgatcc atttcatact aaaaagaagg aataatcaaa gactaaaaaa ttatgacgaa    240
aatttacaaa attatttgga cagaattcaa ctcattgaaa gcgaaaatcc ttcttccatt    300
gaagaaggga aagtggtaac ccacgagaac aatttggcag tctttgattt gactgattta    360
gaaaacgaaa cttttatata tcctttgtaa atattgatgt tttgttgtgt aaatgttcta    420
tctgacactt aataattaga aaattaattt tttaaacttt ccggctgcaa gaaagaggaa    480
ctgtgtctct ttgaaaggca caatttccca aagaatcatt tacaatgaac ctgcaggccg    540
cgagcgccga tgcttcgagc gtcccaaaac cttctcaagc aaggttttca gtataatgtt    600
acatgcgtac acgcgtctgt acagaaaaaa aagaaaaatt tgaaatataa ataacgttct    660
taatactaac ataactataa aaaaataaat agggacctag acttcaggtt gtctaactcc    720
ttccttttcg gttagagcgg atccgctcgt ccaacgccgg cggaccttta gactaatctt    780
ctacacaagg taacaccatc accgatggaa acttgggaga tttcaattct tggatcggaa    840
gccaatcttt tgttcaattc catcaaagcc ttacggttaa ctcttaagtg aactgggaca    900
gtctcttcct cttcagcaac gaaaccgaac cataaggtgt tatcgaaagc aatgatacca    960
ccaactttga ccaacttcat caatctttcc aaagcgtgga cgtaatttgg cttatcagcg   1020
tcaacgaaag cgaagtcaaa ttctggcttt gggttttcag ataacaactt gtctaaggct   1080
tgcaaaccgt cggattggat aaagttaatt ttgtgatcga taccggcgtt cttgatgaat   1140
tccaaaccca tttcgtaagc ttctttatcg atatcaatag cagtaattct accgtcttca   1200
ggcaaagcca aggcggtggt taacaaagag taaccagtga aaacacccaa ttccaaggtg   1260
ttcttagcgt tcatcatctt caacaacatg gacaagaaat gaccttcgtc aacagggact   1320
tccatctcgg acaagttacc gtacttatga acggtagctt ctcttaactt cttcaattct   1380
tcgtgttctc ttgggtaagc ggaagtttca aagatgtact tttcaattc ttcgttcttc    1440
aagataccct tagatggtat aagattttcc atgtctggtt ccattgtaaa gttagttggt   1500
tgcgcgactt cgggtggggt tacttttttt ttggatggac gcaaagaagt ttaataatca   1560
tattacatgg caataccacc atatacatat ccatatctaa tcttacttat atgttgtgga   1620
aatgtaaaga gccccattat cttagcctaa aaaaaccttc tctttggaac tttcagtaat   1680
acgcttaact gctcattgct atattgaagt acggattaga agccgccgag cgggcgacag   1740
ccctccgacg gaagactctc ctccgtgcgt cctggtcttc accggtcgcg ttcctgaaac   1800
gcagatgtgc ctcgcgccgc actgctccga acaataaaga ttctacaata ctagctttta   1860
tggttatgaa gaggaaaaat tggcagtaac ctggccccac aaaccttcaa atcaacgaat   1920
caaattaaca accataggat aataatgcga ttagtttttt agccttattt ctggggtaat   1980
taatcagcga agcgatgatt tttgatctat taacagatat ataaatgcaa aagctgcata   2040
accactttaa ctaatacttt caacattttc ggtttgtatt acttcttatt caaatgtcat   2100
aaaagtatca acaaaaaatt gttaatatac ctctatactt acctcccgcg acctccaaaa   2160
tcgaactacc ttcacaatgg aaccagacat ggaaaatctt ataccatcta agggtatctt   2220
gaagaacgaa gaattgaaaa agtacatctt tgaaacttcc gcttacccaa gagaacacga   2280
```

-continued

```
agaattgaag aagttaagag aagctaccgt tcataagtac ggtaacttgt ccgagatgga   2340

agtccctgtt gacgaaggtc atttcttgtc catgttgttg aagatgatga acgctaagaa   2400

caccttggaa ttgggtgttt tcactggtta ctctttgtta accaccgcct tggctttgcc   2460

tgaagacggt agaattactg ctattgatat cgataaagaa gcttacgaaa tgggtttgga   2520

attcatcaag aacgccggta tcgatcacaa aattaacttt atccaatccg acggtttgca   2580

agccttagac aagttgttat ctgaaaaccc aaagccagaa tttgacttcg ctttcgttga   2640

cgctgataag ccaaattacg tccacgcttt ggaaagattg atgaagttgg tcaaagttgg   2700

tggtatcatt gctttcgata acaccttatg gttcggtttc gttgctgaag aggaagagac   2760

tgtcccagtt cacttaagag ttaaccgtaa ggctttgatg gaattgaaca aaagattggc   2820

ttccgatcca agaattgaaa tctcccaagt ttccatcggt gatggtgtta ccttgtgtag   2880

aagattagtc taaatccccg cgtgcttggc cggccgtgag tatgcttctc tttttttttg   2940

taggccagtg ataggaaaga acaatagaat ataaatacgt cagaatataa tagatatgtt   3000

tttatattta gacctcgtac ataggaataa ttgacgtttt ttttggccaa catttgaaat   3060

tttttttttgt tacctcgcgc tgagcccaaa cgggctccac tacccgaacg cgatcgccga   3120

cgccgccgat aacatattga tgtttttcgt gggtaaccat agttcttgga atgtcaactg   3180

agggtatttg cacttcaaaa aaaaaaattt attaaatgag actatataca gtgagcacaa   3240

cctgtctaat acaacggcaa aaattatata cattggtaga ttttcaaaat tgaactcttt   3300

gtgctaaaga attgtcacaa cagtttaaaa aatagtttga attcttcaaa ttgaccccat   3360

attaataaga cctgatgcga ttccggtctc acccagatta gagagggaat ttaattttct   3420

taggaccgta gctaccaaaa atctttgtgt ggtattgatt atatgatcgt gcttgcgaaa   3480

aaaatagaag actaaaagta gcattagttt actaactttc tcctcgtatc tttcaaattt   3540

gtattcccct caaaagttac tcaggttagg gaaaattcca agtagcttat caagatcaat   3600

tgccattagt tgattcaagg cttcattgtc cggtgtttaa accccagcgc ctggcggg     3658
```

<210> SEQ ID NO 8
<211> LENGTH: 9995
<212> TYPE: DNA
<213> ORGANISM: Artificial Sequence
<220> FEATURE:
<223> OTHER INFORMATION: Synthetic: MS129629 sequence

<400> SEQUENCE: 8

```
gacggcacgg ccacgcgttt aaaccgcctc gcaagtcctg tttctatgcc tttctcttag     60

taattcacga aataaaccta tggtttacga aatgatccac gaaaatcatg ttattattta    120

catcaacata tcgcgaaaat tcatgtcatg tccacattaa catcattgca gagcaacaat    180

tcattttcat agagaaattt gctactatca cccactagta ctaccattgg tacctactac    240

tttgaattgt actaccgctg ggcgttatta ggtgtgaaac cacgaaaagt tcaccataac    300

ttcgaataaa gtcgcggaaa aaagtaaaca gctattgcta ctcaaatgag gtttgcagaa    360

gcttgttgaa gcatgatgaa gcgttctaaa cgcactattc atcattaaat atttaaagct    420

cataaaattg tattcaattc ctattctaaa tggcttttat ttctattaca actattagct    480

ctaaatccat atcctcataa gcagcaatca attctatcta tactttaaac gctcgtccaa    540

cgccggcgga cctggtatac aggatctatc ttttcgataa cgtaacttag tatcacatgt    600

attagtatta atactgcgat aggattgtta gctgttgttt ttatatttgc aatttattta    660

tgatcttttt tgatgatcaa accgttgagt tttgaacat taaaaaatag tgagaaagaa    720
```

```
gaactgaaat gggaattgaa ttgatcagta tctgtagtgg tcggccttga atggaccttc    780
ttctgggata cccaagtatt cagattggac tttactcaat ttagtcaatc taacacccaa    840
gttgcccaag tggaacttag cgacagcttc atccaagatc tttggcaaaa cgtggacacc    900
aacttcgaat gggcctgtct tttggaattc aatgtgcttt tctctgaaag acttatcgtt    960
agacttgaac aaagcaattt gagctaagac ttggttagag aaggaacaag acataacgaa   1020
agatgagtga ccagtagcac aacccaagtt aactaatcta ccgttagcca acaagatgac   1080
gtgtctacca gaagacaaca agtaacggtc gacttgtggt ttgatgttaa tacattcttt   1140
agcgttagcc tttaaccagg cgacatcaat ttcgatgtcg aaatggccaa tgttacaaac   1200
aatggcatct tctggcatgt tgatgaaatg ttcaccgttg ataatatctc tacaaccagt   1260
ggtggtaacg aaaacttgac caatgtggga tgcatcttcc atggtaacaa cttggtagcc   1320
ttccatggca gcttgtaaag cgttgattgg gtcaatttcg gtaaccaaga cacgagcacc   1380
cattcctctt aaggcagcag cacaaccctt accgacatca ccgtaaccag caacaacggc   1440
aaccttacca gccaacatga catcagtggc tctcttaata ccgtcgacta aggattctct   1500
acagccgtac aagttgtcaa acttggactt agtgacggag tcgttaacgt taatggcagg   1560
aacctttaac ttgccttctt tgaccattct gtataagtgg tgaacaccgg tggtagtttc   1620
ttcggaaaga ccaaagcagt cttccaacat ttcagggtgc ttttcatgaa ctaaagtggt   1680
taaatcacca ccatcatcta agatcaagtt caatttcttg ttgtccttga aggcaaacaa   1740
ttgttgttca atacaccaca aatactcttc ttcagtttca cccttccagg caaaaactgg   1800
aacaccggaa gcggcaatag cagcggcggc atgatcttga gtcgaataga tgttacaaga   1860
ggaccaggta acttcggcac ccaaagcaac taaagtttca attaaaacag cagtttgaat   1920
ggtcatgtgc aaacaaccag caatacgggc gcctttcaaa ggttggacgt caccgtaagc   1980
ctttctgatg gccatcaaac ctggcatttc atgttcagcc aattcgattt cctttctacc   2040
gaaggcagcc aaagagatat cagcgatttt gtagttttga gctggagcag acattgtaaa   2100
gttagttggt tgcgcgactt cgggtggggt tacttttttt ttggatggac gcaaagaagt   2160
ttaataatca tattacatgg caataccacc atatacatat ccatatctaa tcttacttat   2220
atgttgtgga aatgtaaaga gccccattat cttagcctaa aaaaaccttc tctttggaac   2280
tttcagtaat acgcttaact gctcattgct atattgaagt acggattaga agccgccgag   2340
cgggcgacag ccctccgacg gaagactctc ctccgtgcgt cctggtcttc accggtcgcg   2400
ttcctgaaac gcagatgtgc ctcgcgccgc actgctccga acaataaaga ttctacaata   2460
ctagctttta tggttatgaa gaggaaaaat tggcagtaac ctggccccac aaaccttcaa   2520
atcaacgaat caaattaaca accataggat aataatgcga ttagtttttt agccttattt   2580
ctggggtaat taatcagcga agcgatgatt tttgatctat taacagatat ataaatgcaa   2640
aagctgcata accactttaa ctaatacttt caacattttc ggtttgtatt acttcttatt   2700
caaatgtcat aaaagtatca acaaaaaatt gttaatatac ctctatactt acctcccgcg   2760
acctccaaaa tcgaactacc ttcacaatgg ttcaatctgc tgtcttaggg ttcccaagaa   2820
tcggtccaaa cagagaatta aagaaggcca ctgaaggtta ctggaacggt aaaatcactg   2880
tcgatgaatt attcaaagtc ggtaaggatt tgagaactca aaactggaag ttgcaaaagg   2940
aggctggtgt tgatatcatc ccatccaatg acttctcctt ttacgaccaa gttttggatt   3000
tgtctttgtt gttcaatgtc attccagacc gttacactaa gtacgatcta tctccaatcg   3060
```

-continued

```
acactttgtt tgctatgggt agaggtttac aaagaaaggc cactgaaact gaaaaggctg   3120
tcgacgtcac tgctttggaa atggttaaat ggttcgactc taactaccat tacgttagac   3180
caactttctc caagaccact caatttaagt tgaacggcca aaagccagtt gacgaatttt   3240
tggaagccaa ggagttaggt attcacacta gacctgtctt gttaggtcca gtttcttact   3300
tattcttggg taaggctgac aaggattctc tagatttgga accattgtcc ctattggaac   3360
aattgttgcc tctatacact gaaatcctat ctaaattggc ttctgctggt gccactgaag   3420
ttcaaattga cgaacctgtc ttagttttgg acttgcctgc caacgcccaa gccgccatta   3480
agaaggctta cacttacttc ggtgaacaaa gcaatctacc aaagattact ttggctactt   3540
acttcggtac cgttgtccct aacttagacg ccatcaaggg cttgccagtt gctgccttac   3600
acgttgactt tgttagagct ccagaacaat ttgatgaagt cgttgccgcc attggtaaca   3660
aacaaacctt gtccgttggt attgttgatg gtagaaacat ttggaagaat gatttcaaga   3720
agtcttccgc tatcgttaac aaggctattg aaaagttggg tgctgacaga gtcgttgttg   3780
ccacttcttc ttctctattg cacacaccag ttgacttgaa caacgaaacc aagttggacg   3840
ctgaaatcaa gggctttttc tctttcgcca ctcaaaaatt ggatgaagtt gttgtgatca   3900
ccaagaacgt ttccggtcaa gacgttgctg ctgccctaga agctaacgct aaatctgttg   3960
aatccagagg taaatccaag tttatccacg atgctgccgt taaggccaga gttgcctcta   4020
tcgacgaaaa aatgtctact agagcagctc catttgaaca aagattgcct gaacaacaaa   4080
aagtcttcaa cttgccattg ttcccaacaa caactattgg ttccttccct caaaccaagg   4140
acatcagaat taacagaaac aaattcaaca agggtaccat ctctgctgaa gaatatgaaa   4200
aattcatcaa ttctgaaatt gaaaaggtca tcagattcca agaagaaatt ggtttggatg   4260
tcttagtcca cggtgaacca gaaagaaacg atatggttca atacttcggt gaacaaatca   4320
acggttatgc tttcactgtt aacggttggg ttcaatctta cggttccaga tatgtcagac   4380
caccaattat tgttggtgac ttgtccagac caaaggctat gtccgtcaag gaatctgttt   4440
acgctcaatc catcacttct aagccagtaa agggtatgtt gactggtcca attacctgtt   4500
tgagatggtc tttcccaaga gacgatgtcg accaaaaaac tcaagctatg caattagctt   4560
tggctttgag agatgaagtc aatgatttgg aagctgccgg tatcaaggtt atccaagttg   4620
atgaaccagc tttaagagaa ggtttaccat tgagagaagg tgctgagaga tctgcttact   4680
acacctgggc tgccgaagct ttcagagttg ctacttctgg tgttgctaac aagactcaaa   4740
tacactctca tttctgttac tctgacttgg atccaaacca tatcaaggct ttggatgctg   4800
atgttgtttc catcgaattc tctaagaagg acgatgctaa ctacattgct gaattcaaaa   4860
actatccaaa ccacattggt ctgggtttat tcgatattca ttctccaaga attccatcaa   4920
aggatgaatt tatcgccaag atttcaacca tcttgaagag ctacccagct gaaaagttct   4980
gggttaaccc agactgtggt ttgaagacta gaggctggga agaaactaga ttgtctttga   5040
ctcatatggt cgaagccgcc aagtacttcc gtgaacaata caagaattaa ggttttaaaa   5100
aggaagcaaa gtaatgatat tttctgaact ttttgttttt tattctggga ttcaacatcg   5160
gtgatttaat tttgtgttc acatttaaaa gtttatttgg gtaatttttt gatatcaatt   5220
ttattacaaa gccataactc ttgcattttt tttattatat ttttatatac acgtacattc   5280
tgtattattt ataacgcatt caatccccgc gtgcttggcc ggccgtcgtt ggatctgcca   5340
aaagagctgg cagaacgtgc tgatttaccc ttgctttcac ataatctgcc cgccgatttt   5400
gctgcgttgc gtaaattgat gatgaatcat cagtaaaatc tattcattat ctcaatcagg   5460
```

ccgggtttgc ttttatgcag cccggctttt ttatgaagaa attatggaga aaaatgacag 5520
ggaaaaagga gaaattctca ataaatgcgg taacttagag attaggattg cggagaataa 5580
caaccgccgt tctcatcgag taatctccgg atatcgaccc ataacgggca atgataaaag 5640
gagtaacctg tgaaaaagat gcaatctatc gtactcgcac tttccctggt tctggtcgct 5700
cccatggcag cacaggctgc ggaaattacg ttagtcccgt cagtaaaatt acagataggc 5760
gatcgtgata atcgtggcta ttactgggat ggaggtcact ggcgcgacca cggctggtgg 5820
aaacaacatt atgaatggcg aggcaatcgc tggcacctac acggaccgcc gccaccgccg 5880
cgccaccata agaaagctcc tcatgatcat cacggcggtc atggtccagg caaacatcac 5940
cgctaaatga caaatgccgg gtaacaatcc ggcattcagc gcctgatgcg acgctggcgc 6000
gtcttatcag gcctacgtta attctgacgg ccggccaagc acgcggggat tagaaaggaa 6060
aaggaatcct gtataatgca aaatgaaatc gatacaaatt tgatttgaga aaaatgagtc 6120
tatatcaaga atatgatggt attgcgtccc tgcatcaaat acggtataat gtacatgttg 6180
acttgtgttg agcaaatgaa aacatgggag gttgaaggca gaaaaaagtc caaaaggaaa 6240
aaagcttaga acttcaaagt cttaggcttt tcccatgggt attcttggtt tgtgaaatgg 6300
ccataagaag cggttggcaa gtagattggt ctagctaagt ccaactcctt gaccaataca 6360
ccaggtctca agtcaaagtt cttgctgata atgtcgataa tttcttcgtc agacttggtc 6420
gcagtaccat aggtgtcaac gtgcaaggac aatggttccg caataccgat ggcataagaa 6480
aattgaactt gaactctctt acataaacca gcggcaacta gggacttggc aacccatcta 6540
gcggcataag cggcagaacg atcaacctta gagtagtcct taccggagaa ggcaccacca 6600
ccgacggatg aggcaccacc gtaagcgtcg acgatgatct ttctaccggt caaaccagcg 6660
tcaccttgag gaccaccgat gacgaatcta ccggaaggtt ggataaagta tttggtgttt 6720
tcgtccaaca tgtctcttgg gatgactttt tcaatgatct cggactttag ttgcgctctt 6780
aagtcctcgg tcgtgatttc gtcagcatgt tgagcggaga cgacgacggt gtcgattctt 6840
tgtggaaccc atctaccgtg gtcatccttg tattcgacgg tgacttgagt cttggtgtct 6900
ggtctcaacc acgctaaaga gccatctctt ctcgcgtcag ccatggccat gtttagttta 6960
tgagccaaaa gaatagtcaa aggcaaaccc tctggagttt catctgtggc gtaaccaaac 7020
atgatacctt ggtcaccggc accgatgtct tccaaatcct tctcctcgtg gacaccttgg 7080
gcgatatctg gagattgttg ctcaatggcg acaaggacgt tacaggtctt atagtcgaaa 7140
cccttggcgg aatcatcgta accaatcttc ttgatggtgt ctctgacgat tttttggtaa 7200
tccaactgtg ccttggtagt aatttcacca aagaccataa tcataccagt ctttgccgcg 7260
gtttcacacg caactttgga gtgagggtcc tcggctaaac aagcgtccaa gatggcgtcg 7320
gaaacttggt cacagatctt atctgggtga ccttcaccaa cggattcaga agtgaataaa 7380
aatgtaccgg ccattgtgaa ggtagttcga ttttggaggt cgcgggaggt aagtatagag 7440
gtatattaac aatttttttgt tgatactttt atgacatttg aataagaagt aatacaaacc 7500
gaaaatgttg aaagtattag ttaaagtggt tatgcagctt ttgcatttat atatctgtta 7560
atagatcaaa aatcatcgct tcgctgatta attaccccag aaataaggct aaaaaactaa 7620
tcgcattatt atcctatggt tgttaatttg attcgttgat ttgaaggttt gtggggccag 7680
gttactgcca atttttcctc ttcataacca taaaagctag tattgtagaa tctttattgt 7740
tcggagcagt gcggcgcgag gcacatctgc gtttcaggaa cgcgaccggt gaagaccagg 7800

-continued acgcacggag gagagtcttc cgtcggaggg ctgtcgcccg ctcggcggct tctaatccgt 7860
acttcaatat agcaatgagc agttaagcgt attactgaaa gttccaaaga gaaggttttt 7920
ttaggctaag ataatggggc tctttacatt tccacaacat ataagtaaga ttagatatgg 7980
atatgtatat ggtggtattg ccatgtaata tgattattaa acttctttgc gtccatccaa 8040
aaaaaaagta accccacccg aagtcgcgca accaactaac tttacaatgt ccaagagcaa 8100
aactttctta tttacctctg aatccgtcgg tgaaggtcac ccagacaaga tttgtgacca 8160
agtttctgat gctattttgg acgcttgttt agaacaagat ccattctcca aggttgcctg 8220
tgaaacagct gccaaaactg gtatgattat ggttttcggt gaaattacca ccaaagctag 8280
acttgactac caacaaatag taagagatac catcaagaag attggttatg acgattctgc 8340
caagggtttc gactacaaga catgtaatgt tttagtagct atcgaacaac aatctccaga 8400
tatcgctcaa ggtctgcact atgaaaagag cttagaagac ttaggtgctg gtgaccaagg 8460
tataatgttt ggttacgcta cagacgaaac tccagaaggg ttaccattga ccattctttt 8520
ggctcacaaa ttgaacatgg ctatggcaga tgctagaaga gatggttctc tcccatggtt 8580
gagaccagac acaaagactc aagtcactgt cgaatacgaa gacgacaatg gtagatgggt 8640
tccaaagagg atagataccg ttgttatttc tgctcaacat gctgatgaaa tttccaccgc 8700
tgacttgaga actcaacttc aaaaagatat tgttgaaaag gtcataccaa aggatatgtt 8760
agacgaaaat accaaatatt tcatccaacc atccggtaga ttcgtcatcg gtggtcctca 8820
aggtgacgct ggtttgaccg gtagaaagat tattgtcgac gcttacggtg gtgcctcatc 8880
cgtcggtggt ggtgccttct ccggtaagga ctattccaag gtcgatcgtt ccgctgctta 8940
cgctgctaga tgggttgcca agtctctagt tgccgctggt ttgtgtaaga gagtccaagt 9000
ccaattttca tatgctattg gtattgctga accattgtct ttacatgtgg acacctatgg 9060
tacagctaca aaatcagatg acgaaatcat tgaaattatt aagaagaact tcgacttgag 9120
accaggtgtg ttagtaaagg aattagattt ggctagacca atttacttac caaccgcttc 9180
ttatggtcac ttcactaatc aagagtactc atgggaaaaa ccaaagaaat tggaatttta 9240
aacatttaga caataaatgt tttattttga tttttataat tatttcaatc cctttcttta 9300
tgctaggctg gtcccgatca cctccctata ttgagaagac gatgccttat cgtttgattc 9360
gctcaactcg agtcatgtaa ttactagaaa atgatacaat agaaaagttt taaacattct 9420
taaacttgac aaacaccaat atcggcgctc gcggcctgca ggttaatgtg tatattagtt 9480
taaaaagttg tatgtaataa aagtaaaatt taatattttg gatgaaaaaa accattttta 9540
gactttttct taactagaat gctggagtag aaatacgcca tctcaagata caaaaagcgt 9600
taccggcact gatttgtttc aaccagtata tagattatta ttgggtcttg atcaactttc 9660
ctcagacata tcagtaacag ttatcaagct aaatatttac gcgaaagaaa aacaaatatt 9720
ttaattgtga tacttgtgaa ttttatttta ttaaggatac aaagttaaga gaaaacaaaa 9780
tttatataca atataagtaa tattcatata tatgtgatga atgcagtctt aacgagaaga 9840
catggccttg gtgacaactc tcttcaaacc aacttcagcc tttctcaatt catcagcaga 9900
tgggtcttcg atttgcaaag cagccaaagc atcggacaaa gcagcttcaa tcttggactt 9960
ggaacctggc ggtttaaacg cgtggccgtg ccgtc 9995

<210> SEQ ID NO 9
<211> LENGTH: 5467
<212> TYPE: DNA
<213> ORGANISM: Artificial Sequence
<220> FEATURE:
<223> OTHER INFORMATION: Synthetic: MS 332389 sequence

<400> SEQUENCE: 9

```
gacggcacgg ccacgcgttt aaaccgccac ccagccaagg tagtctaaaa gctaatttct     60
ctaaaaggga gaaagttggt gattttttat ctcgcattat tatatatgca agaatagtta    120
aggtatagtt ataaagtttt atcttaattg ccacatacgt acattgacac gtagaaggac    180
tccattattt ttttcattct agcatactat tattccttgt aacgtcccag agtattccat    240
ttaattgtcc tccatttctt aacggtgacg aaggatcacc atacaacaac tactaaagat    300
tatagtacac tctcaccttg caactattta tctgacattt gccttacttt tatctccagc    360
ttcccctcga ttttattttt caatttgatt tctaaagctt tttgcttagg cataccaaac    420
catccactca tttaacacct tatttttttt ttcgaagaca gcatccaact ttatacgttc    480
actacctttt tttttacaac aatttcattc ttcatcctat gaacgctcgt ccaacgccgg    540
cggacctgtg tcaaaagtag gcagccaatc tgttttgctg ccatattttt cctaacagga    600
tttgctatgt atgaagtacg ataagtatga aatattagtg cttgtacata cgaccaattt    660
gtaataaata gtgatgtaga gaataaactt aaagaaaact tatgaataaa taattatgga    720
gatataatta cgaataatta tgaataaata gtgctgcctt aattggcact tgcaatggac    780
caagtcttgg cataaccttc aaggtcaaca ggttcccaag gaactcccaa gccttctgca    840
atgactttac ccaaatcttc gtttagcaaa ccaaagtatt gcgtaactct ctttttgact    900
ttaggatctt tgatcttaca agcgtggcaa acaacgttat gaacgaataa tttcttctgt    960
tcatcgttgt ataccttttc atatagagct cttggctgtt cgaagtctag tggactaata   1020
ccataaacgt agtaatattg attaattttg gcatcaacaa tatgctcgtt tctgatttgg   1080
tcttgttcct gttttctcac agaaacttct gttacttcgt caagaactat ccctttgaac   1140
ttatcagata cttcgtcgtt gtcttcattt ttgaatttca gagtttgatt tggtaaactg   1200
gaaatataat ttggctcagg accgaaattg tagtaactca ttgggccgtc cctttggaag   1260
ttcactgctt taaatggaca ctgttcggca gtgtattggg aatcaccttt ggagtatgga   1320
catcccaagt ttcttggtct gttgacgggc aattgctgat agttggctcc caatctatga   1380
cgttgagtgt ctggatagga gaaaagtctg gcttgtagaa cggaatcatt agaaggctta   1440
atacctggga tacaagtgtt cgttggactg aatgcaactt gttcaatttc ttggaaataa   1500
ttgtcaacat tctccgttag ggtgatggta ccaaattttc tcaaagggaa ttccttgtgt   1560
ggccatattt tcgttaggtc atttaccgaa tacctgaact tagttgcttg ttcgggtgtc   1620
attgtttgca cataacagtt aaattttggc ttttcgccat tttgcaattg agtgaacagc   1680
tttgcctgat tataatcagg gtgggagcct gacagttcag cagccttatc tccagtcaag   1740
gtttcaaaac cagtatccga caagacgtgg aattgcacat atgtgtcctt accttctttg   1800
ttgaccatga tgaaggaatg accagagtac gcgttcatac tagcccacga agcaggagta   1860
cctctatcac caaacatgta agttatttga tggattgatt ccggattcaa tgttagataa   1920
tcccagtata tggtagtgtc ctgaaactga ttcagatgag actgagggtc tctcttttgc   1980
gaatgaataa atacgggaaa cttaatagcg tctctgagga agaagacggg agtattgttg   2040
aagacccagt catggttccc ccactcggta tagaatttaa aagaaacacc tcttgggtct   2100
cttgcagtgt ctggtgtacc actttcacca ccaacggtgg aaaaacgaac aagaccagga   2160
catttgtaac ccacattctg gtatggagcg gcgtatgtaa tatcactcaa agaatctgtt   2220
```

-continued agttcgaact ccagtctaca accaccacct ttggcatgga ctacacgctc cggaactctt 2280
tctctatcga aacttgcgat attttccagc agatggaagt cttgcagtaa gatagggccg 2340
tctggtcttg agtattgaga agcgtatggg tgatgagagt acggaaaacc gttttgtaga 2400
gagtaaactt tttcttgctt ttcttctttt ttaccgaaca cgttcattgt aaagttagtt 2460
ggttgcgcga cttcgggtgg ggtaagtata gaggtatatt aacaattttt tgttgatact 2520
tttatgacat ttgaataaga agtaatacaa accgaaaatg ttgaaagtat tagttaaagt 2580
ggttatgcag cttttgcatt tatatatctg ttaatagatc aaaaatcatc gcttcgctga 2640
ttaattaccc cagaaataag gctaaaaaac taatcgcatt attatcctat ggttgttaat 2700
ttgattcgtt gatttgaagg tttgtggggc caggttactg ccaatttttc ctcttcataa 2760
ccataaaagc tagtattgta gaatctttat tgttcggagc agtgcggcgc gaggcacatc 2820
tgcgtttcag gaacgcgacc ggtgaagacc aggacgcacg gaggagagtc ttccgtcgga 2880
gggctgtcgc ccgctcggcg gcttctaatc cgtacttcaa tatagcaatg agcagttaag 2940
cgtattactg aaagttccaa agagaaggtt tttttaggct aagataatgg ggctctttac 3000
atttccacaa catataagta agattagata tggatatgta tatggtggta ttgccatgta 3060
atatgattat taaacttctt tgcgtccatc caaaaaaaaa gtaacctccc gcgacctcca 3120
aaatcgaact accttcacaa tgactagaac cttacctcct ggtgtatccg atgaaagatt 3180
tgatgccgct ttacaaagat ttagagatgt cgtcggtgat aagtgggttt tatctaccgc 3240
tgatgaattg gaggccttca gagatccata ccctgttggt gctgctgaag ccaacttacc 3300
atctgctgtt gtttctccag aatctactga acaagttcaa gatatcgtca gaattgccaa 3360
cgaatacggt atcccattgt ctccagtttc tactggtaag aataacggtt acggtggtgc 3420
tgctccaaga ttgtccggtt ccgtcattgt taaaaccggt gaaagaatga acagaatttt 3480
ggaagttaac gaaaaatacg gttacgcttt gttggaacca ggtgttacct atttcgattt 3540
gtacgaatat ttacaatctc acgattctgg tttgatgttg gattgtccag acttgggttg 3600
gggttctgtt gttggtaaca ccttggaccg tggtgttggt tacactccat atggtgatca 3660
cttcatgtgg caaaccggtt tggaagtcgt cttaccacaa ggtgaagtca tgagaaccgg 3720
tatgggtgcc ttgccaggtt ccgatgcctg gcaattattc ccatacggtt ttggtccatt 3780
cccagatggt atgtttactc aatctaactt aggtattgtt accaagatgg gtattgcctt 3840
gatgcaaaga ccaccagctt cccaatcctt tttgatcacc tttgacaagg aggaagattt 3900
agaacaaatt gttgacatta tgttgccatt gagaattaat atggctccat tgcaaaacgt 3960
tccagtctta agaaacattt tcatggacgc tgctgctgtc tctaagagaa ccgaatggtt 4020
tgacggtgac ggtcctatgc cagctgaagc tattgaaaga atgaagaagg acttagattt 4080
gggtttctgg aacttttatg gtactttgta cggtccacca ccattgatcg aaatgtatta 4140
cggtatgatt aaggaagcct tcggtaagat cccaggtgct agattcttca ctcacgagga 4200
aagagacgat agaggtggtc acgtcttgca agatagacac aagatcaaca atggtattcc 4260
atctttggat gaattgcaat tgttggactg ggttccaaac ggtggtcaca tcggtttctc 4320
tccagtttct gctccagacg gtagagaagc tatgaagcaa tttgaaatgg ttcgtaatag 4380
agccaatgaa tacaacaaag attacgctgc tcaattcatt attggtttga gagaaatgca 4440
ccacgtctgt ttgtttatct atgacaccgc tattccagaa gctagagaag agatcttgca 4500
aatgaccaag gttttagttc gtgaagccgc tgaagctggt tatggtgaat acagaaccca 4560
taacgccttg atggacgacg ttatggctac tttcaactgg ggtgacggtg ccttgttgaa 4620

```
atttcacgaa aagatcaaag atgctttgga cccaaacggt attattgccc ctggtaagtc   4680

tggtatttgg tcccaaagat tcagaggtca aaacttgtaa aacctgcagg ccgcgagcgc   4740

cgatgagtat gcttctcttt ttttttgtag gccagtgata ggaaagaaca atagaatata   4800

aatacgtcag aatataatag atatgttttt atatttagac ctcgtacata ggaataattg   4860

acgttttttt tggccaacat ttgaaatttt tttttgttac ctcgcgctga gcccaaacgg   4920

gctccactac ccgatccccg cgtgcttggc cggccgtctc catgctggac ttactcgtcg   4980

aagatttcct gctactctct atataattag acacccatgt tatagatttc agaaaacaat   5040

gtaataatat atggtagcct cctgaaacta ccaagggaaa aatctcaaca ccaagagctc   5100

atattcgttg gaatagcgat aatatctctt tacctcaatc ttatatgcat gttatttgct   5160

cttataattg gtctctattt agggaaaaaa gtcggtttga gagcttctcg cgatgtgaaa   5220

tctcaatttg aactgcacgc caaagctagc ccatttcacg aacaccagaa agaagaaatc   5280

cccaaggatc gcatgacaga gtatgctctc tcatatcgtt gagtatgaat gccaatacac   5340

tgatcagctt tacaagaaac gtaaaatctg gcacgatggt agactgaaat actttcagtt   5400

aaacaacaga ttcatgcttt atacggaaaa ggataacgtc ggtgtttaaa ccccagcgcc   5460

tggcggg                                                             5467
```

<210> SEQ ID NO 10
<211> LENGTH: 2742
<212> TYPE: DNA
<213> ORGANISM: Artificial Sequence
<220> FEATURE:
<223> OTHER INFORMATION: Synthetic: MS 137140 sequence

<400> SEQUENCE: 10

```
gacggcacgg ccacgcgttt aaaccgccac gagcctgaga caagcccgta accaggcgcg     60

ttgccgcaaa tacagaggcg ccccagacaa caccgcagtg tgaagcactg tcaatttaaa    120

accgtggctt gctggagatg cccagaccaa ccctgttggg tttttctctc gagcacgccg    180

ttataatttt agcgtgttcc gtacctgtgt gcacatcaat aagcggtgta acaaacttga    240

acttgccatc tcatatcgtc atatgagcag ttgcagagaa aggcacttta aataaaaagg    300

cgtggatgat aaaaaatgta tataagttgg atggattttt gggaaaaagt aatgtttttg    360

cagacgtttt aaatactccc tcccttttct tagtaatttt tattatgtat tgactaagtc    420

aaaaataact atagaaaact aaagtttacg agaggaccca aaagttttga ataacacgtg    480

cctttgattt tttgtacctc ccgcgacctc caaaatcgaa ctaccttcac aatgcacata    540

accaaacctc atgctgcaat gttttcttcc ccaggtatgg gtcatgtcat tccagttatc    600

gaattgggta agagattatc tgccaacaac ggtttccacg tcaccgtctt cgtcttggaa    660

actgacgctg cttctgctca atctaagttc ttgaactcta ccggtgttga tattgtcaaa    720

ttgccatctc cagacattta cggtttggtc gacccagacg accacgttgt tactaagatt    780

ggtgttatta tgagagctgc tgttcctgct ttgagatcca aaattgctgc tatgcaccaa    840

aagccaactg ctttgatcgt tgatttgttt ggtaccgatg ccttgtgttt agctaaggaa    900

tttaatatgt tgtcttatgt ttttattcca accaacgccc gtttcttggg tgtttccatt    960

tactacccaa atttagacaa ggacattaag gaagaacata ccgtccaaag aaaccccttta  1020

gctatcccag gttgtgagcc agtcagattc gaagatacct tggatgctta cttggtccca   1080

gatgaaccag tctacagaga tttcgttaga catggtttgg cctacccaaa ggccgacggt   1140
```

```
attttggtta acacttggga agaaatggaa ccaaagtctt taaagtcttt gttaaaccca   1200
aaattgttgg gtagagtcgc tagagttcca gtttacccaa tcggtccatt gtgtagacca   1260
atccaatctt ctgaaaccga tcacccagtc ttggattggt tgaatgaaca acctaacgaa   1320
tctgtcttat acatctcttt tggttccggt ggttgcttgt ctgctaagca attgactgaa   1380
ttagcctggg gtttggagca atctcaacaa agattcgttt gggttgtcag accaccagtc   1440
gatggttctt gttgttccga atacgtttct gctaacggtg gtggtaccga agacaacact   1500
cctgaatact tgccagaagg tttcgtctcc agaacttccg acagaggttt cgttgttcca   1560
tcctgggccc cacaagctga aatcttgtct cacagagctg ttggtggttt cttgactcat   1620
tgtggttggt cctccacctt agaatccgtt gtcggtggtg ttcctatgat cgcttggcca   1680
ttgttcgccg agcaaaacat gaacgccgct ttgttatctg acgaattagg tattgctgtt   1740
agattggacg accctaagga agacatttcc agatggaaga tcgaagcctt agttagaaag   1800
gtcatgactg aaaaggaagg tgaagctatg agaagaaagg ttaagaagtt gagagactct   1860
gccgaaatgt ctttgtctat cgatggtggt ggtttggctc atgaatcttt gtgtagagtt   1920
accaaggaat gtcaaagatt tttggaacgt gttgttgact tgtccagagg tgcttaaatc   1980
cccgcgtgct tggccggccg tgagtatgct tctctttttt tttgtaggcc agtgatagga   2040
aagaacaata gaatataaat acgtcagaat ataatagata tgtttttata tttagacctc   2100
gtacatagga ataattgacg ttttttttgg ccaacatttg aaattttttt ttgttacctc   2160
gcgctgagcc caaacgggct ccactacccg aacgcgatcg ccgacgccgc cgatgtcgcc   2220
ctcagtccgc tcattttagc tgaattttct aatgttattt ttcatcagca aaacttaaca   2280
gaacgttaat ttatctaccc cttttagttc attatctctt ttttatccaa cattttacag   2340
agatctctca cttaagtcta agtaaagaca ttattttata tggtacactt atagaatata   2400
cgataataat aataaaaact atgtaacata accttcagaa tttaatatta gtttcctttt   2460
tacctcattg cactaataaa aaaattctac agaatctccg aaaaagaaaa tccagcttac   2520
tctttttgtt ttcttcttca cacgtgagct tttccgccgg catacgttcc gttccgtgtc   2580
gtcttgcata aaatttccga atcacatgtt cgtaaaacaa ccggaagtgc cccgaatata   2640
aagtcaattc tcaccgctgt tgtaactgga gctttaaggt gttatctaag gaaggataaa   2700
agaacttaaa caaccggtgt ttaaacccca gcgcctggcg gg                     2742
```

<210> SEQ ID NO 11
<211> LENGTH: 8672
<212> TYPE: DNA
<213> ORGANISM: Artificial Sequence
<220> FEATURE:
<223> OTHER INFORMATION: Synthetic: MS146176 sequence

<400> SEQUENCE: 11

```
gacggcacgg ccacgcgttt aaaccgcccg aacaagctta tccctattac agaattccaa     60
ggaggaaatc attcaacttg aaagtaaatg gatgtctatg caatctgtta aaacaactgc    120
cctacccctt caagagacta cgaatacatc atcgacctta acttctctga cgtccagcat    180
aattcccaag agtataccta taatcacgaa aggtgaagtc gccactaaac cagcatctta    240
ctgaattatt ttcaacagaa cacatcgcat ccaactgaac aaactgttac cgctgttgat    300
accaaggaac attcagtgaa cgtagggaag aacgaacatt ctccatattt ttgcatacta    360
gatacaaggg ggaagaatgc aattatttca caaaccgaaa gaaaaagaat cacaagctat    420
gtttgctatt atcaattttt cttatgatta atttaacata aattatggcc tttttcattc    480
```

```
cggctgcgct tgttctccaa tttttttttt ttttttgaga aaacttttcg attacctgcc    540
ttgatacgct gccagaatac atgtcggaaa gcttccttcc ggaatggctt aagtaggttg    600
caatttcttt ttctattagt agctaaaaat gggtcacgtg atctatattc gaaaggggcg    660
gttgcctcag gaaggcaccg gcggtctttc gtccgtgcgg agatatctgc gccgttcagg    720
ggtccatgtg ccttggacga tattaaggca gaaggcagta tcggggcgga tcactccgaa    780
ccgagattag ttaagccctt cccatctcaa gatggggagc aaatggcatt atactcctgc    840
tagaaagtta actgtgcaca tattcttaaa ttatacaatg ttctggagag ctattgttta    900
aaaaacaaac atttcgcagg ctaaaatgtg gagataggat tagttttgta gacatatata    960
aacaatcagt aattggattg aaaatttggt gttgtgaatt gctcttcatt atgcacctta   1020
ttcaattatc atcaagaata gcaatagtta agtaaacaca agattaacat aataaaaaaa   1080
ataattcttt cataatgccc agtaaattgg ctataacttc catgtccttg ggcaggtgtt   1140
atgcaggcca ttctttcaca actaagttag acatggctag gaaatatggt taccagggtt   1200
tggagttgtt tcatgaggac ttagccgatg tcgcatacag gttgtcaggt gaaacaccta   1260
gtccatgcgg tcccagtcca gctgctcaat tatcagccgc tagacagata ttgaggatgt   1320
gccaggttag aaacatcgaa atagtgtgct tgcaaccctt ttcacaatat gatggtttat   1380
tggatagaga ggagcacgag aggaggttgg agcaattaga gttttggatt gaattggccc   1440
acgagttgga tactgacatc attcaaattc cagccaattt cttgcccgcc gaagaagtca   1500
cagaagatat ttcattaatt gtgagtgact tacaggaagt tgccgatatg ggtttacagg   1560
caaaccctcc aataaggttt gtatatgagg cattatgctg gtccactaga gttgacactt   1620
gggagaggtc ttgggaagtt gtccaaagag taaatagacc taactttggc gtttgcttag   1680
acacttttaa catcgcaggt agagtttatg ctgaccccac agttgcctca ggcagaacac   1740
caaacgctga agaagcaatt agaaagtcaa ttgccaggtt ggtcgaaagg gtcgatgtat   1800
ctaaagtctt ctacgttcaa gtagtggacg ccgaaaagtt aaagaaacca ttagttcccg   1860
gtcatagatt ctatgaccct gagcaaccag ccagaatgtc atggtcaaga aattgtaggt   1920
tgttctacgg cgaaaaagac agaggcgctt acttacctgt taaagaaatc gcttgggctt   1980
ttttcaatgg attgggcttc gaaggttggg tgtccttgga attatttaac agaagaatgt   2040
cagatactgg atttggagtt ccagaggagt tagctaggag aggcgccgta tcatgggcca   2100
aattagttag agatatgaaa atcacagtgg attctccaac tcaacaacaa gctacacagc   2160
agcctattag aatgttgtcc ttatctgcag ccttataaaa agcttcgaca catacataat   2220
aactcgataa ggtatggtat cttatttcat tgtggggtag tttttacgaa aaaaatgaaa   2280
agttgtaagt atagtatata tttttttttct atgtaagttt tatatccccg cgtgcttggc   2340
cggccgttca catgtaggga ccgaattgtt tacaagttct ctgtaccacc atggagacat   2400
caaagattga aaatctatgg aaagatatgg acggtagcaa caagaatata gcacgagccg   2460
cgaagttcat ttcgttactt ttgatatcgc tcacaactat tgcgaagcgc ttcagtgaaa   2520
aaatcataag gaaaagttgt aaatattatt ggtagtattc gtttggtaaa gtagaggggg   2580
taatttttcc cctttatttt gttcatacat tcttaaattg ctttgcctct ccttttggaa   2640
agctatactt cggagcactg ttgagcgaag gctcattaga tatattttct gtcattttcc   2700
ttaacccaaa aataagggaa agggtccaaa aagcgctcgg acaactgttg accgtgatcc   2760
gaaggactgg ctatacagtg ttcacaaaat agccaagctg aaaataatgt gtagctatgt   2820
```

```
tcagttagtt tggctagcaa agatataaaa gcaggtcgga aatatttatg ggcattatta   2880
tgcagagcat caacatgata aaaaaaaaca gttgaatatt ccctcaaaaa tggaaagaat   2940
tgttgtaaca ttgggtgaaa ggtcttatcc aatcactatt gcatctggtt tatttaacga   3000
accagccagt tttttaccat tgaaatccgg tgagcaagtg atgttagtca ctaacgaaac   3060
attagctccc ttgtatttag acaaggtaag gggtgttttg gaacaagcag gcgtaaacgt   3120
cgattctgtg atattaccag acggtgaaca atacaaaagt ttggcagttt tagatactgt   3180
attcactgcc ttattacaga aaccacatgg tagagatact acattggttg ccttaggagg   3240
cggagttgtc ggcgatttaa caggtttcgc tgccgcatca tatcagagag gtgttagatt   3300
cattcaggtc ccaactactt tgttatccca agtagactca tcagttggag gaaagactgc   3360
tgtcaatcat cctttaggaa agaacatgat tggtgccttc taccagccag catcagtcgt   3420
tgttgattta gattgtttga agacattacc tccaagagag ttggcaagtg gtttggcaga   3480
agtaataaaa tatggtatca tattggatgg tgcatttttt aattggttgg aagaaaattt   3540
agatgcatta ttgaggttag acggtcctgc tatggcttat tgtattagaa ggtgttgtga   3600
attaaaggct gaggttgtag cagccgacga gagagaaact ggtttaagag ctttgttgaa   3660
cttaggtcat acatttggtc atgctatcga agctgaaatg ggttacggta attggttgca   3720
tggtgaagcc gttgcagccg gtatggttat ggctgccagg acatctgaaa gattgggtca   3780
attcagttct gcagaaacac aaaggataat aacccttattg aaaagggcag gtttacctgt   3840
gaatggtcct agagagatga gtgctcaagc ttatttgccc cacatgttga gagataagaa   3900
ggttttagca ggtgaaatga ggttaatttt gcccttagca attggaaaaa gtgaagtcag   3960
atccggtgtt tcacatgaat tagtattgaa cgccatagct gattgccaat cagcctaaat   4020
aaatgactta attttaacta tatatcgcca aacatgtaaa ttaaaaaaag aagcgagaag   4080
tatatacatg tgtgtatgaa taaataattc gtttactatt gatacgtatt gcaagatatg   4140
attaacctgc aggccgcgag cgccgatgat catctaccca tgccgaaatt cgggccgttg   4200
gccggattgc gcgttgtctt ctccggtatc gaaatcgccg gaccgtttgc cgggcaaatg   4260
ttcgcagaat ggggcgcgga agttatctgg atcgagaacg tcgcctgggc cgacaccatt   4320
cgcgttcaac cgaactaccc gcaactctcc cgccgcaatt tgcacgcgct gtcgttaaat   4380
attttcaaag atgaaggccg cgaagcgttt ctgaaattaa tggaaaccac cgatatcttc   4440
atcgaagcca gtaaaggtcc ggcctttgcc cgtcgtggca ttaccgatga agtactgtgg   4500
cagcacaacc cgaaactggt tatcgctcac ctgtccggtt ttggtcagta cggcaccgag   4560
gagtacacca atcttccggc ctataacact atcgcccagg cctttagtgg ttacctgatt   4620
cagaacggtg atgttgacca gccaatgcct gccttcccgt ataccgccga ttacttttct   4680
ggcctgaccg ccaccacggc ggcgctggca gcactgcata aagtgcgtga aaccggtaaa   4740
ggcgaaagta tcgacatcgc catgtatgaa gtgatgctgc gtatgggcca gtacttcatg   4800
atggattact tcaacggcgg cgaaatgtgc ccgcgcatga gcaaaggtaa agatccctac   4860
tacgccgatc ggcgctcgcg gcctgcaggt tcaatgctgc ttcgtatagg cgctatttaa   4920
ttaagtagtt atataaagag aacggtgcaa ttgaatagga aaggaatgac ggattttgct   4980
tctatgtttg cttttatttg aagcgtgggt tcttatttat gcttggtgta atatggtcaa   5040
aactgttctc aaatcattta ctgagatctg tcctggagca gaagcttttt tgacagcacc   5100
aaatgtagca gcagatccga acacttcacc agctaatcta gaaatcacac cggtttttgc   5160
catagacata gttatgatag gtctatcagc gtattgttct tgcatttcca atgtggcagc   5220
```

-continued taacaatgtt aagacatcag aggtagactg tggcattaaa gcaattttgg gtatatcagc 5280
atcaaaggat tgcatttttc ttaatctggc tatgatttcc tctgcttctg ggtcttgtg 5340
gaaatcatga ttagacataa ctaccttaac atcgtgagcg tgagcgtaag ctacagtttc 5400
cttaacctgg tcatcaccag taaacaactc caaatctatc atatccacta aaccactatc 5460
aatagcagct ctgttcaaag caatgtaggc ttcggtacta attgcttgtt caccaccttc 5520
cttagctgat ctgaaagtga acaataatgg tttttcaggc atagtctctc ttaatatctt 5580
tgctgcagcc attactgatt cgacatttga caagtctgca tagtgatcca ctctccattc 5640
taatatgtca aaatctgctt ctctataagc taaggcctca ctctttacag aggctatgtc 5700
tttagccatt aaactaacaa ttattttagg ggctcctgtt ccaataacca aatctttcac 5760
tgtaactgtc ttcatttttg agggaatatt caactgtttt tttttatcat gttgatgctc 5820
tgcataataa tgcccataaa tatttccgac ctgcttttat atctttgcta gccaaactaa 5880
ctgaacatag ctacacatta ttttcagctt ggctattttg tgaacactgt atagccagtc 5940
cttcggatca cggtcaacag ttgtccgagc gctttttgga ccctttccct tatttttggg 6000
ttaaggaaaa tgacagaaaa tatatctaat gagccttcgc tcaacagtgc tccgaagtat 6060
agctttccaa aaggagaggc aaagcaattt aagaatgtat gaacaaaata aaggggaaaa 6120
attacccccct ctactttacc aaacgaatac taccaataat atttacaact tttccttatg 6180
attttttcac tgaagcgctt cgcaatagtt gtgagcgata tcaaaagtaa cgaaatgaac 6240
ttcgcggctc gtgctatatt cttgttgcta ccgtccatat ctttccatag attttcaatc 6300
tttgatgtct ccatggtggt acagagaact tgtaaacaat tcggtcccta catgtgaacg 6360
gccggccaag cacgcgggga taggatggta aaaagtctga gtggttcttt taattaaggt 6420
agcaaaagtt gatgaaactg gaacttcaaa acagtaataa tatagtaaca ataagaaata 6480
aaagagatat taacgacact aaaattttag gccactcttg ctgtcaattg gccattcaaa 6540
tcctgatgaa tttctctcaa caatgcgtcg gtcatttccc atgaaataca tgcgtctgta 6600
acagacacgc catacttcat ttctgatctt ggctgttcgg atgattggtt accctcatga 6660
atatttgatt cgatcatcaa accgatgata gatctgtttc catcttttat ctgtgcaact 6720
acagattcag cgacggcggg ttgtctcctg taatccttat tagagttacc gtgagaacag 6780
tcgaccatca aggaaggtct taaacctgct tgttccattt ccttttcgca ctgtgccacg 6840
tcggcaggtg aatagtttgg ggccttacca cccctcaata ttacatgacc atctgggtta 6900
ccctgagttt gtaataatgc gacctgacca gcttgattga taccgacaaa tctatgtggt 6960
tgagctgcgg ccctcatggc atttatggca gttgccaatg aaccgtctgt gccgtttttg 7020
aagccaactg gcatactcaa accagatgcc atttctctgt gagtttgtga ttcggtggtt 7080
ctagcaccta ttgcagacca ggagaataaa tcgcccaaat attgaggact gtttaaatcc 7140
aaggcttcgg tagctaaagg caaacccata tttactaatt ccaacaacaa tttccttgcg 7200
atttgcaaac cagcttccac atcaaaagat ccatccatat gtgggtcgtt aatcaatccc 7260
ttccaaccta cagtggtcct tggcttttca aaataaaccc tcataaccaa atacaaggag 7320
tcggagactt cagctgccaa ggccttaaat cttcttgcgt attccaatgc tgtttcagga 7380
tcgtggatac tacatgggcc acatacaacc aataaccttg gatctctacc ggctataata 7440
tcagaaatac tctttcttga atcggctatc tgagcctctt gttgcaaaga taagggaaag 7500
gcagctttta attgctcagg tgtcatcaaa acctgttcat ctgttatatg tacgttattt 7560

-continued

```
aaggcatctt tctgcattat gaaagaatta ttttttttat tatgttaatc ttgtgtttac   7620
ttaactattg ctattcttga tgataattga ataaggtgca taatgaagag caattcacaa   7680
caccaaattt tcaatccaat tactgattgt ttatatatgt ctacaaaact aatcctatct   7740
ccacatttta gcctgcgaaa tgtttgtttt ttaaacaata gctctccaga acattgtata   7800
atttaagaat atgtgcacag ttaactttct agcaggagta taatgccatt tgctccccat   7860
cttgagatgg gaagggctta actaatctcg gttcggagtg atccgccccg atactgcctt   7920
ctgccttaat atcgtccaag gcacatggac ccctgaacgg cgcagatatc tccgcacgga   7980
cgaaagaccg ccggtgcctt cctgaggcaa ccgccccttt cgaatataga tcacgtgacc   8040
catttttagc tactaataga aaaagaaatt gcaacctact taagccattc cggaaggaag   8100
ctttccgaca tgtattctgg cagcgtatca aggcaggtaa tcgagcatag taaaaaaata   8160
gatgcagaat ttactcacct caaggagggg caaagtaata agaaaagtta ccataggcta   8220
gttgaatgtc caagatcgta aagaatgaag aaaaaaggag taaaaagtat gaataagata   8280
aatgaaaata taaaaataaa aaccaactaa tacatgaaga aaaaaaagca gacaaaaaca   8340
ttttatggac ctgatgcaat ctagtagtcc atagaataat caccactaga aaattcttcc   8400
tcttcattac taccgtttgc cattatagga atatgatttg ctgcaggatt ctgcggaggt   8460
attatatagg gcactggcgg cacctgtgga ataaacccaa atgatgggaa cattggcatc   8520
atccagttag cgttattttg gtttgcactt attaagttgt aactgttcac gggctttgtg   8580
ttggtattag ggtactgcag tggtatgaaa taattttccc tcgagacttg ctgttgcgat   8640
tggtggcggt ttaaacgcgt ggccgtgccg tc                                 8672
```

<210> SEQ ID NO 12
<211> LENGTH: 8123
<212> TYPE: DNA
<213> ORGANISM: Artificial Sequence
<220> FEATURE:
<223> OTHER INFORMATION: Synthetic: MS146277 sequence

<400> SEQUENCE: 12

```
gacggcacgg ccacgcgttt aaaccgccaa aaactcacaa gaagttcggt gtccttattt     60
gcgatgggaa ttgctaatat catatcacca caaatatgga gagagaagga ctctcctcgc    120
tttttacctg cctggattgt tcaaatcgtt ttatcattct ctcttgcacc agccattttg    180
ttactgatcc atttcatact aaaaagaagg aataatcaaa gactaaaaaa ttatgacgaa    240
aatttacaaa attatttgga cagaattcaa ctcattgaaa gcgaaaatcc ttcttccatt    300
gaagaaggga aagtggtaac ccacgagaac aatttggcag tctttgattt gactgattta    360
gaaaacgaaa cttttatata tcctttgtaa atattgatgt tttgttgtgt aaatgttcta    420
tctgacactt aataattaga aaattaattt tttaaacttt ccggctgcaa gaaagaggaa    480
ctgtgtctct ttgaaaggca caatttccca aagaatcatt tacaatgtcg attacctgcc    540
ttgatacgct gccagaatac atgagtgagt tctattcacg caatcggtag tatcaaagaa    600
gattatttgg gtgctattta atcacttgtt actccgcaac gcttttctga acgcccgcct    660
tcgcctttca ttatcattct catcccaaaa gaactgtgca tgttatttgc aatacttcat    720
atacgctctg tattattaat agtatcatta attacgtcaa ttgaaattca aaatatcatc    780
tttgacagta acatctatcc tcttagacaa ctagggccat tgcagtgtct cgaaaccatt    840
aatatcactg aaaagatgaa aagaaaggca aatatatatt gatcactaat tttctaagct    900
aaagaatcta ttccccctct gttaaatgga attgtgtgaa ataaaatatt ataaaatcag    960
```

```
aactttgggg gggaaacata aaaaaatgag aaaaagaaaa cgaactaact aatgtttaag   1020
taaaagaaca aaaaggtaga ccaatgtagc gctcttactt tattagacta atcttctaca   1080
caaggtaaca ccatcaccga tggaaacttg ggagatttca attcttggat cggaagccaa   1140
tcttttgttc aattccatca aagccttacg gttaactctt aagtgaactg ggacagtctc   1200
ttcctcttca gcaacgaaac cgaaccataa ggtgttatcg aaagcaatga taccaccaac   1260
tttgaccaac ttcatcaatc tttccaaagc gtggacgtaa tttggcttat cagcgtcaac   1320
gaaagcgaag tcaaattctg gctttgggtt ttcagataac aacttgtcta aggcttgcaa   1380
accgtcggat tggataaagt taattttgtg atcgataccg gcgttcttga tgaattccaa   1440
acccatttcg taagcttctt tatcgatatc aatagcagta attctaccgt cttcaggcaa   1500
agccaaggcg gtggttaaca aagagtaacc agtgaaaaca cccaattcca aggtgttctt   1560
agcgttcatc atcttcaaca acatggacaa gaaatgacct tcgtcaacag ggacttccat   1620
ctcggacaag ttaccgtact tatgaacggt agcttctctt aacttcttca attcttcgtg   1680
ttctcttggg taagcggaag tttcaaagat gtactttttc aattcttcgt tcttcaagat   1740
accettagat ggtataagat tttccatgtc tggttccatt tatattgaat tttcaaaaat   1800
tcttactttt tttttggatg gacgcaaaga agtttaataa tcatattaca tggcaatacc   1860
accatataca tatccatatc taatcttact tatatgttgt ggaaatgtaa agagccccat   1920
tatcttagcc taaaaaaacc ttctctttgg aactttcagt aatacgctta actgctcatt   1980
gctatattga agtacggatt agaagccgcc gagcgggcga cagccctccg acggaagact   2040
ctcctccgtg cgtcctggtc ttcaccggtc gcgttcctga aacgcagatg tgcctcgcgc   2100
cgcactgctc cgaacaataa agattctaca atactagctt ttatggttat gaagaggaaa   2160
aattggcagt aacctggccc cacaaacctt caaatcaacg aatcaaatta acaaccatag   2220
gataataatg cgattagttt tttagcctta tttctggggt aattaatcag cgaagcgatg   2280
atttttgatc tattaacaga tatataaatg caaaagctgc ataaccactt taactaatac   2340
tttcaacatt ttcggtttgt attacttctt attcaaatgt cataaaagta tcaacaaaaa   2400
attgttaata tacctctata ctttaacgtc aaggagaaaa aactataatg gatatggcaa   2460
gtaatggttc tgccggtgag gttagagaag ttcactcctc cgaaactacc aagactttat   2520
tgaaatccga tgctttatac gattatatgt tgaagactat ggtctatcca agagagaacg   2580
aatttatgag agaattgaga caaatcactt ccgaacatat cttcggtttc atgtcttctc   2640
caccagatga aggtttgtta ttgtccttgt tgttaaaggt tatgggtgct aagagaacca   2700
tcgaagtcgg tgtctacact ggttgttccg tcttgactac tgccttagct atcccagacg   2760
atggtagaat cattgctatt gacgtttccc gtgaatactt tgacttgggt ttgccagtta   2820
ttaagaaggc cggtgttgcc cataaggttg atttccgtga aggtcctgct ggtccaattt   2880
tggacaaatt gattgctgat gaagacgaag gttcttttga tttcgctttc gttgatgccg   2940
ataagtacaa ctacggttcc taccacgaac aattgttgag attggttaga gttggtggtg   3000
ttttggctta cgacaatacc ttatggggtg gtaccgtctc catgccagat gacactccat   3060
tgaccgaaga agacagaaag aagagagact ccattcgtgg tttcaatgcc atgattgctg   3120
ccgacgccag agtcgaacca gttcaattac caatcgccga cggtattacc ttgtgcagac   3180
gtgtcgtcta aagtttcagg cagaacaaga cccttttcaa aaatatgtaa gccattatta   3240
aaaaaaagga tattttgtat aattgtttaa taaaataaca tctttttaaa caatcataaa   3300
```

-continued

```
tagcacttct tatcatacaa cctcaaatca tatcggtcca aatttgctca aattgtacat   3360
gagatataac tttttcttct aatgctttca tttcagagtt tgtttttttt ttttcttttt   3420
tttttttttc cttaccggag tctgaatctc ttacttcctt aacttagatg ttagtgacta   3480
aaatctgatg gacagtatca aaatgtaaat attgtaccta aaaagaaaaa agtattaaag   3540
tggtttgcca taaattttaa acaagtgaaa agtttcaata tttatattta catgattgtg   3600
gacaagcggc attgtctaca ggctgtgcaa aattatatag tacagataaa tgtaaccaga   3660
acaacgaaga aaaggtccct atgttgcaac gcgatcgccg acgccgccga tgctgattat   3720
cagggtaaaa atgtcgtcat tatcggcctg ggcctcaccg ggctttcctg cgtggacttt   3780
ttcctcgctc gcggtgtgac gccgcgcgtt atggatacgc gtatgacacc gcctggcctg   3840
gataaattac ccgaagccgt agaacgccac acgggcagtc tgaatgatga atggctgatg   3900
gcggcagatc tgattgtcgc cagtcccggt attgcactgg cgcatccatc cttaagcgct   3960
gccgctgatg ccggaatcga aatcgttggc gatatcgagc tgttctgtcg cgaagcacaa   4020
gcaccgattg tggcgattac cggttctaac ggcaaaagca cggtcaccac gctagtgggt   4080
gaaatggcga aagcggcggg ggttaacgtt ggtgtgggtg gcaatattgg cctgcctgcg   4140
ttgatgctac tggatgatga gtgtgaactg tacgtgctgg aactgtcgag cttccagctg   4200
gaaaccacct ccagcttaca ggcggtagca gcgaccattc tgaacgtgac tgaagatcat   4260
atggatcgct atccgtttgg tttacaacag tatcgtgcag caaaactgcg catttacgaa   4320
aacgcgaaag tttgcgtggt taatgctgat gatgccttaa caatgccgat tcgcggtgcg   4380
gatgaacgct gcgtcagctt tggcgtcaac aatcggcggc gtcggcgatc gcgttgcaac   4440
atagggacct tttcttcgtt gttctggtta catttatctg tactatataa ttttgcacag   4500
cctgtagaca atgccgcttg tccacaatca tgtaaatata aatattgaaa cttttcactt   4560
gtttaaaatt tatggcaaac cactttaata ctttttttctt tttaggtaca atatttacat   4620
tttgatactg tccatcagat tttagtcact aacatctaag ttaaggaagt aagagattca   4680
gactccggta aggaaaaaaa aaaaaaagaa aaaaaaaaaa caaactctga aatgaaagca   4740
ttagaagaaa aagttatatc tcatgtacaa tttgagcaaa tttggaccga tatgatttga   4800
ggttgtatga taagaagtgc tatttatgat tgtttaaaaa gatgttattt tattaaacaa   4860
ttatacaaaa tatccttttt tttaataatg gcttacatat ttttgaaaag ggtcttgttc   4920
tgcctgaaac tttagacgac acgtctgcac aaggtaatac cgtcggcgat tggtaattga   4980
actggttcga ctctggcgtc ggcagcaatc atggcattga aaccacgaat ggagtctctc   5040
ttctttctgt cttcttcggt caatggagtg tcatctggca tggagacggt accaccccat   5100
aaggtattgt cgtaagccaa aacaccacca actctaacca atctcaacaa ttgttcgtgg   5160
taggaaccgt agttgtactt atcggcatca acgaaagcga aatcaaaaga accttcgtct   5220
tcatcagcaa tcaatttgtc caaaattgga ccagcaggac cttcacggaa atcaacctta   5280
tgggcaacac cggccttctt aataactggc aaacccaagt caaagtattc acgggaaacg   5340
tcaatagcaa tgattctacc atcgtctggg atagctaagg cagtagtcaa gacggaacaa   5400
ccagtgtaga caccgacttc gatggttctc ttagcaccca taacctttaa caacaaggac   5460
aataacaaac cttcatctgg tggagaagac atgaaaccga agatatgttc ggaagtgatt   5520
tgtctcaatt ctctcataaa ttcgttctct cttggataga ccatagtctt caacatataa   5580
tcgtataaag catcggattt caataaagtc ttggtagttt cggaggagtg aacttctcta   5640
acctcaccgg cagaaccatt acttgccata tccattatag tttttctcc ttgacgttaa   5700
```

-continued agtatagagg tatattaaca attttttgtt gatactttta tgacatttga ataagaagta 5760
atacaaaccg aaaatgttga aagtattagt taaagtggtt atgcagcttt tgcatttata 5820
tatctgttaa tagatcaaaa atcatcgctt cgctgattaa ttaccccaga aataaggcta 5880
aaaaactaat cgcattatta tcctatggtt gttaatttga ttcgttgatt tgaaggtttg 5940
tggggccagg ttactgccaa tttttcctct tcataaccat aaaagctagt attgtagaat 6000
ctttattgtt cggagcagtg cggcgcgagg cacatctgcg tttcaggaac gcgaccggtg 6060
aagaccagga cgcacggagg agagtcttcc gtcggagggc tgtcgcccgc tcggcggctt 6120
ctaatccgta cttcaatata gcaatgagca gttaagcgta ttactgaaag ttccaaagag 6180
aaggtttttt taggctaaga taatggggct ctttacattt ccacaacata taagtaagat 6240
tagatatgga tatgtatatg gtggtattgc catgtaatat gattattaaa cttctttgcg 6300
tccatccaaa aaaaaagtaa gaatttttga aaattcaata taaatggaac cagacatgga 6360
aaatcttata ccatctaagg gtatcttgaa gaacgaagaa ttgaaaaagt acatctttga 6420
aacttccgct tacccaagag aacacgaaga attgaagaag ttaagagaag ctaccgttca 6480
taagtacggt aacttgtccg agatggaagt ccctgttgac gaaggtcatt tcttgtccat 6540
gttgttgaag atgatgaacg ctaagaacac cttggaattg ggtgttttca ctggttactc 6600
tttgttaacc accgccttgg ctttgcctga agacggtaga attactgcta ttgatatcga 6660
taaagaagct tacgaaatgg gtttggaatt catcaagaac gccggtatcg atcacaaaat 6720
taactttatc caatccgacg gtttgcaagc cttagacaag ttgttatctg aaaacccaaa 6780
gccagaattt gacttcgctt tcgttgacgc tgataagcca aattacgtcc acgctttgga 6840
aagattgatg aagttggtca aagttggtgg tatcattgct ttcgataaca ccttatggtt 6900
cggtttcgtt gctgaagagg aagagactgt cccagttcac ttaagagtta accgtaaggc 6960
tttgatggaa ttgaacaaaa gattggcttc cgatccaaga attgaaatct cccaagtttc 7020
catcggtgat ggtgttacct tgtgtagaag attagtctaa taaagtaaga gcgctacatt 7080
ggtctacctt tttgttcttt tacttaaaca ttagttagtt cgttttcttt ttctcatttt 7140
tttatgtttc ccccccaaag ttctgatttt ataatatttt atttcacaca attccattta 7200
acagaggggg aatagattct ttagcttaga aaattagtga tcaatatata tttgcctttc 7260
ttttcatctt ttcagtgata ttaatggttt cgagacactg caatggccct agttgtctaa 7320
gaggatagat gttactgtca aagatgatat tttgaatttc aattgacgta attaatgata 7380
ctattaataa tacagagcgt atatgaagta ttgcaaataa catgcacagt tcttttggga 7440
tgagaatgat aatgaaaggc gaaggcgggc gttcagaaaa gcgttgcgga gtaacaagtg 7500
attaaatagc acccaaataa tcttctttga tactaccgat tgcgtgaata gaactcactc 7560
atgtattctg gcagcgtatc aaggcaggta atcgaaacat attgatgttt ttcgtgggta 7620
accatagttc ttggaatgtc aactgagggt atttgcactt caaaaaaaaa aatttattaa 7680
atgagactat atacagtgag cacaacctgt ctaatacaac ggcaaaaatt atatacattg 7740
gtagattttc aaaattgaac tctttgtgct aaagaattgt cacaacagtt taaaaaatag 7800
tttgaattct tcaaattgac cccatattaa taagacctga tgcgattccg gtctcaccca 7860
gattagagag ggaatttaat tttcttagga ccgtagctac caaaaatctt tgtgtggtat 7920
tgattatatg atcgtgcttg cgaaaaaaat agaagactaa aagtagcatt agtttactaa 7980
ctttctcctc gtatctttca aatttgtatt cccctcaaaa gttactcagg ttagggaaaa 8040
ttccaagtag cttatcaaga tcaattgcca ttagttgatt caaggcttca ttgtcggcgg 8100
tttaaacgcg tggccgtgcc gtc 8123

<210> SEQ ID NO 13
<211> LENGTH: 8216
<212> TYPE: DNA
<213> ORGANISM: Artificial Sequence
<220> FEATURE:
<223> OTHER INFORMATION: Synthetic: MS153767 sequence

<400> SEQUENCE: 13
gacggcacgg ccacgcgttt aaaccgcctg catacttcaa gttcagggtt ggacctgcca 60
atgaaaattt tagatatgtt tggctcaggt cttcctgtta ttgcaatgaa ctatccagtg 120
cttgacgaat tagtacaaca caatgtaaat gggttaaaat ttgttgatag aagggagctt 180
catgaatctc tgatttttgc tatgaaagat gctgatttat accaaaaatt gaagaaaaat 240
gtaacgcagg aagctgagaa cagatggcaa tcaaattggg aacgaacaat gagagatttg 300
aagctaattc attgagtcaa tggtaactca gcctttcttt tttgaaaatt actattttcg 360
actctttttt tatacagtta catagtacta cctctaatac acattcatga ttaacaatgt 420
ttcaaacaat ataaagtccc gataacgacc ttttgaagtg gtgacgttac cgctcttcgt 480
tgacaagatt caagagggct gtcagaataa cagctatcat ggtggaatcg attacctgcc 540
ttgatacgct gccagaatac atgtcacatg tagggaccga attgtttaca agttctctgt 600
accaccatgg agacatcaaa gattgaaaat ctatggaaag atatggacgg tagcaacaag 660
aatatagcac gagccgcgaa gttcatttcg ttacttttga tatcgctcac aactattgcg 720
aagcgcttca gtgaaaaaat cataaggaaa agttgtaaat attattggta gtattcgttt 780
ggtaaagtag agggggtaat tttcccctt tattttgttc atacattctt aaattgcttt 840
gcctctcctt ttggaaagct atacttcgga gcactgttga gcgaaggctc attagatata 900
ttttctgtca ttttccttaa cccaaaaata agggaaaggg tccaaaaagc gctcggacaa 960
ctgttgaccg tgatccgaag gactggctat acagtgttca caaaatagcc aagctgaaaa 1020
taatgtgtag ctatgttcag ttagtttggc tagcaaagat ataaaagcag gtcggaaata 1080
tttatgggca ttattatgca gagcatcaac atgataaaaa aaaacagttg aatattccct 1140
caaaaatgga tacaagagaa gatcaattag aaagacgtat tgctgcctta actgctaacg 1200
accctcaatt cgccgctgcc agaccagacg aagccgttgc cactgccgtc caaagacctg 1260
gtttgagatt accagaagtc atcgaaaccg tcttgcaagg ttacgctgac cgtccagcct 1320
taggtcaaag agctgtcgaa tttgttaaag atccaaacac tggtagaacc tccgcccatt 1380
tgttaccaag attcgacacc atcacctaca gagaattggc tgatagagtc ggtgctttag 1440
cttctgcttg ggctagagaa gccgtttccc caggtgacag agttgccatt ttgggtttca 1500
cttccgttga ctatactacc attgatgtta ctttggctag aattggtgct gtctctgttc 1560
cattacaaac ctctgctgcc ttggctcaat taagaccaat tgttgtcgaa accgaaccaa 1620
ctgttatcgc tgcttccgtt gattacttgt ccgacgctgt tgaattaatt agaactggtc 1680
acgccccagc cagattggtt gtttttgatc atcacccaga agttgacgat cacagagaag 1740
ctttggacgc tgctagaggt cgtttggctg gtcacgctgt cattgttgaa actttggctg 1800
aagtcttgga gagaggtact tctttgccag ctccaactgt tgctgccgaa gataatgatt 1860
tggctttgtt aatctacacc tctggttcca ctggtgctcc aaagggtgct atgtacccac 1920
aaagaaatgt tgctaagatg tggcaaagat cttccagaaa ctggttcggt ccttctgccg 1980

-continued

```
cttctattac cttgaacttt atgccaatgt cccatgttat gggtagaggt attttgtacg   2040
gtaccttagg taacggtggt actgcctact tcggtgctac ctctgacttg tctactttgt   2100
tggaagactt gactttggtc agacctaccg aattgaactt cgttccaaga gtctgggaca   2160
ctttgcatgc cgagttcttg actagagtcg acagattgac cgctgaaggt gccgacagag   2220
cttccgctga ggctttggtc atgggtgact tgagagacaa cttattgggt ggtcgtgcca   2280
ttttcgccat gactggttcc gctccaatct cttctcaatt gaaaacttgg gttgagtcct   2340
tgttgggtat ccatttattg gacggttatg gttctactga agctggtatg gttttgtacg   2400
atggtgtcgt ccaaagacct ccagtcattg actacaagtt agctgatgtc ccagatttgg   2460
gttacttttc tactgataga ccattcccaa gaggtgaatt attattgaaa actgaaaaca   2520
tgttccctgg ttactacaaa agaccagaaa tcaccgctgg tgtcttcgat gatgacggtt   2580
actaccgtac tggtgatgtt gttgctgaag tcggtccaga tcgtttggtt tacgtcgata   2640
gaagaaacaa tgttttaaaa ttagctcaag gtgagttcgt tactgttgcc aagttggaag   2700
ctggtttcaa caactcccca ttggtcagac aaatctacat ttacggtaac tctgctcatc   2760
catacttatt ggctgttgtt gttcctactg atgtcaatgc ctccaagtcc gctattgctg   2820
aatccttgca aagagtcgct aaggacgctg gtttacaatc ctatgaagtt cctagagact   2880
tcttgattga accagaacca tttaccttgg aaaacggttt gttaactggt attagaaagt   2940
tggcttggcc taagttgaag gagagatacg gtgaacgttt ggaacaattg tacgctgaat   3000
tggacagatc ccaagctgac gaattgtctg aattaagaag atctggtgcc caaagaccag   3060
ttttggaaac tgtcaccaga gctgccggtg ctttgttagg tgctgctgct tctgaattac   3120
aaccagatgc tcacttcact gacttgggtg gtgactcctt gtccgctttg actttcggta   3180
acttgttgag agaaatcttt gacgtcgacg tcccagtcgg tgttatcgtt tctccagctt   3240
ctgacttgca agccattgct ggttacattg aagccgaaag acaaggttct aaaagaccaa   3300
ccttcgcctc cgttcatggt agagctgagg aaggtgaagc tgttgaggtt agagctagag   3360
atttgcgttt ggataagttc ttggacgcca gaaccttgga gtacgttcca gccttgccag   3420
gtccatccac cgaattgcgt actgttttgt tgactggtgc tactggtttc ttgggtagat   3480
atttggcttt ggaatggttg gagagaatgg acgctgttga cggtaccgtt atcgctttag   3540
tcagagctaa ggacgacgcc gctgctagag agagattgga cagaactttc gactctgacc   3600
ctaagttgag agcccactac agagctttgg ccgctgacca tttggaagtt gttgctggtg   3660
acaagggtga agctaactta ggtttgtctc aacaagtttg gcaaagatta gccgacactg   3720
ttgacgttat cgttgaccca gccgctttgg tcaaccacgt tttaccatac tctgaattgt   3780
ttggtccaaa tgttttgggt actgccgaat tgatcagatt ggctttgact accaagatca   3840
agccatacac ttacgtttcc accatcggtg ttggtgacca aatcgagcca ggtaagttta   3900
ctgaagatgc tgacatcaga gttatttctc caactagaag aatttctgac tcttacgcta   3960
acggttacgg taactccaag tgggctggtg aagtcttgtt gagagaagct catgacagat   4020
gtggtttgcc agtcgctgtt ttcagatgtg atatgatctt ggccgacacc acctacgccg   4080
gtcaattaaa cttgccagat atgttcactc gtttaatgtt gtccttggcc gctactggta   4140
ttgccccaag atctttctac gaattggatg ctgaaggtaa cagacaacgt gctcattacg   4200
acggtttgcc agtcgaattc attgctaagg ctgtctctac tttgggtgct caaactgttg   4260
agggttatca aacctaccac gtcatgaacc ctcatgacga cggtattggt ttggacgaat   4320
```

```
acgttgactg gttgattgaa gctggttacc ctattcgtag agttgacgac tacgctgatt   4380
ggttacaaag atttgaaacc gctatgagag ctttgccaga cagacaaaga agatactcct   4440
tgttgccttt gttacataac taccaaaagc cagaaaagcc aatgagaggt tctatggctc   4500
caactgatag atttagagct gctgttcaag aagccaaaat tggtccagac aaggatattc   4560
cacacgtcac cagagaagtt atcgtcaagt atgctactga tttgcaattg ttgggtttat   4620
tggatgaaaa aagagtctaa aaggcttttt tataaacttt ttataattaa cattaaagca   4680
aaaacaacat tgtaaagatt aacaaataaa tgaaaaaaac aacgaaataa cttaggtttt   4740
aggctaaaaa aaacagaagg aattttgaac gataaacttt tcgactgcac acgaaacatt   4800
attactaatt tgtgtaacca ctatataagg aatcgtgttt attaattgaa tttattccgg   4860
gaatattcaa gttatgtata tctcttttca tattcttaaa tacacatact cataatatct   4920
tgtcgaaaat acgcggtgta gggagttatg gtggataact ttttcacgat tagaagaaaa   4980
ggaaaatttc attattcgta gcttaacatg gcaaaaacga gaaagacata taatcaaaac   5040
gtgagtttcc tgtggaaaaa aaaaaaaggg aacctctggt tacgatgata tacctgcgtg   5100
aaaaaggaca gttattacca atacatacaa aggcaacctg caggccgcga gcgccgataa   5160
gattattact tgctataagt gcgtgcctga tgaacaggat attgcggtca ataatgctga   5220
tggttcatta gacttcagca aagccgatgc caaaataagc caatacgatc tcaacgctat   5280
tgaagcggct tgccagctaa agcaacaggc agcagaggcg caggtgacag ccttaagtgt   5340
gggcggtaaa gccctgacca acgccaaagg gcgtaaagat gtgctatcgc gcggcccgga   5400
tgaactgatt gtggtgattg atgaccagtt cgagcaggca ctgccgcaac aaacggcgag   5460
cgcactggct gcagccgccc agaaagcagg ctttgatctg atcctctgtg gcgatggttc   5520
ttccgacctt tatgcccagc aggttggtct gctggtgggc gaaatcctca atattccggc   5580
agttaacggc gtcagcaaaa ttatctccct gacggcagat accctcaccg ttgagcgcga   5640
actggaagat gaaaccgaaa ccttaagcat tccgctgcct gcggttgttg ctgtttccac   5700
tgatatcaac tccccacaaa ttccttcgat gaaagccatt ctcggcgcgg cgaaaaagcc   5760
cgtccaggta tggtcggcgg cggatattgg ttttaacgca gaggcagcct ggtcagaaca   5820
acaggttgcc gcgccgaaac agcgcgaacg tcagcgcaat cggcgctcgc ggcctgcagg   5880
ttccgttaca ggaatggatg atccaccaat tatatcgacg gggggctagaa tcttagatct   5940
cagtactcgc attctagcgt atgtttcttg aaacttgtaa gggactttcg tcgaggccgg   6000
agtgacaagg atcgaggggt ccaatggtgt ggcccacctg ttgggcacat tgccgtttct   6060
aaccacaatc cattcgaagt actgcttatt tggcagcgat ttaacccagt cgatatccac   6120
gggttgaggg acaacctctt cttgtttgat tttggtcctt ttctccggta ggagttctga   6180
ttctggccca gtttcagtct ttaccagcgg tcttttcctc agaattgcca tagatgagta   6240
tttactgatc ttttgcatat tttttttttt tttttaagta tatatagata caaatatatg   6300
atgaatcatt aaagaggagg ttattactaa gtgaaagaaa aagaaaaaaa aaaagatcaa   6360
aaccaaactt cgtattcgag cctaaaaaac agaatataat gttaagcgta agcgatagca   6420
gtcaagatga aaccgtcagc aatcaaccat ctaccatcaa aagacaacaa tggggtacca   6480
ccatcgttag tttgaccagg aaccaataat tcggagtgga aagtaccgtt accagaatca   6540
gcagaaccat cttcaatttc gaaagtaatg tgagcttcct cgaaacctaa ccatctggca   6600
gtcaatggcc accaagcctt gtaagtagct tctttggcac aaaataacaa tctgtctaaa   6660
tgtaaagcag aatcggtagt cttcaaccat tctctttctg gtggcaagga aacggaatcc   6720
```

aagacacctt ctggcaaggt agcgtgtggt tcggcgtcga taccgatgga tctgaatctc 6780
atcttatgag caacagcagc ggctctgtaa ccgtcacagt gagtcaaaga accgacaaca 6840
cctcttggcc aaataggagc accacgttca cctttaccga tagcgactgg tggttcaccc 6900
aattcagcca aagctaatct agcacaatgt ctggcaccaa taaagtctct tcttctcttt 6960
tcgacagatt tggcgattaa atgttcctcg gctgggtgag cttttaagtc ttcagggtac 7020
tctaacaatt cagcagactc aactccagca ggaagaatgg tttcaatcat ttttgaggga 7080
atattcaact gttttttttt atcatgttga tgctctgcat aataatgccc ataaatattt 7140
ccgacctgct tttatatctt tgctagccaa actaactgaa catagctaca cattattttc 7200
agcttggcta ttttgtgaac actgtatagc cagtccttcg gatcacggtc aacagttgtc 7260
cgagcgcttt ttggaccctt tcccttattt ttgggttaag gaaaatgaca gaaaatatat 7320
ctaatgagcc ttcgctcaac agtgctccga agtatagctt tccaaaagga gaggcaaagc 7380
aatttaagaa tgtatgaaca aaataaaggg gaaaaattac cccctctact ttaccaaacg 7440
aatactacca ataatattta caacttttcc ttatgatttt ttcactgaag cgcttcgcaa 7500
tagttgtgag cgatatcaaa agtaacgaaa tgaacttcgc ggctcgtgct atattcttgt 7560
tgctaccgtc catatctttc catagatttt caatctttga tgtctccatg gtggtacaga 7620
gaacttgtaa acaattcggt ccctacatgt gacatgtatt ctggcagcgt atcaaggcag 7680
gtaatcgaaa gatggcaaat agccttgtca aatttcctac ggaatgttat tttcattacg 7740
tccttctttt tcaatgtact tattcataaa tgggacacta tcttgttgca aaaggtactt 7800
tgtattttgg tattaacatc tcgcctattt ttcatacaga aacactactt atcgctatct 7860
atttgatgtg gtattgcttg gccatgagga taccttgagc tacgttttga acacgtgcat 7920
ccaacttgta gccttgttga tccaacttaa ccatttcatc aggaaacttg tgcaactcaa 7980
cgctaaagca ttcgataaat tcattatctt ccaattgagt aactggtttt tggttttcag 8040
gtaaactcat atcaacttcg acagtaacca gacagaggtt ggtgtttgtg aaaccaggat 8100
cgttaaaaac tgttgggctt ttagaaatta ttttaccact gtaaccagtc tcttctttta 8160
attctcttaa ggcagcagtg tcaatatcgg cggtttaaac gcgtggccgt gccgtc 8216

<210> SEQ ID NO 14
<211> LENGTH: 11527
<212> TYPE: DNA
<213> ORGANISM: Artificial Sequence
<220> FEATURE:
<223> OTHER INFORMATION: Synthetic: MS141850 sequence

<400> SEQUENCE: 14
gacggcacgg ccacgcgttt aaaccgccga aatcacctcc aaagttatgt tgccgattag 60
gcaaatactc taaaagtata gtactaaaga actacgtaaa ggtaaaataa aacacctgaa 120
tttcatttct gaaatgaagt accatcatga aatatgatga aagtcaagac tcgttgggtc 180
aatatacacc acaaaaaaag gtacacacga atggtttaac cctttcggtt ccttctgtaa 240
atcgaaaaat gccctttata cagcgggttg gtctcccatc aaagttgaga agcgattaga 300
aattaggtta cctaatgaat ccataaataa atggaaaacg ctattttgtt cgaacgatgg 360
aataaaaata tgaacgggtg tcattgaaat tcggtgtatt ttttgatcgg gcctgatctg 420
gctcgggttt ggcacaattt ggcttggtta gttcggcaaa gcttatttaa agaacctttt 480
tggatagcca attgagagac ttgaaataga aagatcgtaa gtatttttac gctcgtccaa 540

-continued

```
cgccggcgga cctgggtgtt aaccaaacac atgttgaaat gctagttaaa aaagaatggt    600
aaaacaatgg aaaaggaagg agcaaaatct ggtaaaaaag aagaaccata ataatagtga    660
ataaaaaaaa aaaaatgcaa tgtaatgttg aatgtaatgc aaagaggggg ggttgacaat    720
tctgttaaag aactgttatc gttgtctgtg ttattatagg cttagtagga tggaatggat    780
ttgatcatct ggagaaatgt agtcattgtc aacaatattg accaagcagt aatcgtcaat    840
caaggactga atgaattggg cactatgcgg tttatcgtat ttattcatgt ttagtttcca    900
ttcattcaag atatgataga actcctcctt ccacgctaag aacgaaattt tctcgacaat    960
ggtaggttga agaatttctc tgccggggaa aataccccaa gtcacagcgt tggacttgga   1020
gttgtctgga tgattactta gcaggtcacc ttgagagtcg atggcgaagt aggtcaagaa   1080
ctcattgttt ttcaaggtgt caatcaactt gggcaactta gtcttgggca acataaattc   1140
caaatattgc ttctggtaaa cgtaaccatc cttgggtccc caaccatgaa ttttgtcatt   1200
ggacctaatg ccgttgactt gaggttgaga gtttatagtg atgatagaat gctggttcag   1260
ctcaatcaag tgtgctttga ttggatttat ttcatcattg atggggatat cactccaagg   1320
taaacacttc aagtttccat tcaagtagtt gatgaccaag aaggcgacgt cgttgatgga   1380
agtaggggtg gaccataatt cgagacattt gttcgctgat tgcctgatca agtctgaacc   1440
acacagatcc aagtcaccga acgcaggaga agacgaatca ccgaatctac cgttggggaa   1500
ttcgtccacg gcccattgag aggttcttgc gacataggag taaggtcttc tcttccagaa   1560
gataggtctg acttcctcgt ttttacgctt tggattcaaa gattttctcc atggcaacac   1620
ggccaatgga tgtgcattga actctgattc cgtaggtaga atgttcaatc tttccagaat   1680
catgagaggc gctttttcca agttcatggt gtagatgtgc aagtgagaaa cgtaaccact   1740
gtcgagcaat ttttgacaca tttccacgat caagttagtt ccgatatcac ggaccaactc   1800
gtcatcgtcc ttgataggat ccaatcggga cgagaaatgt tgagggatgg agatttggcc   1860
ccattgggcc cttctcaaga aggccgcgta ggtagtgatc ggcatgatcc cgggaataat   1920
gggcacgtcc atgcccgcag ctctaacttg ggaacaccag ttgatgaaat tatcaacatc   1980
gtaaaacatc tgagtgatga tgaagtcgcc gccggcgtcg atcttctgct tcaaatactc   2040
gagatcaagc ttcacgtctt tgttaggcaa ctccggatgg cactccgggt agccggcaac   2100
gccgatagcg aaatggtcac cgtacttgga cttgatatac ttaatcaagt ccttggcata   2160
ctggaagcca ccttcaacgg gagtccagtt ttctgcgtcc ctaggaggat ctcctctcag   2220
cgctaggatg ttctggcaac cggagtgata agcgttttct aaagcgtcgt caatcatcga   2280
aatgggcata ttggtgcagg taaggtgcat gcacgtttcc aaaccaagca cagactgcgc   2340
tgtcgcaacc aagtccgtgg acagatgtga caaccgtcca ccgcctgcat tccaggtgat   2400
gtcaataaat tggggcaaag aagcctcgta catccggtcc atccggtcat acaggttctg   2460
tacaccttgt gtagtcttcg ggacgaagta ctcgaatgag taagtgggct tgccagaggt   2520
ctgtctatgt tgctctaatt tttctgtgat cttcattgta aagttagttg gttgcgcgac   2580
ttcgggtggg gttacttttt ttttggatgg acgcaaagaa gtttaataat catattacat   2640
ggcaatacca ccatatacat atccatatct aatcttactt atatgttgtg gaaatgtaaa   2700
gagccccatt atcttagcct aaaaaaacct tctctttgga actttcagta atacgcttaa   2760
ctgctcattg ctatattgaa gtacggatta gaagccgccg agcgggcgac agccctccga   2820
cggaagactc tcctccgtgc gtcctggtct tcaccggtcg cgttcctgaa acgcagatgt   2880
gcctcgcgcc gcactgctcc gaacaataaa gattctacaa tactagcttt tatggttatg   2940
```

aagaggaaaa attggcagta acctggcccc acaaaccttc aaatcaacga atcaaattaa 3000
caaccatagg ataataatgc gattagtttt ttagccttat ttctggggta attaatcagc 3060
gaagcgatga tttttgatct attaacagat atataaatgc aaaagctgca taaccacttt 3120
aactaatact ttcaacattt tcggtttgta ttacttctta ttcaaatgtc ataaaagtat 3180
caacaaaaaa ttgttaatat acctctatac ttacctcccg cgacctccaa aatcgaacta 3240
ccttcacaat ggttcaatct gctgtcttag ggttcccaag aatcggtcca aacagagaat 3300
taaagaaggc cactgaaggt tactggaacg gtaaaatcac tgtcgatgaa ttattcaaag 3360
tcggtaagga tttgagaact caaaactgga agttgcaaaa ggaggctggt gttgatatca 3420
tcccatccaa tgacttctcc ttttacgacc aagttttgga tttgtctttg ttgttcaatg 3480
tcattccaga ccgttacact aagtacgatc tatctccaat cgacactttg tttgctatgg 3540
gtagaggttt acaaagaaag gccactgaaa ctgaaaaggc tgtcgacgtc actgctttgg 3600
aaatggttaa atggttcgac tctaactacc attacgttag accaactttc tccaagacca 3660
ctcaatttaa gttgaacggc caaaagccag ttgacgaatt tttggaagcc aaggagttag 3720
gtattcacac tagacctgtc ttgttaggtc cagtttctta cttattcttg ggtaaggctg 3780
acaaggattc tctagatttg gaaccattgt ccctattgga acaattgttg cctctataca 3840
ctgaaatcct atctaaattg gcttctgctg gtgccactga agttcaaatt gacgaacctg 3900
tcttagtttt ggacttgcct gccaacgccc aagccgccat taagaaggct tacacttact 3960
tcggtgaaca aagcaatcta ccaaagatta ctttggctac ttacttcggt accgttgtcc 4020
ctaacttaga cgccatcaag ggcttgccag ttgctgcctt acacgttgac tttgttagag 4080
ctccagaaca atttgatgaa gtcgttgccg ccattggtaa caaacaaacc ttgtccgttg 4140
gtattgttga tggtagaaac atttggaaga atgatttcaa gaagtcttcc gctatcgtta 4200
acaaggctat tgaaaagttg ggtgctgaca gagtcgttgt tgccacttct tcttctctat 4260
tgcacacacc agttgacttg aacaacgaaa ccaagttgga cgctgaaatc aagggctttt 4320
tctctttcgc cactcaaaaa ttggatgaag ttgttgtgat caccaagaac gtttccggtc 4380
aagacgttgc tgctgcccta gaagctaacg ctaaatctgt tgaatccaga ggtaaatcca 4440
agtttatcca cgatgctgcc gttaaggcca gagttgcctc tatcgacgaa aaaatgtcta 4500
ctagagcagc tccatttgaa caaagattgc ctgaacaaca aaaagtcttc aacttgccat 4560
tgttcccaac aacaactatt ggttccttcc ctcaaaccaa ggacatcaga attaacagaa 4620
acaaattcaa caagggtacc atctctgctg aagaatatga aaaattcatc aattctgaaa 4680
ttgaaaaggt catcagattc caagaagaaa ttggtttgga tgtcttagtc cacggtgaac 4740
cagaaagaaa cgatatggtt caatacttcg gtgaacaaat caacggttat gctttcactg 4800
ttaacggttg ggttcaatct tacggttcca gatatgtcag accaccaatt attgttggtg 4860
acttgtccag accaaaggct atgtccgtca aggaatctgt ttacgctcaa tccatcactt 4920
ctaagccagt aaagggtatg ttgactggtc caattacctg tttgagatgg tctttcccaa 4980
gagacgatgt cgaccaaaaa actcaagcta tgcaattagc tttggctttg agagatgaag 5040
tcaatgattt ggaagctgcc ggtatcaagg ttatccaagt tgatgaacca gctttaagag 5100
aaggtttacc attgagagaa ggtgctgaga gatctgctta ctacacctgg gctgccgaag 5160
ctttcagagt tgctacttct ggtgttgcta acaagactca aatacactct catttctgtt 5220
actctgactt ggatccaaac catatcaagg ctttggatgc tgatgttgtt tccatcgaat 5280

-continued

```
tctctaagaa ggacgatgct aactacattg ctgaattcaa aaactatcca aaccacattg   5340
gtctgggttt attcgatatt cattctccaa gaattccatc aaaggatgaa tttatcgcca   5400
agatttcaac catcttgaag agctacccag ctgaaaagtt ctgggttaac ccagactgtg   5460
gtttgaagac tagaggctgg gaagaaacta gattgtcttt gactcatatg gtcgaagccg   5520
ccaagtactt ccgtgaacaa tacaagaatt aaggttttaa aaaggaagca aagtaatgat   5580
attttctgaa ctttttgttt tttattctgg gattcaacat cggtgattta atttttgtgt   5640
tcacatttaa aagtttattt gggtaatttt ttgatatcaa ttttattaca aagccataac   5700
tcttgcattt tttttattat atttttatat acacgtacat tctgtattat ttataacgca   5760
ttcaaacgcg atcgccgacg ccgccgatga tcatctaccc atgccgaaat tcgggccgtt   5820
ggccggattg cgcgttgtct tctccggtat cgaaatcgcc ggaccgtttg ccgggcaaat   5880
gttcgcagaa tggggcgcgg aagttatctg gatcgagaac gtcgcctggg ccgacaccat   5940
tcgcgttcaa ccgaactacc cgcaactctc ccgccgcaat ttgcacgcgc tgtcgttaaa   6000
tattttcaaa gatgaaggcc gcgaagcgtt tctgaaatta atggaaacca ccgatatctt   6060
catcgaagcc agtaaaggtc cggcctttgc ccgtcgtggc attaccgatg aagtactgtg   6120
gcagcacaac ccgaaactgg ttatcgctca cctgtccggt tttggtcagt acggcaccga   6180
ggagtacacc aatcttccgg cctataacac tatcgcccag gcctttagtg gttacctgat   6240
tcagaacggt gatgttgacc agccaatgcc tgccttcccg tataccgccg attacttttc   6300
tggcctgacc gccaccacgg cggcgctggc agcactgcat aaagtgcgtg aaaccggtaa   6360
aggcgaaagt atcgacatcg ccatgtatga agtgatgctg cgtatgggcc agtacttcat   6420
gatggattac ttcaacggcg gcgaaatgtg cccgcgcatg agcaaaggta aagatcccta   6480
ctacgccgat cggcggcgtc ggcgatcgcg ttgaatgaaa atagagatca gaaattttgt   6540
gattatttgg aatctaaatt acaacgtgac aaacaacttg taaatggcgg ctccaagaaa   6600
aggaaagcca atgattagca tatgcctctt cttcttagaa gggcgttctg cccgttatgt   6660
atacgttaaa tattacatta ttttcgcatt tttgtattta tattcagtga aatattaggc   6720
ttggtcgagt aacatttccc atagctcgtc ggtttctttg aagtcgtgat gaacaattga   6780
gacaagacag tagtctttat gcactagtct tagaagaata ttggctgggg tgttccttgg   6840
aaataacttg gcccactcgg accagatact aaacgcttca tctctccatg ccttgaatga   6900
ctcttcttca atgattgtag tctgtttgac cggactgttg ggaaaaacac cccatgttac   6960
aacgctagag ctgtgcgggt ctaggttcgt ttcaaatgaa ccagatgaat cgcccgcgta   7020
ataactgaat ttccgacgcc cgtaatggtc tagcttgggt ttcaaagttg tttcccattg   7080
ctgtctatga ataaacattt ctacgaatgc cttctgatac aacctccctt tcgcgggccc   7140
ccagccgaat attttatcac tactcaatgt agcatttgtg gcaggttgcg atgccaaagt   7200
caaatatccg cgatagttta gttggattag ttcttcttgt attaacgccg tttcagctga   7260
taaacccagg tcagaccagg gaatcgcatc cgttgaacct tccaaatatt tttataaaaat  7320
atcttttaaa tcgccaattg tctttggtat accccatagt tcaagcgctt tgcttttgct   7380
taccttgatg gatggcccat aaccgtctat ttcaccatat gcgggagacc tggagtcacc   7440
aaatctacca ttggggaact catcccaagt ggcatcacga cccaaagttc cgtgaccttt   7500
agaaatagat attaaagcct ttttagatgg catggaacca ttctcattat tatagcgtaa   7560
gccttttcca gtgacgatag ccctattgaa aatcaacttg gccgaatcaa gacttgaatg   7620
ccttctcctt ttccggtttg ctacagtttc ttcattcgaa tcatccaaca caatatcccc   7680
```

```
gtcagcatct tctattggca cattttctat gcttcctatt tcgccactgg tttcatcttc   7740
tccctcttct tcgctagatt catttacgat atgggataag acgggagatt gcgagacaat   7800
ttgagcaata gccttttcca aatttaatgt atagaaatga aaccctttaa ttctaccaga   7860
tgttctttga tatatttcct gaatcaattc gataagaatg tccacaccaa tggacttcac   7920
ggcattatca tccgattgga tttctggggg gaacctactc agtattgcag gtggaataga   7980
tgcatgtgat aactttgctg ctctgtggaa aagcagatag gagttaatag gcatcaaccc   8040
agggaaaagg ggcaaatctt gcgaaatccg ttcccgaaat agcatttcaa aagttaagaa   8100
tttttcaacg tcgtaaaaca gttgtgttat cacaaaatcg gccccagctt caactttttc   8160
ttttaaatat accaaatcct tcaatgggtc ttgctcgtga ccttctgctt caccttcaca   8220
atgaccttct ggatatgctg caacaccgac gcagaacttg tctccgtagc tttgcttgat   8280
ataacgaact aaatcaaccg catatttaaa aggtgattcg ttcgattgag aatctagcca   8340
atcttcccca ataggtgggt cacctcgaag agccaaaata ttcctgattc ctgcattata   8400
acatctatcc agcgcatcat caatgatggc tttttctgtg tttgtacagg tcaaatgcat   8460
acaaactggt atatttagtg tctgctgtgc caaggaagct aatgtcagag tcttttccgc   8520
agtagtacca cctgctcccc aagtaaccgt gataaacagt ggatctaaag cagtcatacg   8580
atgcatacgt tccatcaaat ttctcgtccc taattcagtc tttggaggga agaattctaa   8640
cgatataaaa ggggaagccc tcgcatgata taaatctctg atggacattg tgaaggtagt   8700
tcgattttgg aggtcgcggg aggtaagtat agaggtatat taacaatttt ttgttgatac   8760
ttttatgaca tttgaataag aagtaataca aaccgaaaat gttgaaagta ttagttaaag   8820
tggttatgca gcttttgcat ttatatatct gttaatagat caaaaatcat cgcttcgctg   8880
attaattacc ccagaaataa ggctaaaaaa ctaatcgcat tattatccta tggttgttaa   8940
tttgattcgt tgatttgaag gtttgtgggg ccaggttact gccaattttt cctcttcata   9000
accataaaag ctagtattgt agaatcttta ttgttcggag cagtgcggcg cgaggcacat   9060
ctgcgtttca ggaacgcgac cggtgaagac caggacgcac ggaggagagt cttccgtcgg   9120
agggctgtcg cccgctcggc ggcttctaat ccgtacttca atatagcaat gagcagttaa   9180
gcgtattact gaaagttcca aagagaaggt ttttttaggc taagataatg gggctcttta   9240
catttccaca acatataagt aagattagat atggatatgt atatggtggt attgccatgt   9300
aatatgatta ttaaacttct ttgcgtccat ccaaaaaaaa agtaacccca cccgaagtcg   9360
cgcaaccaac taactttaca atgccttaca ctctatccga cgctcatcat aagttgatca   9420
cctctcattt ggtggacacc gaccctgaag tggactccat tatcaaggat gaaattgaaa   9480
gacaaaagca ctccatcgat ttgattgctt ctgaaaattt cacctcaacc tccgttttcg   9540
atgcccttgg aactccattg tccaacaaat attctgaagg ttatccaggt gctcgttact   9600
acggtggtaa tgaacacatt gacagaatgg aaattctatg tcaacaaaga gctttaaaag   9660
ctttccatgt tactccagac aaatggggtg ttaacgtcca aactttatct ggttctcctg   9720
ctaacttgca agtttatcaa gctattatga agcctcatga aagattgatg ggtctatacc   9780
taccagatgg tggtcatttg tctcacggtt acgctactga aaacagaaaa atttctgctg   9840
tttccacata cttcgaatct ttcccataca gagttaaccc agaaaccggt attatcgact   9900
acgatacttt agaaaagaac gccatcctat atagaccaaa ggttcttgtt gctggtactt   9960
cagcatactg tcgtttaatt gactacaaga gaatgagaga aatcgccgac aaatgtggtg  10020
```

-continued

```
cttacttgat ggtagacatg gcccacattt caggtttgat cgccgcaggt gtcatcccat  10080
ctcctttcga atacgctgat atcgttacca ccaccactca caagtctttg agaggtccac  10140
gtggtgctat gattttcttc agaagaggtg tgagatctat caaccctaag accggtaagg  10200
aagtcctata cgacttggaa aacccaatta acttctctgt tttcccaggt caccaaggtg  10260
gtccacacaa ccataccatt gctgctttgg ccactgcttt gaagcaagct gccactccag  10320
aattcaagga ataccaaact caagtcttga agaatgctaa ggctttggaa agtgaattta  10380
agaacttggg ctacagatta gtttccaacg gtaccgattc tcacatggtt ctggtatcct  10440
tgagagaaaa gggtgttgat ggtgctcgtg ttgaatacat ttgtgaaaag attaacattg  10500
ctttgaacaa aaactctatt ccaggtgaca aatctgcttt ggttccaggt ggtgtccgta  10560
ttggggctcc agccatgacc actagaggaa tgggtgaaga agatttccac agaattgttc  10620
aatacattaa caaggctgta gaattcgctc aacaagttca acaaagcttg ccaaaggatg  10680
cttgtagatt aaaggacttc aaagccaagg tcgacgaagg ctctgatgtt ttgaacacct  10740
ggaaaaagga aatttacgac tggqctggcg aatacccatt ggctgtgtaa agaaatcacc  10800
acaacgacac ttaatcccaa aaaaataaac attactgtat aagtattcat tttctcctct  10860
tctcattatg tatatatgta cctatatgta tgtatgtatg tgcgtacgat tttctaacg  10920
ttaacttcat ttctttttga ttatgtgccc tccttgagtt aagatgtgct tgtccaggtc  10980
cgccggcgtt ggacgagcga attaagcttt cgagaaaaac tttcttttaa cccctctaat  11040
ctaaatataa acatatagct tatagaaatg aatgaatatt ttaaatagtt acggatacaa  11100
agagttcatt atagtgcggg cagttagtac ggtatcgatt tatcattgga gatctgcagt  11160
gttacagaag cactgctcac cagttgtcta cggaaggacg ttgagatagt tttaccacgt  11220
ttgagctaaa agtttctacc acaagagcct ttatttgcac atggcagtga atgcatgatt  11280
aaggatatga agaagaaagg aataactagg aataaatttt atttagagag ggtatgatga  11340
aaggagagcc tcgttattta tgacctgcat tttatcagc atcttctttc cagctcccgc  11400
taaacatgtg ctttacaaaa gccattttgt cgtcactaga ctgggcgccc atctgcccca  11460
catctggtga aaaacttgtt attggtagaa ccatcacatg gcggtttaaa cgcgtggccg  11520
tgccgtc                                                             11527
```

<210> SEQ ID NO 15
<211> LENGTH: 1912
<212> TYPE: DNA
<213> ORGANISM: Artificial Sequence
<220> FEATURE:
<223> OTHER INFORMATION: Synthetic: R21 sequence

<400> SEQUENCE: 15

```
tcgacactag taatacacat catcgtccta caagttcatc aaagtgttgg acagacaact    60
ataccagcat ggatctcttg tatcggttct tttctcccgc tctctcgcaa taacaatgaa   120
cactgggtca atcatagcct acacaggtga acagagtagc gtttatacag ggtttatacg   180
gtgattccta cggcaaaaat ttttcatttc taaaaaaaaa aagaaaaatt tttctttcca   240
acgctagaag gaaaagaaaa atctaattaa attgatttgg tgattttctg agagttccct   300
ttttcatata tcgaattttg aatataaaag gagatcgaaa aaatttttct attcaatctg   360
ttttctggtt ttatttgata gtttttttgt gtattattat tatggattag tactggttta   420
tatgggtttt tctgtataac ttctttttat tttagtttgt ttaatcttat tttgagttac   480
attatagttc cctaactgca agagaagtaa cattaaaaat gaaaaagcct gaactcaccg   540
```

cgacgtctgt cgagaagttt ctgatcgaaa agttcgacag cgtctccgac ctgatgcagc 600
tctcggaggg cgaagaatct cgtgctttca gcttcgatgt aggagggcgt ggatatgtcc 660
tgcgggtaaa tagctgcgcc gatggtttct acaaagatcg ttatgtttat cggcactttg 720
catcggccgc gctcccgatt ccggaagtgc ttgacattgg ggaattcagc gagagcctga 780
cctattgcat ctcccgccgt gcacagggtg tcacgttgca agacctgcct gaaaccgaac 840
tgcccgctgt tctgcagccg gtcgcggagg ccatggatgc gatcgctgcg gccgatctta 900
gccagacgag cgggttcggc ccattcggac cgcaaggaat cggtcaatac actacatggc 960
gtgatttcat atgcgcgatt gctgatcccc atgtgtatca ctggcaaact gtgatggacg 1020
acaccgtcag tgcgtccgtc gcgcaggctc tcgatgagct gatgctttgg gccgaggact 1080
gccccgaagt ccggcacctc gtgcacgcgg atttcggctc caacaatgtc ctgacggaca 1140
atggccgcat aacagcggtc attgactgga gcgaggcgat gttcggggat tcccaatacg 1200
aggtcgccaa catcttcttc tggaggccgt ggttggcttg tatggagcag cagacgcgct 1260
acttcgagcg gaggcatccg gagcttgcag gatcgccgcg gctccgggcg tatatgctcc 1320
gcattggtct tgaccaactc tatcagagct tggttgacgg caatttcgat gatgcagctt 1380
gggcgcaggg tcgatgcgac gcaatcgtcc gatccggagc cgggactgtc gggcgtacac 1440
aaatcgcccg cagaagcgcg gccgtctgga ccgatggctg tgtagaagta ctcgccgata 1500
gtggaaaccg acgccccagc actcgtccga gggcaaagga ataggtttaa cttgatacta 1560
ctagattttt tctcttcatt tataaaattt ttggttataa ttgaagcttt agaagtatga 1620
aaaaatcctt tttttcatt ctttgcaacc aaaataagaa gcttctttta ttcattgaaa 1680
tgatgaatat aaacctaaca aaagaaaaag actcgaatat caaacattaa aaaaaaataa 1740
aagaggttat ctgttttccc atttagttgg agtttgcatt ttctaataga tagaactctc 1800
aattaatgtg gatttagttt ctctgttcgt tttttttgt tttgttctca ctgtatttac 1860
atttctattt agtatttagt tattcatata atcttaactt ctcgaggagc tc 1912

<210> SEQ ID NO 16
<211> LENGTH: 4761
<212> TYPE: DNA
<213> ORGANISM: Artificial Sequence
<220> FEATURE:
<223> OTHER INFORMATION: Synthetic: MS150540 sequence

<400> SEQUENCE: 16
gacggcacgg ccacgcgttt aaaccgcccc atggcaaaga atgctttcca tgacgatcat 60
cgtagtgccc aattgggtgc ctctatgatg ggtatggctt gggcaagtgt ctttttatgt 120
atcgtggaat ttatcctgct ggtcttctgg tctgttaggg caaggttggc ctctacttac 180
tccatcgaca attcaagata cagaacctcc tccagatgga atcccttcca tagagagaag 240
gagcaagcaa ctgacccaat attgactgcc actggacctg aagacatgca acaaagtgca 300
agcatagtgg ggccttcttc caatgctaat ccggtcactg ccactgctgc tacggaaaac 360
caacctaaag gtattaactt cttcactata agaaaatcac acgagcgccc ggacgatgtc 420
tctgtttaaa tggcgcaagt tttccgcttt gtaatatata tttataccc tttcttctct 480 cccctgcaat ataatagttt caaatcagat tcaagtttga gggtagttaa ttaatagtct 540
tggatgtaat tcttattgtt atactgaata cgctaaaacc actcacaaca agtatggagt 600
atattgtgtc tctttatata ctgagtactt atgcaatatg cgctcactca ggatgaaatg 660

-continued

```
tacacagccg aaagtatatt gaaagctgcc tctgtggaaa cttctatcta atgttgtctc    720
cagatgtaga ctatgaggcc tgaagaagtc tttaaacacc tgttggagag tataaggaga    780
ctgctacaac aacgtcttcc ccacaaaaat tatgtggagg ccggtatgat acctgcacaa    840
acgttaagtt acacatgaaa aagagactga cataactttg atctctgaaa atatgttttc    900
ccctgagtag cttcactgct tggataccaa tacgaataga ccttggctat agtaagttgc    960
atctgtaccg tagagattct tgcaacctcg cttaaactct cgcttttata taatatttct   1020
ccttattgcg cgcttcgttg aaaatttcgc taaacacggg gtttaagttt aagtttacag   1080
gatttatccg gaagttttcg cggaccccac acaattaaga attggctcga agagtgataa   1140
cgcatacttt tcttttcttt tttcagttcc tagcgtacct aacgtaggta acatgatttg   1200
gatcgtggga tgatacaaac aacgtaagat gagtagttcc ttcctcaatt cttctttcag   1260
catcattttc ttgaggcgct ctgggcaagg tataaaaagt tccattaata cgtctctaaa   1320
aaattaaacc atctatctct taagcagttt ttttgataat ctcaaatgta catcaacctc   1380
ccgcgacctc caaaatcgaa ctaccttcac aatggactac aacaagagat cttcggtctc   1440
aaccgtgcct aatgcagctc ccataagagt cggattcgtc ggtctcaacg cagccaaagg   1500
atgggcaatc aagacacatt accccgccat actgcaacta tcgtcacaat ttcaaatcac   1560
tgccttatac agtccaaaaa ttgagacttc tattgccacc atccagcgtc taaaattgag   1620
taatgccact gcttttccca ctttagagtc atttgcatca tcttccacta tagatatgat   1680
agtgatagct atccaagtgg ccagtcatta tgacgttgtt atgcctctct tggaattctc   1740
caaaaataat ccgaacctca agtatctttt cgtagaatgg gcccttgcat gttcactaga   1800
tcaagccgaa tccatttata aggctgctgc tgaacgtggg gttcaaacca tcatctcttt   1860
acaaggtcgt aaatcaccat atattttgag agcaaaagaa ttaatatctc aaggctatat   1920
cggcgacatt aattctatcg agattgctgg aaatggcggt tggtacggct acgaaaggcc   1980
tgttaaatca ccaaaataca tctatgaaat cgggaacggt gtagatctgg taaccacaac   2040
atttggtcac acaatcgata ttttacaata catgacaagt tcgtactttt ccaggataaa   2100
tgcaatggtt ttcaataata ttccagagca agagctgata gatgagcgtg gtaaccgatt   2160
gggccagcga gtcccaaaga cagtaccgga tcatctttta ttccaaggca cattgttaaa   2220
tggcaatgtt ccagtgtcat gcagtttcaa aggtggcaaa cctaccaaaa aatttaccaa   2280
aaatttggtc attgatattc acggtaccaa gggagatttg aaacttgaag gcgatgccgg   2340
attcgcagaa atttcaaatc tggtccttta ctacagtgga actagagcaa acgacttccc   2400
gctagctaat ggacaacaag ctcctttaga cccggggtat gatgcaggta aagaaatcat   2460
ggaagtatat catttacgaa attataatgc cattgtcggt aatattcatc gactgtatca   2520
atctatctct gacttccact tcaatacaaa gaaaattcct gaattaccct cacaatttgt   2580
aatgcaaggt ttcgatttcg aaggctttcc caccttgatg gatgctctga tattacacag   2640
gttaatcgag agcgtttata aaagtaacat gatgggctcc acattaaacg ttagcaatat   2700
ctcgcattat agtttaatga aaatcgaaga aggtaagtta gtcacttgga tcaacggtga   2760
caagggttac aatggtttgg ctgaagctgg taagaagttt gaaaaagaca ctggtatcaa   2820
ggttaccgtc gaacatccag ttgagttgga agaaaagttc ccacaagtcg ccgctactgg   2880
tgatggtcca gatattatct tctgggctca cgacagattc ggtggttacg ctcaatctgg   2940
tttgttagcc gaaattactc ctggcaaggc tttccaagac aaattatacc cattcacctg   3000
ggatgctgtc agatataacg gtaaattgat cgcttaccca atcgctgtcg aagctttgtc   3060
```

```
cttgatctac aacaaggatt tgttacctaa cccaccaaaa acttgggaag aaatcccagc   3120
tttggacaag gaattgaaag ctaaaggtaa atccgctttg atcttcaact tacaagaacc   3180
atatttcact tggcctttga ttgctgctga tggtggtaat gcctttaagt acgaaaacgg   3240
taagtacgat attaaggacg tcggtgttga cagcgccggt gctaaggctg gtttaacttt   3300
cttggtcgat ttgatcaaga acaagcatat gaacgccgac actgactact ctatcgctga   3360
agtcgctttc aataagggtg agactgctat gactattaac ggtccttggg cttggtctaa   3420
tatcgatact tctaaggtca actacggtgt taccgttttg ccaaccttca aaggtcaacc   3480
atccaagcca tttgttggtg ttttgtccgc tggtatcaac gctgcttctc ctaacaagga   3540
attggctaag gaattcttgg aaaactattt gttgactgat gaaggtttag aagctgttaa   3600
caaggacaag ccattgggtg ccgttgcctt gaagtcttac gaagaagaat tggccaagga   3660
ccctagaatt gctgctacta tggaaaatgc ccaaaaaggt gagatcatgc caaacattcc   3720
acaaatgtct gctttctggt atgctgttag aactgccgtc attaacgctg cttccggtag   3780
acaaactgtt gatgaagcct tgaaagatgc ctaaactaac tcctcttcca acaacaataa   3840
taacaacaac aacaacaact tggtatcga aggtagataa aagcatcttg ccctgtgctt    3900
ggcccccagt gcagcgaacg ttataaaaac gaatactgag tatatatcta tgtaaaacaa   3960
ccatatcatt tcttgttctg aactttgttt acctaactag ttttaaattt cccttttcg    4020
tgcatgcggg tgttcttatt tattagcata ctacatttga aatatcaaat ttccttagta   4080
gaaaagtgag agaaggtggc actgacacac ttaaccttca tacagatctg ggtaagatta   4140
ttacttgcta taagtgcgtg cctgatgaac aggatattgc ggtcaataat gctgatggtt   4200
cattagactt cagcaaagcc gatgccaaaa taagccaata cgatctcaac gctattgaag   4260
cggcttgcca gctaaagcaa caggcagcag aggcgcaggt gacagcctta agtgtgggcg   4320
gtaaagccct gaccaacgcc aaagggcgta aagatgtgct atcgcgcggc ccggatgaac   4380
tgattgtggt gattgatgac cagttcgagc aggcactgcc gcaacaaacg gcgagcgcac   4440
tggctgcagc cgcccagaaa gcaggctttg atctgatcct ctgtggcgat ggttcttccg   4500
acctttatgc ccagcaggtt ggtctgctgg tgggcgaaat cctcaatatt ccggcagtta   4560
acggcgtcag caaaattatc tccctgacgg cagataccct caccgttgag cgcgaactgg   4620
aagatgaaac cgaaacctta agcattccgc tgcctgcggt tgttgctgtt tccactgata   4680
tcaactcccc acaaattcct tcgatgaaag ccattctcgg cgcggcgaaa aagcggtgtt   4740
taaaccccag cgcctggcgg g                                             4761
```

<210> SEQ ID NO 17
<211> LENGTH: 8624
<212> TYPE: DNA
<213> ORGANISM: Artificial Sequence
<220> FEATURE:
<223> OTHER INFORMATION: Synthetic: MS159820 sequence

<400> SEQUENCE: 17

```
gacggcacgg ccacgcgttt aaaccgcccg aacaagctta tccctattac agaattccaa     60
ggaggaaatc attcaacttg aaagtaaatg gatgtctatg caatctgtta aaacaactgc    120
cctacccctt caagagacta cgaatacatc atcgacctta acttctctga cgtccagcat    180
aattcccaag agtataccta taatcacgaa aggtgaagtc gccactaaac cagcatctta    240
ctgaattatt ttcaacagaa cacatcgcat ccaactgaac aaactgttac cgctgttgat    300
```

accaaggaac attcagtgaa cgtagggaag aacgaacatt ctccatattt ttgcatacta 360
gatacaaggg ggaagaatgc aattatttca caaaccgaaa gaaaaagaat cacaagctat 420
gtttgctatt atcaattttt cttatgatta atttaacata aattatggcc tttttcattc 480
cggctgcgct tgttctccaa tttttttttt ttttttgaga aaactttcat actaggtaac 540
tagagggggg tataaaactt acatagaaaa aaaatatata ctatacttac aacttttcat 600
ttttttcgta aaaactaccc cacaatgaaa taagatacca taccttatcg agttattatg 660
tatgtgtcga agctttttat aaggctgcag ataaggacaa cattctaata ggctgctgtg 720
tagcttgttg ttgagttgga gaatccactg tgattttcat atctctaact aatttggccc 780
atgatacggc gcctctccta gctaactcct ctggaactcc aaatccagta tctgacattc 840
ttctgttaaa taattccaag gacacccaac cttcgaagcc caatccattg aaaaaagccc 900
aagcgatttc tttaacaggt aagtaagcgc ctctgtcttt ttcgccgtag aacaacctac 960
aatttcttga ccatgacatt ctggctggtt gctcagggtc atagaatcta tgaccgggaa 1020
ctaatggttt ctttaacttt tcggcgtcca ctacttgaac gtagaagact ttagatacat 1080
cgaccctttc gaccaacctg gcaattgact ttctaattgc ttcttcagcg tttggtgttc 1140
tgcctgaggc aactgtgggg tcagcataaa ctctacctgc gatgttaaaa gtgtctaagc 1200
aaacgccaaa gttaggtcta tttactcttt ggacaacttc ccaagacctc tcccaagtgt 1260
caactctagt ggaccagcat aatgcctcat atacaaacct tattggaggg tttgcctgta 1320
aacccatatc ggcaacttcc tgtaagtcac tcacaattaa tgaaatatct tctgtgactt 1380
cttcggcggg caagaaattg gctggaattt gaatgatgtc agtatccaac tcgtgggcca 1440
attcaatcca aaactctaat tgctccaacc tcctctcgtg ctcctctcta tccaataaac 1500
catcatattg tgaaaagggt tgcaagcaca ctatttcgat gtttctaacc tggcacatcc 1560
tcaatatctg tctagcggct gataattgag cagctggact gggaccgcat ggactaggtg 1620
tttcacctga caacctgtat gcgacatcgg ctaagtcctc atgaaacaac tccaaaccct 1680
ggtaaccata tttcctagcc atgtctaact tagttgtgaa agaatggcct gcataacacc 1740
tgcccaagga catggaagtt atagccaatt tactgggcat tgtaaagtta gttggttgcg 1800
cgacttcggg tggggtatgt taatcttgtg tttacttaac tattgctatt cttgatgata 1860
attgaataag gtgcataatg aagagcaatt cacaacacca aattttcaat ccaattactg 1920
attgtttata tatgtctaca aaactaatcc tatctccaca ttttagcctg cgaaatgttt 1980
gtttttttaaa caatagctct ccagaacatt gtataattta agaatatgtg cacagttaac 2040
tttctagcag gagtataatg ccatttgctc cccatcttga gatgggaagg gcttaactaa 2100
tctcggttcg gagtgatccg ccccgatact gccttctgcc ttaatatcgt ccaaggcaca 2160
tggacccctg aacggcgcag atatctccgc acggacgaaa gaccgccggt gccttcctga 2220
ggcaaccgcc cctttcgaat atagatcacg tgacccattt ttagctacta atagaaaaag 2280
aaattgcaac ctacttaagc cattccggaa ggaagctttc cgatcacatg tagggaccga 2340
attgtttaca agttctctgt accaccatgg agacatcaaa gattgaaaat ctatggaaag 2400
atatggacgg tagcaacaag aatatagcac gagccgcgaa gttcatttcg ttacttttga 2460
tatcgctcac aactattgcg aagcgcttca gtgaaaaaat cataaggaaa agttgtaaat 2520
attattggta gtattcgttt ggtaaagtag agggggtaat ttttcccctt tattttgttc 2580
atacattctt aaattgcttt gcctctcctt ttggaaagct atacttcgga gcactgttga 2640
gcgaaggctc attagatata ttttctgtca ttttccttaa cccaaaaata agggaaaggg 2700

```
tccaaaaagc gctcggacaa ctgttgaccg tgatccgaag gactggctat acagtgttca   2760
caaaatagcc aagctgaaaa taatgtgtag ctatgttcag ttagtttggc tagcaaagat   2820
ataaaagcag gtcggaaata tttatgggca ttattatgca gagcatcaac atgataaaaa   2880
aaaacagttg aatattccct caaaaatgga aagaattgtt gtaacattgg gtgaaaggtc   2940
ttatccaatc actattgcat ctggtttatt taacgaacca gccagttttt taccattgaa   3000
atccggtgag caagtgatgt tagtcactaa cgaaacatta gctcccttgt atttagacaa   3060
ggtaaggggt gttttggaac aagcaggcgt aaacgtcgat tctgtgatat taccagacgg   3120
tgaacaatac aaaagtttgg cagttttaga tactgtattc actgccttat tacagaaacc   3180
acatggtaga gatactacat tggttgcctt aggaggcgga gttgtcggcg atttaacagg   3240
tttcgctgcc gcatcatatc agagaggtgt tagattcatt caggtcccaa ctactttgtt   3300
atcccaagta gactcatcag ttggaggaaa gactgctgtc aatcatcctt taggaaagaa   3360
catgattggt gccttctacc agccagcatc agtcgttgtt gatttagatt gtttgaagac   3420
attacctcca agagagttgg caagtggttt ggcagaagta ataaaatatg gtatcatatt   3480
ggatggtgca ttttttaatt ggttggaaga aaatttagat gcattattga ggttagacgg   3540
tcctgctatg gcttattgta ttagaaggtg ttgtgaatta aaggctgagg ttgtagcagc   3600
cgacgagaga gaaactggtt taagagcttt gttgaactta ggtcatacat ttggtcatgc   3660
tatcgaagct gaaatgggtt acggtaattg gttgcatggt gaagccgttg cagccggtat   3720
ggttatggct gccaggacat ctgaaagatt gggtcaattc agttctgcag aaacacaaag   3780
gataataacc ttattgaaaa gggcaggttt acctgtgaat ggtcctagag agatgagtgc   3840
tcaagcttat ttgccccaca tgttgagaga taagaaggtt ttagcaggtg aaatgaggtt   3900
aattttgccc ttagcaattg gaaaaagtga agtcagatcc ggtgtttcac atgaattagt   3960
attgaacgcc atagctgatt gccaatcagc ctaaataaat gacttaattt taactatata   4020
tcgccaaaca tgtaaattaa aaaaagaagc gagaagtata tacatgtgtg tatgaataaa   4080
taattcgttt actattgata cgtattgcaa gatatgatta acctgcaggc cgcgagcgcc   4140
gatgatcatc tacccatgcc gaaattcggg ccgttggccg gattgcgcgt tgtcttctcc   4200
ggtatcgaaa tcgccggacc gtttgccggg caaatgttcg cagaatgggg cgcggaagtt   4260
atctggatcg agaacgtcgc ctgggccgac accattcgcg ttcaaccgaa ctacccgcaa   4320
ctctcccgcc gcaatttgca cgcgctgtcg ttaaatattt tcaaagatga aggccgcgaa   4380
gcgtttctga aattaatgga aaccaccgat atcttcatcg aagccagtaa aggtccggcc   4440
tttgcccgtc gtggcattac cgatgaagta ctgtggcagc acaacccgaa actggttatc   4500
gctcacctgt ccggttttgg tcagtacggc accgaggagt acaccaatct tccggcctat   4560
aacactatcg cccaggcctt tagtggttac ctgattcaga acggtgatgt tgaccagcca   4620
atgcctgcct tcccgtatac cgccgattac ttttctggcc tgaccgccac cacggcggcg   4680
ctggcagcac tgcataaagt gcgtgaaacc ggtaaaggcg aaagtatcga catcgccatg   4740
tatgaagtga tgctgcgtat gggccagtac ttcatgatgg attacttcaa cggcggcgaa   4800
atgtgcccgc gcatgagcaa aggtaaagat ccctactacg ccgacggccg gccaagcacg   4860
cggggatcaa tgctgcttcg tataggcgct atttaattaa gtagttatat aaagagaacg   4920
gtgcaattga ataggaaagg aatgacggat tttgcttcta tgtttgcttt tatttgaagc   4980
gtgggttctt atttatgctt ggtgtaatat ggtcaaaact gttctcaaat catttactga   5040
```

-continued

```
gatctgtcct ggagcagaag ctttttttgac agcaccaaat gtagcagcag atccgaacac   5100
ttcaccagct aatctagaaa tcacaccggt tttgccata gacatagtta tgataggtct   5160
atcagcgtat tgttcttgca tttccaatgt ggcagctaac aatgttaaga catcagaggt   5220
agactgtggc attaaagcaa ttttgggtat atcagcatca aaggattgca tttttcttaa   5280
tctggctatg atttcctctg cttctggggt cttgtggaaa tcatgattag acataactac   5340
cttaacatcg tgagcgtgag cgtaagctac agtttcctta acctggtcat caccagtaaa   5400
caactccaaa tctatcatat ccactaaacc actatcaata gcagctctgt tcaaagcaat   5460
gtaggcttcg gtactaattg cttgttcacc accttcctta gctgatctga aagtgaacaa   5520
taatggtttt tcaggcatag tctctcttaa tatctttgct gcagccatta ctgattcgac   5580
atttgacaag tctgcatagt gatccactct ccattctaat atgtcaaaat ctgcttctct   5640
ataagctaag gcctcactct ttacagaggc tatgtcttta gccattaaac taacaattat   5700
tttaggggct cctgttccaa taaccaaatc tttcactgta actgtcttca tttttgaggg   5760
aatattcaac tgtttttttt tatcatgttg atgctctgca taataatgcc cataaatatt   5820
tccgacctgc ttttatatct ttgctagcca aactaactga acatagctac acattatttt   5880
cagcttggct attttgtgaa cactgtatag ccagtccttc ggatcacggt caacagttgt   5940
ccgagcgctt tttggaccct ttcccttatt tttgggttaa ggaaaatgac agaaaatata   6000
tctaatgagc cttcgctcaa cagtgctccg aagtatagct ttccaaaagg agaggcaaag   6060
caatttaaga atgtatgaac aaaataaagg ggaaaaatta ccccctctac tttaccaaac   6120
gaatactacc aataatattt acaacttttc cttatgattt tttcactgaa gcgcttcgca   6180
atagttgtga gcgatatcaa aagtaacgaa atgaacttcg cggctcgtgc tatattcttg   6240
ttgctaccgt ccatatcttt ccatagattt tcaatctttg atgtctccat ggtggtacag   6300
agaacttgta aacaattcgg tccctacatg tgatcggaaa gcttccttcc ggaatggctt   6360
aagtaggttg caatttcttt ttctattagt agctaaaaat gggtcacgtg atctatattc   6420
gaaaggggcg gttgcctcag gaaggcaccg gcggtctttc gtccgtgcgg agatatctgc   6480
gccgttcagg ggtccatgtg ccttggacga tattaaggca gaaggcagta tcggggcgga   6540
tcactccgaa ccgagattag ttaagccctt cccatctcaa gatggggagc aaatggcatt   6600
atactcctgc tagaaagtta actgtgcaca tattcttaaa ttatacaatg ttctggagag   6660
ctattgttta aaaaacaaac atttcgcagg ctaaaatgtg gagataggat tagttttgta   6720
gacatatata aacaatcagt aattggattg aaaatttggt gttgtgaatt gctcttcatt   6780
atgcacctta ttcaattatc atcaagaata gcaatagtta agtaaacaca agattaacat   6840
accccacccg aagtcgcgca accaactaac tttacaatgc agaaagatgc cttaaataac   6900
gtacatataa cagatgaaca ggttttgatg acacctgagc aattaaaagc tgcctttccc   6960
ttatctttgc aacaagaggc tcagatagcc gattcaagaa agagtatttc tgatattata   7020
gccggtagag atccaaggtt attggttgta tgtggcccat gtagtatcca cgatcctgaa   7080
acagcattgg aatacgcaag aagatttaag gccttggcag ctgaagtctc cgactccttg   7140
tatttggtta tgagggttta ttttgaaaag ccaaggacca ctgtaggttg gaagggattg   7200
attaacgacc cacatatgga tggatctttt gatgtggaag ctggtttgca aatcgcaagg   7260
aaattgttgt tggaattagt aaatatgggt ttgcctttag ctaccgaagc cttggattta   7320
aacagtcctc aatatttggg cgatttattc tcctggtctg caataggtgc tagaaccacc   7380
gaatcacaaa ctcacagaga aatggcatct ggtttgagta tgccagttgg cttcaaaaac   7440
```

```
ggcacagacg gttcattggc aactgccata aatgccatga gggccgcagc tcaaccacat   7500
agatttgtcg gtatcaatca agctggtcag gtcgcattat tacaaactca gggtaaccca   7560
gatggtcatg taatattgag ggtggtaagg gccccaaact attcacctgc cgacgtggca   7620
cagtgcgaaa aggaaatgga acaagcaggt ttaagacctt ccttgatggt cgactgttct   7680
cacggtaact ctaataagga ttacaggaga caacccgccg tcgctgaatc tgtagttgca   7740
cagataaaag atggaaacag atctatcatc ggtttgatga tcgaatcaaa tattcatgag   7800
ggtaaccaat catccgaaca gccaagatca gaaatgaagt atggcgtgtc tgttacagac   7860
gcatgtattt catgggaaat gaccgacgca ttgttgagag aaattcatca ggatttgaat   7920
ggccaattga cagcaagagt ggcctaaaat tttagtgtcg ttaatatctc ttttatttct   7980
tattgttact atattattac tgttttgaag ttccagtttc atcaactttt gctaccttaa   8040
ttaaaagaac cactcagact ttttaccatc ctacccccct ctagttacct agtatggcat   8100
agtaaaaaaa tagatgcaga atttactcac ctcaaggagg ggcaaagtaa taagaaaagt   8160
taccataggc tagttgaatg tccaagatcg taaagaatga agaaaaaagg agtaaaaagt   8220
atgaataaga taaatgaaaa tataaaaata aaaaccaact aatacatgaa gaaaaaaaag   8280
cagacaaaaa cattttatgg acctgatgca atctagtagt ccatagaata atcaccacta   8340
gaaaattctt cctcttcatt actaccgttt gccattatag gaatatgatt tgctgcagga   8400
ttctgcggag gtattatata gggcactggc ggcacctgtg gaataaaccc aaatgatggg   8460
aacattggca tcatccagtt agcgttattt tggtttgcac ttattaagtt gtaactgttc   8520
acgggctttg tgttggtatt agggtactgc agtggtatga aataattttc cctcgagact   8580
tgctgttgcg attggtggcg gtttaaacgc gtggccgtgc cgtc                    8624
```

<210> SEQ ID NO 18
<211> LENGTH: 9013
<212> TYPE: DNA
<213> ORGANISM: Artificial Sequence
<220> FEATURE:
<223> OTHER INFORMATION: Synthetic: MS156217 sequence

<400> SEQUENCE: 18

```
gacggcacgg ccacgcgttt aaaccgccaa aaactcacaa gaagttcggt gtccttattt     60
gcgatgggaa ttgctaatat catatcacca caaatatgga gagagaagga ctctcctcgc    120
tttttacctg cctggattgt tcaaatcgtt ttatcattct ctcttgcacc agccattttg    180
ttactgatcc atttcatact aaaaagaagg aataatcaaa gactaaaaaa ttatgacgaa    240
aatttacaaa attatttgga cagaattcaa ctcattgaaa gcgaaaatcc ttcttccatt    300
gaagaaggga aagtggtaac ccacgagaac aatttggcag tctttgattt gactgattta    360
gaaaacgaaa cttttatata tcctttgtaa atattgatgt tttgttgtgt aaatgttcta    420
tctgacactt aataattaga aaattaattt tttaaacttt ccggctgcaa gaaagaggaa    480
ctgtgtctct ttgaaaggca caatttccca aagaatcatt tacaatgcga aaaaaagata    540
tcaggagggg tagtgagttc tattcacgca atcggtagta tcaaagaaga ttatttgggt    600
gctatttaat cacttgttac tccgcaacgc ttttctgaac gcccgccttc gcctttcatt    660
atcattctca tcccaaaaga actgtgcatg ttatttgcaa tacttcatat acgctctgta    720
ttattaatag tatcattaat tacgtcaatt gaaattcaaa atatcatctt tgacagtaac    780
atctatcctc ttagacaact agggccattg cagtgtctcg aaaccattaa tatcactgaa    840
```

aagatgaaaa gaaaggcaaa tatatattga tcactaattt tctaagctaa agaatctatt 900
ccccctctgt taaatggaat tgtgtgaaat aaaatattat aaaatcagaa ctttgggggg 960
gaaacataaa aaaatgagaa aaagaaaacg aactaactaa tgtttaagta aaagaacaaa 1020
aaggtagacc aatgtagcgc tcttacttta ttagactaat cttctacaca aggtaacacc 1080
atcaccgatg gaaacttggg agatttcaat tcttggatcg gaagccaatc ttttgttcaa 1140
ttccatcaaa gccttacggt taactcttaa gtgaactggg acagtctctt cctcttcagc 1200
aacgaaaccg aaccataagg tgttatcgaa agcaatgata ccaccaactt tgaccaactt 1260
catcaatctt tccaaagcgt ggacgtaatt tggcttatca gcgtcaacga aagcgaagtc 1320
aaattctggc tttgggtttt cagataacaa cttgtctaag gcttgcaaac cgtcggattg 1380
gataaagtta attttgtgat cgataccggc gttcttgatg aattccaaac ccatttcgta 1440
agcttcttta tcgatatcaa tagcagtaat tctaccgtct tcaggcaaag ccaaggcggt 1500
ggttaacaaa gagtaaccag tgaaaacacc caattccaag gtgttcttag cgttcatcat 1560
cttcaacaac atggacaaga aatgaccttc gtcaacaggg acttccatct cggacaagtt 1620
accgtactta tgaacggtag cttctcttaa cttcttcaat tcttcgtgtt ctcttgggta 1680
agcggaagtt tcaaagatgt actttttcaa ttcttcgttc ttcaagatac ccttagatgg 1740
tataagattt tccatgtctg gttccattgt aaagttagtt ggttgcgcga cttcgggtgg 1800
ggtatgttaa tcttgtgttt acttaactat tgctattctt gatgataatt gaataaggtg 1860
cataatgaag agcaattcac aacaccaaat tttcaatcca attactgatt gtttatatat 1920
gtctacaaaa ctaatcctat ctccacattt tagcctgcga aatgtttgtt ttttaaacaa 1980
tagctctcca gaacattgta taatttaaga atatgtgcac agttaacttt ctagcaggag 2040
tataatgcca tttgctcccc atcttgagat gggaagggct taactaatct cggttcggag 2100
tgatccgccc cgatactgcc ttctgcctta atatcgtcca aggcacatgg acccctgaac 2160
ggcgcagata tctccgcacg gacgaaagac cgccggtgcc ttcctgaggc aaccgcccct 2220
ttcgaatata gatcacgtga cccattttta gctactaata gaaaaagaaa ttgcaaccta 2280
cttaagccat tccggaagga agctttccga tcacatgtag ggaccgaatt gtttacaagt 2340
tctctgtacc accatggaga catcaaagat tgaaaatcta tggaaagata tggacggtag 2400
caacaagaat atagcacgag ccgcgaagtt catttcgtta cttttgatat cgctcacaac 2460
tattgcgaag cgcttcagtg aaaaaatcat aaggaaaagt tgtaaatatt attggtagta 2520
ttcgtttggt aaagtagagg gggtaatttt tccccttttat tttgttcata cattcttaaa 2580
ttgctttgcc tctccttttg gaaagctata cttcggagca ctgttgagcg aaggctcatt 2640
agatatattt tctgtcattt tccttaaccc aaaaataagg gaaagggtcc aaaaagcgct 2700
cggacaactg ttgaccgtga tccgaaggac tggctataca gtgttcacaa aatagccaag 2760
ctgaaaataa tgtgtagcta tgttcagtta gtttggctag caaagatata aaagcaggtc 2820
ggaaatattt atgggcatta ttatgcagag catcaacatg ataaaaaaaa acagttgaat 2880
attccctcaa aaatggatat ggcaagtaat ggttctgccg gtgaggttag agaagttcac 2940
tcctccgaaa ctaccaagac tttattgaaa tccgatgctt tatacgatta tatgttgaag 3000
actatggtct atccaagaga gaacgaattt atgagagaat tgagacaaat cacttccgaa 3060
catatcttcg gtttcatgtc ttctccacca gatgaaggtt tgttattgtc cttgttgtta 3120
aaggttatgg gtgctaagag aaccatcgaa gtcggtgtct acactggttg ttccgtcttg 3180
actactgcct tagctatccc agacgatggt agaatcattg ctattgacgt ttcccgtgaa 3240

-continued

```
tactttgact tgggtttgcc agttattaag aaggccggtg ttgcccataa ggttgatttc   3300

cgtgaaggtc ctgctggtcc aattttggac aaattgattg ctgatgaaga cgaaggttct   3360

tttgatttcg ctttcgttga tgccgataag tacaactacg gttcctacca cgaacaattg   3420

ttgagattgg ttagagttgg tggtgttttg gcttacgaca ataccttatg gggtggtacc   3480

gtctccatgc cagatgacac tccattgacc gaagaagaca gaaagaagag agactccatt   3540

cgtggtttca atgccatgat tgctgccgac gccagagtcg aaccagttca attaccaatc   3600

gccgacggta ttaccttgtg cagacgtgtc gtctaaagtt tcaggcagaa caagaccctt   3660

ttcaaaaata tgtaagccat tattaaaaaa aaggatattt tgtataattg tttaataaaa   3720

taacatcttt ttaaacaatc ataaatagca cttcttatca tacaacctca aatcatatcg   3780

gtccaaattt gctcaaattg tacatgagat ataacttttt cttctaatgc tttcatttca   3840

gagtttgttt tttttttttc ttttttttt ttttccttac cggagtctga atctcttact   3900

tccttaactt agatgttagt gactaaaatc tgatggacag tatcaaaatg taaatattgt   3960

acctaaaaag aaaaaagtat taaagtggtt tgccataaat tttaaacaag tgaaaagttt   4020

caatatttat atttacatga ttgtggacaa gcggcattgt ctacaggctg tgcaaaatta   4080

tatagtacag ataaatgtaa ccagaacaac gaagaaaagg tccctatgtt gcaacgcgat   4140

cgccgacgcc gccgatgctg attatcaggg taaaaatgtc gtcattatcg gcctgggcct   4200

caccgggctt tcctgcgtgg actttttcct cgctcgcggt gtgacgccgc gcgttatgga   4260

tacgcgtatg acaccgcctg gcctggataa attacccgaa gccgtagaac gccacacggg   4320

cagtctgaat gatgaatggc tgatggcggc agatctgatt gtcgccagtc ccggtattgc   4380

actggcgcat ccatccttaa gcgctgccgc tgatgccgga atcgaaatcg ttggcgatat   4440

cgagctgttc tgtcgcgaag cacaagcacc gattgtggcg attaccggtt ctaacggcaa   4500

aagcacggtc accacgctag tgggtgaaat ggcgaaagcg gcgggggtta acgttggtgt   4560

gggtggcaat attggcctgc ctgcgttgat gctactggat gatgagtgtg aactgtacgt   4620

gctggaactg tcgagcttcc agctggaaac cacctccagc ttacaggcgg tagcagcgac   4680

cattctgaac gtgactgaag atcatatgga tcgctatccg tttggtttac aacagtatcg   4740

tgcagcaaaa ctgcgcattt acgaaaacgc gaaagtttgc gtggttaatg ctgatgatgc   4800

cttaacaatg ccgattcgcg gtgcggatga acgctgcgtc agctttggcg tcaacaatcg   4860

gcggcgtcgg cgatcgcgtt gcaacatagg gaccttttct tcgttgttct ggttacattt   4920

atctgtacta tataattttg cacagcctgt agacaatgcc gcttgtccac aatcatgtaa   4980

atataaatat tgaaactttt cacttgttta aaatttatgg caaaccactt taatactttt   5040

ttctttttag gtacaatatt tacattttga tactgtccat cagattttag tcactaacat   5100

ctaagttaag gaagtaagag attcagactc cggtaaggaa aaaaaaaaaa aagaaaaaaa   5160

aaaaacaaac tctgaaatga aagcattaga agaaaaagtt atatctcatg tacaatttga   5220

gcaaatttgg accgatatga tttgaggttg tatgataaga agtgctattt atgattgttt   5280

aaaaagatgt tattttatta aacaattata caaaatatcc ttttttttaa taatggctta   5340

catatttttg aaaagggtct tgttctgcct gaaactttag acgacacgtc tgcacaaggt   5400

aataccgtcg gcgattggta attgaactgg ttcgactctg gcgtcggcag caatcatggc   5460

attgaaacca cgaatggagt ctctcttctt tctgtcttct tcggtcaatg gagtgtcatc   5520

tggcatggag acggtaccac cccataaggt attgtcgtaa gccaaaacac caccaactct   5580
```

```
aaccaatctc aacaattgtt cgtggtagga accgtagttg tacttatcgg catcaacgaa   5640
agcgaaatca aaagaacctt cgtcttcatc agcaatcaat ttgtccaaaa ttggaccagc   5700
aggaccttca cggaaatcaa ccttatgggc aacaccggcc ttcttaataa ctggcaaacc   5760
caagtcaaag tattcacggg aaacgtcaat agcaatgatt ctaccatcgt ctgggatagc   5820
taaggcagta gtcaagacgg aacaaccagt gtagacaccg acttcgatgg ttctcttagc   5880
acccataacc tttaacaaca aggacaataa caaaccttca tctggtggag aagacatgaa   5940
accgaagata tgttcggaag tgatttgtct caattctctc ataaattcgt tctctcttgg   6000
atagaccata gtcttcaaca tataatcgta taaagcatcg gatttcaata aagtcttggt   6060
agtttcggag gagtgaactt ctctaacctc accggcagaa ccattacttg ccatatccat   6120
ttttgaggga atattcaact gttttttttt atcatgttga tgctctgcat aataatgccc   6180
ataaatattt ccgacctgct tttatatctt tgctagccaa actaactgaa catagctaca   6240
cattattttc agcttggcta ttttgtgaac actgtatagc cagtccttcg gatcacggtc   6300
aacagttgtc cgagcgcttt ttggaccctt tcccttattt ttgggttaag gaaaatgaca   6360
gaaaatatat ctaatgagcc ttcgctcaac agtgctccga agtatagctt tccaaaagga   6420
gaggcaaagc aatttaagaa tgtatgaaca aaataaaggg gaaaaattac cccctctact   6480
ttaccaaacg aatactacca ataatattta caacttttcc ttatgatttt ttcactgaag   6540
cgcttcgcaa tagttgtgag cgatatcaaa agtaacgaaa tgaacttcgc ggctcgtgct   6600
atattcttgt tgctaccgtc catatctttc catagatttt caatctttga tgtctccatg   6660
gtggtacaga gaacttgtaa acaattcggt ccctacatgt gatcggaaag cttccttccg   6720
gaatggctta agtaggttgc aatttctttt tctattagta gctaaaaatg ggtcacgtga   6780
tctatattcg aaaggggcgg ttgcctcagg aaggcaccgg cggtctttcg tccgtgcgga   6840
gatatctgcg ccgttcaggg gtccatgtgc cttggacgat attaaggcag aaggcagtat   6900
cggggcggat cactccgaac cgagattagt taagcccttc ccatctcaag atggggagca   6960
aatggcatta tactcctgct agaaagttaa ctgtgcacat attcttaaat tatacaatgt   7020
tctggagagc tattgtttaa aaaacaaaca tttcgcaggc taaaatgtgg agataggatt   7080
agttttgtag acatatataa acaatcagta attggattga aaatttggtg ttgtgaattg   7140
ctcttcatta tgcaccttat tcaattatca tcaagaatag caatagttaa gtaaacacaa   7200
gattaacata ccccacccga agtcgcgcaa ccaactaact ttacaatgga accagacatg   7260
gaaaatctta taccatctaa gggtatcttg aagaacgaag aattgaaaaa gtacatcttt   7320
gaaacttccg cttacccaag agaacacgaa gaattgaaga agttaagaga agctaccgtt   7380
cataagtacg gtaacttgtc cgagatggaa gtccctgttg acgaaggtca tttcttgtcc   7440
atgttgttga agatgatgaa cgctaagaac accttggaat tgggtgtttt cactggttac   7500
tctttgttaa ccaccgcctt ggctttgcct gaagacggta gaattactgc tattgatatc   7560
gataaagaag cttacgaaat gggtttggaa ttcatcaaga acgccggtat cgatcacaaa   7620
attaacttta tccaatccga cggtttgcaa gccttagaca agttgttatc tgaaaaccca   7680
aagccagaat ttgacttcgc tttcgttgac gctgataagc caaattacgt ccacgctttg   7740
gaaagattga tgaagttggt caaagttggt ggtatcattg ctttcgataa caccttatgg   7800
ttcggtttcg ttgctgaaga ggaagagact gtcccagttc acttaagagt taaccgtaag   7860
gctttgatgg aattgaacaa aagattggct tccgatccaa gaattgaaat ctcccaagtt   7920
tccatcggtg atggtgttac cttgtgtaga agattagtct aataaagtaa gagcgctaca   7980
```

```
ttggtctacc tttttgttct tttacttaaa cattagttag ttcgttttct ttttctcatt   8040
tttttatgtt tcccccccaa agttctgatt ttataatatt ttatttcaca caattccatt   8100
taacagaggg ggaatagatt ctttagctta gaaaattagt gatcaatata tatttgcctt   8160
tcttttcatc ttttcagtga tattaatggt ttcgagacac tgcaatggcc ctagttgtct   8220
aagaggatag atgttactgt caaagatgat attttgaatt tcaattgacg taattaatga   8280
tactattaat aatacagagc gtatatgaag tattgcaaat aacatgcaca gttcttttgg   8340
gatgagaatg ataatgaaag gcgaaggcgg gcgttcagaa aagcgttgcg gagtaacaag   8400
tgattaaata gcacccaaat aatcttcttt gatactaccg attgcgtgaa tagaactcac   8460
tacccctcct gatatctttt tttcgaacat attgatgttt ttcgtgggta accatagttc   8520
ttggaatgtc aactgagggt atttgcactt caaaaaaaaa aatttattaa atgagactat   8580
atacagtgag cacaacctgt ctaatacaac ggcaaaaatt atatacattg gtagattttc   8640
aaaattgaac tctttgtgct aaagaattgt cacaacagtt taaaaaatag tttgaattct   8700
tcaaattgac cccatattaa taagacctga tgcgattccg gtctcaccca gattagagag   8760
ggaatttaat tttcttagga ccgtagctac caaaaatctt tgtgtggtat tgattatatg   8820
atcgtgcttg cgaaaaaaat agaagactaa aagtagcatt agtttactaa ctttctcctc   8880
gtatctttca aatttgtatt cccctcaaaa gttactcagg ttagggaaaa ttccaagtag   8940
cttatcaaga tcaattgcca ttagttgatt caaggcttca ttgtcggcgg tttaaacgcg   9000
tggccgtgcc gtc                                                      9013
```

<210> SEQ ID NO 19
<211> LENGTH: 8216
<212> TYPE: DNA
<213> ORGANISM: Artificial Sequence
<220> FEATURE:
<223> OTHER INFORMATION: Synthetic: MS153767 sequence

<400> SEQUENCE: 19

```
gacggcacgg ccacgcgttt aaaccgcctg catacttcaa gttcagggtt ggacctgcca     60
atgaaaattt tagatatgtt tggctcaggt cttcctgtta ttgcaatgaa ctatccagtg    120
cttgacgaat tagtacaaca caatgtaaat gggttaaaat ttgttgatag aagggagctt    180
catgaatctc tgatttttgc tatgaaagat gctgatttat accaaaaatt gaagaaaaat    240
gtaacgcagg aagctgagaa cagatggcaa tcaaattggg aacgaacaat gagagatttg    300
aagctaattc attgagtcaa tggtaactca gcctttcttt tttgaaaatt actattttcg    360
actctttttt tatacagtta catagtacta cctctaatac acattcatga ttaacaatgt    420
ttcaaacaat ataaagtccc gataacgacc ttttgaagtg gtgacgttac cgctcttcgt    480
tgacaagatt caagagggct gtcagaataa cagctatcat ggtggaatcg attacctgcc    540
ttgatacgct gccagaatac atgtcacatg tagggaccga attgtttaca agttctctgt    600
accaccatgg agacatcaaa gattgaaaat ctatggaaag atatggacgg tagcaacaag    660
aatatagcac gagccgcgaa gttcatttcg ttacttttga tatcgctcac aactattgcg    720
aagcgcttca gtgaaaaaat cataaggaaa agttgtaaat attattggta gtattcgttt    780
ggtaaagtag agggggtaat ttttcccctt tattttgttc atacattctt aaattgcttt    840
gcctctcctt ttggaaagct atacttcgga gcactgttga gcgaaggctc attagatata    900
ttttctgtca ttttccttaa cccaaaaata agggaaaggg tccaaaaagc gctcggacaa    960
```

-continued

```
ctgttgaccg tgatccgaag gactggctat acagtgttca caaaatagcc aagctgaaaa   1020
taatgtgtag ctatgttcag ttagtttggc tagcaaagat ataaaagcag gtcggaaata   1080
tttatgggca ttattatgca gagcatcaac atgataaaaa aaaacagttg aatattccct   1140
caaaaatgga tacaagagaa gatcaattag aaagacgtat tgctgcctta actgctaacg   1200
accctcaatt cgccgctgcc agaccagacg aagccgttgc cactgccgtc caaagacctg   1260
gtttgagatt accagaagtc atcgaaaccg tcttgcaagg ttacgctgac cgtccagcct   1320
taggtcaaag agctgtcgaa tttgttaaag atccaaacac tggtagaacc tccgcccatt   1380
tgttaccaag attcgacacc atcacctaca gagaattggc tgatagagtc ggtgctttag   1440
cttctgcttg ggctagagaa gccgtttccc caggtgacag agttgccatt ttgggtttca   1500
cttccgttga ctatactacc attgatgtta ctttggctag aattggtgct gtctctgttc   1560
cattacaaac ctctgctgcc ttggctcaat taagaccaat tgttgtcgaa accgaaccaa   1620
ctgttatcgc tgcttccgtt gattacttgt ccgacgctgt tgaattaatt agaactggtc   1680
acgccccagc cagattggtt gtttttgatc atcacccaga agttgacgat cacagagaag   1740
ctttggacgc tgctagaggt cgtttggctg gtcacgctgt cattgttgaa actttggctg   1800
aagtcttgga gagaggtact tctttgccag ctccaactgt tgctgccgaa gataatgatt   1860
tggctttgtt aatctacacc tctggttcca ctggtgctcc aaagggtgct atgtacccac   1920
aaagaaatgt tgctaagatg tggcaaagat cttccagaaa ctggttcggt ccttctgccg   1980
cttctattac cttgaacttt atgccaatgt cccatgttat gggtagaggt attttgtacg   2040
gtaccttagg taacggtggt actgcctact tcggtgctac ctctgacttg tctactttgt   2100
tggaagactt gactttggtc agacctaccg aattgaactt cgttccaaga gtctgggaca   2160
ctttgcatgc cgagttcttg actagagtcg acagattgac cgctgaaggt gccgacagag   2220
cttccgctga ggctttggtc atgggtgact tgagagacaa cttattgggt ggtcgtgcca   2280
ttttcgccat gactggttcc gctccaatct cttctcaatt gaaaacttgg gttgagtcct   2340
tgttgggtat ccatttattg gacggttatg gttctactga agctggtatg gttttgtacg   2400
atggtgtcgt ccaaagacct ccagtcattg actacaagtt agctgatgtc ccagatttgg   2460
gttacttttc tactgataga ccattcccaa gaggtgaatt attattgaaa actgaaaaca   2520
tgttccctgg ttactacaaa agaccagaaa tcaccgctgg tgtcttcgat gatgacggtt   2580
actaccgtac tggtgatgtt gttgctgaag tcggtccaga tcgtttggtt tacgtcgata   2640
gaagaaacaa tgttttaaaa ttagctcaag gtgagttcgt tactgttgcc aagttggaag   2700
ctggtttcaa caactcccca ttggtcagac aaatctacat ttacggtaac tctgctcatc   2760
catacttatt ggctgttgtt gttcctactg atgtcaatgc ctccaagtcc gctattgctg   2820
aatccttgca aagagtcgct aaggacgctg gtttacaatc ctatgaagtt cctagagact   2880
tcttgattga accagaacca tttaccttgg aaaacggttt gttaactggt attagaaagt   2940
tggcttggcc taagttgaag gagagatacg gtgaacgttt ggaacaattg tacgctgaat   3000
tggacagatc ccaagctgac gaattgtctg aattaagaag atctggtgcc caaagaccag   3060
ttttggaaac tgtcaccaga gctgccggtg ctttgttagg tgctgctgct tctgaattac   3120
aaccagatgc tcacttcact gacttgggtg gtgactcctt gtccgctttg actttcggta   3180
acttgttgag agaaatcttt gacgtcgacg tcccagtcgg tgttatcgtt tctccagctt   3240
ctgacttgca agccattgct ggttacattg aagccgaaag acaaggttct aaaagaccaa   3300
ccttcgcctc cgttcatggt agagctgagg aaggtgaagc tgttgaggtt agagctagag   3360
```

```
atttgcgttt ggataagttc ttggacgcca gaaccttgga gtacgttcca gccttgccag   3420
gtccatccac cgaattgcgt actgttttgt tgactggtgc tactggtttc ttgggtagat   3480
atttggcttt ggaatggttg gagagaatgg acgctgttga cggtaccgtt atcgctttag   3540
tcagagctaa ggacgacgcc gctgctagag agagattgga cagaactttc gactctgacc   3600
ctaagttgag agcccactac agagctttgg ccgctgacca tttggaagtt gttgctggtg   3660
acaagggtga agctaactta ggtttgtctc aacaagtttg gcaaagatta gccgacactg   3720
ttgacgttat cgttgaccca gccgctttgg tcaaccacgt tttaccatac tctgaattgt   3780
ttggtccaaa tgttttgggt actgccgaat tgatcagatt ggctttgact accaagatca   3840
agccatacac ttacgtttcc accatcggtg ttggtgacca aatcgagcca ggtaagttta   3900
ctgaagatgc tgacatcaga gttatttctc caactagaag aatttctgac tcttacgcta   3960
acggttacgg taactccaag tgggctggtg aagtcttgtt gagagaagct catgacagat   4020
gtggtttgcc agtcgctgtt ttcagatgtg atatgatctt ggccgacacc acctacgccg   4080
gtcaattaaa cttgccagat atgttcactc gtttaatgtt gtccttggcc gctactggta   4140
ttgccccaag atctttctac gaattggatg ctgaaggtaa cagacaacgt gctcattacg   4200
acggtttgcc agtcgaattc attgctaagg ctgtctctac tttgggtgct caaactgttg   4260
agggttatca aacctaccac gtcatgaacc ctcatgacga cggtattggt ttggacgaat   4320
acgttgactg gttgattgaa gctggttacc ctattcgtag agttgacgac tacgctgatt   4380
ggttacaaag atttgaaacc gctatgagag ctttgccaga cagacaaaga agatactcct   4440
tgttgccttt gttacataac taccaaaagc cagaaaagcc aatgagaggt tctatggctc   4500
caactgatag atttagagct gctgttcaag aagccaaaat tggtccagac aaggatattc   4560
cacacgtcac cagagaagtt atcgtcaagt atgctactga tttgcaattg ttgggtttat   4620
tggatgaaaa aagagtctaa aaggcttttt tataaacttt ttataattaa cattaaagca   4680
aaaacaacat tgtaaagatt aacaaataaa tgaaaaaaac aacgaaataa cttaggtttt   4740
aggctaaaaa aaacagaagg aattttgaac gataaacttt tcgactgcac acgaaacatt   4800
attactaatt tgtgtaacca ctatataagg aatcgtgttt attaattgaa tttattccgg   4860
gaatattcaa gttatgtata tctcttttca tattcttaaa tacacatact cataatatct   4920
tgtcgaaaat acgcggtgta gggagttatg gtggataact tttcacgat tagaagaaaa    4980
ggaaaatttc attattcgta gcttaacatg gcaaaaacga gaaagacata taatcaaaac   5040
gtgagtttcc tgtggaaaaa aaaaaaaggg aacctctggt tacgatgata tacctgcgtg   5100
aaaaaggaca gttattacca atacatacaa aggcaacctg caggccgcga gcgccgataa   5160
gattattact tgctataagt gcgtgcctga tgaacaggat attgcggtca ataatgctga   5220
tggttcatta gacttcagca aagccgatgc caaaataagc caatacgatc tcaacgctat   5280
tgaagcggct tgccagctaa agcaacaggc agcagaggcg caggtgacag ccttaagtgt   5340
gggcggtaaa gccctgacca acgccaaagg gcgtaaagat gtgctatcgc gcggcccgga   5400
tgaactgatt gtggtgattg atgaccagtt cgagcaggca ctgccgcaac aaacggcgag   5460
cgcactggct gcagccgccc agaaagcagg ctttgatctg atcctctgtg gcgatggttc   5520
ttccgacctt tatgcccagc aggttggtct gctggtgggc gaaatcctca atattccggc   5580
agttaacggc gtcagcaaaa ttatctccct gacggcagat accctcaccg ttgagcgcga   5640
actggaagat gaaaccgaaa ccttaagcat tccgctgcct gcggttgttg ctgtttccac   5700
```

-continued

```
tgatatcaac tccccacaaa ttccttcgat gaaagccatt ctcggcgcgg cgaaaaagcc   5760
cgtccaggta tggtcggcgg cggatattgg ttttaacgca gaggcagcct ggtcagaaca   5820
acaggttgcc gcgccgaaac agcgcgaacg tcagcgcaat cggcgctcgc ggcctgcagg   5880
ttccgttaca ggaatggatg atccaccaat tatatcgacg gggctagaa tcttagatct   5940
cagtactcgc attctagcgt atgtttcttg aaacttgtaa gggactttcg tcgaggccgg   6000
agtgacaagg atcgaggggt ccaatggtgt ggcccacctg ttgggcacat tgccgtttct   6060
aaccacaatc cattcgaagt actgcttatt tggcagcgat ttaacccagt cgatatccac   6120
gggttgaggg acaacctctt cttgtttgat tttggtcctt ttctccggta ggagttctga   6180
ttctggccca gtttcagtct ttaccagcgg tcttttcctc agaattgcca tagatgagta   6240
tttactgatc ttttgcatat tttttttttt tttttaagta tatatagata caaatatatg   6300
atgaatcatt aaagaggagg ttattactaa gtgaaagaaa aagaaaaaaa aaaagatcaa   6360
aaccaaactt cgtattcgag cctaaaaaac agaatataat gttaagcgta agcgatagca   6420
gtcaagatga aaccgtcagc aatcaaccat ctaccatcaa aagacaacaa tggggtacca   6480
ccatcgttag tttgaccagg aaccaataat tcggagtgga aagtaccgtt accagaatca   6540
gcagaaccat cttcaatttc gaaagtaatg tgagcttcct cgaaacctaa ccatctggca   6600
gtcaatggcc accaagcctt gtaagtagct tctttggcac aaaataacaa tctgtctaaa   6660
tgtaaagcag aatcggtagt cttcaaccat tctctttctg gtggcaagga aacggaatcc   6720
aagacacctt ctggcaaggt agcgtgtggt tcggcgtcga taccgatgga tctgaatctc   6780
atcttatgag caacagcagc ggctctgtaa ccgtcacagt gagtcaaaga accgacaaca   6840
cctcttggcc aaataggagc accacgttca cctttaccga tagcgactgg tggttcaccc   6900
aattcagcca aagctaatct agcacaatgt ctggcaccaa taaagtctct tcttctcttt   6960
tcgacagatt tggcgattaa atgttcctcg gctgggtgag cttttaagtc ttcagggtac   7020
tctaacaatt cagcagactc aactccagca ggaagaatgg tttcaatcat ttttgaggga   7080
atattcaact gttttttttt atcatgttga tgctctgcat aataatgccc ataaatattt   7140
ccgacctgct tttatatctt tgctagccaa actaactgaa catagctaca cattattttc   7200
agcttggcta ttttgtgaac actgtatagc cagtccttcg gatcacggtc aacagttgtc   7260
cgagcgcttt ttggaccctt tcccttattt ttgggttaag gaaaatgaca gaaaatatat   7320
ctaatgagcc ttcgctcaac agtgctccga agtatagctt tccaaaagga gaggcaaagc   7380
aatttaagaa tgtatgaaca aaataaaggg gaaaaattac cccctctact ttaccaaacg   7440
aatactacca ataatattta caacttttcc ttatgatttt ttcactgaag cgcttcgcaa   7500
tagttgtgag cgatatcaaa agtaacgaaa tgaacttcgc ggctcgtgct atattcttgt   7560
tgctaccgtc catatctttc catagatttt caatctttga tgtctccatg gtggtacaga   7620
gaacttgtaa acaattcggt ccctacatgt gacatgtatt ctggcagcgt atcaaggcag   7680
gtaatcgaaa gatggcaaat agccttgtca aatttcctac ggaatgttat tttcattacg   7740
tccttctttt tcaatgtact tattcataaa tgggacacta tcttgttgca aaaggtactt   7800
tgtattttgg tattaacatc tcgcctattt ttcatacaga aacactactt atcgctatct   7860
atttgatgtg gtattgcttg gccatgagga taccttgagc tacgttttga acacgtgcat   7920
ccaacttgta gccttgttga tccaacttaa ccatttcatc aggaaacttg tgcaactcaa   7980
cgctaaagca ttcgataaat tcattatctt ccaattgagt aactggtttt tggttttcag   8040
gtaaactcat atcaacttcg acagtaacca gacagaggtt ggtgtttgtg aaaccaggat   8100
```

cgttaaaaac tgttgggctt ttagaaatta ttttaccact gtaaccagtc tcttctttta 8160
attctcttaa ggcagcagtg tcaatatcgg cggtttaaac gcgtggccgt gccgtc 8216

<210> SEQ ID NO 20
<211> LENGTH: 2942
<212> TYPE: DNA
<213> ORGANISM: Artificial Sequence
<220> FEATURE:
<223> OTHER INFORMATION: Synthetic: MS172561 sequence

<400> SEQUENCE: 20
gacggcacgg ccacgcgttt aaaccgccat aataaaatgg aagccgcgag tacgaacaat 60
gatgtgttct gggaatacct cgtcaaaaca agacaatggc aaggattttc tttcatcagg 120
cagaaagatc tggatctgaa tggcatcatt ttgtgatgtg taaaagcggg accttgttat 180
ttcgactttt tgcatcatgt tgatgcaatt tgctactttt ccgacggtgc gctccaacgg 240
atgggtattt ccttaataac aaggcatttc tctggaagtt ggcttactgt ttgaaatcac 300
agccggtcac aaaataaagt aaaaaaacta tctctctcca caagaagtaa ttacaggttg 360
tatactacat atgatcgtat ttctttatga acactaagga gtttcccgct gtgtaccgca 420
atatccacac aaaaggaagg aagaaacttc tgtggcttga cagataaata actgcagtag 480
tcggtgcgta ctaattgttt ggtcgtgtct gaaaaatctt gaattttcct cccgcgtgcg 540
agataaaagg gttggcaata ccaccatata catatcccata tctaatctta cttatatgtt 600
gtggaaatgt aaagagcccc attatcttag cctaaaaaaa ccttctcttt ggaactttca 660
gtaatacgct taactgctca ttgctatatt gaagtacgga ttagaagccg ccgagcgggc 720
gacagccctc cgacggaaga ctctcctccg tgcgtcctgg tcttcaccgg tcgcgttcct 780
gaaacgcaga tgtgcctcgc gccgcactgc tccgaacaat aaagattcta caatactagc 840
ttttatggtt atgaagagga aaaattggca gtaacctggc cccacaaacc ttcaaatcaa 900
cgaatcaaat taacaaccat aggataataa tgcgattagt tttttagcct tatttctggg 960
gtaattaatc agcgaagcga tgatttttga tctattaaca gatatataaa tgcaaaagct 1020
gcataaccac tttaactaat actttcaaca ttttcggttt gtattacttc ttattcaaat 1080
gtcataaaag tatcaacaaa aaattgttaa tatacctcta tacttacctc ccgcgacctc 1140
caaaatcgaa ctaccttcac aatgcccagt aaattggcta taacttccat gtccttgggc 1200
aggtgttatg caggccattc tttcacaact aagttagaca tggctaggaa atatggttac 1260
cagggtttgg agttgtttca tgaggactta gccgatgtcg catacaggtt gtcaggtgaa 1320
acacctagtc catgcggtcc cagtccagct gctcaattat cagccgctag acagatattg 1380
aggatgtgcc aggttagaaa catcgaaata gtgtgcttgc aacccttttc acaatatgat 1440
ggtttattgg atagagagga gcacgagagg aggttggagc aattagagtt ttggattgaa 1500
ttggcccacg agttggatac tgacatcatt caaattccag ccaatttctt gcccgccgaa 1560
gaagtcacag aagatatttc attaattgtg agtgacttac aggaagttgc cgatatgggt 1620
ttacaggcaa accctccaat aaggtttgta tatgaggcat tatgctggtc cactagagtt 1680
gacacttggg agaggtcttg ggaagttgtc caaagagtaa atagacctaa ctttggcgtt 1740
tgcttagaca cttttaacat cgcaggtaga gtttatgctg accccacagt tgcctcaggc 1800
agaacaccaa acgctgaaga agcaattaga aagtcaattg ccaggttggt cgaaagggtc 1860
gatgtatcta aagtcttcta cgttcaagta gtggacgccg aaaagttaaa gaaaccatta 1920

-continued gttcccggtc atagattcta tgaccctgag caaccagcca gaatgtcatg gtcaagaaat 1980
tgtaggttgt tctacggcga aaaagacaga ggcgcttact tacctgttaa agaaatcgct 2040
tgggcttttt tcaatggatt gggcttcgaa ggttgggtgt ccttggaatt atttaacaga 2100
agaatgtcag atactggatt tggagttcca gaggagttag ctaggagagg cgccgtatca 2160
tgggccaaat tagttagaga tatgaaaatc acagtggatt ctccaactca acaacaagct 2220
acacagcagc ctattagaat gttgtcctta tctgcagcct tataaaaagc ttcgacacat 2280
acataataac tcgataaggt atggtatctt atttcattgt ggggtagttt ttacgaaaaa 2340
aatgaaaagt tgtaagtata gtatatattt tttttctatg taagttttat aacctgcagg 2400
ccgcgagcgc cgatagtact cccctacgat tttagatact ttagagagcc caccttcaga 2460
atcggaagga ggataatttt gtaaagccct tctgtttttt ctcttgcata acttatattt 2520
ccacatcaaa aagtagtgtg ctaagaaaaa ggagacgaga aaaaggatta cggcactctc 2580
tgcatctaga catataccaa aagttgggtt tgctcacgaa aataccataa ttgtggtgtc 2640
aaaaaaatcc tgcctcataa taccactgca gcaattgtgg atgactaaaa aataacttgc 2700
attccacgat gttattttac tttataaagc acctgcaatt tttttttttg tattaactca 2760
tcgagtatgt ctgatgtgta aactgaacca ggcttaatat cgtttctaat tcttgttgtg 2820
agaaaacttt cctgcctagt gtatttcgtc agggcgaacc ttcggatagg caccgaactc 2880
cgagattctt gctccaattt aagaaataag ctttcggtgt ttaaacccca gcgcctggcg 2940
gg 2942

<210> SEQ ID NO 21
<211> LENGTH: 8441
<212> TYPE: DNA
<213> ORGANISM: Artificial Sequence
<220> FEATURE:
<223> OTHER INFORMATION: Synthetic: MS167660 sequence

<400> SEQUENCE: 21
gacggcacgg ccacgcgttt aaaccgccaa aaactcacaa gaagttcggt gtccttattt 60
gcgatgggaa ttgctaatat catatcacca caaatatgga gagagaagga ctctcctcgc 120
tttttacctg cctggattgt tcaaatcgtt ttatcattct ctcttgcacc agccattttg 180
ttactgatcc atttcatact aaaaagaagg aataatcaaa gactaaaaaa ttatgacgaa 240
aatttacaaa attatttgga cagaattcaa ctcattgaaa gcgaaaatcc ttcttccatt 300
gaagaaggga aagtggtaac ccacgagaac aatttggcag tctttgattt gactgattta 360
gaaaacgaaa cttttatata tcctttgtaa atattgatgt tttgttgtgt aaatgttcta 420
tctgacactt aataattaga aaattaattt tttaaacttt ccggctgcaa gaaagaggaa 480
ctgtgtctct ttgaaaggca caatttccca aagaatcatt tacaatgcgg agattaccga 540
gcattctggg tagtgagttc tattcacgca atcggtagta tcaaagaaga ttatttgggt 600
gctatttaat cacttgttac tccgcaacgc ttttctgaac gcccgccttc gcctttcatt 660
atcattctca tcccaaaaga actgtgcatg ttatttgcaa tacttcatat acgctctgta 720
ttattaatag tatcattaat tacgtcaatt gaaattcaaa atatcatctt tgacagtaac 780
atctatcctc ttagacaact agggccattg cagtgtctcg aaaccattaa tatcactgaa 840
aagatgaaaa gaaaggcaaa tatatattga tcactaattt tctaagctaa agaatctatt 900
ccccctctgt taaatggaat tgtgtgaaat aaaatattat aaaatcagaa ctttgggggg 960
gaaacataaa aaaatgagaa aaagaaaacg aactaactaa tgtttaagta aaagaacaaa 1020

```
aaggtagacc aatgtagcgc tcttacttta ttagactaat cttctacaca aggtaacacc   1080
atcaccgatg gaaacttggg agatttcaat tcttggatcg gaagccaatc ttttgttcaa   1140
ttccatcaaa gccttacggt taactcttaa gtgaactggg acagtctctt cctcttcagc   1200
aacgaaaccg aaccataagg tgttatcgaa agcaatgata ccaccaactt tgaccaactt   1260
catcaatctt tccaaagcgt ggacgtaatt tggcttatca gcgtcaacga aagcgaagtc   1320
aaattctggc tttgggtttt cagataacaa cttgtctaag gcttgcaaac cgtcggattg   1380
gataaagtta attttgtgat cgataccggc gttcttgatg aattccaaac ccatttcgta   1440
agcttcttta tcgatatcaa tagcagtaat tctaccgtct tcaggcaaag ccaaggcggt   1500
ggttaacaaa gagtaaccag tgaaaacacc caattccaag gtgttcttag cgttcatcat   1560
cttcaacaac atggacaaga aatgaccttc gtcaacaggg acttccatct cggacaagtt   1620
accgtactta tgaacggtag cttctcttaa cttcttcaat tcttcgtgtt ctcttgggta   1680
agcggaagtt tcaaagatgt acttttttcaa ttcttcgttc ttcaagatac ccttagatgg   1740
tataagattt tccatgtctg gttccattgt aaagttagtt ggttgcgcga cttcgggtgg   1800
ggtatgttaa tcttgtgttt acttaactat tgctattctt gatgataatt gaataaggtg   1860
cataatgaag agcaattcac aacaccaaat tttcaatcca attactgatt gtttatatat   1920
gtctacaaaa ctaatcctat ctccacattt tagcctgcga aatgtttgtt ttttaaacaa   1980
tagctctcca gaacattgta taatttaaga atatgtgcac agttaacttt ctagcaggag   2040
tataatgcca tttgctcccc atcttgagat gggaagggct taactaatct cggttcggag   2100
tgatccgccc cgatactgcc ttctgcctta atatcgtcca aggcacatgg acccctgaac   2160
ggcgcagata tctccgcacg gacgaaagac cgccggtgcc ttcctgaggc aaccgcccct   2220
ttcgaatata gatcacgtga cccattttta gctactaata gaaaaagaaa ttgcaaccta   2280
cttaagccat tccggaagga agctttccga tcacatgtag ggaccgaatt gtttacaagt   2340
tctctgtacc accatggaga catcaaagat tgaaaatcta tggaaagata tggacggtag   2400
caacaagaat atagcacgag ccgcgaagtt catttcgtta cttttgatat cgctcacaac   2460
tattgcgaag cgcttcagtg aaaaaatcat aaggaaaagt tgtaaatatt attggtagta   2520
ttcgtttggt aaagtagagg gggtaatttt tccccttttat tttgttcata cattcttaaa   2580
ttgctttgcc tctccttttg gaaagctata cttcggagca ctgttgagcg aaggctcatt   2640
agatatattt tctgtcattt tccttaaccc aaaaataagg gaaagggtcc aaaaagcgct   2700
cggacaactg ttgaccgtga tccgaaggac tggctataca gtgttcacaa aatagccaag   2760
ctgaaaataa tgtgtagcta tgttcagtta gtttggctag caaagatata aaagcaggtc   2820
ggaaatattt atgggcatta ttatgcagag catcaacatg ataaaaaaaa acagttgaat   2880
attccctcaa aaatggctat aaacaacgaa ggccaacaac aaaaccaaaa ccaacaattg   2940
atcggtcaca aagatttggc tcataagacc ttgttacaat ctgacgcctt ataccaatac   3000
attttggata cctctgttca cccaagagaa cacccatgtt tgaaggaatt gcgtgaaatg   3060
actgaaaagc acccaagaaa cttgatggcc acccctgctg atgaaggtca attgttgtct   3120
atgttaatca aattgatcaa tgctaagaac accttagaaa ttggtgtttt taccggttac   3180
tctttgttgt ctactgcttt agctttgcca tctgacggta agattttggc tttggacgtt   3240
tctcgtgaat actacgaatt gggtttacca attatcgaaa aggctggtgt cgctcacaag   3300
atcgactttc gtgaaggtcc tgctttgcca ttattggacc aattattgca agatgtcacc   3360
```

-continued

```
aaggaaaaca acaagggtat ttttgatttt gttttcgtcg atgccgataa ggacaactat   3420
ttaaactacc acaagagagt tatcgatttg gtcaagattg gtggtttgat cggttacgac   3480
aacaccttat ggtccggttc cgttgtcgct ccaccagacg ctccattaat ggattatgtt   3540
aagcattaca gaccacatgt tattgccttg aacaagtact tggctcaaga ctcccgtatt   3600
gaaatttgtc aattgccagt cggtgatggt atcaccttgt gtagaagaac cacttaagag   3660
tatgcttctc tttttttttg taggccagtg ataggaaaga acaatagaat ataaatacgt   3720
cagaatataa tagatatgtt tttatattta gacctcgtac ataggaataa ttgacgtttt   3780
ttttggccaa catttgaaat tttttttgt tacctcgcgc tgagcccaaa cgggctccac   3840
tacccgaacg cgatcgccga cgccgccgat gctgattatc agggtaaaaa tgtcgtcatt   3900
atcggcctgg gcctcaccgg gctttcctgc gtggactttt tcctcgctcg cggtgtgacg   3960
ccgcgcgtta tggatacgcg tatgacaccg cctggcctgg ataaattacc cgaagccgta   4020
gaacgccaca cgggcagtct gaatgatgaa tggctgatgg cggcagatct gattgtcgcc   4080
agtcccggta ttgcactggc gcatccatcc ttaagcgctg ccgctgatgc cggaatcgaa   4140
atcgttggcg atatcgagct gttctgtcgc gaagcacaag caccgattgt ggcgattacc   4200
ggttctaacg gcaaaagcac ggtcaccacg ctagtgggtg aaatggcgaa agcggcgggg   4260
gttaacgttg gtgtgggtgg caatattggc ctgcctgcgt tgatgctact ggatgatgag   4320
tgtgaactgt acgtgctgga actgtcgagc ttccagctgg aaaccacctc cagcttacag   4380
gcggtagcag cgaccattct gaacgtgact gaagatcata tggatcgcta tccgtttggt   4440
ttacaacagt atcgtgcagc aaaactgcgc atttacgaaa acgcgaaagt ttgcgtggtt   4500
aatgctgatg atgccttaac aatgccgatt cgcggtgcgg atgaacgctg cgtcagcttt   4560
ggcgtcaaca atcggcggcg tcggcgatcg cgttcgggta gtggagcccg tttgggctca   4620
gcgcgaggta acaaaaaaaa atttcaaatg ttggccaaaa aaaacgtcaa ttattcctat   4680
gtacgaggtc taaatataaa aacatatcta ttatattctg acgtatttat attctattgt   4740
tctttcctat cactggccta caaaaaaaaa gagaagcata ctcttaagtg gttcttctac   4800
acaaggtgat accatcaccg actggcaatt gacaaatttc aatacgggag tcttgagcca   4860
agtacttgtt caaggcaata acatgtggtc tgtaatgctt aacataatcc attaatggag   4920
cgtctggtgg agcgacaacg gaaccggacc ataaggtgtt gtcgtaaccg atcaaaccac   4980
caatcttgac caaatcgata actctcttgt ggtagtttaa atagttgtcc ttatcggcat   5040
cgacgaaaac aaaatcaaaa atacccttgt tgttttcctt ggtgacatct tgcaataatt   5100
ggtccaataa tggcaaagca ggaccttcac gaaagtcgat cttgtgagcg acaccagcct   5160
tttcgataat tggtaaaccc aattcgtagt attcacgaga aacgtccaaa gccaaaatct   5220
taccgtcaga tggcaaagct aaagcagtag acaacaaaga gtaaccggta aaaacaccaa   5280
tttctaaggt gttcttagca ttgatcaatt tgattaacat agacaacaat tgaccttcat   5340
cagcaggggt ggccatcaag tttcttgggt gcttttcagt catttcacgc aattccttca   5400
aacatgggtg ttctcttggg tgaacagagg tatccaaaat gtattggtat aaggcgtcag   5460
attgtaacaa ggtcttatga gccaaatctt tgtgaccgat caattgttgg ttttggtttt   5520
gttgttggcc ttcgttgttt atagccattt ttgagggaat attcaactgt ttttttttat   5580
catgttgatg ctctgcataa taatgcccat aaatatttcc gacctgcttt tatatctttg   5640
ctagccaaac taactgaaca tagctacaca ttattttcag cttggctatt ttgtgaacac   5700
tgtatagcca gtccttcgga tcacggtcaa cagttgtccg agcgcttttt ggaccctttc   5760
```

```
ccttattttt gggttaagga aaatgacaga aaatatatct aatgagcctt cgctcaacag   5820
tgctccgaag tatagctttc caaaaggaga ggcaaagcaa tttaagaatg tatgaacaaa   5880
ataaagggga aaaattaccc cctctacttt accaaacgaa tactaccaat aatatttaca   5940
acttttcctt atgatttttt cactgaagcg cttcgcaata gttgtgagcg atatcaaaag   6000
taacgaaatg aacttcgcgg ctcgtgctat attcttgttg ctaccgtcca tatctttcca   6060
tagattttca atctttgatg tctccatggt ggtacagaga acttgtaaac aattcggtcc   6120
ctacatgtga tcggaaagct tccttccgga atggcttaag taggttgcaa tttctttttc   6180
tattagtagc taaaaatggg tcacgtgatc tatattcgaa aggggcggtt gcctcaggaa   6240
ggcaccggcg gtctttcgtc cgtgcggaga tatctgcgcc gttcaggggt ccatgtgcct   6300
tggacgatat taaggcagaa ggcagtatcg gggcggatca ctccgaaccg agattagtta   6360
agcccttccc atctcaagat ggggagcaaa tggcattata ctcctgctag aaagttaact   6420
gtgcacatat tcttaaatta tacaatgttc tggagagcta ttgtttaaaa aacaaacatt   6480
tcgcaggcta aaatgtggag ataggattag ttttgtagac atatataaac aatcagtaat   6540
tggattgaaa atttggtgtt gtgaattgct cttcattatg caccttattc aattatcatc   6600
aagaatagca atagttaagt aaacacaaga ttaacatacc ccacccgaag tcgcgcaacc   6660
aactaacttt acaatggaac cagacatgga aaatcttata ccatctaagg gtatcttgaa   6720
gaacgaagaa ttgaaaaagt acatctttga aacttccgct tacccaagag aacacgaaga   6780
attgaagaag ttaagagaag ctaccgttca taagtacggt aacttgtccg agatggaagt   6840
ccctgttgac gaaggtcatt tcttgtccat gttgttgaag atgatgaacg ctaagaacac   6900
cttggaattg ggtgttttca ctggttactc tttgttaacc accgccttgg ctttgcctga   6960
agacggtaga attactgcta ttgatatcga taaagaagct tacgaaatgg gtttggaatt   7020
catcaagaac gccggtatcg atcacaaaat taactttatc caatccgacg gtttgcaagc   7080
cttagacaag ttgttatctg aaaacccaaa gccagaattt gacttcgctt tcgttgacgc   7140
tgataagcca aattacgtcc acgctttgga aagattgatg aagttggtca aagttggtgg   7200
tatcattgct ttcgataaca ccttatggtt cggtttcgtt gctgaagagg aagagactgt   7260
cccagttcac ttaagagtta accgtaaggc tttgatggaa ttgaacaaaa gattggcttc   7320
cgatccaaga attgaaatct cccaagtttc catcggtgat ggtgttacct tgtgtagaag   7380
attagtctaa taaagtaaga gcgctacatt ggtctacctt tttgttcttt tacttaaaca   7440
ttagttagtt cgttttcttt ttctcatttt tttatgtttc ccccccaaag ttctgatttt   7500
ataatatttt atttcacaca attccattta acagaggggg aatagattct ttagcttaga   7560
aaattagtga tcaatatata tttgcctttc ttttcatctt ttcagtgata ttaatggttt   7620
cgagacactg caatggccct agttgtctaa gaggatagat gttactgtca aagatgatat   7680
tttgaatttc aattgacgta attaatgata ctattaataa tacagagcgt atatgaagta   7740
ttgcaaataa catgcacagt tcttttggga tgagaatgat aatgaaaggc gaaggcgggc   7800
gttcagaaaa gcgttgcgga gtaacaagtg attaaatagc acccaaataa tcttctttga   7860
tactaccgat tgcgtgaata gaactcacta cccagaatgc tcggtaatct ccgaacatat   7920
tgatgttttt cgtgggtaac catagttctt ggaatgtcaa ctgagggtat ttgcacttca   7980
aaaaaaaaaa tttattaaat gagactatat acagtgagca caacctgtct aatacaacgg   8040
caaaaattat atacattggt agattttcaa aattgaactc tttgtgctaa agaattgtca   8100
```

caacagttta aaaaatagtt tgaattcttc aaattgaccc catattaata agacctgatg 8160
cgattccggt ctcacccaga ttagagaggg aatttaattt tcttaggacc gtagctacca 8220
aaaatctttg tgtggtattg attatatgat cgtgcttgcg aaaaaaatag aagactaaaa 8280
gtagcattag tttactaact ttctcctcgt atctttcaaa tttgtattcc cctcaaaagt 8340
tactcaggtt agggaaaatt ccaagtagct tatcaagatc aattgccatt agttgattca 8400
aggcttcatt gtcggcggtt taaacgcgtg gccgtgccgt c 8441

<210> SEQ ID NO 22
<211> LENGTH: 2855
<212> TYPE: DNA
<213> ORGANISM: Artificial Sequence
<220> FEATURE:
<223> OTHER INFORMATION: Synthetic: MS188586 sequence

<400> SEQUENCE: 22
gacggcacgg ccacgcgttt aaaccgcctt atggcagctg ctgttgactg cggtggcgtc 60
ccgtttccac accgtacgtg agcacatgtc tggattgcta gctgcgtaca tagtgacagg 120
ccttgtctac gctcgcgacg cagccgcgct acgtccagta tgactcagga aaagttggcg 180
atagaccacg agcgactgaa aaaataacag cgacttttct cccggtagcg ggccgtcgtt 240
tagtcattct atccctcgga ttatagactg tgaatattgc atatgcaact ttgactcaaa 300
tttttccaaa atttgatata tatatatata tatatatgtt tgtatgtata tatatatata 360
cgtatatata tcatatatac gaaaagtaga aaaaaaaagg tgatatttcg ctcgtggaaa 420
agctaatgcc acagcttgtg tttcgtgtag tttgccttgc tccccttgat tgaaatagtc 480
tccctaaact aaagttatca gcaaacagaa ccaccacagt tactactaca accacatcgc 540
aatatgaaga tcacagaaaa attagagcaa catagacaga cctctggcaa gcccacttac 600
tcattcgagt acttcgtccc gaagactaca caaggtgtac agaacctgta tgaccggatg 660
gaccggatgt acgaggcttc tttgccccaa tttattgaca tcacctggaa tgcaggcggt 720
ggacggttgt cacatctgtc cacggacttg gttgcgacag cgcagtctgt gcttggtttg 780
gaaacgtgca tgcaccttac ctgcaccaat atgcccattt cgatgattga cgacgcttta 840
gaaaacgctt atcactccgg ttgccagaac atcctagcgc tgagaggaga tcctcctagg 900
gacgcagaaa actggactcc cgttgaaggt ggcttccagt atgccaagga cttgattaag 960
tatatcaagt ccaagtacgg tgaccatttc gctatcggcg ttgccggcta cccggagtgc 1020
catccggagt tgcctaacaa agacgtgaag cttgatctcg agtatttgaa gcagaagatc 1080
gacgccggcg gcgacttcat catcactcag atgttttacg atgttgataa tttcatcaac 1140
tggtgttccc aagttagagc tgcgggcatg gacgtgccca ttattcccgg gatcatgccg 1200
atcactacct acgcggcctt cttgagaagg gcccaatggg gccaaatctc catccctcaa 1260
catttctcgt cccgattgga tcctatcaag gacgatgacg agttggtccg tgatatcgga 1320
actaacttga tcgtggaaat gtgtcaaaaa ttgctcgaca gtggttacgt ttctcacttg 1380
cacatctaca ccatgaactt ggaaaaagcg cctctcatga ttctggaaag attgaacatt 1440
ctacctacgg aatcagagtt caatgcacat ccattggccg tgttgccatg gagaaaatct 1500
ttgaatccaa agcgtaaaaa cgaggaagtc agacctatct tctgggcgaa tagacccaaa 1560
tcttatattt cacgtactaa gggttggaat gactttccac acggtagatg gggtgattct 1620
cactccgccg cttactctac tttatccgac taccaattcg ctcgtccaaa gggtagagac 1680
aagaagttgc aacaagaatg ggtcgttcct ttgaaatcta tcgaagacgt ccaagaaaag 1740
ttcaaggaat tgtgtattgg taacttaaag tcttctccat ggtctgaatt ggatggtttg 1800
caaccagaaa ccaagattat caacgagcaa ttgggtaaga ttaactctaa cggtttcttg 1860
accattaact ctcaaccatc tgttaacgct gctaagtccg attctccagc tattggttgg 1920
ggtggtccag gtggttacgt ttaccaaaaa gcttacttgg aattcttctg ttccaaggat 1980
aagttggaca ccttggtcga aaagtccaag gccttccctt ctatcactta catggctgtt 2040
aacaagtctg aaaactgggt ttctaacact ggtgaatctg atgttaacgc cgttacttgg 2100
ggtgtcttcc cagctaagga agtcatccaa ccaaccattg tcgacccagc ttccttcaaa 2160
gtttggaagg atgaagcttt cgaaatctgg tctagatctt gggctaactt gtatccagaa 2220
gatgacccat ctcgtaagtt gttagaagag gttaagaact cttactactt ggtttcttta 2280
gtcgataaca actacattaa cggtgatatc ttctctgttt ttgcctaata acacagacaa 2340
cgataacagt tctttaacag aattgtcaac cccccctctt tgcattacat tcaacattac 2400
attgcatttt ttttttttta ttcactatta ttatggttct tctttttac cagattttgc 2460 tccttccttt tccattgttt taccattctt ttttaactag catttcaaca tgtgtttggt 2520
taacacccct tcttttttt caggaaaatc ctttcatttc ttctcatact ttcaacaaag 2580
ttttttaaag gtactttaaa atagttcaac accctcttcc ttcatttatt tattctcttc 2640
atattcaaca tactcgaaaa ggaagaacac taaaagtact tacattttca catgtatgta 2700
tacctatata tatatatata tatactctta tagatatatt tacaaattaa aggaaaaaat 2760
aataaaataa cctccctgtc acaagttaaa acacggcccc atcacttata aatagtctcg 2820
actcgtgcgg tgtttaaacc ccagcgcctg gcggg 2855

<210> SEQ ID NO 23
<211> LENGTH: 11309
<212> TYPE: DNA
<213> ORGANISM: Artificial Sequence
<220> FEATURE:
<223> OTHER INFORMATION: Synthetic: MS173680 sequence

<400> SEQUENCE: 23
gacggcacgg ccacgcgttt aaaccgccga aatcacctcc aaagttatgt tgccgattag 60
gcaaatactc taaaagtata gtactaaaga actacgtaaa ggtaaaataa aacacctgaa 120
tttcatttct gaaatgaagt accatcatga aatatgatga aagtcaagac tcgttgggtc 180
aatatacacc acaaaaaaag gtacacacga atggtttaac cctttcggtt ccttctgtaa 240
atcgaaaaat gccctttata cagcgggttg gtctcccatc aaagttgaga agcgattaga 300
aattaggtta cctaatgaat ccataaataa atggaaaacg ctattttgtt cgaacgatgg 360
aataaaaata tgaacgggtg tcattgaaat tcggtgtatt ttttgatcgg gcctgatctg 420
gctcgggttt ggcacaattt ggcttggtta gttcggcaaa gcttatttaa agaacctttt 480
tggatagcca attgagagac ttgaaataga aagatcgtaa gtatttttac gctcgtccaa 540
cgccggcgga cctatgaaga tcacagaaaa attagagcaa catagacaga cctctggcaa 600
gcccacttac tcattcgagt acttcgtccc gaagactaca caaggtgtac agaacctgta 660
tgaccggatg gaccggatgt acgaggcttc tttgccccaa tttattgaca tcacctggaa 720
tgcaggcggt ggacggttgt cacatctgtc cacggacttg gttgcgacag cgcagtctgt 780
gcttggtttg gaaacgtgca tgcaccttac ctgcaccaat atgcccattt cgatgattga 840
cgacgcttta gaaaacgctt atcactccgg ttgccagaac atcctagcgc tgagaggaga 900

-continued

```
tcctcctagg gacgcagaaa actggactcc cgttgaaggt ggcttccagt atgccaagga    960
cttgattaag tatatcaagt ccaagtacgg tgaccatttc gctatcggcg ttgccggcta   1020
cccggagtgc catccggagt tgcctaacaa agacgtgaag cttgatctcg agtatttgaa   1080
gcagaagatc gacgccggcg gcgacttcat catcactcag atgttttacg atgttgataa   1140
tttcatcaac tggtgttccc aagttagagc tgcgggcatg gacgtgccca ttattcccgg   1200
gatcatgccg atcactacct acgcggcctt cttgagaagg gcccaatggg gccaaatctc   1260
catccctcaa catttctcgt cccgattgga tcctatcaag gacgatgacg agttggtccg   1320
tgatatcgga actaacttga tcgtggaaat gtgtcaaaaa ttgctcgaca gtggttacgt   1380
ttctcacttg cacatctaca ccatgaactt ggaaaaagcg cctctcatga ttctggaaag   1440
attgaacatt ctacctacgg aatcagagtt caatgcacat ccattggccg tgttgccatg   1500
gagaaaatct ttgaatccaa agcgtaaaaa cgaggaagtc agacctatct tctgggcgaa   1560
tagacccaaa tcttatattt cacgtactaa gggttggaat gactttccac acggtagatg   1620
gggtgattct cactccgccg cttactctac tttatccgac taccaattcg ctcgtccaaa   1680
gggtagagac aagaagttgc aacaagaatg ggtcgttcct ttgaaatcta tcgaagacgt   1740
ccaagaaaag ttcaaggaat tgtgtattgg taacttaaag tcttctccat ggtctgaatt   1800
ggatggtttg caaccagaaa ccaagattat caacgagcaa ttgggtaaga ttaactctaa   1860
cggtttcttg accattaact ctcaaccatc tgttaacgct gctaagtccg attctccagc   1920
tattggttgg ggtggtccag gtggttacgt ttaccaaaaa gcttacttgg aattcttctg   1980
ttccaaggat aagttggaca ccttggtcga aaagtccaag gccttccctt ctatcactta   2040
catggctgtt aacaagtctg aaaactgggt ttctaacact ggtgaatctg atgttaacgc   2100
cgttacttgg ggtgtcttcc cagctaagga agtcatccaa ccaaccattg tcgacccagc   2160
ttccttcaaa gtttggaagg atgaagcttt cgaaatctgg tctagatctt gggctaactt   2220
gtatccagaa gatgacccat ctcgtaagtt gttagaagag gttaagaact cttactactt   2280
ggtttcttta gtcgataaca actacattaa cggtgatatc ttctctgttt ttgcctaatg   2340
taaagttagt tggttgcgcg acttcgggtg gggttacttt ttttttggat ggacgcaaag   2400
aagtttaata atcatattac atggcaatac caccatatac atatccatat ctaatcttac   2460
ttatatgttg tggaaatgta aagagcccca ttatcttagc ctaaaaaaac cttctctttg   2520
gaactttcag taatacgctt aactgctcat tgctatattg aagtacggat tagaagccgc   2580
cgagcgggcg acagccctcc gacggaagac tctcctccgt gcgtcctggt cttcaccggt   2640
cgcgttcctg aaacgcagat gtgcctcgcg ccgcactgct ccgaacaata aagattctac   2700
aatactagct tttatggtta tgaagaggaa aaattggcag taacctggcc ccacaaacct   2760
tcaaatcaac gaatcaaatt aacaaccata ggataataat gcgattagtt ttttagcctt   2820
atttctgggg taattaatca gcgaagcgat gatttttgat ctattaacag atatataaat   2880
gcaaaagctg cataaccact ttaactaata ctttcaacat tttcggtttg tattacttct   2940
tattcaaatg tcataaaagt atcaacaaaa aattgttaat atacctctat acttacctcc   3000
cgcgacctcc aaaatcgaac taccttcaca atggttcaat ctgctgtctt agggttccca   3060
agaatcggtc caaacagaga attaaagaag gccactgaag gttactggaa cggtaaaatc   3120
actgtcgatg aattattcaa agtcggtaag gatttgagaa ctcaaaactg gaagttgcaa   3180
aaggaggctg gtgttgatat catcccatcc aatgacttct ccttttacga ccaagttttg   3240
gatttgtctt tgttgttcaa tgtcattcca gaccgttaca ctaagtacga tctatctcca   3300
```

```
atcgacactt tgtttgctat gggtagaggt ttacaaagaa aggccactga aactgaaaag   3360
gctgtcgacg tcactgcttt ggaaatggtt aaatggttcg actctaacta ccattacgtt   3420
agaccaactt tctccaagac cactcaattt aagttgaacg gccaaaagcc agttgacgaa   3480
tttttggaag ccaaggagtt aggtattcac actagacctg tcttgttagg tccagtttct   3540
tacttattct tgggtaaggc tgacaaggat tctctagatt tggaaccatt gtccctattg   3600
gaacaattgt tgcctctata cactgaaatc ctatctaaat tggcttctgc tggtgccact   3660
gaagttcaaa ttgacgaacc tgtcttagtt ttggacttgc ctgccaacgc ccaagccgcc   3720
attaagaagg cttacactta cttcggtgaa caaagcaatc taccaaagat tactttggct   3780
acttacttcg gtaccgttgt ccctaactta gacgccatca agggcttgcc agttgctgcc   3840
ttacacgttg actttgttag agctccagaa caatttgatg aagtcgttgc cgccattggt   3900
aacaaacaaa ccttgtccgt tggtattgtt gatggtagaa acatttggaa gaatgatttc   3960
aagaagtctt ccgctatcgt taacaaggct attgaaaagt tgggtgctga cagagtcgtt   4020
gttgccactt cttcttctct attgcacaca ccagttgact tgaacaacga aaccaagttg   4080
gacgctgaaa tcaagggctt tttctctttc gccactcaaa aattggatga agttgttgtg   4140
atcaccaaga acgtttccgg tcaagacgtt gctgctgccc tagaagctaa cgctaaatct   4200
gttgaatcca gaggtaaatc caagtttatc cacgatgctg ccgttaaggc cagagttgcc   4260
tctatcgacg aaaaaatgtc tactagagca gctccatttg aacaaagatt gcctgaacaa   4320
caaaaagtct tcaacttgcc attgttccca acaacaacta ttggttcctt ccctcaaacc   4380
aaggacatca gaattaacag aaacaaattc aacaagggta ccatctctgc tgaagaatat   4440
gaaaaattca tcaattctga aattgaaaag gtcatcagat tccaagaaga aattggtttg   4500
gatgtcttag tccacggtga accagaaaga aacgatatgg ttcaatactt cggtgaacaa   4560
atcaacggtt atgctttcac tgttaacggt tgggttcaat cttacggttc cagatatgtc   4620
agaccaccaa ttattgttgg tgacttgtcc agaccaaagg ctatgtccgt caaggaatct   4680
gtttacgctc aatccatcac ttctaagcca gtaaagggta tgttgactgg tccaattacc   4740
tgtttgagat ggtctttccc aagagacgat gtcgaccaaa aaactcaagc tatgcaatta   4800
gctttggctt tgagagatga agtcaatgat ttggaagctg ccggtatcaa ggttatccaa   4860
gttgatgaac cagctttaag agaaggttta ccattgagag aaggtgctga gagatctgct   4920
tactacacct gggctgccga agctttcaga gttgctactt ctggtgttgc taacaagact   4980
caaatacact ctcatttctg ttactctgac ttggatccaa accatatcaa ggctttggat   5040
gctgatgttg tttccatcga attctctaag aaggacgatg ctaactacat tgctgaattc   5100
aaaaactatc caaaccacat tggtctgggt ttattcgata ttcattctcc aagaattcca   5160
tcaaaggatg aatttatcgc caagatttca accatcttga agagctaccc agctgaaaag   5220
ttctgggtta acccagactg tggtttgaag actagaggct gggaagaaac tagattgtct   5280
ttgactcata tggtcgaagc cgccaagtac ttccgtgaac aatacaagaa ttaaggtttt   5340
aaaaaggaag caaagtaatg atattttctg aactttttgt tttttattct gggattcaac   5400
atcggtgatt taatttttgt gttcacattt aaaagtttat ttgggtaatt ttttgatatc   5460
aattttatta caaagccata actcttgcat ttttttattt atatttttat atacacgtac   5520
attctgtatt atttataacg cattcaaacg cgatcgccga cgccgccgat gatcatctac   5580
ccatgccgaa attcgggccg ttggccggat tgcgcgttgt cttctccggt atcgaaatcg   5640
```

-continued

```
ccggaccgtt tgccgggcaa atgttcgcag aatggggcgc ggaagttatc tggatcgaga   5700
acgtcgcctg ggccgacacc attcgcgttc aaccgaacta cccgcaactc tcccgccgca   5760
atttgcacgc gctgtcgtta aatattttca aagatgaagg ccgcgaagcg tttctgaaat   5820
taatggaaac caccgatatc ttcatcgaag ccagtaaagg tccggccttt gcccgtcgtg   5880
gcattaccga tgaagtactg tggcagcaca acccgaaact ggttatcgct cacctgtccg   5940
gttttggtca gtacggcacc gaggagtaca ccaatcttcc ggcctataac actatcgccc   6000
aggcctttag tggttacctg attcagaacg gtgatgttga ccagccaatg cctgccttcc   6060
cgtataccgc cgattacttt tctggcctga ccgccaccac ggcggcgctg gcagcactgc   6120
ataaagtgcg tgaaaccggt aaaggcgaaa gtatcgacat cgccatgtat gaagtgatgc   6180
tgcgtatggg ccagtacttc atgatggatt acttcaacgg cggcgaaatg tgcccgcgca   6240
tgagcaaagg taaagatccc tactacgccg atcggcggcg tcggcgatcg cgttgaatga   6300
aaatagagat cagaaatttt gtgattattt ggaatctaaa ttacaacgtg acaaacaact   6360
tgtaaatggc ggctccaaga aaaggaaagc caatgattag catatgcctc ttcttcttag   6420
aagggcgttc tgcccgttat gtatacgtta aatattacat tattttcgca tttttgtatt   6480
tatattcagt gaaatattag gcttggtcga gtaacatttc ccatagctcg tcggtttctt   6540
tgaagtcgtg atgaacaatt gagacaagac agtagtcttt atgcactagt cttagaagaa   6600
tattggctgg ggtgttcctt ggaaataact tggcccactc ggaccagata ctaaacgctt   6660
catctctcca tgccttgaat gactcttctt caatgattgt agtctgtttg accggactgt   6720
tgggaaaaac accccatgtt acaacgctag agctgtgcgg gtctaggttc gtttcaaatg   6780
aaccagatga atcgcccgcg taataactga atttccgacg cccgtaatgg tctagcttgg   6840
gtttcaaagt tgtttcccat tgctgtctat gaataaacat ttctacgaat gccttctgat   6900
acaacctccc tttcgcgggc ccccagccga atattttatc actactcaat gtagcatttg   6960
tggcaggttg cgatgccaaa gtcaaatatc cgcgatagtt tagttggatt agttcttctt   7020
gtattaacgc cgtttcagct gataaaccca ggtcagacca gggaatcgca tccgttgaac   7080
cttccaaata ttttataaaa atatctttta aatcgccaat tgtctttggt ataccccata   7140
gttcaagcgc tttgcttttg cttaccttga tggatggccc ataaccgtct atttcaccat   7200
atgcgggaga cctggagtca ccaaatctac cattggggaa ctcatcccaa gtggcatcac   7260
gacccaaagt tccgtgacct ttagaaatag atattaaagc ctttttagat ggcatggaac   7320
cattctcatt attatagcgt aagccttttt cagtgacgat agccctattg aaaatcaact   7380
tggccgaatc aagacttgaa tgccttctcc ttttccggtt tgctacagtt tcttcattcg   7440
aatcatccaa cacaatatcc ccgtcagcat cttctattgg cacattttct atgcttccta   7500
tttcgccact ggtttcatct tctccctctt cttcgctaga ttcatttacg atatgggata   7560
agacgggaga ttgcgagaca atttgagcaa tagccttttc caaatttaat gtatagaaat   7620
gaaacccttt aattctacca gatgttcttt gatatatttc ctgaatcaat tcgataagaa   7680
tgtccacacc aatggacttc acggcattat catccgattg gatttctggg gggaacctac   7740
tcagtattgc aggtggaata gatgcatgtg ataactttgc tgctctgtgg aaaagcagat   7800
aggagttaat aggcatcaac ccagggaaaa ggggcaaatc ttgcgaaatc cgttcccgaa   7860
atagcatttc aaaagttaag aatttttcaa cgtcgtaaaa cagttgtgtt atcacaaaat   7920
cggccccagc ttcaactttt tcttttaaat ataccaaatc cttcaatggg tcttgctcgt   7980
gaccttctgc ttcaccttca caatgacctt ctggatatgc tgcaacaccg acgcagaact   8040
```

-continued

```
tgtctccgta gctttgcttg atataacgaa ctaaatcaac cgcatattta aaaggtgatt   8100
cgttcgattg agaatctagc caatcttccc caataggtgg gtcacctcga agagccaaaa   8160
tattcctgat tcctgcatta taacatctat ccagcgcatc atcaatgatg gctttttctg   8220
tgtttgtaca ggtcaaatgc atacaaactg gtatatttag tgtctgctgt gccaaggaag   8280
ctaatgtcag agtcttttcc gcagtagtac cacctgctcc ccaagtaacc gtgataaaca   8340
gtggatctaa agcagtcata cgatgcatac gttccatcaa atttctcgtc cctaattcag   8400
tctttggagg gaagaattct aacgatataa aaggggaagc cctcgcatga tataaatctc   8460
tgatggacat tgtgaaggta gttcgatttt ggaggtcgcg ggaggtaagt atagaggtat   8520
attaacaatt ttttgttgat acttttatga catttgaata agaagtaata caaaccgaaa   8580
atgttgaaag tattagttaa agtggttatg cagcttttgc atttatatat ctgttaatag   8640
atcaaaaatc atcgcttcgc tgattaatta ccccagaaat aaggctaaaa aactaatcgc   8700
attattatcc tatggttgtt aatttgattc gttgatttga aggtttgtgg ggccaggtta   8760
ctgccaattt ttcctcttca taaccataaa agctagtatt gtagaatctt tattgttcgg   8820
agcagtgcgg cgcgaggcac atctgcgttt caggaacgcg accggtgaag accaggacgc   8880
acggaggaga gtcttccgtc ggagggctgt cgcccgctcg gcggcttcta atccgtactt   8940
caatatagca atgagcagtt aagcgtatta ctgaaagttc caaagagaag gtttttttag   9000
gctaagataa tggggctctt tacatttcca caacatataa gtaagattag atatggatat   9060
gtatatggtg gtattgccat gtaatatgat tattaaactt ctttgcgtcc atccaaaaaa   9120
aaagtaaccc cacccgaagt cgcgcaacca actaacttta caatgcctta cactctatcc   9180
gacgctcatc ataagttgat cacctctcat ttggtggaca ccgaccctga agtggactcc   9240
attatcaagg atgaaattga aagacaaaag cactccatcg atttgattgc ttctgaaaat   9300
ttcacctcaa cctccgtttt cgatgccctt ggaactccat tgtccaacaa atattctgaa   9360
ggttatccag gtgctcgtta ctacggtggt aatgaacaca ttgacagaat ggaaattcta   9420
tgtcaacaaa gagctttaaa agctttccat gttactccag acaaatgggg tgttaacgtc   9480
caaactttat ctggttctcc tgctaacttg caagtttatc aagctattat gaagcctcat   9540
gaaagattga tgggtctata cctaccagat ggtggtcatt tgtctcacgg ttacgctact   9600
gaaaacagaa aaatttctgc tgtttccaca tacttcgaat ctttcccata cagagttaac   9660
ccagaaaccg gtattatcga ctacgatact ttagaaaaga acgccatcct atatagacca   9720
aaggttcttg ttgctggtac ttcagcatac tgtcgtttaa ttgactacaa gagaatgaga   9780
gaaatcgccg acaaatgtgg tgcttacttg atggtagaca tggcccacat ttcaggtttg   9840
atcgccgcag gtgtcatccc atctcctttc gaatacgctg atatcgttac caccaccact   9900
cacaagtctt tgagaggtcc acgtggtgct atgattttct tcagaagagg tgtgagatct   9960
atcaacccta agaccggtaa ggaagtccta tacgacttgg aaaacccaat taacttctct  10020
gttttcccag gtcaccaagg tggtccacac aaccatacca ttgctgcttt ggccactgct  10080
ttgaagcaag ctgccactcc agaattcaag gaataccaaa ctcaagtctt gaagaatgct  10140
aaggctttgg aaagtgaatt taagaacttg ggctacagat tagtttccaa cggtaccgat  10200
tctcacatgg ttctggtatc cttgagagaa aagggtgttg atggtgctcg tgttgaatac  10260
atttgtgaaa agattaacat tgctttgaac aaaaactcta ttccaggtga caaatctgct  10320
ttggttccag gtggtgtccg tattggggct ccagccatga ccactagagg aatgggtgaa  10380
```

gaagatttcc acagaattgt tcaatacatt aacaaggctg tagaattcgc tcaacaagtt 10440
caacaaagct tgccaaagga tgcttgtaga ttaaaggact tcaaagccaa ggtcgacgaa 10500
ggctctgatg ttttgaacac ctggaaaaag gaaatttacg actgggctgg cgaataccca 10560
ttggctgtgt aaagaaatca ccacaacgac acttaatccc aaaaaaataa acattactgt 10620
ataagtattc attttctcct cttctcatta tgtatatatg tacctatatg tatgtatgta 10680
tgtgcgtacg atttttctaa cgttaacttc atttcttttt gattatgtgc cctccttgag 10740
ttaagatgtg cttgtccagg tccgccggcg ttggacgagc gaattaagct ttcgagaaaa 10800
actttctttt aacccctcta atctaaatat aaacatatag cttatagaaa tgaatgaata 10860
ttttaaatag ttacggatac aaagagttca ttatagtgcg ggcagttagt acggtatcga 10920
tttatcattg gagatctgca gtgttacaga agcactgctc accagttgtc tacggaagga 10980
cgttgagata gttttaccac gtttgagcta aaagtttcta ccacaagagc ctttatttgc 11040
acatggcagt gaatgcatga ttaaggatat gaagaagaaa ggaataacta ggaataaatt 11100
ttatttagag agggtatgat gaaaggagag cctcgttatt tatgacctgc atttttatca 11160
gcatcttctt tccagctccc gctaaacatg tgctttacaa aagccatttt gtcgtcacta 11220
gactgggcgc ccatctgccc cacatctggt gaaaaacttg ttattggtag aaccatcaca 11280
tggcggttta aacgcgtggc cgtgccgtc 11309

<210> SEQ ID NO 24
<211> LENGTH: 2128
<212> TYPE: DNA
<213> ORGANISM: Artificial Sequence
<220> FEATURE:
<223> OTHER INFORMATION: Synthetic: MS 116593 sequence

<400> SEQUENCE: 24
gacggcacgg ccacgcgttt aaaccgccct aatacccagc caaggtagtc taaaagctaa 60
tttctctaaa agggagaaag ttggtgattt tttatctcgc attattatat atgcaagaat 120
agttaaggta tagttataaa gttttatctt aattgccaca tacgtacatt gacacgtaga 180
aggactccat tatttttttc attctagcat actattattc cttgtaacgt cccagagtat 240
tccatttaat tgtcctccat ttcttaacgg tgacgaagga tcaccataca acaactacta 300
aagattatag tacactctca ccttgcaact atttatctga catttgcctt acttttatct 360
ccagcttccc ctcgatttta tttttcaatt tgatttctaa agctttttgc ttaggcatac 420
caaaccatcc actcatttaa caccttattt tttttttcga agacagcatc caactttata 480
cgttcactac cttttttttt acaacaattt cattcttcat cctatgaacg ctcgtccaac 540
gccggcggac cttggaactt tcagtaatac gcttaactgc tcattgctat attgaagtac 600
ggattagaag ccgccgagcg ggcgacagcc ctccgacgga agactctcct ccgtgcgtcc 660
tggtcttcac cggtcgcgtt cctgaaacgc agatgtgcct cgcgccgcac tgctccgaac 720
aataaagatt ctacaatact agcttttatg gttatgaaga ggaaaaattg gcagtaacct 780
ggccccacaa accttcaaat caacgaatca aattaacaac cataggataa taatgcgatt 840
agttttttag ccttatttct ggggtaatta atcagcgaag cgatgatttt tgatctatta 900
acagatatat aaatgcaaaa gctgcataac cactttaact aatactttca acattttcgg 960
tttgtattac ttcttattca aatgtcataa aagtatcaac aaaaaattgt taatatacct 1020
ctatacttta acgtcaagga gaaaaaacta tagatgcacg agcgcaacgc tcacaaacag 1080
gccccttttc ctttgtcgat atcatgtaat tagttatgtc acgcttacat tcacgccctc 1140

-continued

```
cccccacatc cgctctaacc gaaaaggaag gagttagaca acctgaagtc taggtcccta   1200
tttatttttt tatagttatg ttagtattaa gaacgttatt tatatttcaa atttttcttt   1260
tttttctgta caaacgcgtg tacgcatgta acattatact gaaaaccttg cttgagaagg   1320
ttttgggacg ctcgaaggct ttaatttgca agcttcgcag tttacactct catcgtcgct   1380
ctcatcatcg cttccgttgt tgttttcctt agtagcgtct gcttccagag agtatttatc   1440
tcttattacc tctaaaggtt ctgcttgatt tctgactttg ttcgcctcat gtgcatattt   1500
ttcttggttc ttttgggaca aaatatgcgt aaaggacttt tgttgttccc tcacattcca   1560
gtttagttgt cgactgatcc ccgcgtgctt ggccggccgt ctccatgctg gacttactcg   1620
tcgaagattt cctgctactc tctatataat tagacaccca tgttatagat ttcagaaaac   1680
aatgtaataa tatatggtag cctcctgaaa ctaccaaggg aaaaatctca acaccaagag   1740
ctcatattcg ttggaatagc gataatatct ctttacctca atcttatatg catgttattt   1800
gctcttataa ttggtctcta tttagggaaa aaagtcggtt tgagagcttc tcgcgatgtg   1860
aaatctcaat ttgaactgca cgccaaagct agcccatttc acgaacacca gaaagaagaa   1920
atccccaagg atcgcatgac agagtatgct ctctcatatc gttgagtatg aatgccaata   1980
cactgatcag ctttacaaga aacgtaaaat ctggcacgat ggtagactga aatactttca   2040
gttaaacaac agattcatgc tttatacgga aaaggataac gttttgttag ctagtgaatt   2100
cggtgtttaa accccagcgc ctggcggg                                      2128
```

MODIFIED HOST CELLS FOR HIGH EFFICIENCY PRODUCTION OF VANILLIN

CROSS-REFERENCE TO RELATED APPLICATIONS

This application claims priority to U.S. Provisional Application No. 62/881,869, filed Aug. 1, 2019, the entire contents of which is herein incorporated by reference in its entirety for all purposes.

Incorporated by reference is a sequence listing entitled "107345.00795 ST.25" dated Aug. 31, 2020, which is 197 kb. The sequence listing listing does not go beyond the sequences of the application as originally filed.

FIELD OF THE INVENTION

The present disclosure relates to particular genetic modifications, host cells comprising the same, and methods of their use for the production of vanillin and/or glucovanillin and any compound that can be synthesized or biosynthesized from either or both.

BACKGROUND

Vanillin is the largest-volume flavor ingredient in the world. Only about 1% of the vanilla flavor ingredient supply comes from vanilla extract from the vanilla orchid. There is strong demand, insufficient supply, and a high price for "natural" vanillin. An alternative, low cost, high-volume source of "natural" vanillin would be a lucrative addition to the flavorings market. Vanillin produced de novo through fermentation of sugar by yeast has the potential to generate "natural" vanillin at a lower cost than alternatives currently in the market.

There are several approaches that are being used to generate "natural" vanillin by bioconversion from natural precursors, including precursors other than glucose. One path is bioconversion of ferulic acid which is found abundantly in certain parts of certain plants. Microorganisms have been identified which catabolize ferulic acid by a pathway which generates vanillin as an intermediate. These microorganisms can be engineered to reduce further catabolism of vanillin to unwanted side products to optimize vanillin production. Gallage et al., *Molecular Plant,* 8:40-57 (2015). In a similar approach, the more cost-effective substrate eugenol can be catabolized by microorganisms to ferulic acid and further to vanillin. Gallage et al.

There is no known microorganism that can natively convert glucose to vanillin. Gallage et al. In 1998, an enzymatic route from glucose to vanillin was developed which converts a natively produced metabolite 3-dehydroshikimate into vanillin with three additional enzymatic steps: 1.) dehydration to produce protocatechuic acid (3,4-dihydroxybenzoic acid) 2.) O-methylation of the 3-hydroxyl group, and 3.) reduction of the carboxylic acid to an aldehyde. Li and Frost, *J. Am. Chem. Soc.,* 120:10545-10546 (1998). This process was demonstrated by producing vanillic acid (steps 1 and 2) in *E. coli* by expression of heterologous enzymes catalyzing 3-DHS dehydratase (AroZ) and catechol-O-methyltransferase (COMT). An enzymatic conversion using an aromatic carboxylic acid reductase (ACAR) purified from fungi was used to convert vanillic acid to vanillin in vitro.

Hansen et al. demonstrated de novo biosynthesis of vanillin from glucose in a single recombinant organism, *Saccharomyces cerevisiae*, by expressing the above enzymes in combination with a heterologous PPTase which was identified to be necessary to activate the ACAR enzyme in this organism. Hansen et al., *Appl. Environ. Microbiol.* 75:2765-2774 (2009). In addition they expressed a UDP-glucosyltransferase to convert the toxic vanillin product into the far less toxic glucovanillin.

A number of other modifications have been reported to improve the efficiency of vanillin biosynthesis in yeast. In order to improve titer of glucovanillin, Hansen et al. demonstrated that it was important to reduce endogenous reductase activity through the deletion of native reductases (i.e. ADH6) to reduce conversion of vanillin to vanillyl alcohol, and to eliminate native β-glucosidase activity by deleting EXG1 to reduce hydrolysis of the glucose moiety during fermentation. In subsequent filings, the use of a vanillyl alcohol oxidase was reported to further mitigate the loss of carbon from reduction of vanillin to vanillyl alcohol. US2014/0245496 A1; WO 2015 121379 A2. In order to mitigate loss of carbon to the undesired isomer, isovanillin (produced by methylation of the 4-OH instead of 3-OH), the human variant Hs.COMT was used as a starting point for enzyme evolution. Mutants were obtained which were highly specific for the correct vanillin isomer. In order to increase flux to PCA and reduce flux to shikimate pathway metabolites, a mutant version of Aro1 was generated, annotated as mutant AROM which contains a mutation in the E domain and reduces activity of this reaction that uses 3-DHS as a substrate to make shikimate.

Further genetic modifications that can provide low cost, high-volume sources of "natural" vanillin would be a significant addition to the flavorings market.

SUMMARY OF THE INVENTION

Provided herein are genetically modified host cells, compositions, and methods for the improved production of vanillin and/or glucovanillin. These compositions and methods are based in part on the expression and/or deletion of certain gene products in host cells that have been genetically modified to produce vanillin and/or glucovanillin. Certain expressed gene products include enzymes that facilitate S-adenosylmethionine regeneration. While not intending to be bound by any particular theory of operation, the examples herein demonstrate that S-adenosylmethionine is an effective cosubstrate for methylation of protocatechuic acid into vanillic acid by O-methyltransferase. Increasing S-adenosylmethionine regeneration improves the yield and productivity of vanillic acid production.

In one aspect, provided herein are genetically modified host cell capable of producing vanillin or glucovanillin, and/or one or more derivatives thereof, comprising one, two, three, or four of: (a) one or more nucleic acids capable of overexpressing one or more genes selected from SAM1, SAM2, SAH1, and MET6; (b) one or more nucleic acids expressing heterologous OMT, for example, either *Hordeum vulgare* OMT or *Brassica napus* OMT, or both *Hordeum vulgare* OMT and *Brassica napus* OMT; (c) one or more nucleic acids expressing *Rhodococcus jostii* EAO; and (d) one or more nucleic acids expressing chimeric MET13. Each feature is described in detail below.

In one aspect, provided herein are genetically modified host cells and methods of their use for the production of vanillin and/or glucovanillin. In certain embodiments, provided herein are genetically modified host cells capable of producing vanillin or glucovanillin where the host cell overexpresses one or more genes selected from SAM1, SAM2, SAH1, and MET6. In particular embodiments, the genetically modified host cell expresses further enzymes sufficient to produce vanillin or glucovanillin. Useful enzymes are described herein.

In another aspect, provided herein are genetically modified host cells and methods of their use for the production of vanillin or glucovanillin. In certain embodiments, provided herein are genetically modified host cells capable of producing vanillin or glucovanillin where the host cell overexpresses one or more genes selected from SHM2, MET12, MET13, and one or more copies of MET6. In particular embodiments, the genetically modified host cell expresses further enzymes sufficient to produce vanillin or glucovanillin. Useful enzymes are described herein.

In another aspect, provided herein are genetically modified host cells and methods of their use for the production of vanillin or glucovanillin. In certain embodiments, provided herein are genetically modified host cells capable of producing vanillin or glucovanillin where the host cell expresses an O-methyltransferase (OMT). In certain embodiments, the O-methyltransferase is selected from *Hordeum vulgare* OMT and *Brassica napus* OMT. In certain embodiments, the O-methyltransferase is *Hordeum vulgare* OMT. In certain embodiments, the O-methyltransferase is *Brassica napus* OMT. In certain embodiments, provided herein is a genetically modified host cell capable of producing vanillin or glucovanillin where the host cell expresses both *Hordeum vulgare* OMT and *Brassica napus* OMT. In particular embodiments, the genetically modified host cell expresses further enzymes sufficient to produce vanillin or glucovanillin. Useful enzymes are described herein.

In another aspect, provided herein are genetically modified host cells and methods of their use for the production of vanillin or glucovanillin. In certain embodiments, provided herein are genetically modified host cells capable of producing vanillin or glucovanillin where the host cell expresses a eugenol alcohol oxidase (EAO). In certain embodiments, the EAO is *Rhodococcus jostii* EAO. In particular embodiments, the genetically modified host cell expresses further enzymes sufficient to produce vanillin or glucovanillin. Useful enzymes are described herein.

In another aspect, provided herein are genetically modified host cells and methods of their use for the production of vanillin or glucovanillin. In certain embodiments, provided herein are genetically modified host cells capable of producing vanillin or glucovanillin where the host cell expresses a MET13 chimera. In certain embodiments, the MET13 chimera comprises a yeast N-terminal domain and an *Arabidopsis* MTHFR C-terminal domain. The *Arabidopsis* MTHFR enzyme is less sensitive or not sensitive to SAM inhibition. Similarly, the chimera provided herein is less sensitive or not sensitive to SAM inhibition. In certain embodiments, the yeast N-terminal domain is from *S. cerevisiae* and the MTHFR C-terminal domain is from *A. thaliana*. In particular embodiments, the genetically modified host cell expresses further enzymes sufficient to produce vanillin or glucovanillin. Useful enzymes are described herein.

In another aspect, provided herein is a method for producing vanillin or glucovanillin involving: culturing a population of the host cells of the invention in a medium with a carbon source under conditions suitable for making vanillin or glucovanillin to yield a culture broth; and recovering the vanillin or glucovanillin from the culture broth.

The compositions and methods are useful for producing vanillin and/or glucovanillin for any purpose, including as flavorings and food ingredients. They are also useful for producing any compound that can be synthesized or biosynthesized from vanillin and/or glucovanillin. The compounds can be produced synthetically, or biosynthetically with downstream enzymes or pathways, or a combination thereof. Such compounds include vanillic acid, vanillyl alcohol, ferulic acid, eugenol, and heliotropin.

DETAILED DESCRIPTION OF THE EMBODIMENTS

Terminology

Figure 1:
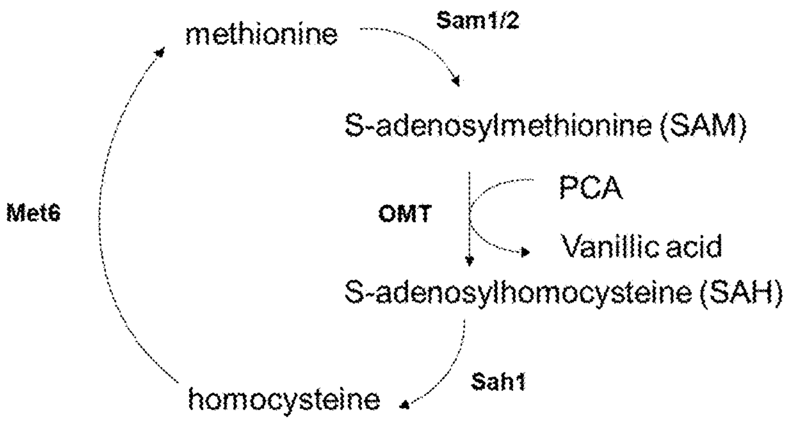
FIG. 1 is a schematic showing an enzymatic pathway from a native yeast whereby SAH is recycled back to SAM which is used as a co-substrate for the methylation reaction catalyzed by OMT.

As used herein, the term "about" refers to a reasonable range about a value as determined by the practitioner of skill. In certain embodiments, the term about refers to ±one, two, or three standard deviations. In certain embodiments, the term about refers to ±5%, 10%, 20%, or 25%. In certain embodiments, the term about refers to ±0.1, 0.2, or 0.3 logarithmic units, e.g. pH units.

As used herein, the term "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus.

On the other hand, the term "native" or "endogenous" as used herein with reference to molecules, and in particular enzymes and nucleic acids, indicates molecules that are expressed in the organism in which they originated or are found in nature. It is understood that expression of native enzymes or polynucleotides may be modified in recombinant microorganisms. In particular embodiments, codon optimized genes express native enzymes.

As used herein, the term "heterologous nucleic acid expression cassette" refers to a nucleic acid sequence that comprises a coding sequence operably linked to one or more regulatory elements sufficient to expresses the coding sequence in a host cell. Non-limiting examples of regulatory elements include promoters, enhancers, silencers, terminators, and poly-A signals.

As used herein, gene names are typically capitalized and italicized, e.g. SAM1. Protein names are typically initially capitalized and not italicized, e.g. Sam1 or Sam1p. However, where the term protein is indicated, then the protein is intended. For instance, those of skill will recognize that "SAM1 protein" is intended to refer to Sam1p.

As used herein, the terms "S-adenosylmethionine synthetase" and "SAM1" or "Sam1" refer to an encoding nucleic acid and an S-adenosylmethionine synthetase that catalyzes transfer of the adenosyl group of ATP to the sulfur atom of methionine. In certain embodiments, its EC number is 2.5.1.6. In certain embodiments, its sequence is according to GenBank locus AAB67461 or *S. cerevisiae* YLR180W.

As used herein, the terms "S-adenosylmethionine synthetase" and "SAM2" or "Sam2" or "ETH2" or "Eth2" refer to an encoding nucleic acid and an S-adenosylmethionine synthetase that catalyzes transfer of the adenosyl group of ATP to the sulfur atom of methionine. In certain embodiments, its EC number is 2.5.1.6. In certain embodiments, its sequence is according to NCBI Reference Sequence AAT93205.1 or *S. cerevisiae* YDR502C. Sam1 and Sam2 are paralogs and will be identified by their abbreviations herein.

As used herein, the terms "S-adenosyl-L-homocysteine hydrolase" and "SAH1" or "Sah1" refer to an encoding nucleic acid and an S-adenosyl-L-homocysteine hydrolase that catabolizes S-adenosyl-L-homocysteine which is formed after donation of the activated methyl group of S-adenosyl-L-methionine (AdoMet) to an acceptor. In certain embodiments, its EC number is 3.3.1.1. In certain embodiments, its sequence is according to GenBank locus X07238 or *S. cerevisiae* YER043C.

As used herein, the terms "cobalamin-independent methionine synthase" and "MET6" or "Met6" refer to an encoding nucleic acid and a cobalamin-independent methionine synthase that is involved in methionine biosynthesis and regeneration and requires a minimum of two glutamates on the methyltetrahydrofolate substrate. In certain embodiments, its EC number is 2.1.1.14. In certain embodiments, its sequence is according to GenBank locus AY692801 or *S. cerevisiae* YER091C.

As used herein, the terms "cytosolic serine hydroxymethyltransferase" and "SHM2" or "Shm2" refer to an encoding nucleic acid and a cytosolic serine hydroxymethyltransferase that converts serine to glycine plus 5,10 methylenetetrahydrofolate. In certain embodiments, its EC number is 2.1.2.1. In certain embodiments, its sequence is according to GenBank locus AAB68164 or *S. cerevisiae* YLR058C.

As used herein, the term "MET12" or "Met12" refers to an encoding nucleic acid and an isozyme of methylenetetrahydrofolate reductase (MTHFR). In certain embodiments, its EC number is 1.5.1.20. In certain embodiments, its sequence is according to NCBI Reference Sequence NP_013159 or *S. cerevisiae* YPL023C.

As used herein, the term "MET13" or "Met13" refers to an encoding nucleic acid and an isozyme of methylenetetrahydrofolate reductase (MTHFR). In certain embodiments, its EC number is 1.5.1.20. In certain embodiments, its sequence is according to GenBank locus Z72647 or *S. cerevisiae* YGL125W.

As used herein, the terms "NADPH-dependent medium chain alcohol dehydrogenase" and "ADH6" or "Adh6" refer to an encoding nucleic acid and an alcohol dehydrogenase. In certain embodiments, its EC number is 1.1.1.2. In certain embodiments, its sequence is according to GenBank locus CAA90836 or *S. cerevisiae* YMR318C.

As used herein, the terms "3-methylbutanal reductase" and "NADPH-dependent methylglyoxal reductase" and "GRE2" or "Gre2" refer to an encoding nucleic acid and a 3-methylbutanal reductase and NADPH-dependent methylglyoxal reductase. In certain embodiments, its EC number is 1.1.1.265 or 1.1.1.283. In certain embodiments, its sequence is according to NCBI reference sequence NP_014490 or *S. cerevisiae* YOL151W.

As used herein, the term "YGL039W" refers to an encoding nucleic acid and an aldehyde reductase. Its systematic name is YGL039W. In certain embodiments, its sequence is according to GenBank reference Z72561.

As used herein, the terms "dihydrofolate reductase" and "DHFR" refer to an encoding nucleic acid and a dihydrofolate reductase. In certain embodiments, its EC number is 1.5.1.3. In certain embodiments, DHFR is from *Mus musculus*. In certain embodiments, the DHFR sequence is according to NCBI reference sequence NP_034179.

As used herein, the terms "3-dehydroquinate synthase" and "AroB" refer to an encoding nucleic acid and a 3-dehydroquinate synthase. In certain embodiments, its EC number is 4.2.3.4. In certain embodiments, AroB is from *E. coli*. In certain embodiments, the AroB sequence is according to UniProtKB P07639.

As used herein, the terms "3-dehydroquinate dehydratase" and "AroD" refer to an encoding nucleic acid and a 3-dehydroquinate dehydratase. In certain embodiments, its EC number is 4.2.1.10. In certain embodiments, AroD is from *E. coli*. In certain embodiments, the AroD sequence is according to UniProtKB P05194.

As used herein, the terms "phospho-2-dehydro-3-deoxyheptonate aldolase, Tyr-sensitive" and "AroF" refer to an encoding nucleic acid and a phospho-2-dehydro-3-deoxyheptonate aldolase. In certain embodiments, its EC number is 2.5.1.54. In certain embodiments, AroF is from *E. coli*. In certain embodiments, the AroF sequence is according to UniProtKB P00888. In certain embodiments, the AroF is feedback resistant (J. Bacteriol. November 1990 172:6581-6584).

As used herein, the terms "3-dehydroshikimate dehydratase" and "AroZ" refer to an encoding nucleic acid and a 3-dehydroshikimate dehydratase. In certain embodiments, its EC number is 4.2.1.118. In certain embodiments, AroZ is from *Podospora pauciseta*. In certain embodiments, the AroZ sequence is according to Hansen et al., Appl Environ Microbiol. 2009 (May) 75 (9): 2765-74.

As used herein, the terms "phosphopantetheinyl transferase" and "PPTASE" refer to an encoding nucleic acid and a phosphopantetheinyl transferase. In certain embodiments, its EC number is 2.7.8.7. In certain embodiments, PPTASE is from *Corynebacterium glutamicum*. In certain embodiments, the PPTASE sequence is according to UniProtKB Q8NP45.

As used herein, the terms "aromatic carboxylic acid reductase" and "ACAR" refer to an encoding nucleic acid and an aromatic carboxylic acid reductase. In certain embodiments, its EC number is 1.2,1.30. In certain embodiments, ACAR is from *Nocardia iowensis*. In certain embodiments, the ACAR sequence is according to UniProtKB Q6RKB1. In certain embodiments, ACAR is from Table 3 below.

As used herein, the terms "O-methyl transferase" and "OMT" refer to an encoding nucleic acid and an O-methyl transferase. In certain embodiments, OMT is from *Hordeum vulgare* or from *Brassica napus*. In certain embodiments, the OMT sequence is according to UniProtKB F2E2Z7 (*Hordeum vulgare*) or A0A078HEB0 (*Brassica napus*). In certain embodiments, OMT is from Table 2 below.

As used herein, the terms "eugenol alcohol oxidase" and "EAO" refer to an encoding nucleic acid and a eugenol alcohol oxidase. In certain embodiments, EAO is from *Rhodococcus jostii*. In certain embodiments, the EAO sequence is according to UniProtKB Q0SBK1.

As used herein, the terms "UDP-glycosyltransferase" and "UGT" refer to an encoding nucleic acid and a UDP-glycosyltransferase. In certain embodiments, its EC number is 2.4.1.126. In certain embodiments, the UGT is from *Arabidopsis thaliana*. In certain embodiments, the UGT is *A. thaliana* UGT72E2. In certain embodiments, the UGT sequence is according to UniProtKB Q9LVR1.

As used herein, the term "parent cell" refers to a cell that has an identical genetic background as a genetically modified host cell disclosed herein except that it does not comprise one or more particular genetic modifications engineered into the modified host cell, for example, one or more modifications selected from the group consisting of: heterologous expression of an enzyme of a vanillin pathway, heterologous expression of an enzyme of a glucovanillin pathway; or heterologous expression of SAM1, SAM2, SAH1, MET6, SHM2, MET12, MET13, a MET13 chimera, AroB, AroD, AroF, AroZ, PPTASE, ACAR, OMT, EAO, or UGT; or deletion of ADH6, GRE2, or YGL039W.

As used herein, the term "naturally occurring" refers to what is found in nature. For example, gene product that is present in an organism that can be isolated from a source in nature and that has not been intentionally modified by a human in the laboratory is naturally occurring gene product. Conversely, as used herein, the term "non-naturally occurring" refers to what is not found in nature but is created by human intervention. In certain embodiments, naturally occurring genomic sequences are modified, e.g. codon optimized, for use in the organisms provided herein.

The term "medium" refers to a culture medium and/or fermentation medium.

The term "fermentation composition" refers to a composition which comprises genetically modified host cells and products or metabolites produced by the genetically modified host cells. An example of a fermentation composition is a whole cell broth, which can be the entire contents of a vessel (e.g., a flasks, plate, or fermentor), including cells, aqueous phase, and compounds produced from the genetically modified host cells.

As used herein, the term "production" generally refers to an amount of vanillin or a derivative thereof produced by a genetically modified host cell provided herein. Derivatives can include glucovanillin, vanillyl alcohol, and/or vanillic acid. In some embodiments, production is expressed as a yield of vanillin or glucovanillin by the host cell. In other embodiments, production is expressed as the productivity of the host cell in producing the vanillin or glucovanillin.

As used herein, the term "productivity" refers to production of a vanillin or a derivative thereof by a host cell, expressed as the amount of vanillin or glucovanillin produced (by weight) per amount of fermentation broth in which the host cell is cultured (by volume) over time (per hour). Derivatives can include glucovanillin, vanillyl alcohol, and/or vanillic acid.

As used herein, the term "yield" refers to production of a vanillin or a derivative thereof by a host cell, expressed as the amount of vanillin or glucovanillin produced per amount of carbon source consumed by the host cell, by weight. Derivatives can include glucovanillin, vanillyl alcohol, and/or vanillic acid.

As used herein, the term "titer" refers to production of a vanillin or a derivative thereof by a host cell, expressed as the amount of vanillin or glucovanillin or other derivative produced per volume of media. Derivatives can include glucovanillin, vanillyl alcohol, and/or vanillic acid.

As used herein, the term "an undetectable level" of a compound (e.g., vanillic acid, or other compounds) means a level of a compound that is too low to be measured and/or analyzed by a standard technique for measuring the compound. For instance, the term includes the level of a compound that is not detectable by the typical analytical methods known in the art.

The term "vanillin" refers to the compound vanillin, including any stereoisomer of vanillin. The chemical name of vanillin is 4-hydroxy-3-methoxybenzaldehyde. In particular embodiments, the term refers to the compound according to the following structure:

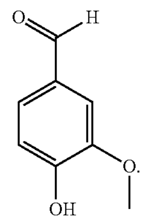

The term "vanillyl alcohol" refers to the compound vanillyl alcohol, including any stereoisomer of vanillyl alcohol. The chemical name of vanillyl alcohol is 4-(hydroxymethyl)-2-methoxyphenol. In particular embodiments, the term refers to the compound according to the following structure:

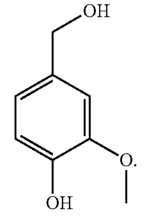

The term "vanillic acid" refers to the compound vanillic acid, including any stereoisomer of vanillic acid. The chemical name of vanillic acid is 4-hydroxy-3-methoxybenzoic acid. In particular embodiments, the term refers to the compound according to the following structure:

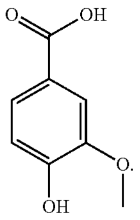

The term "glucovanillin" refers to the compound glucovanillin, including any stereoisomer of glucovanillin. The chemical name of glucovanillin is 3-methoxy-4-[(2S,3R,4S,5S,6R)-3,4,5-trihydroxy-6-(hydroxymethyl) oxan-2-yl]oxybenzaldehyde. In particular embodiments, the term refers to the compound according to the following structure:

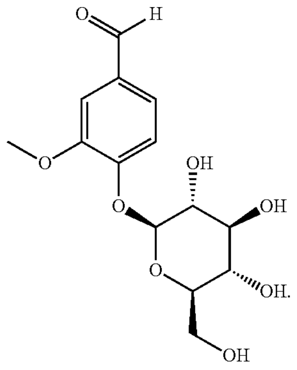 [SMILES: COc1cc(C=O)ccc1O[C@@H]1O[C@H](CO)[C@@H](O)[C@H](O)[C@H]1O]

The term "protecatechuic acid" refers to the compound protecatechuic acid, including any stereoisomer of protecatechuic acid. The chemical name of protecatechuic acid is 3,4-dihydroxybenzoic acid. In particular embodiments, the term refers to the compound according to the following structure:

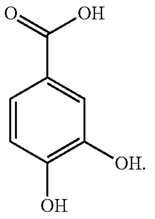 [SMILES: O=C(O)c1ccc(O)c(O)c1]

As used herein, the term "variant" refers to a polypeptide differing from a specifically recited "reference" polypeptide (e.g., a wild-type sequence) by amino acid insertions, deletions, mutations, and/or substitutions, but retains an activity that is substantially similar to the reference polypeptide. In some embodiments, the variant is created by recombinant DNA techniques or by mutagenesis. In some embodiments, a variant polypeptide differs from its reference polypeptide by the substitution of one basic residue for another (i.e. Arg for Lys), the substitution of one hydrophobic residue for another (i.e. Leu for Ile), or the substitution of one aromatic residue for another (i.e. Phe for Tyr), etc. In some embodiments, variants include analogs wherein conservative substitutions resulting in a substantial structural analogy of the reference sequence are obtained. Examples of such conservative substitutions, without limitation, include glutamic acid for aspartic acid and vice-versa; glutamine for asparagine and vice-versa; serine for threonine and vice-versa; lysine for arginine and vice-versa; or any of isoleucine, valine or leucine for each other.

As used herein, the term "sequence identity" or "percent identity," in the context or two or more nucleic acid or protein sequences, refers to two or more sequences or subsequences that are the same or have a specified percentage of amino acid residues or nucleotides that are the same. For example, the sequence can have a percent identity of at least 60%, at least 65%, at least 70%, at least 75%, at least 80%, at least 85%, at least 90%, at least 91% at least 92%, at least 93%, at least 94%, at least 95%, at least 96%, at least 97%, at least 98%, at least 99%, or higher identity over a specified region to a reference sequence when compared and aligned for maximum correspondence over a comparison window, or designated region as measured using a sequence comparison algorithm or by manual alignment and visual inspection. For example, percent of identity is determined by calculating the ratio of the number of identical nucleotides (or amino acid residues) in the sequence divided by the length of the total nucleotides (or amino acid residues) minus the lengths of any gaps.

For convenience, the extent of identity between two sequences can be ascertained using computer programs and mathematical algorithms known in the art. Such algorithms that calculate percent sequence identity generally account for sequence gaps and mismatches over the comparison region. Programs that compare and align sequences, like Clustal W (Thompson et al., (1994) *Nucleic Acids Res.,* 22:4673-4680), ALIGN (Myers et al., (1988) *CABIOS,* 4:11-17), FASTA (Pearson et al., (1988) *PNAS,* 85:2444-2448; Pearson (1990), *Methods Enzymol.,* 183:63-98) and gapped BLAST (Altschul et al., (1997) *Nucleic Acids Res.,* 25:3389-3402) are useful for this purpose. The BLAST or BLAST 2.0 (Altschul et al., *J. Mol. Biol.* 215:403-10, 1990) is available from several sources, including the National Center for Biological Information (NCBI) and on the Internet, for use in connection with the sequence analysis programs BLASTP, BLASTN, BLASTX, TBLASTN, and TBLASTX. Additional information can be found at the NCBI web site.

In certain embodiments, the sequence alignments and percent identity calculations can be determined using the BLAST program using its standard, default parameters. For nucleotide sequence alignment and sequence identity calculations, the BLASTN program is used with its default parameters (Gap opening penalty=5, Gap extension penalty=2, Nucleic match=2, Nucleic mismatch=−3, Expectation value=10.0, Word size=11, Max matches in a query range=0). For polypeptide sequence alignment and sequence identity calculations, BLASTP program is used with its default parameters (Alignment matrix=BLOSUM62; Gap costs: Existence=11, Extension=1; Compositional adjustments=Conditional compositional score, matrix adjustment; Expectation value=10.0; Word size=6; Max matches in a query range=0). Alternatively, the following program and parameters can be used: Align Plus software of Clone Manager Suite, version 5 (Sci-Ed Software); DNA comparison: Global comparison, Standard Linear Scoring matrix, Mismatch penalty=2, Open gap penalty=4, Extend gap penalty=1. Amino acid comparison: Global comparison, BLOSUM 62 Scoring matrix. In the embodiments described herein, the sequence identity is calculated using BLASTN or BLASTP programs using their default parameters. In the embodiments described herein, the sequence alignment of two or more sequences are performed using Clustal W using the suggested default parameters (Dealign input sequences: no; Mbed-like clustering guide-tree: yes; Mbed-like clustering iteration: yes; number of combined iterations: default(0); Max guide tree iterations: default; Max HMM iterations: default; Order: input).

Nucleic Acids, Expression Cassettes, and Host Cells

In one aspect, provided herein are nucleic acids, expression vectors, and host cells which express one or more enzymes useful for the production of vanillin and/or glucovanillin. In another aspect, provided herein are host cells comprising one or more deletions in genes wherein the one or more deletions are useful for the production of vanillin and/or glucovanillin. In a further aspect, provided herein are host cells that comprise one or more of the deletions and further comprise one or more of the enzymes. The enzymes and deletions are described in detail herein. In certain embodiments, the host cells can produce vanillin and/or glucovanillin from a carbon source in a culture medium. In certain embodiments, the host cells provide improved yield and/or productivity compared to a parent strain. In certain embodiments, the host cells provide byproducts, intermediates, and/or side products, e.g. vanillic acid, compared to a parent strain. Exemplary byproducts, intermediates, and/or side products include vanillic acid, vanillyl alcohol, glucovanillic acid, glucovanillyl alcohol, and protocatechuic aldehyde.

In certain embodiments, host cells according to the embodiments herein produce at least 5%, at least 10%, at least 15%, at least 20%, or at least 25% more total vanillin or glucovanillin compared to a parent strain. In certain embodiments, host cells according to the embodiments herein produce at least 5%, at least 10%, at least 15%, at least 20%, at least 25% more total vanillin compared to a parent strain. In certain embodiments, host cells according to the embodiments herein produce at least 5%, at least 10%, at least 15%, at least 20%, at least 25% more total glucovanillin compared to a parent strain. In certain embodiments, host cells according to the embodiments herein produce 2-fold, 3-fold, 4-fold, 5-fold, or 10-fold less vanillic acid compared to a parent strain. In certain embodiments, the percent increases are with respect to vanillin or glucovanillin titer (g/L). In certain embodiments, the percent increases are with respect to vanillin or glucovanillin yield (weight %). In certain embodiments, the percent increases are with respect to vanillin or glucovanillin productivity (g/L/h). In certain embodiments, the percent increases are with respect to vanillin or glucovanillin total mass produced (g). Those of skill will recognize that the total vanillin and/or glucovanillin produced can be measured as a sum of the actual compounds produced and any downstream compounds produced from the vanillin and/or glucovanillin, as shown in the Examples and Figures herein. In certain embodiments, host cells according to the embodiments herein produce increased vanillin and/or glucovanillin, and produce less vanillic acid, compared to a parent strain.

In advantageous embodiments, the host cell comprises one or more enzymatic pathways capable of making vanillin and/or glucovanillin, said pathways taken individually or together.

In one aspect, provided herein are genetically modified host cell capable of producing vanillin or glucovanillin, and/or one or more derivatives thereof, comprising one, two, three, or four of: (a) one or more nucleic acids capable of overexpressing one or more genes selected from SAM1, SAM2, SAH1, and MET6; (b) one or more nucleic acids expressing OMT, for instance according to Table 2, for example either *Hordeum vulgare* OMT or *Brassica napus* OMT, or both *Hordeum vulgare* OMT and *Brassica napus* OMT; (c) one or more nucleic acids expressing *Rhodococcus jostii* EAO; and (d) one or more nucleic acids expressing chimeric MET13. The cells can comprise any of (a) through (d) in any combination. In certain embodiments, the cells comprise (a) and (b). In certain embodiments, the cells comprise (a) and (c). In certain embodiments, the cells comprise (a) and (d). In certain embodiments, the cells comprise (b) and (c). In certain embodiments, the cells comprise (b) and (d). In certain embodiments, the cells comprise (c) and (d). In certain embodiments, the cells comprise (a), (b), and (c). In certain embodiments, the cells comprise (a), (b), and (d). In certain embodiments, the cells comprise (a), (c), and (d). In certain embodiments, the cells comprise (b), (c), and (d). In certain embodiments, the cells comprise (a), (b), (c), and (d).

In another aspect, provided herein are host cells that overexpress one or more genes selected from SAM1, SAM2, SAH1, and MET6. As shown in FIG. 1, protocatechuic acid (PCA) is methylated by an O-methyltransferase with cosubstrate S-adenosylmethionine (SAM) to form vanillic acid and S-adenosylhomocysteine (SAH). In the cell, SAH is regenerated to SAM in the SAM regeneration pathway. As demonstrated in the examples below, overexpression of the SAM regeneration pathway enhanced yield and productivity of vanillin and/or glucovanillin. Accordingly, provided herein are host cells that overexpress one or more of SAM1, SAM2, SAH1, and MET6. In certain embodiments, one gene is overexpressed. In certain embodiments, two genes are overexpressed. In certain embodiments, three genes are overexpressed. In certain embodiments, four genes are overexpressed. In particular embodiments, the host cells are *S. cerevisiae*, and the overexpressed proteins are native. In other host cells, homologs of SAM1, SAM2, SAH1, and/or MET6 can be overexpressed. In certain embodiments, the overexpressed genes are native or codon optimized *S. cerevisiae* genes.

Figure 2:
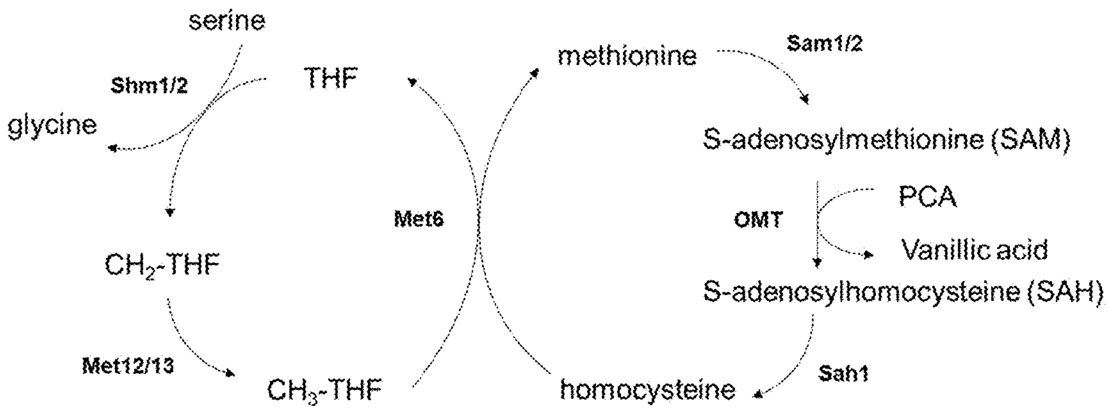
FIG. 2 is a schematic showing an enzymatic pathway from a native yeast whereby Shm2 and Met12/Met13 catalyze the transfer of a $C_1$ unit to tetrahydrofolate (THF) and subsequent reduction to 5-methyltetrahydrofolate, which in turn acts as a methyl donor in a Met6 reaction that regenerates methionine from homocysteine.

In another aspect, provided herein are host cells that overexpress one or more genes selected from SHM2, MET12, MET13, and MET6. As shown in FIG. 2, in the SAM regeneration pathway, Met6 catalyzes the conversion of homocysteine to methionine. Methionine is then converted to SAM. In the Met6 reaction, a methyl group is provided by cosubstrate methyl-tetrahydrofolate ($CH_3$-THF). THE is then regenerated to methyl tetrahydrofolate by SHM1, SHM2, MET12, and MET13. Accordingly, provided herein are host cells that overexpress one or more of SHM2, MET12, MET13, and MET6. In certain embodiments, one gene is overexpressed. In certain embodiments, two genes are overexpressed. In certain embodiments, three genes are overexpressed. In certain embodiments, four genes are overexpressed. In particular embodiments, the host cells are *S. cerevisiae*, and the overexpressed genes are *S. cerevisiae* genes or optimized *S. cerevisiae* genes. In other host cells, homologs of SHM2, MET12, MET13, and MET6 can be overexpressed. In certain embodiments, the overexpressed genes are native or codon optimized *S. cerevisiae* genes.

In another aspect, provided herein are host cells that express one or more heterologous O-methyltransferases (OMTs). As shown in FIGS. 1 and 2, OMT catalyzes the conversion of protocatechuic acid (PCA) to vanillic acid. The OMT can be any OMT deemed useful by those of skill. In advantageous embodiments, the OMT has specificity for the correct-OH group of protocatechuic acid. In other words, in advantageous embodiments, the OMT forms more vanillic acid and less vanillic acid in this reaction. In certain embodiments, OMT is *Hordeum vulgare* OMT. In certain embodiments, the OMT is *Brassica napus* OMT. As described herein, these OMTs provide excellent specificity for the correct-OH group and minimize formation of vanillic acid. In certain embodiments, provided herein are host cells that express *Hordeum vulgare* OMT. In certain embodiments, provided herein are host cells that express *Brassica napus* OMT. In certain embodiments, provided herein are host cells that overexpress *Hordeum vulgare* OMT. In certain embodiments, provided herein are host cells that overexpress *Brassica napus* OMT. In certain embodiments, provided herein are host cells that express both *Hordeum vulgare* OMT and *Brassica napus* OMT. In certain embodiments, provided herein are host cells that overexpress both *Hordeum vulgare* OMT and *Brassica napus* OMT. In certain embodiments, the host cells express one or more OMTs from Table 2, below.

In certain embodiments, provided herein are genetically modified host cells capable of producing vanillin or glucovanillin where the host cell expresses a MET13 chimera. In certain embodiments, the MET13 chimera comprises a yeast N-terminal domain and an *Arabidopsis* MTHFR C-terminal domain. The *Arabidopsis* MTHFR enzyme typically has little or no sensitivity to SAM inhibition. Accordingly, in certain embodiments, the chimera provided herein is not sensitive to SAM inhibition. In certain embodiments, the N-terminal domain is a catalytic domain. In certain embodiments, the C-terminal domain is a regulatory domain. Details are provided in Roje et al., *J. Biol. Chem.,* 2002; 277 (6): 4056-4061, incorporated by reference in its entirety. In certain embodiments, the two domains are linked by a bridge domain. In certain embodiments, the yeast N-terminal domain is from *S. cerevisiae* and the MTHFR C-terminal domain is from *A. thaliana*. In particular embodiments, the genetically modified host cell expresses further enzymes sufficient to produce vanillin or glucovanillin. Useful enzymes are described herein.

In particular embodiments, the above aspects are combined. In other words, provided herein are host cells that express or overexpress one or more of SAM1, SAM2, SAH1, MET6, SHM2, MET12, MET13, MET13 chimera, and OMT(s). In certain embodiments, two copies of MET6 are overexpressed. In certain embodiments, at least one gene is overexpressed. In certain embodiments, at least two genes are overexpressed. In certain embodiments, at least three genes are overexpressed. In certain embodiments, at least four genes are overexpressed. In certain embodiments, at least five genes are overexpressed. In certain embodiments, at least five genes are overexpressed, including two copies of MET6. In particular embodiments, the host cells are *S. cerevisiae*, and the overexpressed *S. cerevisiae* genes are native or optimized. In other host cells, homologs of SAM1, SAM2, SAH1, MET6, SHM2, MET12, MET13, MET13 chimera, and/or OMT(s) can be overexpressed.

In further embodiments, the above host cells further comprise one or more deletions and/or one or more expressed genes useful for the production of vanillin and/or glucovanillin.

In certain embodiments, the host cells further comprise deletion of ADH6. In host cells other than *S. cerevisiae*, a homolog of ADH6 is deleted. Preferably, all copies of ADH6 are deleted. For instance, in haploid cells with one copy of ADH6, that copy is deleted. In diploid cells with two copies of ADH6, both copies are deleted. In any cells with multiple copies of ADH6, each copy is preferably deleted. The ADH6 gene(s) can be deleted by any technique apparent to those of skill in the art. Useful techniques include those based on homologous recombination and polymerase chain reaction (PCR).

In certain embodiments, the host cells further comprise deletion of GRE2. In host cells other than *S. cerevisiae*, a homolog of GRE2 is deleted. Preferably, all copies of GRE2 are deleted. For instance, in haploid cells with one copy of GRE2, that copy is deleted. In diploid cells with two copies of GRE2, both copies are deleted. In any cells with multiple copies of GRE2, each copy is preferably deleted. The GRE2 gene(s) can be deleted by any technique apparent to those of skill in the art. Useful techniques include those based on homologous recombination and polymerase chain reaction (PCR).

In certain embodiments, the host cells further comprise deletion of YGL039W. In host cells other than *S. cerevisiae*, a homolog of YGL039W is deleted. Preferably, all copies of YGL039W are deleted. For instance, in haploid cells with one copy of YGL039W, that copy is deleted. In diploid cells with two copies of YGL039W, both copies are deleted. In any cells with multiple copies of YGL039W, each copy is preferably deleted. The YGL039W gene(s) can be deleted by any technique apparent to those of skill in the art. Useful techniques include those based on homologous recombination and polymerase chain reaction (PCR).

In particular embodiments, the host cells further comprise enzymes of a pathway useful for the production of vanillin or glucovanillin. Such pathway enzymes have been described previously, including those described in Hansen et al., *Appl. Environ. Microbiol.* (2009) 75 (9): 2765-2774; U.S. Pat. No. 6,372,461 B1; U.S. Pat. No. 10,066,252 B1; U.S. Pat. No. 10,208,293 B2; each of which are incorporated by reference in their entireties.

In certain embodiments, the host cells further comprise a 3-dehydroquinate synthase, or AroB. Useful AroB genes and enzymes are known. Useful AroB polypeptides are also known. Useful AroB genes and enzymes include those of *E. coli*. Examples can be found at UniProtKB P07639. In preferred embodiments, the host cells further express or overexpress *E. coli* AroB.

In certain embodiments, the host cells further comprise a 3-dehydroquinate dehydratase, or AroD. Useful AroD genes and enzymes are known. Useful AroD polypeptides are also known. Useful AroD genes and enzymes include those of *E. coli*. Examples can be found at UniProtKB P05194. In preferred embodiments, the host cells further express or overexpress *E. coli* AroD.

In certain embodiments, the host cells further comprise a phospho-2-dehydro-3-deoxyheptonate aldolase, Tyr-sensitive, or AroF. Useful AroF genes and enzymes are known. Useful AroB polypeptides are also known. Useful AroF genes and enzymes include those of *E. coli*. Examples can be found at UniProtKB P00888. In preferred embodiments, the host cells further express or overexpress *E. coli* AroF. In certain embodiments, the AroF is feedback resistant (*J. Bacteriol.* November 1990 172:6581-6584, incorporated by reference in its entirety).

In certain embodiments, the host cells further comprise a 3-dehydroshikimate dehydratase, or AroZ. Useful AroZ genes and enzymes are known. Useful 3DSD polypeptides are also known. Useful AroZ genes and enzymes include those of *Podospora pauciseta, Ustilago maydis, Rhodoicoccus jostii, Acinetobacter* sp., *Aspergillus niger* and *Neurospora crassa*. Examples can be found at GenBank Accession Nos. CAD60599, XP_001905369.1, XP_761560.1, ABG93191.1, AAC37159.1, and XM_001392464. In preferred embodiments, the host cells further express or overexpress *Podospora pauciseta* AroZ.

In certain embodiments, the host cells further comprise an ACAR. Useful ACAR genes and enzymes are known. Useful ACAR polypeptides are also known. Useful ACAR genes and enzymes include those of *Nocardia* sp. Examples can be found at GenBank Accession No. AY495697. In preferred embodiments, the host cells further express or overexpress *Nocardia iowensis* ACAR. In certain embodiments, the host cells express one or more ACAR enzyme in Table 3 below.

In certain embodiments, the host cells further comprise an PPTASE. Useful PPTASE genes and enzymes are known. Useful PPTASE polypeptides are also known. Useful PPTASE genes and enzymes include those of *E. coli, Corynebacterium glutamicum*, and *Nocardia farcinica*. Examples can be found at GenBank Accession Nos. NP_601186, BAA35224, and YP_120266. In preferred embodiments, the host cells further express or overexpress *Cornybacterium glutamicum* PPTASE.

In certain embodiments, the host cells are capable of converting vanillyl alcohol to vanillin. This reduces the amount of the side product vanillyl alcohol and increases the amount of vanillin. Useful oxidase genes and enzymes are known. Suitable oxidase polypeptides are known. Useful oxidase genes and enzymes include those of *Penicillium simplicissimum* and *Rhodococcus jostii*. In preferred embodiments, the host cells further express or overexpress *Rhodococcus jostii* eugenal alcohol oxidase (EAO).

In certain embodiments, the host cells are capable of glucosylating vanillin to form glucovanillin. Glucovanillin is a storage form of vanillin found in the vanilla pod. It is non-toxic to most organisms, including yeast, and has a higher solubility in water, as compared to vanillin. In addition, the formation of vanillin-β-D-glucoside most likely directs biosynthesis toward vanillin production. Useful UGT genes and enzymes for this conversion are known. Useful UGT enzymes according to the invention are classified under EC 2.4.1. Suitable UGT polypeptides include the UGT71C2, UGT72B1, UGT72E2, UGT84A2, UGT89B1, UGT85B1, and arbutin synthase polypeptides, at, for example, GenBank Accession Nos. AC0005496, NM_116337, and NM_126067. In certain embodiments, the host cells further express or overexpress one or more of UGT71C2, UGT72B1, UGT72E2, UGT84A2, UGT89B1, UGT85B1, and arbutin synthase. In preferred embodiments, the host cells further express or overexpress *A. thaliana* UGT72E2.

Overexpression can be according to any technique apparent to those of skill in the art. In certain embodiments, the genes are overexpressed from a promoter useful in the host cell. In certain embodiments, the genes are overexpressed from a *S. cerevisiae* promoter. In certain embodiments, the promoter is selected from the group consisting of pPGK1, pTDH3, pENO2, pADH1, pTPI1, pTEF1, pTEF2, pTEF3, pGAL1, pGAL2, pGAL7, pGAL10, GALI, pRPL3, pRPL15A, pRPL4, pRPL8B, pSSA1, pSSB1, pCUP1, pTPS1, pHXT7, pADH2, pCYC1, and pPDA1. In certain embodiments, the genes are overexpressed from a GAL promoter. In certain embodiments, the genes are overexpressed from a promoter selected from the group consisting of pGAL1, pGAL2, pGAL7, pGAL10, and variants thereof.

In certain embodiments, one, some, or all of the heterologous promoters in the host cells are inducible. The inducible promoter system can be any recognized by those of skill in the art. In particular embodiments, the promoters are inducible by maltose. In an advantageous embodiment, the host cells comprise a GAL regulon that is inducible by maltose. Examples of the Gal regulon which are further repressed or induced by a maltose are described in PCT Application Publications WO2015/020649, WO2016/210343, and WO2016210350, each of which is incorporated by reference in its entirety. In certain embodiment, a maltose switchable strain is built on top of a non-switchable strain by chromosomally integrating a copy of GAL80 under the control of a maltose-responsive promoter such as pMAL32. In certain embodiments, the GAL80 gene product is mutated for temperature sensitivity, e.g. to facilitate further control. In certain embodiments, the GAL80 gene product is fused to a temperature-sensitive polypeptide. In certain embodiments, the GAL80 gene product is fused to a temperature-sensitive DHFR polypeptide or fragment. Additional description of switchable farnesene producing switchable strains are described in U.S. Patent Application Publication No. US 2016/0177341 and PCT Application Publication No. WO 2016/210350, each of which is incorporated herein by reference in its entirety.

For each of the polypeptides and nucleic acids described above, the host cells can comprise variants thereof. In certain embodiments, the variant can comprise up to 15, 10, 9, 8, 7, 6, 5, 4, 3, 2, or 1 amino acid substitutions relative to the relevant polypeptide. In certain embodiments, the variant can comprise up to 15, 10, 9, 8, 7, 6, 5, 4, 3, 2, or 1 conservative amino acid substitutions relative to the reference polypeptide. In certain embodiments, any of the nucleic acids described herein can be optimized for the host cell, for instance codon optimized. Variants and optimization are described in detail below.

In certain embodiments, the additional enzymes are native, unless specified otherwise above. Native enzymes can be expressed from codon optimized nucleic acids. In advantageous embodiments, the additional enzymes are heterologous. In certain embodiments, two or more enzymes can be combined in one polypeptide.

Cell Strains

Host cells useful compositions and methods provided herein include archae, prokaryotic, or eukaryotic cells.

Suitable prokaryotic hosts include, but are not limited, to any of a variety of gram-positive, gram-negative, or gram-variable bacteria. Examples include, but are not limited to, cells belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphylococcus, Strepromyces, Synnecoccus*, and *Zymomonas*. Examples of prokaryotic strains include, but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei*, and *Staphylococcus aureus*. In a particular embodiment, the host cell is an *Escherichia coli* cell.

Suitable archae hosts include, but are not limited to, cells belonging to the genera: *Aeropyrum, Archaeglobus, Halobacterium, Methanococcus, Methanobacterium, Pyrococ-* cus, Sulfolobus*, and *Thermoplasma*. Examples of archae strains include, but are not limited to: *Archaeoglobus fulgidus, Halobacterium* sp., *Methanococcus jannaschii, Methanobacterium thermoautotrophicum, Thermoplasma acidophilum, Thermoplasma volcanium, Pyrococcus horikoshii, Pyrococcus abyssi*, and *Aeropyrum pernix*.

Suitable eukaryotic hosts include, but are not limited to, fungal cells, algal cells, insect cells, and plant cells. In some embodiments, yeasts useful in the present methods include yeasts that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis*, and *Zygozyma*, among others.

In some embodiments, the host microbe is *Saccharomyces cerevisiae, Pichia pastoris, Schizosaccharomyces pombe, Dekkera bruxellensis, Kluyveromyces lactis* (previously called *Saccharomyces lactis*), *Kluveromyces marxianus, Arxula adeninivorans*, or *Hansenula polymorpha* (now known as *Pichia angusta*). In some embodiments, the host microbe is a strain of the genus *Candida*, such as *Candida lipolytica, Candida guilliermondii, Candida krusei, Candida pseudotropicalis*, or *Candida utilis*.

In a particular embodiment, the host microbe is *Saccharomyces cerevisiae*. In some embodiments, the host is a strain of *Saccharomyces cerevisiae* selected from the group consisting of Baker's yeast, CEN.PK, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1, and AL-1. In some embodiments, the host microbe is a strain of *Saccharomyces cerevisiae* selected from the group consisting of PE-2, CAT-1, VR-1, BG-1, CR-1, and SA-1. In a particular embodiment, the strain of *Saccharomyces cerevisiae* is PE-2. In another particular embodiment, the strain of *Saccharomyces cerevisiae* is CAT-1. In another particular embodiment, the strain of *Saccharomyces cerevisiae* is BG-1.

In some embodiments, the host microbe is a microbe that is suitable for industrial fermentation. In particular embodiments, the microbe is conditioned to subsist under high solvent concentration, high temperature, high pressure, expanded substrate utilization, nutrient limitation, osmotic stress due to sugar and salts, acidity, sulfite and bacterial contamination, or combinations thereof, which are recognized stress conditions of the industrial fermentation environment.

Methods of Producing Vanillin or Glucovanillin

In another aspect, provided herein is a method for the production of a vanillin or glucovanillin, the method comprising the steps of: (a) culturing a population of any of the genetically modified host cells described herein that are capable of producing a vanillin or glucovanillin in a medium with a carbon source under conditions suitable for making the vanillin or glucovanillin compound; and (b) recovering said vanillin or glucovanillin compound from the medium. Those of skill will recognize that the amount of a compound produced can be evaluated by measuring the amount of the compound itself, or more preferably the amount of the compound and derivatives of the compound. For instance, the amount of vanillin produced can be evaluated from the total amount of vanillin, vanillyl alcohol, glucovanillin, and glucovanillyl alcohol produced.

In some embodiments, the genetically modified host cell produces an increased amount of the vanillin or glucovanillin, or derivative thereof such as vanillyl alcohol or glucovanillyl alcohol, compared to a parent cell not comprising the one or more modifications, or a parent cell comprising only a subset of the one or more modifications of the genetically modified host cell, but is otherwise genetically identical. In some embodiments, the increased amount is at least 1%, 5%, 10%, 15%, 20%, 25%, 30%, 35%, 40%, 45%, 50%, 55%, 60%, 65%, 70%, 75%, 80%, 85%, 90%, 95%, 100% or greater than 100%, as measured, for example, in yield, production, and/or productivity, in grams per liter of cell culture, milligrams per gram of dry cell weight, on a per unit volume of cell culture basis, on a per unit dry cell weight basis, on a per unit volume of cell culture per unit time basis, or on a per unit dry cell weight per unit time basis.

In some embodiments, the host cell produces an elevated level of a vanillin or glucovanillin, or derivative thereof such as vanillyl alcohol or glucovanillyl alcohol, that is greater than about 0.25 grams per liter of fermentation medium. In some embodiments, the host cell produces an elevated level of a vanillin or glucovanillin, or derivative thereof such as vanillyl alcohol or glucovanillyl alcohol, that is greater than about 0.5 grams per liter of fermentation medium. In some embodiments, the host cell produces an elevated level of a vanillin or glucovanillin, or derivative thereof such as vanillyl alcohol or glucovanillyl alcohol, that is greater than about 0.75 grams per liter of fermentation medium. In some embodiments, the host cell produces an elevated level of a vanillin or glucovanillin, or derivative thereof such as vanillyl alcohol or glucovanillyl alcohol, that is greater than about 1 grams per liter of fermentation medium. In some embodiments, the host cell produces an elevated level of a vanillin or glucovanillin, or derivative thereof such as vanillyl alcohol or glucovanillyl alcohol, that is greater than about 5 grams per liter of fermentation medium. In some embodiments, the host cell produces an elevated level of a vanillin or glucovanillin, or derivative thereof such as vanillyl alcohol or glucovanillyl alcohol, that is greater than about 10 grams per liter of fermentation medium. In some embodiments, the vanillin or glucovanillin, or derivative thereof such as vanillyl alcohol or glucovanillyl alcohol, is produced in an amount from about 10 to about 50 grams, from about 10 to about 15 grams, more than about 15 grams, more than about 20 grams, more than about 25 grams, or more than about 30 grams per liter of cell culture.

In some embodiments, the host cell produces an elevated level of a vanillin or glucovanillin, or derivative thereof such as vanillyl alcohol or glucovanillyl alcohol, that is greater than about 50 milligrams per gram of dry cell weight. In some such embodiments, the vanillin or glucovanillin, or derivative thereof such as vanillyl alcohol or glucovanillyl alcohol, is produced in an amount from about 50 to about 1500 milligrams, more than about 100 milligrams, more than about 150 milligrams, more than about 200 milligrams, more than about 250 milligrams, more than about 500 milligrams, more than about 750 milligrams, or more than about 1000 milligrams per gram of dry cell weight.

In some embodiments, the host cell produces an elevated level of a vanillin or glucovanillin, or derivative thereof such as vanillyl alcohol or glucovanillyl alcohol, that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of vanillin or glucovanillin, or derivative thereof such as vanillyl alcohol or glucovanillyl alcohol, produced by a parent cell, on a per unit volume of cell culture basis.

In some embodiments, the host cell produces an elevated level of a vanillin or glucovanillin, or derivative thereof such as vanillyl alcohol or glucovanillyl alcohol, that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of vanillin or glucovanillin, or derivative thereof such as vanillyl alcohol or glucovanillyl alcohol, produced by the parent cell, on a per unit dry cell weight basis.

In some embodiments, the host cell produces an elevated level of a vanillin or glucovanillin, or derivative thereof such as vanillyl alcohol or glucovanillyl alcohol, that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of vanillin or glucovanillin, or derivative thereof such as vanillyl alcohol or glucovanillyl alcohol, produced by the parent cell, on a per unit volume of cell culture per unit time basis.

In some embodiments, the host cell produces an elevated level of a vanillin or glucovanillin, or derivative thereof such as vanillyl alcohol or glucovanillyl alcohol, that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of vanillin or glucovanillin, or derivative thereof such as vanillyl alcohol or glucovanillyl alcohol, produced by the parent cell, on a per unit dry cell weight per unit time basis.

In most embodiments, the production of the elevated level of vanillin or glucovanillin by the host cell is inducible by the presence of an inducing compound or the absence of a repressing compound. Such a host cell can be manipulated with ease in the absence of the inducing compound or the presence of the repressing compound. The inducing compound is then added, or the repressing compound is diminished, to induce the production of the elevated level of vanillin or glucovanillin by the host cell. In other embodiments, production of the elevated level of vanillin or glucovanillin by the host cell is inducible by changing culture conditions, such as, for example, the growth temperature, media constituents, and the like. In certain embodiments, the vanillin-producing enzymes are repressed by maltose during a growth phase of the cells, and the vanillin-producing enzymes are expressed during an expression phase of the fermentation. Useful promoters and techniques are described in US 2018/0171341 A1, incorporated by reference in its entirety.

Culture Media and Conditions

Materials and methods for the maintenance and growth of microbial cultures are well known to those skilled in the art of microbiology or fermentation science (see, for example, Bailey et al., *Biochemical Engineering Fundamentals*, second edition, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process.

The methods of producing vanillin and/or glucovanillin provided herein may be performed in a suitable culture medium in a suitable container, including but not limited to a cell culture plate, a microtiter plate, a flask, or a fermentor. Further, the methods can be performed at any scale of fermentation known in the art to support industrial production of microbial products. Any suitable fermentor may be used including a stirred tank fermentor, an airlift fermentor, a bubble fermentor, or any combination thereof. In particular embodiments utilizing *Saccharomyces cerevisiae* as the host cell, strains can be grown in a fermentor as described in detail by Kosaric, et al, in Ullmann's Encyclopedia of Industrial Chemistry, Sixth Edition, Volume 12, pages 398-473, Wiley-VCH Verlag GmbH & Co. KDaA, Weinheim, Germany.

In some embodiments, the culture medium is any culture medium in which a genetically modified microorganism capable of producing vanillin or glucovanillin can subsist, i.e., maintain growth and viability. In some embodiments, the culture medium is an aqueous medium comprising assimilable carbon, nitrogen and phosphate sources. Such a medium can also include appropriate salts, minerals, metals and other nutrients. In some embodiments, the carbon source and some or all of the essential cell nutrients are added incrementally or continuously to the fermentation media. In certain embodiments, a subset of the essential nutrients are maintained in excess while a few, e.g. one or two, required nutrients are maintained at about the minimum levels needed for efficient assimilation by growing cells, for example, in accordance with a predetermined cell growth curve based on the metabolic or respiratory function of the cells which convert the carbon source to a biomass.

Suitable conditions and suitable media for culturing microorganisms are well known in the art. In some embodiments, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter), or a selection agent (e.g., an antibiotic to select for microorganisms comprising the genetic modifications).

In some embodiments, the carbon source is a monosaccharide (simple sugar), a disaccharide, a polysaccharide, a non-fermentable carbon source, or one or more combinations thereof. Non-limiting examples of suitable monosaccharides include glucose, galactose, mannose, fructose, xylose, ribose, and combinations thereof. Non-limiting examples of suitable disaccharides include sucrose, lactose, maltose, trehalose, cellobiose, and combinations thereof. Non-limiting examples of suitable polysaccharides include starch, glycogen, cellulose, chitin, and combinations thereof. Non-limiting examples of suitable non-fermentable carbon sources include acetate, ethanol, and glycerol.

The concentration of a carbon source, such as glucose, in the culture medium is sufficient to promote cell growth, but is not so high as to repress growth of the microorganism used. Typically, cultures are run with a carbon source, such as glucose, being added at levels to achieve the desired level of growth and biomass. In other embodiments, the concentration of a carbon source, such as glucose, in the culture medium is greater than about 1 g/L, preferably greater than about 2 g/L, and more preferably greater than about 5 g/L. In addition, the concentration of a carbon source, such as glucose, in the culture medium is typically less than about 100 g/L, preferably less than about 50 g/L, and more preferably less than about 20 g/L. It should be noted that references to culture component concentrations can refer to both initial and/or ongoing component concentrations. In some cases, it may be desirable to allow the culture medium to become depleted of a carbon source during culture.

Sources of assimilable nitrogen that can be used in a suitable culture medium include, but are not limited to, simple nitrogen sources, organic nitrogen sources and complex nitrogen sources. Such nitrogen sources include anhydrous ammonia, ammonium salts and substances of animal, vegetable and/or microbial origin. Suitable nitrogen sources include, but are not limited to, protein hydrolysates, microbial biomass hydrolysates, peptone, yeast extract, ammonium sulfate, urea, and amino acids. Typically, the concentration of the nitrogen sources, in the culture medium is greater than about 0.1 g/L, preferably greater than about 0.25 g/L, and more preferably greater than about 1.0 g/L. Beyond certain concentrations, however, the addition of a nitrogen source to the culture medium is not advantageous for the growth of the microorganisms. As a result, the concentration of the nitrogen sources, in the culture medium is less than about 20 g/L, preferably less than about 10 g/L and more preferably less than about 5 g/L. Further, in some instances it may be desirable to allow the culture medium to become depleted of the nitrogen sources during culture.

The effective culture medium can contain other compounds such as inorganic salts, vitamins, trace metals or growth promoters. Such other compounds can also be present in carbon, nitrogen or mineral sources in the effective medium or can be added specifically to the medium.

The culture medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. Typically, the concentration of phosphate in the culture medium is greater than about 1.0 g/L, preferably greater than about 2.0 g/L and more preferably greater than about 5.0 g/L. Beyond certain concentrations, however, the addition of phosphate to the culture medium is not advantageous for the growth of the microorganisms. Accordingly, the concentration of phosphate in the culture medium is typically less than about 20 g/L, preferably less than about 15 g/L and more preferably less than about 10 g/L.

The culture medium can also contain a suitable sulfur source. Preferred sulfur sources include, but are not limited to, sulfate salts such as ammonium sulfate ($(NH_4)_2SO_4$), magnesium sulfate ($MgSO_4$), potassium sulfate ($K_2SO_4$), and sodium sulfate ($Na_2SO_4$) and mixtures thereof. Typically, the concentration of sulfate in the culture medium is greater than about 1.0 g/L, preferably greater than about 3.0 g/L and more preferably greater than about 10.0 g/L. Beyond certain concentrations, however, the addition of sulfate to the culture medium is not advantageous for the growth of the microorganisms. Accordingly, the concentration of sulfate in the culture medium is typically less than about 50 g/L, preferably less than about 30 g/L and more preferably less than about 20 g/L.

A suitable culture medium can also include a source of magnesium, preferably in the form of a physiologically acceptable salt, such as magnesium sulfate heptahydrate, although other magnesium sources in concentrations that contribute similar amounts of magnesium can be used. Typically, the concentration of magnesium in the culture medium is greater than about 0.5 g/L, preferably greater than about 1.0 g/L, and more preferably greater than about 2.0 g/L. Beyond certain concentrations, however, the addition of magnesium to the culture medium is not advantageous for the growth of the microorganisms. Accordingly, the concentration of magnesium in the culture medium is typically less than about 10 g/L, preferably less than about 5 g/L, and more preferably less than about 3 g/L. Further, in some instances it may be desirable to allow the culture medium to become depleted of a magnesium source during culture.

In some embodiments, the culture medium can also include a biologically acceptable chelating agent, such as the dihydrate of trisodium citrate. In such instance, the concentration of a chelating agent in the culture medium is greater than about 0.2 g/L, preferably greater than about 0.5 g/L, and more preferably greater than about 1 g/L. Beyond certain concentrations, however, the addition of a chelating agent to the culture medium is not advantageous for the growth of the microorganisms. Accordingly, the concentration of a chelating agent in the culture medium is typically less than about 10 g/L, preferably less than about 5 g/L, and more preferably less than about 2 g/L.

The culture medium can also initially include a biologically acceptable acid or base to maintain the desired pH of the culture medium. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof. In some embodiments, the base used is ammonium hydroxide.

The culture medium can also include a biologically acceptable calcium source, including, but not limited to, calcium chloride. Typically, the concentration of the calcium source, such as calcium chloride, dihydrate, in the culture medium is within the range of from about 5 mg/L to about 2000 mg/L, preferably within the range of from about 20 mg/L to about 1000 mg/L, and more preferably in the range of from about 50 mg/L to about 500 mg/L.

The culture medium can also include sodium chloride. Typically, the concentration of sodium chloride in the culture medium is within the range of from about 0.1 g/L to about 5 g/L, preferably within the range of from about 1 g/L to about 4 g/L, and more preferably in the range of from about 2 g/L to about 4 g/L.

In some embodiments, the culture medium can also include trace metals. Such trace metals can be added to the culture medium as a stock solution that, for convenience, can be prepared separately from the rest of the culture medium. Typically, the amount of such a trace metals solution added to the culture medium is greater than about 1 ml/L, preferably greater than about 5 mL/L, and more preferably greater than about 10 mL/L. Beyond certain concentrations, however, the addition of a trace metals to the culture medium is not advantageous for the growth of the microorganisms. Accordingly, the amount of such a trace metals solution added to the culture medium is typically less than about 100 mL/L, preferably less than about 50 mL/L, and more preferably less than about 30 mL/L. It should be noted that, in addition to adding trace metals in a stock solution, the individual components can be added separately, each within ranges corresponding independently to the amounts of the components dictated by the above ranges of the trace metals solution.

The culture media can include other vitamins, such as pantothenate, biotin, calcium, pantothenate, inositol, pyridoxine-HCl, and thiamine-HCl. Such vitamins can be added to the culture medium as a stock solution that, for convenience, can be prepared separately from the rest of the culture medium. Beyond certain concentrations, however, the addition of vitamins to the culture medium is not advantageous for the growth of the microorganisms.

The fermentation methods described herein can be performed in conventional culture modes, which include, but are not limited to, batch, fed-batch, cell recycle, continuous and semi-continuous. In some embodiments, the fermentation is carried out in fed-batch mode. In such a case, some of the components of the medium are depleted during culture during the production stage of the fermentation. In some embodiments, the culture may be supplemented with relatively high concentrations of such components at the outset, for example, of the production stage, so that growth and/or vanillin or glucovanillin production is supported for a period of time before additions are required. The preferred ranges of these components are maintained throughout the culture by making additions as levels are depleted by culture. Levels of components in the culture medium can be monitored by, for example, sampling the culture medium periodically and assaying for concentrations. Alternatively, once a standard culture procedure is developed, additions can be made at timed intervals corresponding to known levels at particular times throughout the culture. As will be recognized by those in the art, the rate of consumption of nutrient increases during culture as the cell density of the medium increases. Moreover, to avoid introduction of foreign microorganisms into the culture medium, addition is performed using aseptic addition methods, as are known in the art. In addition, a small amount of anti-foaming agent may be added during the culture.

The temperature of the culture medium can be any temperature suitable for growth of the genetically modified cells and/or production of vanillin or glucovanillin. For example, prior to inoculation of the culture medium with an inoculum, the culture medium can be brought to and maintained at a temperature in the range of from about 20° C. to about 45° C., preferably to a temperature in the range of from about 25° C. to about 40° C. In certain embodiments, the cells are eukaryotic, e.g. yeast, and the temperature is in the range of from about 28° C. to about 34° C. In certain embodiments, the cells are prokaryotic, e.g. bacteria, and the temperature is in the range of from about 35° C. to about 40° C., for instance 37° C.

The pH of the culture medium can be controlled by the addition of acid or base to the culture medium. In such cases when ammonia is used to control pH, it also conveniently serves as a nitrogen source in the culture medium. Preferably, the pH is maintained from about 3.0 to about 8.0, more preferably from about 3.5 to about 7.0. In certain embodiments, the cells are eukaryotic, e.g. yeast, and the pH is preferably from about 4.0 to about 6.5. In certain embodiments, the cells are prokaryotic, e.g. bacteria, and the pH is from about 6.5 to about 7.5, e.g. about 7.0.

In some embodiments, the carbon source concentration, such as the glucose, fructose or sucrose, concentration, of the culture medium is monitored during culture. Carbon source concentration of the culture medium can be monitored using known techniques, such as, for example, use of the glucose oxidase enzyme test or high pressure liquid chromatography, which can be used to monitor glucose concentration in the supernatant, e.g., a cell-free component of the culture medium. The carbon source concentration is typically maintained below the level at which cell growth inhibition occurs. Although such concentration may vary from organism to organism, for glucose as a carbon source, cell growth inhibition occurs at glucose concentrations greater than at about 60 g/L, and can be determined readily by trial. Accordingly, when glucose, fructose, or sucrose is used as a carbon source the glucose, fructose, or sucrose is preferably fed to the fermentor and maintained below detection limits. Alternatively, the glucose concentration in the culture medium is maintained in the range of from about 1 g/L to about 100 g/L, more preferably in the range of from about 2 g/L to about 50 g/L, and yet more preferably in the range of from about 5 g/L to about 20 g/L. Although the carbon source concentration can be maintained within desired levels by addition of, for example, a carbon source solution, it is acceptable, and may be preferred, to maintain the carbon source concentration of the culture medium by addition of aliquots of the original culture medium. The use of aliquots of the original culture medium may be desirable because the concentrations of other nutrients in the medium (e.g. the nitrogen and phosphate sources) can be maintained simultaneously. Likewise, the trace metals concentrations can be maintained in the culture medium by addition of aliquots of the trace metals solution.

Other suitable fermentation medium and methods are described in, e.g., WO 2016/196321.

Fermentation Compositions

In another aspect, provided herein are fermentation compositions comprising a genetically modified host cell described herein and vanillin and/or glucovanillin produced from the genetically modified host cell. The fermentation compositions may further comprise a medium. In certain embodiments, the fermentation compositions comprise a genetically modified host cell, and further comprise vanillin or glucovanillin. In certain embodiments, the fermentation compositions provided herein comprise vanillin as a major component of the vanillin and/or glucovanillin produced from the genetically modified host cell. In certain embodiments, the fermentation compositions provided herein comprise glucovanillin as a major component of the vanillin and/or glucovanillin produced from the genetically modified host cell.

Recovery of Vanillin and/or Glucovanillin

Once the vanillin or glucovanillin is produced by the host cell, it may be recovered or isolated for subsequent use using any suitable separation and purification methods known in the art. In some embodiments, a clarified aqueous phase comprising the vanillin or glucovanillin is separated from the fermentation by centrifugation or filtration. In certain embodiments, flocculants and coagulants are added to the clarified aqueous phase, for instance, to the clarified aqueous phase.

The vanillin or glucovanillin produced in these cells may be present in the culture supernatant and/or associated with the host cells. In embodiments where some of the vanillin or glucovanillin is associated with the host cell, the recovery of the vanillin or glucovanillin may comprise a method of improving the release of the vanillin and/or glucovanillin from the cells. In some embodiments, this could take the form of washing the cells with hot water or buffer treatment, with or without a surfactant, and with or without added buffers or salts. In some embodiments, the temperature is any temperature deemed suitable for releasing the vanillin and/or glucovanillin. In some embodiments, the temperature is in a range from 40 to 95° C.; or from 60 to 90° C.; or from 75 to 85° C. In some embodiments, the temperature is 40, 45, 50, 55, 65, 70, 75, 80, 85, 90, or 95° C. In some embodiments physical or chemical cell disruption is used to enhance the release of vanillin and/or glucovanillin from the host cell. Alternatively and/or subsequently, the vanillin or glucovanillin in the culture medium can be recovered using an isolation unit operations including, but not limited to solvent extraction, membrane clarification, membrane concentration, adsorption, chromatography, evaporation, chemical derivatization, crystallization, and drying.

Methods of Making Genetically Modified Cells

Also provided herein are methods for producing a host cell that is genetically engineered to comprise one or more of the modifications described above, e.g., one or more nucleic heterologous nucleic acids and/or biosynthetic pathway enzymes, e.g., for a vanillin or glucovanillin compound. Expression of a heterologous enzyme in a host cell can be accomplished by introducing into the host cells a nucleic acid comprising a nucleotide sequence encoding the enzyme under the control of regulatory elements that permit expression in the host cell. In some embodiments, the nucleic acid is an extrachromosomal plasmid. In other embodiments, the nucleic acid is a chromosomal integration vector that can integrate the nucleotide sequence into the chromosome of the host cell. In other embodiments, the nucleic acid is a linear piece of double stranded DNA that can integrate via homology the nucleotide sequence into the chromosome of the host cell.

Nucleic acids encoding these proteins can be introduced into the host cell by any method known to one of skill in the art without limitation (see, for example, Hinnen et al. (1978) *Proc. Natl. Acad. Sci. USA* 75:1292-3; Cregg et al. (1985) *Mol. Cell. Biol.* 5:3376-3385; Goeddel et al. eds, 1990, Methods in Enzymology, vol. 185, Academic Press, Inc., CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY). Exemplary techniques include, but are not limited to, spheroplasting, electroporation, PEG 1000 mediated transformation, and lithium acetate or lithium chloride mediated transformation.

The amount of an enzyme in a host cell may be altered by modifying the transcription of the gene that encodes the enzyme. This can be achieved for example by modifying the copy number of the nucleotide sequence encoding the enzyme (e.g., by using a higher or lower copy number expression vector comprising the nucleotide sequence, or by introducing additional copies of the nucleotide sequence into the genome of the host cell or by deleting or disrupting the nucleotide sequence in the genome of the host cell), by changing the order of coding sequences on a polycistronic mRNA of an operon or breaking up an operon into individual genes each with its own control elements, or by increasing the strength of the promoter or operator to which the nucleotide sequence is operably linked. Alternatively or in addition, the copy number of an enzyme in a host cell may be altered by modifying the level of translation of an mRNA that encodes the enzyme. This can be achieved for example by modifying the stability of the mRNA, modifying the sequence of the ribosome binding site, modifying the distance or sequence between the ribosome binding site and the start codon of the enzyme coding sequence, modifying the entire intercistronic region located "upstream of" or adjacent to the 5' side of the start codon of the enzyme coding region, stabilizing the 3'-end of the mRNA transcript using hairpins and specialized sequences, modifying the codon usage of enzyme, altering expression of rare codon tRNAs used in the biosynthesis of the enzyme, and/or increasing the stability of the enzyme, as, for example, via mutation of its coding sequence.

The activity of an enzyme in a host cell can be altered in a number of ways, including, but not limited to, expressing a modified form of the enzyme that exhibits increased or decreased solubility in the host cell, expressing an altered form of the enzyme that lacks a domain through which the activity of the enzyme is inhibited, expressing a modified form of the enzyme that has a higher or lower Kcat or a lower or higher Km for the substrate, or expressing an altered form of the enzyme that is more or less affected by feed-back or feed-forward regulation by another molecule in the pathway.

In some embodiments, a nucleic acid used to genetically modify a host cell comprises one or more selectable markers useful for the selection of transformed host cells and for placing selective pressure on the host cell to maintain the foreign DNA.

In some embodiments, the selectable marker is an antibiotic resistance marker. Illustrative examples of antibiotic resistance markers include, but are not limited to, the BLA, NAT1, PAT, AUR1-C, PDR4, SMR1, CAT, mouse dhfr, HPH, DSDA, $KAN^R$, and SH BLE gene products. The BLA gene product from *E. coli* confers resistance to beta-lactam antibiotics (e.g., narrow-spectrum cephalosporins, cephamycins, and carbapenems (ertapenem), cefamandole, and cefoperazone) and to all the anti-gram-negative-bacterium penicillins except temocillin; the NAT1 gene product from *S. noursei* confers resistance to nourseothricin; the PAT gene product from *S. viridochromogenes* Tu94 confers resistance to bialophos; the AUR1-C gene product from *Saccharomyces cerevisiae* confers resistance to Auerobasidin A (AbA); the PDR4 gene product confers resistance to cerulenin; the SMR1 gene product confers resistance to sulfometuron methyl; the CAT gene product from Tn9 transposon confers resistance to chloramphenicol; the mouse dhfr gene product confers resistance to methotrexate; the HPH gene product of *Klebsiella pneumonia* confers resistance to Hygromycin B; the DSDA gene product of *E. coli* allows cells to grow on plates with D-serine as the sole nitrogen source; the $KAN^R$ gene of the Tn903 transposon confers resistance to G418; and the SH BLE gene product from *Streptoalloteichus hindustanus* confers resistance to Zeocin (bleomycin). In some embodiments, the antibiotic resistance marker is deleted after the genetically modified host cell disclosed herein is isolated.

In some embodiments, the selectable marker rescues an auxotrophy (e.g., a nutritional auxotrophy) in the genetically modified microorganism. In such embodiments, a parent microorganism comprises a functional disruption in one or more gene products that function in an amino acid or nucleotide biosynthetic pathway and that when non-functional renders a parent cell incapable of growing in media without supplementation with one or more nutrients. Such gene products include, but are not limited to, the HIS3, LEU2, LYS1, LYS2, MET15, TRP1, ADE2, and URA3 gene products in yeast. The auxotrophic phenotype can then be rescued by transforming the parent cell with an expression vector or chromosomal integration construct encoding a functional copy of the disrupted gene product, and the genetically modified host cell generated can be selected for based on the loss of the auxotrophic phenotype of the parent cell. Utilization of the URA3, TRP1, and LYS2 genes as selectable markers has a marked advantage because both positive and negative selections are possible. Positive selection is carried out by auxotrophic complementation of the URA3, TRP1, and LYS2 mutations, whereas negative selection is based on specific inhibitors, i.e., 5-fluoro-orotic acid (FOA), 5-fluoroanthranilic acid, and aminoadipic acid (aAA), respectively, that prevent growth of the prototrophic strains but allows growth of the URA3, TRP1, and LYS2 mutants, respectively. In other embodiments, the selectable marker rescues other non-lethal deficiencies or phenotypes that can be identified by a known selection method.

Described herein are specific genes and proteins useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutations and silent mutations. Such modified or mutated polynucleotides and polypeptides can be screened for expression of a functional enzyme using methods known in the art.

Due to the inherent degeneracy of the genetic code, other polynucleotides which encode substantially the same or functionally equivalent polypeptides can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, in a process sometimes called "codon optimization" or "controlling for species codon bias." Codon optimization for other host cells can be readily determined using codon usage tables or can be performed using commercially available software, such as CodonOp (www.idtdna.com/CodonOptfrom) from Integrated DNA Technologies.

Optimized coding sequences containing codons preferred by a particular prokaryotic or eukaryotic host (Murray et al., 1989, *Nucl Acids Res.* 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al., 1996, *Nucl Acids Res.* 24:216-8).

Those of skill in the art will recognize that, due to the degenerate nature of the genetic code, a variety of DNA molecules differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA molecules of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for the compositions and methods provided herein are encompassed by the disclosure. In some embodiments, two proteins (or a region of the proteins) are substantially homologous when the amino acid sequences have at least about 30%, 40%, 50%, 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (See, e.g., Pearson W. R., 1994, *Methods in Mol Biol* 25:365-89).

The following six groups each contain amino acids that are conservative substitutions for one another: 1) Serine(S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. A typical algorithm used comparing a molecule sequence to a database containing a large number of sequences from different organisms is the computer program BLAST. When searching a database containing sequences from a large number of different organisms, it is typical to compare amino acid sequences.

Furthermore, any of the genes encoding the foregoing enzymes (or any others mentioned herein (or any of the regulatory elements that control or modulate expression thereof)) may be optimized by genetic/protein engineering techniques, such as directed evolution or rational mutagenesis, which are known to those of ordinary skill in the art. Such action allows those of ordinary skill in the art to optimize the enzymes for expression and activity in yeast.

In addition, genes encoding these enzymes can be identified from other fungal and bacterial species and can be expressed for the modulation of this pathway. A variety of organisms could serve as sources for these enzymes, including, but not limited to, *Saccharomyces* spp., including *S. cerevisiae* and *S. uvarum, Kluyveromyces* spp., including *K. thermotolerans, K. lactis*, and *K. marxianus, Pichia* spp., *Hansenula* spp., including *H. polymorpha, Candida* spp., *Trichosporon* spp., *Yamadazyma* spp., including *Y.* spp. *stipitis, Torulaspora pretoriensis, Issatchenkia orientalis, Schizosaccharomyces* spp., including *S. pombe, Cryptococcus* spp., *Aspergillus* spp., *Neurospora* spp., or *Ustilago* spp. Sources of genes from anaerobic fungi include, but are not limited to, *Piromyces* spp., *Orpinomyces* spp., or *Neocallimastix* spp. Sources of prokaryotic enzymes that are useful include, but are not limited to, *Escherichia. coli, Zymomonas mobilis, Staphylococcus aureus, Bacillus* spp., *Clostridium* spp., *Corynebacterium* spp., *Pseudomonas* spp., *Lactococcus* spp., *Enterobacter* spp., and *Salmonella* spp.

Techniques known to those skilled in the art may be suitable to identify additional homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous UDP glycosyltransferases, or any biosynthetic pathway genes, proteins, or enzymes, techniques may include, but are not limited to, cloning a gene by PCR using primers based on a published sequence of a gene/enzyme of interest, or by degenerate PCR using degenerate primers designed to amplify a conserved region among a gene of interest. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity (e.g. as described herein or in Kiritani, K., *Branched-Chain Amino Acids Methods Enzymology,* 1970), then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above mentioned databases in accordance with the teachings herein.

EXAMPLES

Example 1. Yeast Transformation Methods

Each DNA construct is integrated into *Saccharomyces cerevisiae* (CEN.PK2) with standard molecular biology techniques in an optimized lithium acetate (LiAc) transformation. Briefly, cells are grown overnight in yeast extract peptone dextrose (YPD) media at 30° C. with shaking (200 rpm), diluted to an $OD_{600}$ of 0.1 in 100 mL YPD, and grown to an $OD_{600}$ of 0.6-0.8. For each transformation, 5 mL of culture is harvested by centrifugation, washed in 5 mL of sterile water, spun down again, resuspended in 1 mL of 100 mM LiAc, and transferred to a microcentrifuge tube. Cells are spun down (13,000×g) for 30 seconds, the supernatant is removed, and the cells are resuspended in a transformation mix consisting of 240 μL 50% PEG, 36 μL 1 M LiAc, 10 μL boiled salmon sperm DNA, and 74 μL of donor DNA. Following a heat shock at 42° C. for 40 minutes, cells are recovered overnight in YPD media before plating on selective media. DNA integration is confirmed by colony PCR with primers specific to the integrations.

Example 2: Improvement in the Production of Vanillin by Metabolic Engineering of the SAM Regeneration Pathway for Improved Flux Through the O-Methyltransferase Reaction To achieve methylation of protocatechuic acid into vanillic acid by the O-methyltransferase enzyme, a donor for the methyl group is required. S-adenosylmethionine is the major cosubstrate utilized for methyl transfer reactions. Here the O-methyltransferase enzyme converts one molecule of protocatechuic acid and one molecule of S-adenosylmethionine (SAM) into one molecule of vanillic acid and one molecule of S-adenosylhomocysteine (SAH). SAH can be converted back into SAM by the action of three enzymes, S-adenosyl- L-homocysteine hydrolase, methionine synthase, and SAM synthetase. In yeast these are encoded by SAH1, MET6 and homologs SAM1 and SAM2, respectively. See FIG. 1. In order to increase the amount of vanillic acid and subsequently the amount of vanillin produced it is advantageous to increase the availability of SAM and decrease the concentration of SAH produced, which is inhibitory to most methyltransferase enzymes. In order to increase the regeneration of SAH back to SAM to drive the O-methyltransferase enzyme reaction, a second copy of each of the native yeast genes SAM1, SAM2, SAH1, and MET6 has been integrated into the genome of a vanillin producing strain Y41906 under the control of an inducible promoter that enables these genes to be overexpressed highly during the production phase of fermentation. The resulting strain is Y42688.

Figure 3:
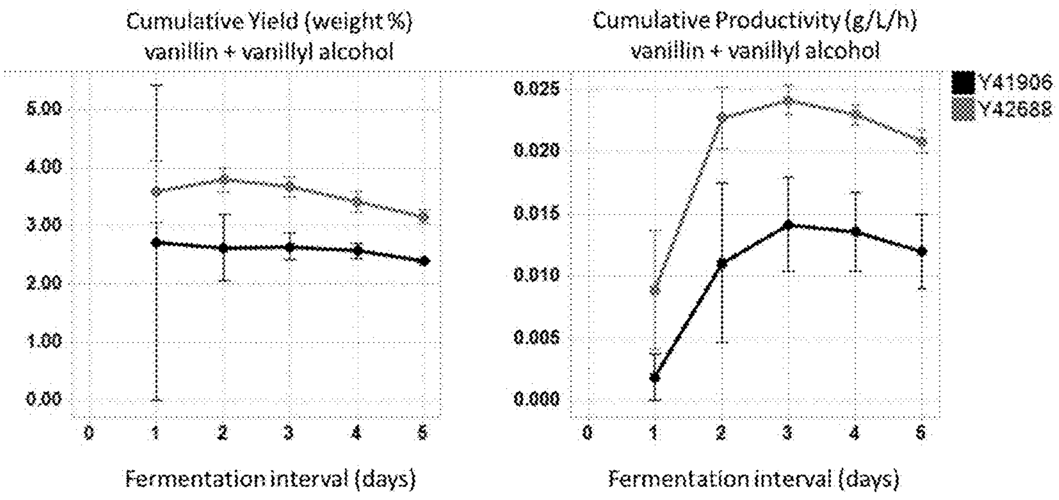
FIG. 3 provides cumulative yield (weight %; vanillin+vanillyl alcohol) and cumulative productivity (g/L/h; vanillin plus vanillyl alcohol) for a 5 day fermentation using the vanillin producing strain Y41906 and an improved derivative Y42688. Cumulative indicates the value for the interval from time zero to the indicated time.

The performance of Y41906 (the parent strain) and Y42688 (the child strain) was tested in a 500 mL fermentor as described below. Samples were taken every 24 hours and concentration of vanillin, and vanillyl alcohol were measured. Here the sum of vanillin plus vanillyl alcohol production was used to calculate the cumulative yield and productivity of the strain. Y42688 achieved a 30% increase in cumulative yield and 75% increase in productivity (0-5 day) compared to parent strain Y41906. See FIG. 3.

Strain Construction to Generate Y41906/Y42688

Y17025

All strains described here are derived from Y17025. Y17025 is a wildtype prototrophic *Saccharomyces cerevisiae* strain Cen.PK113-7d. All DNA-mediated transformation into *S. cerevisiae* was conducted using the standard lithium acetate procedure as described by Gietz R W and Woods R A, *Guide to Yeast Genetics and Molecular and Cell Biology*. Part B. San Diego, Calif.: Academic Press Inc. pp. 87-96 (2002), and in all cases integration of the constructs were confirmed by PCR amplification of genomic DNA.

US_dsMGA1 pGAL7 Pp.AroZ tCYC1 tHUG1 Ec.AroF(FBR) pGAL2 CAIB pGAL2 Ec.AroB tTIP1 tPGK1 Ec.AroD pGAL7 DS_dsMGA1

Y33651

Y33651 was generated from Y17025 from four genomic integrations. First, the native GAL80 locus was replaced with an integration MS106908 (SEQ ID NO: 1) consisting of the GAL80 gene with a temperature sensitive allele fused to the DHFR protein from *Mus musculus* which reduced protein stability. The expression of this GAL80 variant is controlled by a pMAL32 promoter which induces expression when maltose is present. This construct also contains a copy of constitutively driven GAL4 annotated pGAL4oc-GAL4. A non-functional gene fragment derived from the part of the FixA flavoprotein is used as a spacer between these two genes as shown in the diagram below. US and DS refer to the region immediately upstream (US) and immediately downstream (DS) of the coding region.

US_GAL80 pMAL32 D_GAL80ts1 FIXA pGAL4oc-GAL4 DS_GAL80

Next, three reductases, ADH6, GRE2, and YGL039W were deleted by integrating constructs containing homology to the upstream and downstream region of these genes, deleting the ORF (SEQ ID NO: 2, 3 and 4).

US_ADH6 DS_ADH6

US_GRE2 DS_GRE2

US_YGL039W DS_YGL039W

Y41906

Y41906 was generated from Y33651 by one evolution and isolation step and three integrations. Y33651 was evolved for increased tolerance to vanillin by serial propagation in media containing concentration of vanillin which reduced the growth rate of Y33651. Following this serial propagation, Y35127 was identified which had an improved growth rate in media containing vanillin.

This strain was subsequently integrated with three genetic constructs containing the vanillin pathway to produce Y41906 (SEQ ID NO: 5, 6, and 7). MS133489 (SEQ ID NO: 5) is flanked with upstream and downstream homology regions targeting an intergenic region downstream of MGA1. This construct contains four genes which catalyze the conversion of central carbon metabolites erythrose-4-phosphate and phosphoenolpyruvate into protocatechuic acid (PCA). These are a feedback resistant version of *E. coli* Ec.AroF(FBR) (*J. Bacteriol.* November 1990 172:6581-6584) driven by pGAL2 and followed by a HUG1 terminator, *E. coli* Ec.AroB driven by pGAL2 and followed by a TIPI terminator, *E. coli* Ec.AroD driven by pGAL7 and followed by a PGK 1 terminator, and *Podospora pauciseta* Pp.AroZ driven by pGAL7 and followed by a CYC1 terminator. A non-functional gene fragment derived from part of the CaiB gene, a carnitine CoA transferase, is used as a spacer between the first two genes and second two genes. A diagram is shown below.

MS134781 (SEQ ID NO: 6) is integrated at the intergenic region downstream of the ALG1 gene. This integration is flanked by homology regions targeting downstream of the ALG1 gene and contains a phosphopantetheinyl transferase (PPTASE) from *Corynebacterium glutamicum* driven by pGAL10 and followed by VAM5 terminator, followed by PGK 1 terminator, an aromatic carboxylic acid reductase (ACAR) from *Nocardia iowensis* driven by pGAL1 and followed by TIPI terminator, a spacer non-functional gene fragment derived from the part of the FixA flavoprotein, an O-methyl transferase from *Hordeum vulgare* (Hv.OMT) driven by pGAL10 and followed by the CYC1 terminator and O-methyltransferase from *Setaria italic* followed by HUG1 terminator. A diagram is shown below.

US_dsALG1 tPGK1 tVAM5 Cg.PPTASE pGAL10_1 NLACAR tTIP1 FIXA tCYC1 Hv.OMT pGAL10_1 SLOMT tHUG1 DS_dSALG1

MS130477 (SEQ ID NO: 7) contains upstream and downstream homology to integrate into an intergenic region downstream of YCT1. This flanks two copies of O-methyltransferase from *Brassica napus* followed by either CYC1 terminator or HUG1 terminator as shown in the diagram below.

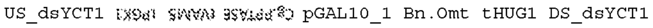

Y42688

Y42686 was generated from Y41906 by one integration. MS129629 (SEQ ID NO: 8). This integration is flanked by homology upstream and downstream of the HO locus resulting in replacement of the HO open reading frame. The integration contains a copy of SAH1 (gene and native terminator) and MET6 (gene and native terminator) driven by a divergent pGAL1_10 promoter, and a copy of SAM1 (gene and native terminator) and mSAM2 (gene and native terminator) driven by a pGAL1_10 promoter. These are separated by a non-coding fragment of *E. coli* K12 designated ECO1. A diagram is shown below.

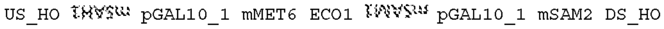

Fermentation Media and Conditions for Y41906/Y42688

Yeast colonies grown on an agar plate were used to inoculate a 500 mL baffled seed flask containing 60 mL of BSM 2.0 containing 4% sucrose, 2% maltose, 5 g/L lysine and grown in a shaker at 28° C., 200 RPM for 21 hours. 60 mL of the seed flask culture was then inoculated into a 0.5-L manufacturing fermentor (MFA) containing 240 mL of MF media described above. The nutrient feed to the fermentor was a 100 g/L pure sucrose feedstock. The initial pulse was 2 g TRS/L at a rate of 5 g/L/h. The fermentor feed rate was then adjusted using an algorithm based on the culture demand for carbon, as indicated by rises in dissolved oxygen. The fermentation was run aerobically at a constant temperature of 30° C. and constant pH of 5.0 (controlled by ammonium hydroxide additions) until the dissolved oxygen reached 0%. The agitation was then controlled in order to maintain an oxygen utilization rate of 15 mmol $O_2$/L/h for the remainder of the fermentation. Culture was removed as needed to prevent overflow. Salts, trace metals and vitamins were also added daily. 0.1 mL L-61 antifoam was added to the fermentation media at the beginning and subsequently added as needed. The amount of vanillin produced and the total sugar consumed by the cells was monitored daily and the ratio of these two values (i.e., the product yield off of sugar) was determined for each 24 hour period. The fermentor was run for 5 days. Cumulative yield indicates the total yield from time 0 to the indicated time point. Similarly, cumulative productivity indicates the total productivity from time 0 to the indicated time point.

Quantification of Vanillin Y41906/Y42688

To quantify the amount of vanillin and vanillyl alcohol produced, the samples were analyzed on a Agilent Vanquish™ Flex Binary UHPLC System with a diode array detector with the following program:

Mobile phase (A): 1.4% sulfuric acid v/v in water

Mobile phase (B): 100% acetonitrile

Gradient is as follows [gradient time, (min) mobile phase A, (%)]: [(0.00, 88), (0.05, 88), (1.25, 85), (2.25, 83), (3.0, 82), (3.5, 88), (4.0, 88)]. Flow rate was 1 mL/min.

Example 3: Further Improvement in the Production of Vanillin by Metabolic Engineering of the SAM Regeneration Pathway for Improved Flux Through the O-Methyltransferase Reaction In order to further improve the regeneration of SAH back to SAM and thereby improve the production of vanillin, additional genes SHM2, MET12, MET13, and a third copy of MET6 were integrated into the genome of a glucovanillin producing strain under the control of an inducible promoter that enables these genes to be overexpressed highly during the production phase of fermentation. These modifications were tested in a strain that produces glucovanillin as a fermentation product. The parent strain Y48967 contains genes required to produce glucovanillin. In addition to the glucovanillin core genes, the cassette to overexpress a second copy of SAM1, SAM2, SAH1, and MET6 has already been integrated (as was done to make Y42688 from Y41906). To this strain was integrated into the genome a cassette overexpressing an additional copy of SHM2, MET12, MET13, and MET6 to generate Y48969. SHM2 and MET12/MET13 catalyze the transfer of a C1 unit to tetrahydrofolate (THF) and subsequent reduction to 5-methyltetrahydrofolate which is required to drive the MET6 reaction to recycle homocysteine back to methionine as shown in FIG. 2.

Figure 4:
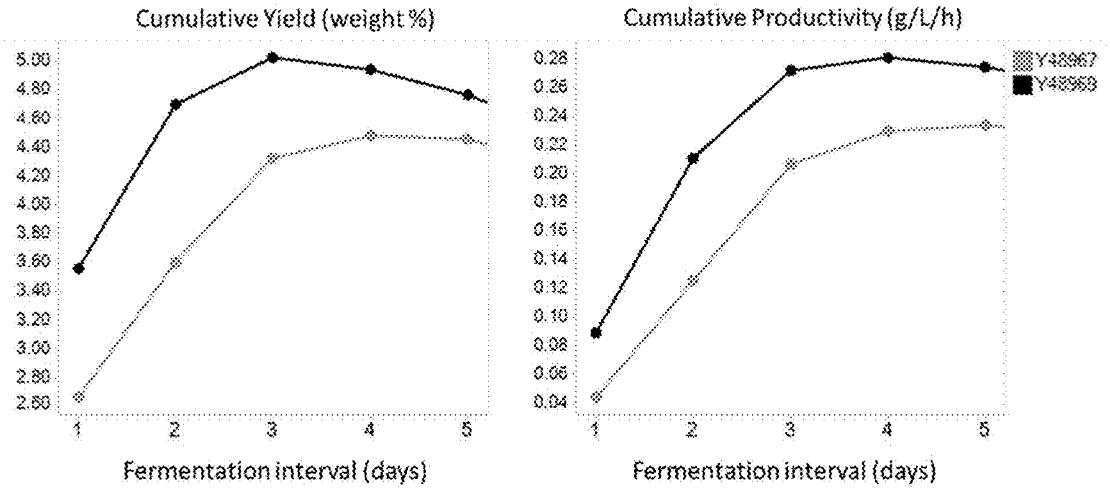
FIG. 4 provides cumulative yield (weight %) and productivity (g/L/h) for vanillin for a 5 day fermentation of glucovanillin producing strain Y48967 and an improved derivative Y48969. Cumulative indicates the value for the interval from time zero to the indicated time.

These strains were both tested in a 0.5 L fermentor as described below. In order to measure the concentration of vanillin produced, samples of the fermentation broth were centrifuged, and the supernatant was treated with a β-glucosidase enzyme to cleave the glucose from the glucovanillin and generate vanillin. The resulting concentration of vanillin was measured by UPLC as described below. This vanillin titer was used to calculate the cumulative yield and productivity of each strain shown in FIG. 4. Y48969 had a 7% increase in 0-5 day cumulative vanillin yield and 17% increase in 0-5 day cumulative vanillin productivity compared to Y48967.

Strain Construction to Generate Y48967/Y48969

Y33653

Y33653 was generated from Y33651 by deletion of the ARI1 gene by integration of MS120569 (SEQ ID NO 10). Diagram is shown below.

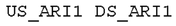

Y44814

Y44814 was constructed from Y33653 with four integrations. MS133973 (SEQ ID NO: 9) was integrated at the BUD9 locus replacing the BUD9 open reading frame. The integration contains a eugenol alcohol oxidase from *Rhodococcus jostii*, Rj.EAO followed by a HUG1 terminator, and mCTT1 containing the native *Saccharomyces cerevisiae* CTT1 gene followed by its native terminator driven by the pGAL1_10 divergent promoter as shown below.

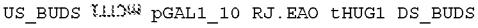

MS137150 (SEQ ID NO: 10) was integrated at the EXG1 locus replacing the native EXG1 gene. This integration contains two copies of *Arabidopsis thaliana* UDP-glycosyltransferase, At.UGT, driven by a divergent pGAL10_1 promoter and followed by either a HUG1 terminator or CYC1 terminator as shown below.

US_EXG1 pGAL10_1 At.UGT tHUG1 DS_EXG1

MS129629 (SEQ ID NO: 8) was integrated as described above.

Y48967

Y48967 was created from Y44814 with three integrations. MS146176 (SEQ ID NO: 11) was integrated downstream of the MGA1 gene. This integration contains Pp.AroZ driven by pGAL2 promoter and followed by tGAS1 terminator, Ec.AroB driven by pGAL7 promoter and followed by tGRS1 terminator, a CAIB spacer as described above, a Ec.AroD gene driven by pGAL7 promoter and followed by CYS4 terminator and a feedback resistant allele of Ec.AroF (described above) driven by pGAL2 promoter and followed by ECM33 terminator as shown in the diagram below.

US_dsMGA1 pGAL2 Pp.AroZ tGAS1 pGAL7 Ec.AroB tGRS1 CAIB tCYS4 Ec.AroD pGAL7 tECM33 Ec.AroF(FBR) pGAL2 DS_dsMGA1

MS146277 (SEQ ID NO: 12) was integrated downstream of the YCT1 gene. This integration contains two copies of Bn.OMT with DIT1 terminator and two copies of Hv.OMT with VMA8 terminator each driven by divergent pGAL1_10 promoters as described below and with a spacer derived from an *E. coli* sequence of a non-functional gene fragment derived from the part of the MurD synthetase gene.

US_dSYCT1 tDIT1 Bn.OMT pGAL10_1 Hv.OMT tVMA8 MURD tVMA8 Hv.OMT pGAL10_1 Bn.OMT tDIT1 DS_dsYCT1

MS146176 (SEQ ID NO: 13) was integrated downstream of the ALG1 gene. This integration contains an ACAR driven by pGAL7 promoter and followed by an EFB1 terminator separated by a FIXA spacer and followed by a PPTase from *Nocardia iowensis* driven by pGAL7 promoter and followed by tSYN8 terminator as shown below.

US_dsALG1 pGAL2 Mx.ACAR tEFB1 FIXA tSYN8 Ni.PPTase pGAL7 DS_dsALG1

Y48969

Y48969 was generated from Y48967 by one integration. MS141850 (SEQ ID NO: 14) was integrated at the YGL039w locus. This contains overexpression of additional copies of four native *Saccharomyces cerevisiae* genes, MET12, MET13, MET6 and SHM2 with their native terminators driven by divergent pGAL1_10 promoters as shown below.

US_YGL039W pGAL10_1 mMET6 ECO1 pGAL10_1 mSHM2 DS_YGL039W

Fermentation Media and Conditions for Y48967/Y48969

A 1 mL vial of frozen cell suspension of a yeast strain containing the desired genetic modifications, was thawed, transferred into a 500-mL baffled flask containing 100 mL of BSM 2.0 containing 4% sucrose, 2% maltose, and 5 g/L lysine and grown in a shaker at 28° C., 200 RPM for 21 hours. 0.5 mL of this culture was then transferred into a second flask containing 100 ml of BSM 2.0 (8 g/L $KH_2PO_4$, 15 g/L $(NH_4)_2SO_4$, 6.15 g/L $MgSO_4$*$7H_2O$, 0.0575 $ZnSO_4$*$7H_2O$, 0.0032 g/L $CuSO_4$, 0.0032 $MnCl_2$*$4H_2O$, 0.0047 g/L $CoCl_2$*$6H_2O$, 0.0048 g/L $NazMoO_4$*$2H_2O$, 0.028 g/L $FeSO_4$*$7H_2O$, 0.029 g/L $CaCl_2$*$2H_2O$, 0.117 g/L EDTA, 0.0006 g/L Biotin, 0.0024 g/L p-Aminobenzoic acid, 0.012 g/L nicotinic acid, 0.03 g/L myoinositol, 0.012 g/L pyridoxine HCl, 0.012 g/L thiamine HCl 0.012 g/L calcium pantothenate, 6 g/L succinic acid) containing 4% sucrose and 2% maltose, and 5 g/L lysine and grown in a shaker at 28° C., 200 RPM for 21 hours. 0.6 mL of this culture was then inoculated into a 0.5-L initial fermentor (IFA) containing 299.4 mL of IF media (8 g/L $KH_2PO_4$, 7 g/L $(NH_4)_2SO_4$, 6.15 g/L $MgSO_4$*$7H_2O$, 3 mL/L 1× Bird Vitamins 3.5 (0.05 g/L biotin, 0.2 p-aminobenzoic acid, 1 g/L nicotinic acid, 2.5 g/L myoinositol, 1 g/L pyridoxine HCl, 1 g/L thiamine HCl, 1 g/L calcium pantothenate), 5 mL/L 1× Bird™ (5.75 g/L $ZnSO_4$*$7H_2O$, 0.32 g/L $CuSO_4$, 0.32 $MnCl_2$*$4H_2O$, 0.47 g/L $CoCl_2$*$6H_2O$, 0.48 g/L $Na_2MoO_4$*$2H_2O$, 2.8 g/L $FeSO_4$*$7H_2O$, 2.9 $CaCl_2$*$2H_2O$, 0.0585 EDTA), 10 g/L Maltose, 20 g/L Lysine). The nutrient feed to the IFA was an undefined Brazilian cane syrup media delivered with an initial pulse equivalent of 20 g TRS/L. The IFA was operated at 28° C. for 24 hours. 50 mL of the IFA culture was then inoculated into a 0.5-L manufacturing fermentor (MFA) containing 200 mL of MF media (8 g/L $KH_2PO_4$, 7 g/L $(NH_4)_2SO_4$, 6.15 g/L $MgSO_4$*$7H_2O$, 3 mL/L 1× Bird Vitamins 3.5 (0.05 g/L biotin, 0.2 p-aminobenzoic acid, 1 g/L nicotinic acid, 2.5 g/L myoinositol, 1 g/L pyridoxine HCl, 1 g/L thiamine HCl, 1 g/L calcium pantothenate), 5 mL/L 1× Bird™ (, 5.75 g/L $ZnSO_4$*$7H_2O$, 0.32 g/L $CuSO_4$, 0.32 $MnCl_2$*$4H_2O$, 0.47 g/L $CoCl_2$*$6H_2O$, 0.48 g/L $Na_2MoO_4$*$2H_2O$, 2.8 g/L $FeSO_4$*$7H_2O$, 2.9 $CaCl_2$*$2H_2O$, 0.0585 EDTA), 5 g/L Maltose, 2 g/L Lysine). The nutrient feed to the fermentor was an undefined Brazilian cane syrup media delivered with an initial pulse equivalent to a 10 g TRS/L delivered at rate of 8.5 g TRS/L/h. The fermentor feed rate was then adjusted using an algorithm based on the culture demand for carbon, as indicated by rises in dissolved oxygen. The fermentation was run aerobically at a constant temperature of 30° C. and constant pH of 5.0 (controlled by ammonium hydroxide additions) until the dissolved oxygen reached 0% The agitation was then controlled in order to maintain an oxygen utilization rate of 110 mmol $O_2$/L/h for the remainder of the fermentation. Culture was removed daily for sampling and to prevent overflow. Salts, trace metals and vitamins were also added daily. 0.2 mL Y-30 antifoam was added to the fermentation media at the beginning and subsequently added as needed. The amount of gluco-vanillin produced and the total sugar consumed by the cells were monitored daily and the ratio of these two values (i.e., the product yield off of sugar) was determined for each 24 hour period. The fermentor was run for 10 days.

Quantification of Vanillin Y48967/Y48969

To quantify the amount of vanillin produced, the samples first treated with a commercially available beta-glucosidase to convert glucovanillin into vanillin for analysis. Samples were then analyzed on a Agilent Vanquish™ Flex Binary UHPLC System with a diode array detector with the following program:

Mobile phase (A): 1.4% sulfuric acid v/v in water

Mobile phase (B): 100% acetonitrile

Gradient is as follows [gradient time, (min) mobile phase A, (%)]: [(0.00, 88), (0.05, 88), (1.25, 85), (2.25, 83), (3.0, 82), (3.5, 88), (4.0, 88)]. Flow rate was 1 mL/min.

Example 4: Further Improvement in the Production of Vanillin by Replacing the Native Methylenetetrahydrofolate Reductase with a Chimera Insensitive to SAM for Improved Flux Through the O-Methyltransferase Reaction Methylenetetrahydrofolate reductase (MTHFR) is a useful step in converting SAH back to SAM to drive the OMT reaction. Yeast MTHFR (Met12 and Met13) are reported to be feedback inhibited by high concentrations of SAM. MTHFR enzymes in plants such as *Arabadopsis* do not have this same feedback inhibition. Roje et al. (Roje et al., *J. Biol. Chem.,* 2002; 277 (6): 4056-4061) constructed a chimeric protein by fusing gene sequence coding for the C-terminal domain of *Arabadopsis* MTHFR with the sequence coding for the N-terminal domain of yeast Met13. This strain accumulated higher intracellular SAM compared to native yeast. It is believed that this modification may also be advantageous to increase intracellular SAM concentrations in glucovanillin producing strains to drive the OMT reaction. Since these strains already contained an overexpressed copy of MET13, we replaced the C-terminus of both the native copy and overexpressed copy of MET13 in Y57481 with the C-terminus of *Arabidopsis* MTHFR to generate Y57482 and tested these strains in fermentation.

Figure 5:
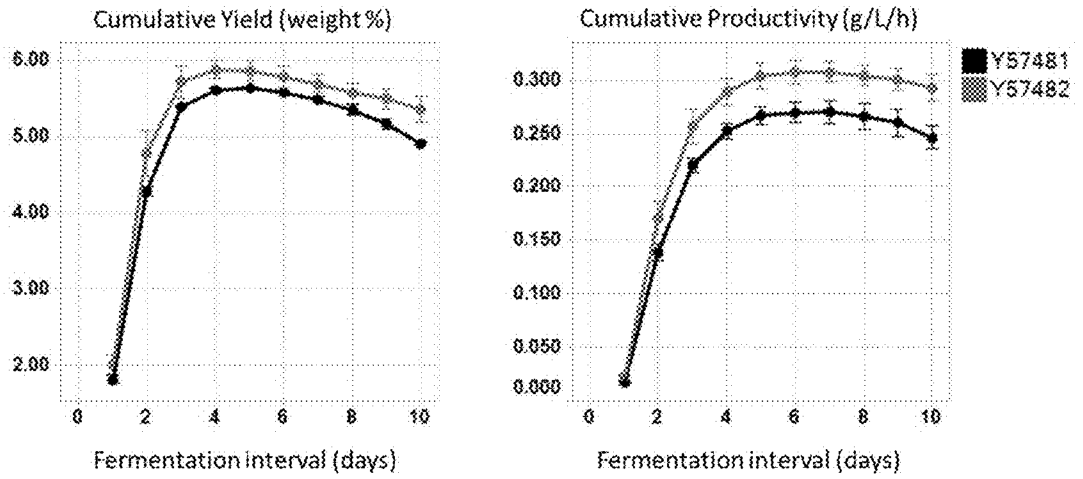
FIG. 5 provides cumulative yield (weight %) and productivity (g/L/h) for vanillin producing strain Y57481 and an improved derivative Y57482. Cumulative indicates the value for the interval from time zero to the indicated time.
Figure 6:
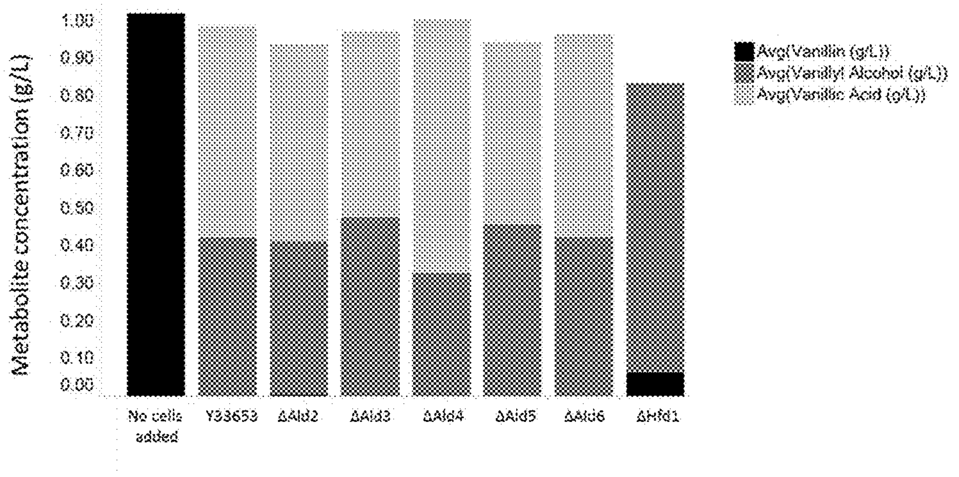
FIG. 6 provides titers (g/L) of vanillin and degradation products vanillyl alcohol and vanillic acid in liquid medium with a starting concentration of 1 g/L vanillin incubated for 24 hours for the strain modifications indicated.
Figure 7:
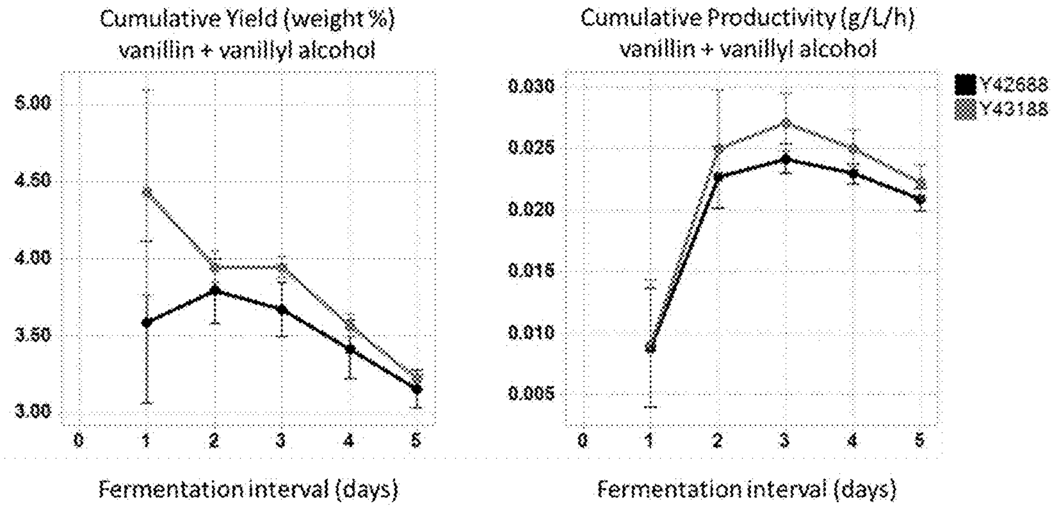
FIG. 7 provides cumulative yield (weight %; vanillin+vanillyl alcohol) and cumulative productivity (g/L/h; vanillin+vanillyl alcohol) for a 5 day fermentation of vanillin producing strain Y42688 and an improved derivative Y43188. Cumulative indicates the value for the interval from time zero to the indicated time.
Figure 8:
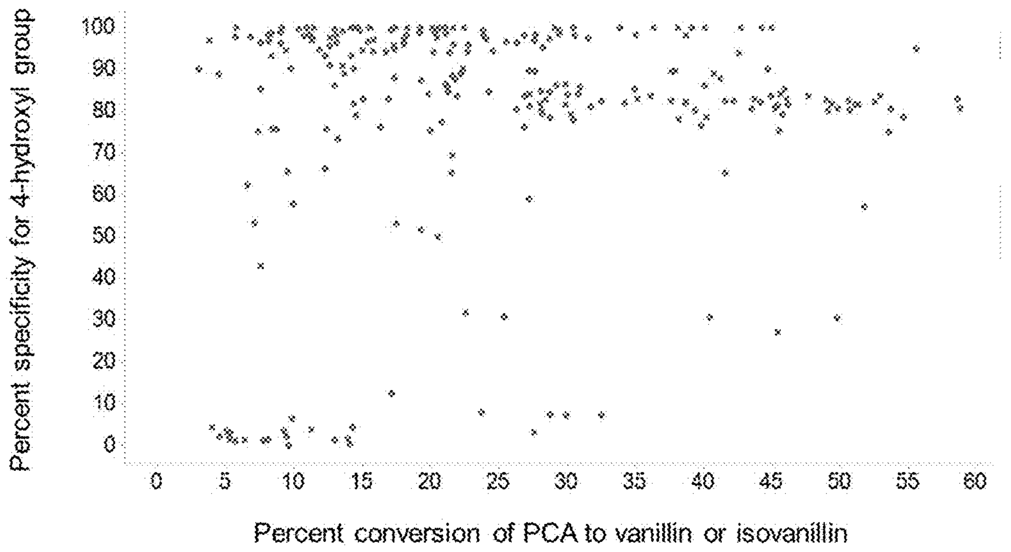
FIG. 8 provides percent specificity for 4-hydroxyl versus percent conversion of PCA to vanillin or isovanillin.

Both strains were tested in a 0.5 L fermentor as described below. In order to measure the concentration of vanillin produced, samples of the fermentation broth were centrifuged, and the supernatant was treated with a β-glucosidase enzyme to cleave the glucose. The resulting concentration of vanillin was measured by UPLC as described below. This vanillin titer was used to calculate the cumulative yield and productivity of each strain shown in FIG. 5. Y57482 had a 9% increase in 0-10 day cumulative vanillin yield and 18% increase in 0-10 day cumulative vanillin productivity compared to Y57481.

Strain Construction to Generate Y57481/Y57482

Y57481

Y57481 was constructed from Y44814 with eight integrations. First, the engineered GAL80 gene with a temperature sensitive allele fused to the DHFR protein from *Mus musculus* in MS106908 (SEQ ID NO: 1) was replaced with a different engineered GAL80 gene MS150540 (SEQ ID NO: 16) comprised of the native GAL80 gene fused to an engineered maltose binding domain which is destabilized in the absence of maltose. The expression of this GAL80 variant is controlled by a pMAL32 promoter which induces expression when maltose is present. The GAL4oc from MS106908 was left intact. The new integration is described below.

US_GAL80 pMAL32 GAL80_MBPLB_v4 FIXA

MS159820 (SEQ ID NO: 17) was integrated downstream of the MGA1 gene. This integration contains Pp.AroZ driven by pGAL2 promoter and followed by tGAS1 terminator, Ec.AroB driven by pGAL7 promoter and followed by tGRS1 terminator, a CAIB spacer as described above, a Ec.AroD gene driven by pGAL2 promoter and followed by CYS4 terminator and a feedback resistant allele of Ec.AroF (described above) driven by pGAL7 promoter and followed by ECM33 terminator as shown in the diagram below.

US_dsMGA1 tGAS1 Pp.AroZ pGAL2 pGAL7 Ec.AroB tGRS1 CAIB tCYS4 Ec.AroD pGAL7 Ec.AroF(FBR) DS_dsMGA1

MS156217 (SEQ ID NO: 18) was integrated downstream of the YCT1 gene. This integration contains two copies of Bn.OMT with DIT1 terminator and two copies of Hv.OMT with VMA8 terminator each driven by divergent pGAL1_10 promoters as described below and with a spacer derived from an *E. coli* sequence of a non-functional gene fragment derived from the part of the MurD synthetase gene.

US_dsYCT1 tDIT1 Bn.OMT pGAL10_1 Hv.OMT tVMA8 MURD tVMA8 Hv.OMT pGAL10_1 Bn.OMT tDIT1 DS_dsYCT1

MS153767 (SEQ ID NO: 19) was integrated downstream of the ALG1 gene. This integration contains an ACAR driven by pGAL7 promoter and followed by a EFB1 terminator separated by a FIXA spacer and followed by a PPTase from *Nocardia iowensis* driven by pGAL7 promoter and followed by tSYN8 terminator as shown below.

US_dsALG1 pGAL7 Mx.ACAR tEFB1 FIXA tSYN8 Ni.PPtase pGAL7 DS_dsALG1

MS141850 (SEQ ID NO: 14) was integrated at the YGL039w locus as described above.

MS172561 (SEQ ID NO: 20) was integrated downstream of the GAT4 locus. This integration contains Pp.AroZ driven by pGAL1 promoter and followed by tGAS1 terminator as described below.

US_dsGAT4 pGAL1 Pp.AroZtGAS1 DS_dsGAT4

MS167660 (SEQ ID NO: 21) was integrated downstream of the YCT1 locus. This integration contains two copies of Bn. OMT with DIT1 terminator and two copies of Ca.OMT with tHUG terminator each driven by divergent pGAL2_7 promoters as described below and with a spacer derived from an *E. coli* sequence of a non-functional gene fragment derived from the part of the MurD synthetase gene.

US_dsYCT1 [illegible] pGAL2_7 Ca.OMT tHUG1 MURD [illegible] pGAL2_7 Bn.OMT tDIT1 DS_dsYCT1

Y57482

Y57482 was generated from Y57481 by two integrations. MS 188586 (SEQ ID NO: 22) was integrated at the MET13 locus and replaces the C-terminal domain of native yeast MET13 with the *Arabidopsis* domain.

N-term MET13 C-term At.MHTFR DS_MET13

MS 173680 (SEQ ID NO: 23) was integrated at the overexpressed MET13 at the YGL039w locus (MS141850 (SEQ ID NO: 14) described below.

US_YGL039W mMET13_chimera pGAL10_1 mMET6 ECO1 mMET12 pGAL10_1 mSHM2 DS_YGL039W

Fermentation Media and Conditions for Y57481/Y57482—

A 0.5 ml of frozen cell suspension of a yeast strain containing the desired genetic modifications, was thawed, transferred into a 500-ml baffled flask containing 100 ml of BSM 3.5 (8 g/L $KH_2PO_4$, 7 g/L $(NH_4)_2SO_4$, 6.15 g/L $MgSO_4$*$7H_2O$, 3 mL/L 1× Bird Vitamins 3.5 (0.05 g/L biotin, 0.2 p-aminobenzoic acid, 1 g/L nicotinic acid, 2.5 g/L myoinositol, 1 g/L pyridozine HCl, 1 g/L thiamine HCl, 1 g/L calcium pantothenate), 5 mL/L 1× Bird™ (5.75 g/L $ZnSO_4$*$7H_2O$, 0.32 g/L $CuSO_4$, 0.32 $MnCl_2$*$4H_2O$, 0.47 g/L $CoCl_2$*$6H_2O$, 0.48 g/L $Na_2MoO_4$*$2H_2O$, 2.8 g/L $FeSO_4$*$7H_2O$, 2.9 $CaCl_2$*$2H_2O$, 0.0585 EDTA) with 0.5M succinate buffer containing 2% sucrose, 4% maltose, and 5 g/L lysine was grown in a shaker at 28° C., 200 RPM for 21 hours. 0.25 mL of this culture was then transferred into a second flask containing 100 ml of BSM 3.5 containing 2% sucrose, 4% maltose, and 5 g/L lysine and grown in a shaker at 28° C., 200 RPM for 21 hours. 0.6 mL of this culture was then inoculated into a 0.5-L initial fermentor (IFA) containing 299.4 mL of IF media (8 g/L $KH_2PO_4$, 7 g/L $(NH_4)2SO_4$, 6.15 g/L $MgSO_4$*$7H_2O$, 6 mL/L 4× Bird Vitamins 3.5 (0.2 g/L Biotin, 0.8 p-Aminobenzoic acid, 4 g/L nicotinic acid, 10 g/L myoinositol, 4 g/L pyridoxine HCl, 4 g/L thiamine HCl 4 g/L calcium pantothenate), 10 mL/L 2× Bird™ (, 11.5 g/L $ZnSO_4$*$7H_2O$, 0.64 g/L $CuSO_4$, 0.64 $MnCl_2$*$4H_2O$, 0.94 g/L CoCl2*$6H_2O$, 0.96 g/L $Na_2MoO_4$*$2H_2O$, 5.6 g/L $FeSO_4$*$7H_2O$, 5.8 $CaCl_2$*$2H_2O$, 0.117 EDTA), 40 g/L Maltose, 5 g/L Lysine). The nutrient feed to the IFA was concentrated pure sucrose delivered with an initial pulse equivalent to a 20 g TRS/L sugar. The IFA was operated at 28° C. for 24 hours. 60 mL of the IF A culture was then inoculated into a 0.5 L manufacturing fermentor (MFA) containing 240 mL of MF media (8 g/L $KH_2PO_4$, 7 g/L $(NH_4)2SO_4$, 6.15 g/L $MgSO_4$*$7H_2O$, 6 mL/L 4× Bird Vitamins 3.5 (0.2 g/L Biotin, 0.8 p-Aminobenzoic acid, 4 g/L nicotinic acid, 10 g/L myoinositol, 4 g/L pyridoxine HCl, 4 g/L thiamine HCl 4 g/L calcium pantothenate), 10 mL/L 2× Bird™ (11.5 g/L $ZnSO_4$*$7H_2O$, 0.64 g/L $CuSO_4$, 0.64 $MnCl_2$*$4H_2O$, 0.94 g/L CoCl2*$6H_2O$, 0.96 g/L $Na_2MoO_4$*$2H_2O$, 5.6 g/L $FeSO_4$*$7H_2O$, 5.8 $CaCl_2$*$2H_2O$, 0.117 EDTA), 5 g/L Maltose, 2 g/L Lysine). The nutrient feed to the fermentor was a defined sucrose feed delivered with an initial pulse of 10 g TRS/L sugar delivered at 1 g/L/h. The fermentor feed rate was then adjusted based on the culture demand for carbon, as indicated by rises in dissolved oxygen. The fermentation was run aerobically at a constant temperature of 30° C. and constant pH of 5.0 (controlled by ammonium hydroxide additions) until the dissolved oxygen reached 0%. The agitation was then controlled in order to maintain an oxygen utilization rate of 110 mmol $O_2$/L/h for the remainder of the fermentation. Culture was removed daily for sampling and to prevent overflow. Salts, trace metals, and vitamins were also added daily. 0.1 mL L-61 antifoam was added to the fermentation media at the beginning and subsequently added as needed. The amount of gluco-vanillin produced and the total sugar consumed by the cells was monitored daily and the ratio of these two values (i.e., the product yield off of sugar) was determined for each 24 hour period. The fermentor was run for 10 days.

Quantification of Vanillin Y57481/Y57482

To quantify the amount of vanillin produced, the samples first treated with a commercially available beta-glucosidase to convert glucovanillin into vanillin for analysis. Samples were then analyzed on a Agilent Vanquish™ Flex Binary UHPLC System with a diode array detector with the following program:

Mobile phase (A): 1.4% sulfuric acid v/v in water

Mobile phase (B): 100% acetonitrile

Gradient is as follows [gradient time, (min) mobile phase A, (%)]: [(0.00, 88), (0.05, 88), (1.25, 85), (2.25, 83), (3.0, 82), (3.5, 88), (4.0, 88)]. Flow rate was 1 mL/min.

Example 5. Screening O-Methyltransferase (OMT) Enzymes for Conversion of PCA to Vanillic Acid with High Specificity and Efficiency To generate a strain for screening for OMT enzymes with high efficiency and specificity Y17025 was transformed with MS106908 (SEQ ID NO: 1) as described previously. Additionally this strain was transformed with a landing pad containing only the GALI promoter and terminator, with an F-CphI restriction sequence in between the promoter and terminator (SEQ ID NO: 24) as shown below to generate Y33462.

US_BUD9 pGAL1 F-CphI cute site terminator DS_BUD9

Figure 9:
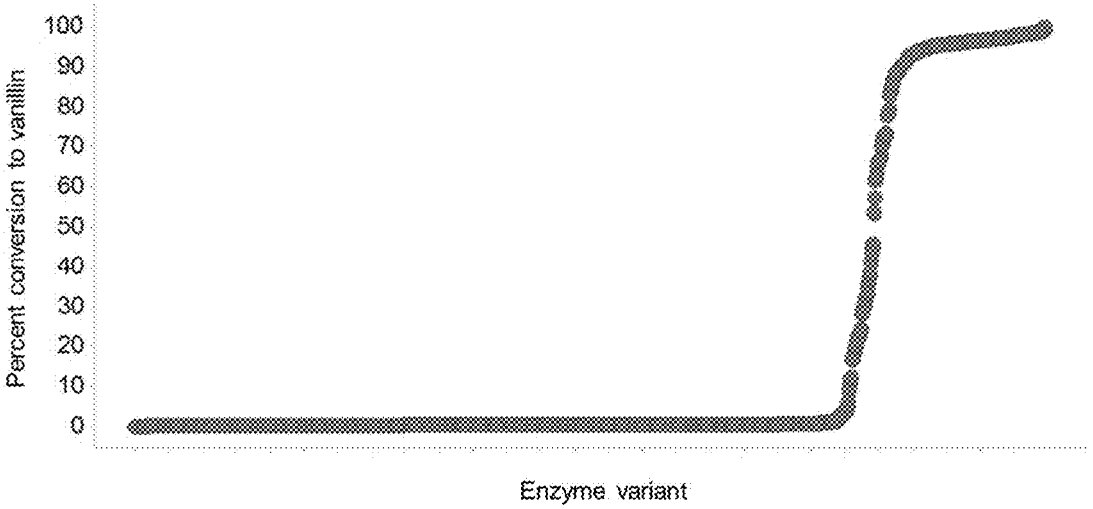
FIG. 9 provides percent conversion to vanillin for a series of enzyme variants.

Over 1,000 OMT enzymes obtained from public databases were codon optimized for optimal expression in *S. cerevisiae*. These OMT genes were then synthesized with the addition of terminal flanking sequences corresponding to the same pGAL1 and yeast terminator that flank the F-CphI sequences in the landing pad described above, to enable integration by homologous recombination into the landing pad. Yeast were transformed with OMT donor DNA, that was PCR amplified from the synthesized DNA described above, using PCR primers that bind to the pGAL1 promoter and yeast terminator, and co-transformed with a plasmid containing the gene for the endonuclease F-Cphl to cut the DNA within the landing pad. Individual yeast colonies were then tested for their ability to convert PCA to vanillic acid by culturing the resulting strains in medium containing PCA. In the primary screen, enzymes were analyzed for ability to convert PCA to vanillic acid. For the secondary screen, enzymes were analyzed for specificity of methylating the 3-hydroxyl group (to create the desired vanillic acid) and not methylating the 4-hydroxyl group (to create the undesired isovanillic acid). For each screen, strains were inoculated into the pre-culture (400 ul of Bird Seed Media (BSM) 2.0+4% raffinose+2% maltose) and incubated at 30° C. and 1,000 rpm for 24 hours, and then subcultured at a 1:25 dilution ratio into the production culture (400 ul BSM 2.0+6% raffinose+10 mM PCA) and incubated at 30° C. and 1,000 rpm for 24 hours). Cultures were then centrifuged at 3,200 rpm for 3 minutes to collect the supernatant and analyzed for total PCA converted to vanillic acid or isovanillic acid. Of these, 241 unique OMTs were able to convert 10% or more of the 10 mM PCA to an isomer of vanillic acid. These 241 strains were retested in a higher resolution assay to determine their specificity for vanillic acid over isovanillic acid. Data from this screen in shown in FIG. 9.

From this data a set of OMTs was identified which have specificity for the 4-hydroxyl group of over 98% and conversion of PCA to vanillic acid over 15% in the conditions tested. These OMTs are identified from the organisms listed in Table 2.

TABLE 2

| Organism sources of OMT enzymes identified with favorable specificity and activity<br>Organism source for OMT enzyme candidates meeting selection criteria |
|---|
| *Brachypodium distachyon* |
| *Brassica napus* |
| *Chelonia mydas* |
| *Cicer arietinum* |
| *Ciona intestinalis* |
| *Coccidioides posadasii* |
| *Cucumis sativus* |
| *Danio rerio* |
| *Dicentrarchus labrax* |
| *Esox lucius* |
| *Hordeum vulgare* |
| *Ictalurus punctatus* |
| *Medicago truncatula* |
| *Oryzias latipes* |
| *Osmerus mordax* |
| *Phoenix dactylifera* |
| *Setaria italica* |
| *Solanum tuberosum* |
| *Sorghum bicolor* |
| *Streptomyces* sp. Root431 |
| *Tuber melanosporum* |

Example 6. Screening Aromatic Carboxylic Acid Reductase (ACAR) Enzymes for Conversion of Vanillic Acid to Vanillin with High Efficiency To generate a strain for screening for ACAR enzymes with high efficiency, Y33462 described in the previous example was transformed with a DNA construct for the expression of a phosphopantothionyl transferase (PPTase) such as a PPTase from *N. iowensis* described in SEQ ID NO: 19.

Over 500 ACAR enzymes obtained from public databases were codon optimized for optimal expression in *S. cerevisiae*. These ACAR genes were then synthesized with the addition of terminal flanking sequences corresponding to the same pGAL1 and yeast terminator that flank the F-CphI sequences in the landing pad described above, to enable integration by homologous recombination into the landing pad. Yeast were transformed with ACAR donor DNA that was PCR amplified from the synthesized DNA described above using primers that bind to the pGAL1 promoter and yeast terminator, and co-transformed with a plasmid containing the endonuclease F-Cphl to cut the DNA in the landing pad. Individual yeast colonies were then tested for their ability to convert vanillic acid to vanillin by culturing the resulting strains in medium containing vanillic acid. Single colonies were cultivated in a preculture (400 ul of Bird Seed Media (BSM) 2.0+4% raffinose+2% maltose) and incubated at 30° C. and 1,000 rpm for 48 hours, and then subcultured at a 1:25 dilution ratio into the production culture (400 μl BSM 2.0+6% raffinose+20 mM vanillic acid) and incubated at 30° C. and 1,000 rpm for 24 hours. $OD_{600}$ values of the production cultures were measured. Cultures were then centrifuged at 3,200 rpm for 3 minutes to collect the supernatant. Vanillic acid, vanillin and vanillyl alcohol titers were quantified. Of these, a subset of those tested had very good conversion of vanillic acid as seen in FIG. 10. Thirty of these active ACAR variants are given in Table 3.

TABLE 3

| Organism sources for ACAR enzymes identified with favorable activity<br>Organism source for ACD1:D22 candidates meeting selection criteria |
|---|
| *Actinokineospora spheciospongiae* |
| *Aspergillus terreus* |
| *Coccomyxa subellipsoidea* |
| *Gordonia effusa* |
| *Hypocrea jecorina* |
| *Kibdelosporangium* sp. MJ126-NF4 |
| *Lichtheimia corymbifera* |
| *Metarhizium brunneum* |
| *Mycobacterium abscessus* |
| *Mycobacterium avium* |
| *Mycobacterium cosmeticum* |
| *Mycobacterium lepromatosis* |
| *Mycobacterium nebraskense* |
| *Mycobacterium obuense* |
| *Mycobacterium* sp. MOTT36Y |
| *Mycobacterium* sp. URHB0044 |
| *Mycobacterium vaccae* |
| *Mycobacterium xenopi* |
| *Neurospora crassa* |
| *Nocardia brasiliensis* |
| *Nocardia gamkensis* |
| *Nocardia lowensis* |
| *Nocardia otitidiscaviarum* |
| *Nocardia seriolae* |
| *Nocardia terpenica* |
| *Nocardia vulneris* |
| *Purpureocillium lilacinum* |
| *Rhodococcus* sp. Leaf258 |
| *Streptomyces* sp. NRRL S-31 |
| *Talaromyces marneffei* |

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

SEQ ID NO: 1
Length: 8262
Type:
Organism: artificial sequence
Other information: MS106908 sequence GACGGCACGGCCACGCGTTTAAACCGCCCCATGGCAAAGAATGCTTTCCATGACGATCATCGTAGTGCCCAATTG
GGTGCCTCTATGATGGGTATGGCTTGGGCAAGTGTCTTTTTATGTATCGTGGAATTTATCCTGCTGGTCTTCTGG
TCTGTTAGGGCAAGGTTGGCCTCTACTTACTCCATCGACAATTCAAGATACAGAACCTCCTCCAGATGGAATCCC
TTCCATAGAGAGAAGGAGCAAGCAACTGACCCAATATTGACTGCCACTGGACCTGAAGACATGCAACAAAGTGCA
AGCATAGTGGGGCCTTCTTCCAATGCTAATCCGGTCACTGCCACTGCTGCTACGGAAAACCAACCTAAAGGTATT
AACTTCTTCACTATAAGAAAATCACACGAGCGCCCGGACGATGTCTCTGTTTAAATGGCGCAAGTTTTCCGCTTT
GTAATATATATTTATACCCCTTTCTTCTCTCCCCTGCAATATAATAGTTTCGCTCGTCCAACGCCGGCGGACCTA
GTTAATTAATAGTCTTGGATGTAATTCTTATTGTTATACTGAATACGCTAAAACCACTCACAACAAGTATGGAGT
ATATTGTGTCTCTTTATATACTGAGTACTTATGCAATATGCGCTCACTCAGGATGAAATGTACACAGCCGAAAGT
ATATTGAAAGCTGCCTCTGTGGAAACTTCTATCTAATGTTGTCTCCAGATGTAGACTATGAGGCCTGAAGAAGTC
TTTAAACACCTGTTGGAGAGTATAAGGAGACTGCTACAACAACGTCTTCCCCACAAAAATTATGTGGAGGCCGGT
ATGATACCTGCACAAACGTTAAGTTACACATGAAAAAGAGACTGACATAACTTTGATCTCTGAAAATATGTTTTC
CCCTGAGTAGCTTCACTGCTTGGATACCAATACGAATAGACCTTGGCTATAGTAAGTTGCATCTGTACCGTAGAG
ATTCTTGCAACCTCGCTTAAACTCTCGCTTTTATATAATATTTCTCCTTATTGCGCGCTTCGTTGAAAATTTCGC
TAAACACGGGGTTTAAGTTTAAGTTTACAGGATTTATCCGGAAGTTTTCGCGGACCCCACACAATTAAGAATTGG
CTCGAAGAGTGATAACGCATACTTTTCTTTTCTTTTTTCAGTTCCTAGCGTACCTAACGTAGGTAACATGATTTG
GATCGTGGGATGATACAAACAACGTAAGATGAGTAGTTCCTTCCTCAATTCTTCTTTCAGCATCATTTTCTTGAG
GCGCTCTGGGCAAGGTATAAAAAGTTCCATTAATACGTCTCTAAAAAATTAAACCATCTATCTCTTAAGCAGTTT
TTTTGATAATCTCAAATGTACATCAACCTCCCGCGACCTCCAAAATCGAACTACCTTCACAATGCAGATTTTCGT
CAAGACTTTGACCGGTAAAACCATAACATTGGAAGTTGAATCTTCCGATACCATCGACAACGTTAAGTCGAAAAT
TCAAGACAAGGAAGGTATCCCTCCAGATCAACAAAGATTGATCTTTGCCGGTAAGCAGCTAGAAGACGGTAGAAC
GCTGTCTGATTACAACATTCAGAAGGAGTCCACCTTACATCTTGTGCTAAGGCTAAGAGGTGGTAGGCACGGATC
CGGCATCATGGTTCGACCATTGAACTGCATCGTCGCCGTGTCCCAAAATATGGGGATTGGCAAGAACGGAGACCT
ACCCTGGCCTCCGCTCAGGAACGAGTTCAAGTACTTCCAAAGAATGACCACAACCTCTTCAGTGGAAGGTAAACA
GAATCTGGTGATTATGGGTAGGAAAACCTGGTTCTCCATTCCTGAGAAGAATCGACTTTTAAAGGACAGAATTAA
TATAGTTCTCAGTAGAGAACTCAAAGAACCACCACGAGGAGCTCATTTTCTTGCCAAAAGTTTGGATGATGCCTT
AAGACTTATTGAACAACCGGAATTGGCAAGTAAAGTAGACATGGTTTGGATAGTCGGAGGCAGTTCTGTTTACCA
GGAAGCCATGAATCAACCAGGCCACCTCAGACTCTTTGTGACAAGGATCATGCAGGAATTTGAAAGTGACACGTT
TTTCCCAGAAATTGATTTGGGGAAATATAAACTTCTCCCAGAATACCCAGGCGTCCTCTCTGAGGTCCAGGAGGA
AAAAGGCATCAAGTATAAGTTTGAAGTCTACGAGAAGAAAGACGGTACCGAACAAAAGCTTATTTCTGAAGAAGA
CTTGGGAGCTGGTGCAGGCGCTGGAGCGGGTGCCATGGACTACAACAAGAGATCTTCGGTCTCAACCGTGCCTAA
TGCAGCTCCCATAAGAGTCGGATTCGTCGGTCTCAACGCAGCCAAAGGATGGGCAATCAAGACACATTACCCCGC
CATACTGCAACTATCGTCACAATTTCAAATCACTGCCTTATACAGTCCAAAAATTGAGACTTCTATTGCCACCAT
CCAGCGTCTAAAATTGAGTAGTGCCACTGCTTTTCCCACTTTAGAGTCATTTGCATCATCTTCCACTATAGATAT
GATAGTGCTAGCTATCCAAGTGGCCAGTCATTATGACGTTGTTATGCCTCTCTTGGAATTCTCCAAAAATAATCC
GAACCTCAAGTATCTTTTCGTAGAATGGGCCCTTGCATGTTCACTAGATCAAGCCGAATCCATTTATAAGGCTGC
TGCTGAACGTGGGGTTCAAACCATCATCTCTTTACAAGGTCGTAAATCACCATATATTTTGAGAGCAAAAGAATT
AATATCTCAAGGCTATATCGGCGACATTAATTCTATCGAGATTGCTGGAAATGGCGGTTGGTACGGCTACGAAAG
GCCTGTTAAATCACCAAAATACATCTATGAAATCGGGAACGGTGTAGATCTGGTAACCACAACATTTGGTCACAC
AATCGATATTTTACAATACATGACAAGTTCGTACTTTTCCAGGATAAATGCAACGGTTTTCAATAATATTCCAGA
GCAAGAGCTGATAGATGAGCGTGGTAACCGATTGGGCCAGCGAGTCCCAAAGACAGTACCGGATCATCTTTTATA -continued

CCAAGGCACATTGTTAAATGGCAATGTTCCAGTGTCATGCAGTTTCAAAGGTGGCAAACCTACCAAAAAATTTAC

CAAAAATTTGGTCATTGATATTCACGGTACCAAGGGAGATTTGAAACTTGAAGGCGACGCCGGATTCGCAGAAAT

TTCAAATCTGGTCCTTTACTACAGTGGAACTAGAGCAAACGACTTCCCGCTAGCTAATGGACAACAAGCTCCTTT

AGACCCGGGGTATGATGCAGGTAAAGAAATCATGAAAGTATATCATTTACGAAATTATAATGCCATTGTCGGTAA

TATTCATCGACTGTATCAATCTATCTCTGACTTCCACTTCAATACAAAGAAAATTCCTGAATTACCCTCACAATT

TGTAATGCAAGGTTTCGATTTCGAAGGCTTTCCCACCTTGATGGATGCTCTGATATTACACAGGTTAATCGAGAG

CGTTTATAAAAGTAACATGATGGGCTCCACATTAAACGTTAGCAATATCTCGCATTATAGTTTATAAAAGCATCT

TGCCCTGTGCTTGGCCCCCAGTGCAGCGAACGTTATAAAAACGAATACTGAGTATATATCTATGTAAAACAACCA

TATCATTTCTTGTTCTGAACTTTGTTTACCTAACTAGTTTTAAATTTCCCTTTTTCGTGCATGCGGGTGTTCTTA

TTTATTAGCATACTACATTTGAAATATCAAATTTCCTTAGTAGAAAAGTGAGAGAAGGTGCACTGACACAAAAAA

TAAAATCCCCGCGTGCTTGGCCGGCCGTAAGATTATTACTTGCTATAAGTGCGTGCCTGATGAACAGGATATTGC

GGTCAATAATGCTGATGGTTCATTAGACTTCAGCAAAGCCGATGCCAAAATAAGCCAATACGATCTCAACGCTAT

TGAAGCGGCTTGCCAGCTAAAGCAACAGGCAGCAGAGGCGCAGGTGACAGCCTTAAGTGTGGGGGGTAAAGCCCT

GACCAACGCCAAAGGGCGTAAAGATGTGCTATCGCGCGGCCCGGATGAACTGATTGTGGTGATTGATGACCAGTT

CGAGCAGGCACTGCCGCAACAAACGGCGAGCGCACTGGCTGCAGCCGCCCAGAAAGCAGGCTTTGATCTGATCCT

CTGTGGCGATGGTTCTTCCGACCTTTATGCCCAGCAGGTTGGTCTGCTGGTGGGCGAAATCCTCAATATTCCGGC

AGTTAACGGCGTCAGCAAAATTATCTCCCTGACGGCAGATACCCTCACCGTTGAGCGCGAACTGGAAGATGAAAC

CGAAACCTTAAGCATTCCGCTGCCTGCGGTTGTTGCTGTTTCCACTGATATCAACTCCCCACAAATTCCTTCGAT

GAAAGCCATTCTCGGCGCGGCGAAAAAGCCCGTCCAGGTATGGTCGGCGGCGGATATTGGTTTTAACGCAGAGGC

AGCCTGGTCAGAACAACAGGTTGCCGCGCCGAAACAGCGCGAACGTCAGCGCAACGGCCGGCCAAGCACGCGGGG

ATTGAGCGAAGCTTCTGAATAAGCCCTCGTAATATATTTTCATGAAGAATTTAGGTCCAAAAAAAAGATGGGCAT

TAATTCTAGTCATTTAAAAAATTCTATAGATCAGAGGTTACATGGCCAAGATTGAAACTTAGAGGAGTATAGTTA

CATAAAAGAAGGCAAAACGATGTATAAATGAAAGAAATTGAGATGGTGCACGATGCACAGTTGAAGTGAACTTGC

GGGGTTTTTCAGTATCTACGATTCATTTTACTCTTTTTTTGGGTTTGGTGGGGTATCTTCATCATCGAATAGATA

GTTATATACATCATCCATTGTAGTGGTATTAAACATCCCTGTAGTGATTCCAAACGCGTTATACGCAGTTTGGTC

CGTCCAACCAGGTGACAGTGGTTTTGAATTATTACCATCATCAATTTTACTAGCCGTGATTTCATTATTCATGAA

GTTATCATGAACGTTAGAGGAGGCAATTGGTTGTGAAAGCGCTTGAGAATTTGTTTGAGTTGTTATGAGGTTCGG

ACCGTTGCTACTGTTAGTGAAAGTGAAGGACAATGAGCTATCAGCAATATTCCCACTTTGATTAAAATTGGCGCC

ACCAAACAAAGCAGACGGGGTCAGTGGCACTAATGATTGCAGCTGTTGCTGTTGCCCTAGAAAAGGCGTGACTGA

GCGATGCGAAGGTGTGCTTCTTGGTATTGTCACTGGAGAGTTACGAGAGGGTGGACGGTTAGATAACAGCTTGAC

TAGATCACTGAAACTTGCTCCTGATTTCAATGGCACAGGTGAAGGCCCTACTGAGCCAGGAGAAACATATTTAAC

ACTGATATTGTTGACATTTTCCTCCGGAAGAGTAGGGTATTGGGCGATAGTTGCAGAACCGACAATATTTTTAAT

GGCGCTACCATTACTATTGTTATAACTGATATGCGGTAATGGGATTGCACACTGTGATAACAGAAACGGCGCACA

TACCTCTTCCAGTACTTGAATGTATTTTTCACAAGTCTGGATTTTAAAAGTGGCCAGTTTTTTTAATAGCATCAG

AACAGTGTTAATTTGTTGTAATAATTGTGCGGTCTCGTTATTCTCAGCATTCGATTTTGAGTTTGAGAGTAGAGT

CTTTATGGGTACTAGGACTGCATTGAACAAGTAATAAGAACAATTCCAGGCAAAATATGGGGTGACATTATGATT

GTCCATATAGCTACTTACAGACATAACAGTTCTTTGTGCTGCATCGCTTAACATGATGGAGCATCGTTTAACTTC

ATAACTTTGATGATCATTTTGATCCTGTTCTAGTTGTGACTTTTTCTGGGTAAAATTAGTGAAAAAATCTCTTAA

TACATAAATGATAAGAGACAACTGTTTCCACTTCAGTTCGAATCTTGTAAAGGATAGCCAAGGGTGTTCCTTCAA

CAAATTGGTTAGAGCGGTGGTGGAAATATCCATTTGTAAAAACTTTGGTGCCTGTCTCGAAACCTCCTCAATCTC

-continued

ATTACAAATCATCAAGCATTTTTTTGCACATATAGGACTTTTTTCTGCAGTTACTGTTTTGTCTAGTTCATAGAT

TTTTGTGAAAACTTGTAAGAGCCTTGCTGTTTCAATGATGCCATGATATATGGTGGGACCTGTTGTGGTACGCTG

CACATCGTCGACAGAAGAAGGGAAGGAGATTGTATTCTGAGAAAGCTGGATGGATCGACCATAAAGCAGGGACAA

TTGGATCTCCCAAGAGTAGACAGACCACCAAATTCGGCGTCTTTGTTCCAGAATGCTGCTATCACTGAAGGACGA

GGGGAGGTCCCTATTCAAGCCCAATGATATGGCCATTCTTATGGAAAAGCTGTGAAAATTATAGCTAGTATTTGT

TTTCTGCCTCCACTGTGTATATCGCGACAGAAGATGTAGGGCTGTCACCAAAATTATGGAACCTGACTCGAAGAC

CTTGCTCGTCAAATGAGATTTAGCATTTTGATAGTAAAAAACATCTATATCAGTAGATTCCCCCTCTATACACCA

GGCTCCAATGGCTAATATGCAGTTAAAAAGGATTTGCCATTGATCCTTCGACGCGATTTCAATCTGGTTATTATA

CAACATCATTAGCGTCGGTGAGTGCACGATAGGGCAGTAGGGGTGAAAATTATTGAGATAACTTTGAAGTAAACG

GGATGTTGTGGATCTAGAAGCCAACGTGTATCTATCCGTAATCATGGTCGGGAGCCTGTTAACGTTAGAGTTCGT

GTAATTTTCCGGTTTAAAGCCAATAGATCGAAGAATACATAAGAGAGAACCGTCGCCAAAGAACCCATTATTGTT

GGGGTCCGTTTTCAGGAAGGGCAAGCCATCCGACATGTCATCCTCTTCAGACCAATCAAATCCATGAAGAGCATC

CCTGGGCATAAAATCCAACGGAATTGTGGAGTTATCATGATGAGCTGCCGAGTCAATCGATACAGTCAACTGTCT

TTGACCTTTGTTACTACTCTCTTCCGATGATGATGTCGCACTTATTCTATGCTGTCTCAATGTTAGAGGCATATC

AGTCTCCACTGAAGCCAATCTATCTGTGACGGCATCTTTATTCACATTATCTTGTACAAATAATCCTGTTAACAA

TGCTTTTATATCCTGTAAAGAATCCATTTTCAAAATCATGTCAAGGTCTTCTCGAGGAAAAATCAGTAGAAATAG

CTGTTCCAGTCTTTCTAGCCTTGATTCCACTTCTGTCAGATGTGCCCTAGTCAGCGGAGACCTTTTGGTTTTGGG

AGAGTAGCGACACTCCCAGTTGTTCTTCAGACACTTGGCGCACTTCGGTTTTTCTTTGGAGCACTTGAGCTTTTT

AAGTCGGCAAATATCGCATGCTTGTTCGATAGAAGACAGTAGCTTCATCTTTCAGGAGGCTTGCTTCTCTGTCCT

CTCTTAAAATGATGGCGTGCATTACGTAGACACAATCTGGAGATGAAGCTGAAAATCTGGATCCGGAAGGATGAC

GGAAAAAATAGCTCATAAAACAGAAAAAGGCCCGAAGTAACAATAGGAAAAATTAATTGCACTAAACAAAGAAAA

CGATATTATGGTGATTAAACTGATACAGAATTATGTAAATACTTTGAAATTATAGAAGGTTTGTAGAATAAAAAA

AATACTGGGCGAATGCTGAGGTCCGCCGGCGTTGGACGAGCGGCTACGTATAACTGTCAAAACTTTGCAGCAGCG

GGCATCCTTCCATCATAGCTTCAAACATATTAGCGTTCCTGATCTTCATACCCGTGCTCAAAATGATCAAACAAA

CTGTTATTGCCAAGAAATAAACGCAAGGCTGCCTTCAAAAACTGATCCATTAGATCCTCATATCAAGCTTCCTCA

TAGAACGCCCAATTACAATAAGCATGTTTTGCTGTTATCACCGGGTGATAGGTTTGCTCAACCATGGAAGGTAGC

ATGGAATCATAATTTGGATACTAATACAAATCGGCCATATAATGCCATTAGTAAATTGCGCTCCCATTTAGGTGG

TTCTCCAGGAATACTAATAAATGCGGTGCATTTGCAAAATGAATTTATTCCAAGGCCAAAACAACACGATGAATG

GCTTTATTTTTTTGTTATTCCTGACATGAAGCTTTATGTAATTAAGGAAACGGACATCGGGCGGTTTAAACGCGT

GGCCGTGCCGTC

SEQ ID NO: 2
Length: 920
Type:
Organism: *Saccharomyces cerevisiae*
Other information: MS73609 sequence

GACGGCACGGCCACGCGTTTAAACCGCCCTGTGACACAATTTGTGTCTCTACTGTGTGAACTTCCATTGCTGACT

AAAGATTCCCCGCTCCGCTTATATGTCCGGTCCGTCCTTGACCGAAGATCACATTGCCAATTTTTCACATCTGGA

AGCGATACGACAATATAGGAGAAAAAGAAAAGTGAAAGGCAAAAAAGCACCAACAGTTCTCGAGGTGAAGTGCCG

TCAATCTTCTGTATAAATTCGGCCAATTCAATCTAATTTAATAGATTTGCGACAGACTTTCACATCCACATTCGA

GGAAGAAATTCAACACAACAACAAGAAAAGCCAAAATCCGCTCGTCCAACGCCGGCGGACCTGTTGTCAAGCTCT

TGATAAATGTAGCTCCTTTCTTTTTAACTGCTCCATGTTTTGGGTCTGTATATAGGAGTGCTGTTTTAATCGATA

-continued

TAGGTTACATTTGAAACTTTTTTTTATGATTATAAGGTACTATTTAAATATTTACAACTCGTACAGTTCTCTTTT

GTTTTTTCTCTTTTTCTCCTTGCTAAGCACCTTTAAGGTGAAAAGAAACACATATCAATACACTAACAAAAAAGG

TGCACGTTCATAGGGTATCGGACAATAACTATATTACTAAGCTACCAAAGCAATAGCGCCAATAACAAAAGCTTT

CATGTTAATGTTCAGGGATGCACCGGTATTTTCTTTTGCCGTGCTGACAGTATATGTTGTGCTTTGTTTAGCGGA

TGAGGATGTTCCATGAATCGCTGCCGTAGGTTTGGTGGTAGATCTGTTTACCTTTTCAGTGGATGAACTTAGTTG

TGATGTTAATAGCGACTTTTGGCTCGAGACAATTATCGTTTCAAGGGTAGTTTCACCCCTCCCGATCCGGTGTTT

AAACCCCAGCGCCTGGCGGG

SEQ ID NO: 3
Length: 1069
Type:
Organism: *Saccharomyces cerevisiae*
Other information: MS120584 sequence

GACGGCACGGCCACGCGTTTAAACCGCCATTACCGCGTGAACTATGTCATATTTGCGATTTTAGGTACAATAAAT

ATTATCATTATTATATTATGTTTGCATGTAGGTTCTACAAATACATTGTTGTACGCTATAGTTTCCTTTCAAAAC

TAGAAAGAATTCGTAACAAAATAATCTCCAATATTTTATAGCACCTTATTAATATCAATGCTGCAATACCTTCTC

ATTTCAACAATTGGCCCTCACCTCTTTTGTACAAAAAACGTCGCCATTGATAAAATAAGTAAGAAGCATATAATT

GGAATGTCCATTACGTAAAAGAAAAAAAATCATGTGTACATATTACGTAATAGAATACGGAATTTTCTCGCGGAA

GTAGATCTTCCGTGGAAAAAAAGGAAAAAGTCCGATCAATATTGAAAAAGGGATCCTTAGTTTCCCAACTATATA

AGGAGGAAAAGTCTATCTCTGTAGCGTTGATATAACGTGTACGATTTTCAAACAAACAGATAGCAGTATCACACG

CCCGTAAATACTTTAAATGAAAATAGATAATATTTATATATATTAACGTTATTACAATTATTTTTTATCATCTGG

TACATCTCTGCGTATTTTTCTCTTCTATATACAGCTTAATATGTCGAAAACGCGAAGCAAGAAAGAAAAGAAAAT

TGACGAAAAAACAATAGAGAAACGTTCAGATAAGCATTTATCTTTGCAACACATCACAAGAAAAGCTGTGCACAA

TGACCGGAGCAGCAACTGCAGCAGAAAACTCTGCCACACAGTTAGAATTCTATAGAAAAGCTTTGAATTTCAACG

TTATTGGGAGATACGATCCAAAAATAAAGCAACTGCTTTTTCACACACCACATGCGTCACTGTATAAATGGGACT

TCAAGAAGGACGAATGGAATAAACTAGAATATCAAGGTGTTTTGGCCATATATTTGAGAGACGTCTCGCAAAATA

CAAATCTTCTACCCGTCTCCCCACAAGAAGTAGATATTTTTGATTCGCAAAATGGTAGTAATAACACGGTGTTTA

AACCCCAGCGCCTGGCGGG

SEQ ID NO: 4
Length: 1048.
Type:
Organism: *Saccharomyces cerevisiae*
Other information: MS120568 sequence

GACGGCACGGCCACGCGTTTAAACCGCCCAAGACTCGTTGGGTCAATATACACCACAAAAAAAGGTACACACGAA

TGGTTTAACCCTTTCGGTTCCTTCTGTAAATCGAAAAATGCCCTTTATACAGCGGGTTGGTCTCCCATCAAAGTT

GAGAAGCGATTAGAAATTAGGTTACCTAATGAATCCATAAATAAATGGAAAACGCTATTTTGTTCGAACGATGGA

ATAAAAATATGAACGGGTGTCATTGAAATTCGGTGTATTTTTTGATCGGGCCTGATCTGGCTCGGGTTTGGCACA

ATTTGGCTTGGTTAGTTCGGCAAAGCTTATTTAAAGAACCTTTTTGGATAGCCAATTGAGAGACTTGAAATAGAA

AGATCGTAAGTATTTTTATGAACGCAAAATCAATCTTGGTAGCCCAGTTAGTTTCTCTTCACTAATTCCGGAGAA

CAAAAACATATCATACGATTGTGTGAGATTCAACAAAAATCGATCAGAAATTTTTTTTGAACAGAATAGTCAATT

AAGCTTTCGAGAAAAACTTTCTTTTAACCCCTCTAATCTAAATATAAACATATAGCTTATAGAAATGAATGAATA

TTTTAAATAGTTACGGATACAAAGAGTTCATTATAGTGCGGGCAGTTAGTACGGTATCGATTTATCATTGGAGAT

CTGCAGTGTTACAGAAGCACTGCTCACCAGTTGTCTACGGAAGGACGTTGAGATAGTTTTACCACGTTTGAGCTA

-continued

AAAGTTTCTACCACAAGAGCCTTTATTTGCACATGGCAGTGAATGCATGATTAAGGATATGAAGAAGAAAGGAAT

AACTAGGAATAAATTTTATTTAGAGAGGGTATGATGAAAGGAGAGCCTCGTTATTTATGACCTGCATTTTTATCA

GCATCTTCTTTCCAGCTCCCGCTAAACATGTGCTTTACAAAAGCCATTTTGTCGTCACTAGACTGGGCGCCCATC

TGCCCCACATCTGGTGAAAAACTTGTTATTGGTAGAACCATCACACGGTGTTTAAACCCCAGCGCCTGGCGGG

SEQ ID NO: 5
Length: 9085
Type:
Organism: Artificial sequence
Other information: MS133489 sequence

GACGGCACGGCCACGCGTTTAAACCGCCCGAACAAGCTTATCCCTATTACAGAATTCCAAGGAGGAAATCATTCA

ACTTGAAAGTAAATGGATGTCTATGCAATCTGTTAAAACAACTGCCCTACCCCTTCAAGAGACTACGAATACATC

ATCGACCTTAACTTCTCTGACGTCCAGCATAATTCCCAAGAGTATACCTATAATCACGAAAGGTGAAGTCGCCAC

TAAACCAGCATCTTACTGAATTATTTTCAACAGAACACATCGCATCCAACTGAACAAACTGTTACCGCTGTTGAT

ACCAAGGAACATTCAGTGAACGTAGGGAAGAACGAACATTCTCCATATTTTTGCATACTAGATACAAGGGGGAAG

AATGCAATTATTTCACAAACCGAAAGAAAAAGAATCACAAGCTATGTTTGCTATTATCAATTTTTCTTATGATTA

ATTTAACATAAATTATGGCCTTTTTCATTCCGGCTGCGCTTGTTCTCCAATTTTTTTTTTTTTTTTGAGAAAACT

TTCGCTCGTCCAACGCCGGCGGACCTTCACATGTAGGGACCGAATTGTTTACAAGTTCTCTGTACCACCATGGAG

ACATCAAAGATTGAAAATCTATGGAAAGATATGGACGGTAGCAACAAGAATATAGCACGAGCCGCGAAGTTCATT

TCGTTACTTTTGATATCGCTCACAACTATTGCGAAGCGCTTCAGTGAAAAAATCATAAGGAAAAGTTGTAAATAT

TATTGGTAGTATTCGTTTGGTAAAGTAGAGGGGGTAATTTTTCCCCTTTATTTTGTTCATACATTCTTAAATTGC

TTTGCCTCTCCTTTTGGAAAGCTATACTTCGGAGCACTGTTGAGCGAAGGCTCATTAGATATATTTTCTGTCATT

TTCCTTAACCCAAAAATAAGGGAAAGGGTCCAAAAAGCGCTCGGACAACTGTTGACCGTGATCCGAAGGACTGGC

TATACAGTGTTCACAAAATAGCCAAGCTGAAAATAATGTGTAGCTATGTTCAGTTAGTTTGGCTAGCAAAGATAT

AAAAGCAGGTCGGAAATATTTATGGGCATTATTATGCAGAGCATCAACATGATAAAAAAAAACAGTTGAATATTC

CCTCAAAAATGCCCAGTAAATTGGCTATAACTTCCATGTCCTTGGGCAGGTGTTATGCAGGCCATTCTTTCACAA

CTAAGTTAGACATGGCTAGGAAATATGGTTACCAGGGTTTGGAGTTGTTTCATGAGGACTTAGCCGATGTCGCAT

ACAGGTTGTCAGGTGAAACACCTAGTCCATGCGGTCCCAGTCCAGCTGCTCAATTATCAGCCGCTAGACAGATAT

TGAGGATGTGCCAGGTTAGAAACATCGAAATAGTGTGCTTGCAACCCTTTTCACAATATGATGGTTTATTGGATA

GAGAGGAGCACGAGAGGAGGTTGGAGCAATTAGAGTTTTGGATTGAATTGGCCCACGAGTTGGATACTGACATCA

TTCAAATTCCAGCCAATTTCTTGCCCGCCGAAGAAGTCACAGAAGATATTTCATTAATTGTGAGTGACTTACAGG

AAGTTGCCGATATGGGTTTACAGGCAAACCCTCCAATAAGGTTTGTATATGAGGCATTATGCTGGTCCACTAGAG

TTGACACTTGGGAGAGGTCTTGGGAAGTTGTCCAAAGAGTAAATAGACCTAACTTTGGCGTTTGCTTAGACACTT

TTAACATCGCAGGTAGAGTTTATGCTGACCCCACAGTTGCCTCAGGCAGAACACCAAACGCTGAAGAAGCAATTA

GAAAGTCAATTGCCAGGTTGGTCGAAAGGGTCGATGTATCTAAAGTCTTCTACGTTCAAGTAGTGGACGCCGAAA

AGTTAAAGAAACCATTAGTTCCCGGTCATAGATTCTATGACCCTGAGCAACCAGCCAGAATGTCATGGTCAAGAA

ATTGTAGGTTGTTCTACGGCGAAAAAGACAGAGGCGCTTACTTACCTGTTAAAGAAATCGCTTGGGCTTTTTTCA

ATGGATTGGGCTTCGAAGGTTGGGTGTCCTTGGAATTATTTAACAGAAGAATGTCAGATACTGGATTTGGAGTTC

CAGAGGAGTTAGCTAGGAGAGGCGCCGTATCATGGGCCAAATTAGTTAGAGATATGAAAATCACAGTGGATTCTC

CAACTCAACAACAAGCTACACAGCAGCCTATTAGAATGTTGTCCTTATCTGCAGCCTTATAAAAGGCGGCCGCTG

GCGAGGGAGATGATCCGCTCTAACCGAAAAGGAAGGAGTTAGACAACCTGAAGTCTAGGTCCCTATTTATTTTTT

TATAGTTATGTTAGTATTAAGAACGTTATTTATATTTCAAATTTTTCTTTTTTTTCTGTACAGACGCGTGTACGC

-continued

ATGTAACATTATACTGAAAACCTTGCTTGAGAAGGTTTTGGGACGCTCGAAGCAACCTGCAGGCCGCGAGCGCCG

ATCGGGTAGTGGAGCCCGTTTGGGCTCAGCGCGAGGTAACAAAAAAAAATTTCAAATGTTGGCCAAAAAAAACGT

CAATTATTCCTATGTACGAGGTCTAAATATAAAAACATATCTATTATATTCTGACGTATTTATATTCTATTGTTC

TTTCCTATCACTGGCCTACAAAAAAAAAGAGAAGCATACTCAACGCGATCGCCGACGCCGCCGATTTAGGCCACT

CTTGCTGTCAATTGGCCATTCAAATCCTGATGAATTTCTCTCAACAATGCGTCGGTCATTTCCCATGAAATACAT

GCGTCTGTAACAGACACGCCATACTTCATTTCTGATCTTGGCTGTTCGGATGATTGGTTACCCTCATGAATATTT

GATTCGATCATCAAACCGATGATAGATCTGTTTCCATCTTTTATCTGTGCAACTACAGATTCAGCGACGGCGGGT

TGTCTCCTGTAATCCTTATTAGAGTTACCGTGAGAACAGTCGACCATCAAGGAAGGTCTTAAACCTGCTTGTTCC

ATTTCCTTTTCGCACTGTGCCACGTCGGCAGGTGAATAGTTTGGGGCCTTACCACCCCTCAATATTACATGACCA

TCTGGGTTACCCTGAGTTTGTAATAATGCGACCTGACCAGCTTGATTGATACCGACAAATCTATGTGGTTGAGCT

GCGGCCCTCATGGCATTTATGGCAGTTGCCAATGAACCGTCTGTGCCGTTTTTGAAGCCAACTGGCATACTCAAA

CCAGATGCCATTTCTCTGTGAGTTTGTGATTCGGTGGTTCTAGCACCTATTGCAGACCAGGAGAATAAATCGCCC

AAATATTGAGGACTGTTTAAATCCAAGGCTTCGGTAGCTAAAGGCAAACCCATATTTACTAATTCCAACAACAAT

TTCCTTGCGATTTGCAAACCAGCTTCCACATCAAAAGATCCATCCATATGTGGGTCGTTAATCAATCCCTTCCAA

CCTACAGTGGTCCTTGGCTTTTCAAAATAAACCCTCATAACCAAATACAAGGAGTCGGAGACTTCAGCTGCCAAG

GCCTTAAATCTTCTTGCGTATTCCAATGCTGTTTCAGGATCGTGGATACTACATGGGCCACATACAACCAATAAC

CTTGGATCTCTACCGGCTATAATATCAGAAATACTCTTTCTTGAATCGGCTATCTGAGCCTCTTGTTGCAAAGAT

AAGGGAAAGGCAGCTTTTAATTGCTCAGGTGTCATCAAAACCTGTTCATCTGTTATATGTACGTTATTTAAGGCA

TCTTTCTGCATTGTAAAGTTAGTTGGTTGCGCGACTTCGGGTGGGGTATGTTAATCTTGTGTTTACTTAACTATT

GCTATTCTTGATGATAATTGAATAAGGTGCATAATGAAGAGCAATTCACAACACCAAATTTTCAATCCAATTACT

GATTGTTTATATATGTCTACAAAACTAATCCTATCTCCACATTTTAGCCTGCGAAATGTTTGTTTTTTAAACAAT

AGCTCTCCAGAACATTGTATAATTTAAGAATATGTGCACAGTTAACTTTCTAGCAGGAGTATAATGCCATTTGCT

CCCCATCTTGAGATGGGAAGGGCTTAACTAATCTCGGTTCGGAGTGATCCGCCCCGATACTGCCTTCTGCCTTAA

TATCGTCCAAGGCACATGGACCCCTGAACGGCGCAGATATCTCCGCACGGACGAAAGACCGCCGGTGCCTTCCTG

AGGCAACCGCCCCTTTCGAATATAGATCACGTGACCCATTTTTAGCTACTAATAGAAAAAGAAATTGCAACCTAC

TTAAGCCATTCCGGAAGGAAGCTTTCCGAATCCCCGCGTGCTTGGCCGGCCGTGATCATCTACCCATGCCGAAAT

TCGGGCCGTTGGCCGGATTGCGCGTTGTCTTCTCCGGTATCGAAATCGCCGGACCGTTTGCCGGGCAAATGTTCG

CAGAATGGGGCGCGGAAGTTATCTGGATCGAGAACGTCGCCTGGGCCGACACCATTCGCGTTCAACCGAACTACC

CGCAACTCTCCCGCCGCAATTTGCACGCGCTGTCGTTAAATATTTTCAAAGATGAAGGCCGCGAAGCGTTTCTGA

AATTAATGGAAACCACCGATATCTTCATCGAAGCCAGTAAAGGTCCGGCCTTTGCCCGTCGTGGCATTACCGATG

AAGTACTGTGGCAGCACAACCCGAAACTGGTTATCGCTCACCTGTCCGGTTTTGGTCAGTACGGCACCGAGGAGT

ACACCAATCTTCCGGCCTATAACACTATCGCCCAGGCCTTTAGTGGTTACCTGATTCAGAACGGTGATGTTGACC

AGCCAATGCCTGCCTTCCCGTATACCGCCGATTACTTTTCTGGCCTGACCGCCACCACGGCGGCGCTGGCAGCAC

TGCATAAAGTGCGTGAAACCGGTAAAGGCGAAAGTATCGACATCGCCATGTATGAAGTGATGCTGCGTATGGGCC

AGTACTTCATGATGGATTACTTCAACGGCGGCGAAATGTGCCCGCGCATGAGCAAAGGTAAAGATCCCTACTACG

CCGACGGCCGGCCAAGCACGCGGGGATTCGGAAAGCTTCCTTCCGGAATGGCTTAAGTAGGTTGCAATTTCTTTT

TCTATTAGTAGCTAAAAATGGGTCACGTGATCTATATTCGAAAGGGGGCGTTGCCTCAGGAAGGCACCGGCGGTC

TTTCGTCCGTGCGGAGATATCTGCGCCGTTCAGGGGTCCATGTGCCTTGGACGATATTAAGGCAGAAGGCAGTAT

CGGGGCGGATCACTCCGAACCGAGATTAGTTAAGCCCTTCCCATCTCAAGATGGGGAGCAAATGGCATTATACTC

CTGCTAGAAAGTTAACTGTGCACATATTCTTAAATTATACAATGTTCTGGAGAGCTATTGTTTAAAAAACAAACA

-continued

TTTCGCAGGCTAAAATGTGGAGATAGGATTAGTTTTGTAGACATATATAAACAATCAGTAATTGGATTGAAAATT

TGGTGTTGTGAATTGCTCTTCATTATGCACCTTATTCAATTATCATCAAGAATAGCAATAGTTAAGTAAACACAA

GATTAACATACCCCACCCGAAGTCGCGCAACCAACTAACTTTACAATGGAAAGAATTGTTGTAACATTGGGTGAA

AGGTCTTATCCAATCACTATTGCATCTGGTTTATTTAACGAACCAGCCAGTTTTTTACCATTGAAATCCGGTGAG

CAAGTGATGTTAGTCACTAACGAAACATTAGCTCCCTTGTATTTAGACAAGGTAAGGGGTGTTTTGGAACAAGCA

GGCGTAAACGTCGATTCTGTGATATTACCAGACGGTGAACAATACAAAAGTTTGGCAGTTTTAGATACTGTATTC

ACTGCCTTATTACAGAAACCACATGGTAGAGATACTACATTGGTTGCCTTAGGAGGCGGAGTTGTCGGCGATTTA

ACAGGTTTCGCTGCCGCATCATATCAGAGAGGTGTTAGATTCATTCAGGTCCCAACTACTTTGTTATCCCAAGTA

GACTCATCAGTTGGAGGAAAGACTGCTGTCAATCATCCTTTAGGAAAGAACATGATTGGTGCCTTCTACCAGCCA

GCATCAGTCGTTGTTGATTTAGATTGTTTGAAGACATTACCTCCAAGAGAGTTGGCAAGTGGTTTGGCAGAAGTA

ATAAAATATGGTATCATATTGGATGGTGCATTTTTTAATTGGTTGGAAGAAAATTTAGATGCATTATTGAGGTTA

GACGGTCCTGCTATGGCTTATTGTATTAGAAGGTGTTGTGAATTAAAGGCTGAGGTTGTAGCAGCCGACGAGAGA

GAAACTGGTTTAAGAGCTTTGTTGAACTTAGGTCATACATTTGGTCATGCTATCGAAGCTGAAATGGGTTACGGT

AATTGGTTGCATGGTGAAGCCGTTGCAGCCGGTATGGTTATGGCTGCCAGGACATCTGAAAGATTGGGTCAATTC

AGTTCTGCAGAAACACAAAGGATAATAACCTTATTGAAAAGGGCAGGTTTACCTGTGAATGGTCCTAGAGAGATG

AGTGCTCAAGCTTATTTGCCCCACATGTTGAGAGATAAGAAGGTTTTAGCAGGTGAAATGAGGTTAATTTTGCCC

TTAGCAATTGGAAAAAGTGAAGTCAGATCCGGTGTTTCACATGAATTAGTATTGAACGCCATAGCTGATTGCCAA

TCAGCCTAAATCGGCGGCGTCGGCGATCGCGTTAAGGGAACCTTTTACAACAAATATTTGAAAAATTACCTCCAT

TATTATACCTTCTCTTTATGTAATTGTTAGTTCGAAAATTTTTTCTTCATTAATATAATCAACTTCTAAAACTTT

CTAAAAACGTTCTCTTTTTCGAGATTAGTGCTTCTTCCCAATCCGTAAGAAATGTTTCCTTTCTTGACAAATCGG

CGCTCGCGGCCTGCAGGTTAAACTTAAAATACGCTGAACCCGAACATAGAAATATCGAATGGGAAAAAAAAACTG

CATAAAGGCATTAAAAGAGGAGCGAATTTTTTTTTAATAAAAATCTTAATAATCATTAAAAGATAAATAATAGTC

TATATATACGTATATAAATAAAAAATATTCAAAAAATAAAATAAACTATTATTTTAGCGTAAAGGATGGGGAAAG

AGAAAAGAAAAAAATTGATCTATCGATTTCAATTCAATTCAATATCTCCCTCGCCAGCGGCCGCCTTTTATGCTT

GGTGTAATATGGTCAAAACTGTTCTCAAATCATTTACTGAGATCTGTCCTGGAGCAGAAGCTTTTTTGACAGCAC

CAAATGTAGCAGCAGATCCGAACACTTCACCAGCTAATCTAGAAATCACACCGGTTTTTGCCATAGACATAGTTA

TGATAGGTCTATCAGCGTATTGTTCTTGCATTTCCAATGTGGCAGCTAACAATGTTAAGACATCAGAGGTAGACT

GTGGCATTAAAGCAATTTTGGGTATATCAGCATCAAAGGATTGCATTTTTCTTAATCTGGCTATGATTTCCTCTG

CTTCTGGGGTCTTGTGGAAATCATGATTAGACATAACTACCTTAACATCGTGAGCGTGAGCGTAAGCTACAGTTT

CCTTAACCTGGTCATCACCAGTAAACAACTCCAAATCTATCATATCCACTAAACCACTATCAATAGCAGCTCTGT

TCAAAGCAATGTAGGCTTCGGTACTAATTGCTTGTTCACCACCTTCCTTAGCTGATCTGAAAGTGAACAATAATG

GTTTTTCAGGCATAGTCTCTCTTAATATCTTTGCTGCAGCCATTACTGATTCGACATTTGACAAGTCTGCATAGT

GATCCACTCTCCATTCTAATATGTCAAAATCTGCTTCTCTATAAGCTAAGGCCTCACTCTTTACAGAGGCTATGT

CTTTAGCCATTAAACTAACAATTATTTTAGGGGCTCCTGTTCCAATAACCAAATCTTTCACTGTAACTGTCTTCA

TTTTTGAGGGAATATTCAACTGTTTTTTTTTATCATGTTGATGCTCTGCATAATAATGCCCATAAATATTTCCGA

CCTGCTTTTATATCTTTGCTAGCCAAACTAACTGAACATAGCTACACATTATTTTCAGCTTGGCTATTTTGTGAA

CACTGTATAGCCAGTCCTTCGGATCACGGTCAACAGTTGTCCGAGCGCTTTTTGGACCCTTTCCCTTATTTTTGG

GTTAAGGAAAATGACAGAAAATATATCTAATGAGCCTTCGCTCAACAGTGCTCCGAAGTATAGCTTTCCAAAAGG

AGAGGCAAAGCAATTTAAGAATGTATGAACAAAATAAAGGGGAAAAATTACCCCCTCTACTTTACCAAACGAATA

CTACCAATAATATTTACAACTTTTCCTTATGATTTTTTCACTGAAGCGCTTCGCAATAGTTGTGAGCGATATCAA

AAGTAACGAAATGAACTTCGCGGCTCGTGCTATATTCTTGTTGCTACCGTCCATATCTTTCCATAGATTTTCAAT

-continued

CTTTGATGTCTCCATGGTGGTACAGAGAACTTGTAAACAATTCGGTCCCTACATGTGAAGGTCCGCCGGCGTTGG

ACGAGCGGCATAGTAAAAAAATAGATGCAGAATTTACTCACCTCAAGGAGGGGCAAAGTAATAAGAAAAGTTACC

ATAGGCTAGTTGAATGTCCAAGATCGTAAAGAATGAAGAAAAAAAGGAGTAAAAAGTATGAATAAGATAAATGAAA

ATATAAAAATAAAAACCAACTAATACATGAAGAAAAAAAAGCAGACAAAAACATTTTATGGACCTGATGCAATCT

AGTAGTCCATAGAATAATCACCACTAGAAAATTCTTCCTCTTCATTACTACCGTTTGCCATTATAGGAATATGAT

TTGCTGCAGGATTCTGCGGAGGTATTATATAGGGCACTGGCGGCACCTGTGGAATAAACCCAAATGATGGGAACA

TTGGCATCATCCAGTTAGCGTTATTTTGGTTTGCACTTATTAAGTTGTAACTGTTCACGGGCTTTGTGTTGGTAT

TAGGGTACTGCAGTGGTATGAAATAATTTTCCCTCGAGACTTGCTGTTGCGATTGGTGGCGGTTTAAACGCGTGG

CCGTGCCGTC

SEQ ID NO: 6
Length: 10078
Type:
Organism: artificial sequence
Other information: MS134781 sequence

GACGGCACGGCCACGCGTTTAAACCGCCTGCATACTTCAAGTTCAGGGTTGGACCTGCCAATGAAAATTTTAGAT

ATGTTTGGCTCAGGTCTTCCTGTTATTGCAATGAACTATCCAGTGCTTGACGAATTAGTACAACACAATGTAAAT

GGGTTAAAATTTGTTGATAGAAGGGAGCTTCATGAATCTCTGATTTTTGCTATGAAAGATGCTGATTTATACCAA

AAATTGAAGAAAAATGTAACGCAGGAAGCTGAGAACAGATGGCAATCAAATTGGGAACGAACAATGAGAGATTTG

AAGCTAATTCATTGAGTCAATGGTAACTCAGCCTTTCTTTTTTGAAAATTACTATTTTCGACTCTTTTTTTATAC

AGTTACATAGTACTACCTCTAATACACATTCATGATTAACAATGTTTCAAACAATATAAAGTCCCGATAACGACC

TTTTGAAGTGGTGACGTTACCGCTCTTCGTTGACAAGATTCAAGAGGGCTGTCAGAATAACAGCTATCATGGTGG

AACGCTCGTCCAACGCCGGCGGACCTAAACTTAAAATACGCTGAACCCGAACATAGAAATATCGAATGGGAAAAA

AAAACTGCATAAAGGCATTAAAAGAGGAGCGAATTTTTTTTTAATAAAAATCTTAATAATCATTAAAAGATAAAT

AATAGTCTATATATACGTATATAAATAAAAAATATTCAAAAAATAAAATAAACTATTATTTTAGCGTAAAGGATG

GGGAAAGAGAAAAGAAAAAAATTGATCTATCGATTTCAATTCAATTCAATATCCCCGCGTGCTTGGCCGGCCGTT

ACAAGATGGTCCTCGGAGGTCACAATTATCACCTCTCCGCATTCACAATCACAGTGTATTATCTCTATGAATAAA

AAAGTTGAAAATTCTAAAAAAAAAACAGAAATATATATTAATCTAAGTTAGTATTATAAATCGATTAAGTGACGG

CGGTAGCAGCGATAACGTAACCATCTCTTAAAACCCACTTACCGGAGATAAATGGAACTGGAGTTGGTCTAACCA

ATAAGTAGGAGACGAAGGTACCATCGTCTCTTAAATCAATCTCGGCTTGTTCGAAACCCAACCAACGATGGGTCA

AAGGAAACCAGGCTTTGTAAGTGGCTTCTTTAGCACAAAACAACAATCTGTCAGCACAGTGAACACCTTGTTCCT

CTAAACGTTTCAATTGTGGGATTTCACCAACTCTAGCGATAGAACCCAAGACATCCTTTGGCAATGGTTCAGCTG

GTTCGGCGTCCAAACCCATAGATCTGACTAATAATCTTGGAGCGACAACAGCAGCTCTGAAACCATCGGTGTGGG

TCAAAGAACCAGAAACGGAAGAAGGCCATAAAGGCATACCTCTTTCACCTCTCAAAATTGGATCACCAGAGTCTC

TACCCAAGGCTTGCAAGGCTTGGTGGGCACACCATCTAGCGTCACCAAATTCGGCCTTTCTGATGTCGACGGAAT

GAGCGACCAAGGCTTTTTCCAATGGATGCAATTGGTGGAAGTGGTCCAAGTTGACAGCGTCACCAGTTTTGATAA

AAGAAAACTTAGCGGAGTTTGGAAACAAAGATTCGTCCAACATTGTAAAGTTAGTTGGTTGCGCGACTTCGGGTG

GGGTTACTTTTTTTTTGGATGGACGCAAAGAAGTTTAATAATCATATTACATGGCAATACCACCATATACATATC

CATATCTAATCTTACTTATATGTTGTGGAAATGTAAAGAGCCCCATTATCTTAGCCTAAAAAAACCTTCTCTTTG

GAACTTTCAGTAATACGCTTAACTGCTCATTGCTATATTGAAGTACGGATTAGAAGCCGCCGAGCGGGCGACAGC

CCTCCGACGGAAGACTCTCCTCCGTGCGTCCTGGTCTTCACCGGTCGCGTTCCTGAAACGCAGATGTGCCTCGCG

CCGCACTGCTCCGAACAATAAAGATTCTACAATACTAGCTTTTATGGTTATGAAGAGGAAAAAATTGGCAGTAACC

-continued

TGGCCCCACAAACCTTCAAATCAACGAATCAAATTAACAACCATAGGATAATAATGCGATTAGTTTTTTAGCCTT

ATTTCTGGGGTAATTAATCAGCGAAGCGATGATTTTTGATCTATTAACAGATATATAAATGCAAAAGCTGCATAA

CCACTTTAACTAATACTTTCAACATTTTCGGTTTGTATTACTTCTTATTCAAATGTCATAAAAGTATCAACAAAA

AATTGTTAATATACCTCTATACTTACCTCCCGCGACCTCCAAAATCGAACTACCTTCACAATGGCTGTTGACTCT

CCAGACGAAAGATTGCAAAGAAGAATTGCTCAATTATTCGCTGAGGACGAACAAGTCAAGGCCGCTAGACCATTG

GAAGCTGTTTCTGCTGCCGTTTCTGCTCCAGGTATGAGATTAGCCCAAATCGCTGCCACTGTCATGGCTGGTTAT

GCTGATAGACCAGCTGCTGGTCAAAGAGCTTTCGAATTAAACACCGACGACGCTACCGGTAGAACCTCTTTACGT

TTGTTACCTAGATTCGAAACTATTACCTACCGTGAATTATGGCAAAGAGTCGGTGAAGTTGCTGCTGCTTGGCAC

CATGATCCAGAAAACCCATTGCGTGCCGGTGACTTCGTTGCTTTGTTAGGTTTCACCTCTATTGACTACGCCACT

TTGGACTTGGCCGATATCCATTTGGGTGCCGTTACTGTCCCATTACAAGCTTCCGCTGCTGTTTCCCAATTAATT

GCTATTTTGACTGAGACCTCTCCACGTTTATTAGCTTCTACTCCAGAACACTTAGATGCTGCTGTTGAATGCTTA

TTGGCCGGTACCACCCCAGAAAGATTGGTCGTTTTCGATTATCATCCAGAAGATGATGATCAAAGAGCTGCTTTC

GAATCTGCTAGAAGAAGATTAGCTGATGCTGGTTCTTTGGTTATCGTTGAAACCTTGGACGCTGTCAGAGCCAGA

GGTAGAGATTTGCCAGCCGCCCCATTGTTCGTTCCAGACACTGATGACGACCCATTAGCTTTGTTAATTTACACT

TCTGGTTCTACCGGTACTCCAAAGGGTGCTATGTACACCAACAGATTAGCTGCTACCATGTGGCAAGGTAACTCC

ATGTTACAAGGTAATTCTCAAAGAGTCGGTATTAACTTGAATTACATGCCAATGTCCCACATTGCTGGTAGAATT

TCTTTGTTTGGTGTCTTAGCCAGAGGTGGTACTGCTTATTTCGCCGCCAAGTCCGATATGTCTACCTTGTTCGAA

GATATTGGTTTGGTTAGACCTACTGAAATTTTCTTCGTCCCAAGAGTTTGCGATATGGTCTTCCAAAGATACCAA

TCTGAATTAGACAGAAGATCTGTTGCTGGTGCTGACTTAGACACCTTGGATCGTGAGGTTAAAGCTGATTTGAGA

CAAAACTACTTGGGTGGTCGTTTCTTGGTTGCTGTTGTCGGTTCTGCTCCATTGGCCGCTGAAATGAAGACTTTC

ATGGAATCTGTTTTGGATTTGCCTTTGCATGACGGTTACGGTTCCACCGAAGCTGGTGCTTCCGTCTTGTTGGAC

AACCAAATTCAAAGACCACCAGTTTTGGACTACAAGTTGGTTGATGTCCCTGAGTTAGGTTACTTCAGAACTGAC

AGACCTCACCCAAGAGGTGAGTTATTGTTGAAGGCCGAAACTACTATCCCTGGTTACTACAAAAGACCTGAAGTT

ACCGCCGAAATTTTCGACGAAGATGGTTTTTACAAGACTGGTGATATTGTTGCTGAATTAGAACACGACAGATTG

GTTTATGTTGATCGTAGAAACAATGTCTTGAAGTTGTCTCAAGGTGAATTCGTCACTGTTGCTCACTTGGAAGCT

GTTTTTGCTTCTTCCCCATTAATCAGACAAATCTTCATCTATGGTTCCTCCGAAAGATCCTACTTGTTGGCTGTT

ATTGTCCCAACTGATGATGCTTTGAGAGGTAGAGATACTGCTACTTTGAAGTCTGCTTTAGCTGAATCTATCCAA

AGAATTGCTAAGGATGCTAACTTGCAACCTTACGAAATTCCAAGAGATTTCTTGATTGAAACTGAACCATTCACT

ATCGCTAACGGTTTATTGTCCGGTATTGCCAAGTTGTTGCGTCCTAACTTGAAGGAAAGATACGGTGCCCAATTG

GAACAAATGTACACCGACTTGGCTACTGGTCAAGCTGACGAGTTATTGGCCTTGAGAAGAGAAGCTGCTGATTTA

CCAGTTTTGGAAACCGTTTCTAGAGCTGCCAAGGCCATGTTAGGTGTTGCTTCCGCTGACATGAGACCAGACGCC

CACTTTACCGACTTGGGTGGTGATTCCTTGTCTGCTTTATCCTTTTCCAACTTGTTGCACGAAATTTTTGGTGTC

GAAGTCCCAGTTGGTGTTGTCGTCTCCCCAGCTAACGAATTGAGAGACTTAGCCAATTACATCGAAGCTGAACGT

AACTCTGGTGCTAAGAGACCAACCTTCACCTCCGTTCATGGTGGTGGTTCCGAGATTAGAGCTGCCGACTTAACC

TTGGATAAGTTCATTGATGCTAGAACTTTAGCTGCCGCTGACTCCATTCCACACGCTCCTGTCCCAGCTCAAACT

GTTTTGTTGACCGGTGCTAACGGTTATTTGGGTAGATTCTTATGTTTGGAATGGTTGGAAAGATTGGATAAGACC

GGTGGTACCTTGATCTGCGTTGTTCGTGGTTCCGATGCCGCCGCTGCCAGAAAGAGATTGGACTCCGCTTTCGAC

TCCGGTGATCCAGGTTTGTTGGAACACTATCAACAATTGGCCGCTCGTACCTTGGAAGTTTTGGCTGGTGACATT

GGTGACCCAAACTTGGGTTTGGACGATGCTACTTGGCAACGTTTAGCTGAAACCGTCGATTTGATTGTTCACCCA

GCCGCTTTGGTCAACCACGTTTTACCATATACCCAATTATTCGGTCCAAACGTTGTTGGTACTGCTGAAATTGTT

-continued

CGTTTAGCTATCACTGCTAGAAGAAAGCCAGTTACTTATTTATCCACCGTTGGTGTTGCTGATCAAGTTGACCCA

GCTGAATACCAAGAAGACTCTGATGTCAGAGAAATGTCCGCCGTCCGTGTTGTTAGAGAATCCTATGCTAACGGT

TATGGTAACTCTAAGTGGGCTGGTGAAGTTTTGTTGAGAGAAGCTCATGATTTGTGCGGTTTGCCAGTCGCTGTC

TTCCGTTCTGACATGATCTTGGCTCACTCCAGATACGCTGGTCAATTAAACGTTCAAGATGTTTTCACCCGTTTG

ATCTTGTCCTTGGTTGCCACTGGTATCGCTCCATACTCCTTCTACAGAACTGACGCCGACGGTAACAGACAAAGA

GCTCATTACGATGGTTTGCCAGCTGACTTCACTGCTGCTGCTATTACCGCTTTGGGTATTCAAGCTACCGAAGGT

TTCCGTACTTACGATGTTTTGAACCCATACGACGATGGTATTTCTTTGGATGAATTCGTTGACTGGTTAGTTGAA

TCTGGTCATCCAATCCAAAGAATCACCGACTACTCTGATTGGTTCCACAGATTTGAAACTGCCATCAGAGCTTTG

CCAGAAAAGCAAAGACAAGCTTCTGTCTTACCATTGTTGGATGCCTACAGAAACCCATGTCCTGCTGTCCGTGGT

GCTATCTTGCCAGCTAAGGAATTTCAAGCCGCTGTCCAAACTGCTAAGATCGGTCCAGAACAAGACATCCCACAT

TTGTCCGCCCCATTGATTGACAAGTACGTTTCTGATTTGGAATTGTTGCAATTATTGTAAAACCTGCAGGCCGCG

AGCGCCGATAAGGGAACCTTTTACAACAAATATTTGAAAAATTACCTCCATTATTATACCTTCTCTTTATGTAAT

TGTTAGTTCGAAAATTTTTTCTTCATTAATATAATCAACTTCTAAAACTTTCTAAAAACGTTCTCTTTTTCGAGA

TTAGTGCTTCTTCCCAATCCGTAAGAAATGTTTCCTTTCTTGACAAAACGCGATCGCCGACGCCGCCGATAAGAT

TATTACTTGCTATAAGTGCGTGCCTGATGAACAGGATATTGCGGTCAATAATGCTGATGGTTCATTAGACTTCAG

CAAAGCCGATGCCAAAATAAGCCAATACGATCTCAACGCTATTGAAGCGGCTTGCCAGCTAAAGCAACAGGCAGC

AGAGGCGCAGGTGACAGCCTTAAGTGTGGGCGGTAAAGCCCTGACCAACGCCAAAGGGCGTAAAGATGTGCTATC

GCGCGGCCCGGATGAACTGATTGTGGTGATTGATGACCAGTTCGAGCAGGCACTGCCGCAACAAACGGCGAGCGC

ACTGGCTGCAGCCGCCCAGAAAGCAGGCTTTGATCTGATCCTCTGTGGCGATGGTTCTTCCGACCTTTATGCCCA

GCAGGTTGGTCTGCTGGTGGGCGAAATCCTCAATATTCCGGCAGTTAACGGCGTCAGCAAAATTATCTCCCTGAC

GGCAGATACCCTCACCGTTGAGCGCGAACTGGAAGATGAAACCGAAACCTTAAGCATTCCGCTGCCTGCGGTTGT

TGCTGTTTCCACTGATATCAACTCCCCACAAATTCCTTCGATGAAAGCCATTCTCGGCGCGGCGAAAAAGCCCGT

CCAGGTATGGTCGGCGGCGGATATTGGTTTTAACGCAGAGGCAGCCTGGTCAGAACAACAGGTTGCCGCGCCGAA

ACAGCGCGAACGTCAGCGCAATCGGCGGCGTCGGCGATCGCGTTGCTTCGAGCGTCCCAAAACCTTCTCAAGCAA

GGTTTTCAGTATAATGTTACATGCGTACACGCGTCTGTACAGAAAAAAAAGAAAAATTTGAAATATAAATAACGT

TCTTAATACTAACATAACTATAAAAAAATAAATAGGGACCTAGACTTCAGGTTGTCTAACTCCTTCCTTTTCGGT

TAGAGCGGATCATCGGCGCTCGCGGCCTGCAGGTTTTAGACGACACGTCTGCACAAGGTAATACCGTCGGCGATT

GGTAATTGAACTGGTTCGACTCTGGCGTCGGCAGCAATCATGGCATTGAAACCACGAATGGAGTCTCTCTTCTTT

CTGTCTTCTTCGGTCAATGGAGTGTCATCTGGCATGGAGACGGTACCACCCCATAAGGTATTGTCGTAAGCCAAA

ACACCACCAACTCTAACCAATCTCAACAATTGTTCGTGGTAGGAACCGTAGTTGTACTTATCGGCATCAACGAAA

GCGAAATCAAAAGAACCTTCGTCTTCATCAGCAATCAATTTGTCCAAAATTGGACCAGCAGGACCTTCACGGAAA

TCAACCTTATGGGCAACACCGGCCTTCTTAATAACTGGCAAACCCAAGTCAAAGTATTCACGGGAAACGTCAATA

GCAATGATTCTACCATCGTCTGGGATAGCTAAGGCAGTAGTCAAGACGGAACAACCAGTGTAGACACCGACTTCG

ATGGTTCTCTTAGCACCCATAACCTTTAACAACAAGGACAATAACAAACCTTCATCTGGTGGAGAAGACATGAAA

CCGAAGATATGTTCGGAAGTGATTTGTCTCAATTCTCTCATAAATTCGTTCTCTCTTGGATAGACCATAGTCTTC

AACATATAATCGTATAAAGCATCGGATTTCAATAAAGTCTTGGTAGTTTCGGAGGAGTGAACTTCTCTAACCTCA

CCGGCAGAACCATTACTTGCCATATCCATTGTGAAGGTAGTTCGATTTTGGAGGTCGCGGGAGGTAAGTATAGAG

GTATATTAACAATTTTTTGTTGATACTTTTATGACATTTGAATAAGAAGTAATACAAACCGAAAATGTTGAAAGT

ATTAGTTAAAGTGGTTATGCAGCTTTTGCATTTATATATCTGTTAATAGATCAAAAATCATCGCTTCGCTGATTA

ATTACCCCAGAAATAAGGCTAAAAAACTAATCGCATTATTATCCTATGGTTGTTAATTTGATTCGTTGATTTGAA

GGTTTGTGGGGCCAGGTTACTGCCAATTTTTCCTCTTCATAACCATAAAAGCTAGTATTGTAGAATCTTTATTGT

-continued

TCGGAGCAGTGCGGCGCGAGGCACATCTGCGTTTCAGGAACGCGACCGGTGAAGACCAGGACGCACGGAGGAGAG

TCTTCCGTCGGAGGGCTGTCGCCCGCTCGGCGGCTTCTAATCCGTACTTCAATATAGCAATGAGCAGTTAAGCGT

ATTACTGAAAGTTCCAAAGAGAAGGTTTTTTTAGGCTAAGATAATGGGGCTCTTTACATTTCCACAACATATAAG

TAAGATTAGATATGGATATGTATATGGTGGTATTGCCATGTAATATGATTATTAAACTTCTTTGCGTCCATCCAA

AAAAAAAGTAACCCCACCCGAAGTCGCGCAACCAACTAACTTTACAATGGGTGCAGCCACTACTAGAAGACCATT

TGATGGTAGAAGACGTAGATCCTCCTGGCGTCCAGAATCCCCAGCCAGAGGTGCCGTCGGTATCCACTCTGCTAG

AAAGGTTGCTCAAGGTGCTAGATCCACTGCTATGGCTGCTGATGGTGAAGTTAAGAACATTCATACTAACGACTC

TACTAAAACTTTATTAAAAAATGAAGCTTTGTACGAATACATGTTAAACACTATGGTTTATCCAAGAGAAAACGA

ACACTTAAGAGAATTAAGACACATTACCGAACAACACGCTTACGGTTTTATGTTGTCTCCTCCAGACGAAGAACA

ATTGTTGTCCTTATTGTTAAAGGTTATGGGTGCTCGTAACACTATTGAAGTCGGTGTTTTCACCGGTGGTTCTGT

TTTGGCCGCTGCCTTGGCTATTCCAGATGATGGTCGTATTGTCGCTATTGACGTTTCTAGAGAGTATTATGACTT

GGGTAGACCAGTCATTGAAAAAGCCGGTGTTGCCCACAAAGTTGACTTCAGAGAAGGTCCAGCTTTGGGTCATTT

GGACGCCTTATTGGCTGATGAAGGTAACGCCGGTGCTTTTGATTTTGCTTTCGTCGATGCTGACAAGGGTAACTA

TGGTAATTATCACGAACAATTGTTGAGATTGGTTAGAGTCGGTGGTGTTATTGCTTACGATAACACTTTGTGGGG

TGGTTCTGTTGCTATGCCAGATGACGCCCCATTAACTGAAAAGGATAGAGAAGTTCGTGAAGCTATTAGAGCCTT

TAACGCTAGAATTGCTGCTGATACTAGAGTCGAAGCTGTTCAATTACCAGTCGCTGATGGTATCACCTTGTGTAG

AAGAGTCGTCTAAACGGCCGGCCAAGCACGCGGGGATGAGTATGCTTCTCTTTTTTTTTGTAGGCCAGTGATAGG

AAAGAACAATAGAATATAAATACGTCAGAATATAATAGATATGTTTTTATATTTAGACCTCGTACATAGGAATAA

TTGACGTTTTTTTTGGCCAACATTTGAAATTTTTTTTTGTTACCTCGCGCTGAGCCCAAACGGGCTCCACTACCC

GAGGTCCGCCGGCGTTGGACGAGCGAAGATGGCAAATAGCCTTGTCAAATTTCCTACGGAATGTTATTTTCATTA

CGTCCTTCTTTTTCAATGTACTTATTCATAAATGGGACACTATCTTGTTGCAAAAGGTACTTTGTATTTTGGTAT

TAACATCTCGCCTATTTTTCATACAGAAACACTACTTATCGCTATCTATTTGATGTGGTATTGCTTGGCCATGAG

GATACCTTGAGCTACGTTTTGAACACGTGCATCCAACTTGTAGCCTTGTTGATCCAACTTAACCATTTCATCAGG

AAACTTGTGCAACTCAACGCTAAAGCATTCGATAAATTCATTATCTTCCAATTGAGTAACTGGTTTTTGGTTTTC

AGGTAAACTCATATCAACTTCGACAGTAACCAGACAGAGGTTGGTGTTTGTGAAACCAGGATCGTTAAAAACTGT

TGGGCTTTTAGAAATTATTTTACCACTGTAACCAGTCTCTTCTTTTAATTCTCTTAAGGCAGCAGTGTCAATATC

GGCGGTTTAAACGCGTGGCCGTGCCGTC

SEQ ID NO: 7
Length: 3658
Type:
Organism; artificial sequence
Other information: MS130477 sequence

GACGGCACGGCCACGCGTTTAAACCGCCAAAAACTCACAAGAAGTTCGGTGTCCTTATTTGCGATGGGAATTGCT

AATATCATATCACCACAAATATGGAGAGAGAAGGACTCTCCTCGCTTTTTACCTGCCTGGATTGTTCAAATCGTT

TTATCATTCTCTCTTGCACCAGCCATTTTGTTACTGATCCATTTCATACTAAAAAGAAGGAATAATCAAAGACTA

AAAAATTATGACGAAAATTTACAAAATTATTTGGACAGAATTCAACTCATTGAAAGCGAAAATCCTTCTTCCATT

GAAGAAGGGAAAGTGGTAACCCACGAGAACAATTTGGCAGTCTTTGATTTGACTGATTTAGAAAACGAAACTTTT

ATATATCCTTTGTAAATATTGATGTTTTGTTGTGTAAATGTTCTATCTGACACTTAATAATTAGAAAATTAATTT

TTTAAACTTTCCGGCTGCAAGAAAGAGGAACTGTGTCTCTTTGAAAGGCACAATTTCCCAAAGAATCATTTACAA

TGAACCTGCAGGCCGCGAGCGCCGATGCTTCGAGCGTCCCAAAACCTTCTCAAGCAAGGTTTTCAGTATAATGTT

ACATGCGTACACGCGTCTGTACAGAAAAAAAAGAAAAATTTGAAATATAAATAACGTTCTTAATACTAACATAAC

-continued

TATAAAAAAATAAATAGGGACCTAGACTTCAGGTTGTCTAACTCCTTCCTTTTCGGTTAGAGCGGATCCGCTCGT

CCAACGCCGGCGGACCTTTAGACTAATCTTCTACACAAGGTAACACCATCACCGATGGAAACTTGGGAGATTTCA

ATTCTTGGATCGGAAGCCAATCTTTTGTTCAATTCCATCAAAGCCTTACGGTTAACTCTTAAGTGAACTGGGACA

GTCTCTTCCTCTTCAGCAACGAAACCGAACCATAAGGTGTTATCGAAAGCAATGATACCACCAACTTTGACCAAC

TTCATCAATCTTTCCAAAGCGTGGACGTAATTTGGCTTATCAGCGTCAACGAAAGCGAAGTCAAATTCTGGCTTT

GGGTTTTCAGATAACAACTTGTCTAAGGCTTGCAAACCGTCGGATTGGATAAAGTTAATTTTGTGATCGATACCG

GCGTTCTTGATGAATTCCAAACCCATTTCGTAAGCTTCTTTATCGATATCAATAGCAGTAATTCTACCGTCTTCA

GGCAAAGCCAAGGCGGTGGTTAACAAAGAGTAACCAGTGAAAACACCCAATTCCAAGGTGTTCTTAGCGTTCATC

ATCTTCAACAACATGGACAAGAAATGACCTTCGTCAACAGGGACTTCCATCTCGGACAAGTTACCGTACTTATGA

ACGGTAGCTTCTCTTAACTTCTTCAATTCTTCGTGTTCTCTTGGGTAAGCGGAAGTTTCAAAGATGTACTTTTTC

AATTCTTCGTTCTTCAAGATACCCTTAGATGGTATAAGATTTTCCATGTCTGGTTCCATTGTAAAGTTAGTTGGT

TGCGCGACTTCGGGTGGGGTTACTTTTTTTTTGGATGGACGCAAAGAAGTTTAATAATCATATTACATGGCAATA

CCACCATATACATATCCATATCTAATCTTACTTATATGTTGTGGAAATGTAAAGAGCCCCATTATCTTAGCCTAA

AAAAACCTTCTCTTTGGAACTTTCAGTAATACGCTTAACTGCTCATTGCTATATTGAAGTACGGATTAGAAGCCG

CCGAGCGGGCGACAGCCCTCCGACGGAAGACTCTCCTCCGTGCGTCCTGGTCTTCACCGGTCGCGTTCCTGAAAC

GCAGATGTGCCTCGCGCCGCACTGCTCCGAACAATAAAGATTCTACAATACTAGCTTTTATGGTTATGAAGAGGA

AAAATTGGCAGTAACCTGGCCCCACAAACCTTCAAATCAACGAATCAAATTAACAACCATAGGATAATAATGCGA

TTAGTTTTTTAGCCTTATTTCTGGGGTAATTAATCAGCGAAGCGATGATTTTTGATCTATTAACAGATATATAAA

TGCAAAAGCTGCATAACCACTTTAACTAATACTTTCAACATTTTCGGTTTGTATTACTTCTTATTCAAATGTCAT

AAAAGTATCAACAAAAAATTGTTAATATACCTCTATACTTACCTCCCGCGACCTCCAAAATCGAACTACCTTCAC

AATGGAACCAGACATGGAAAATCTTATACCATCTAAGGGTATCTTGAAGAACGAAGAATTGAAAAAGTACATCTT

TGAAACTTCCGCTTACCCAAGAGAACACGAAGAATTGAAGAAGTTAAGAGAAGCTACCGTTCATAAGTACGGTAA

CTTGTCCGAGATGGAAGTCCCTGTTGACGAAGGTCATTTCTTGTCCATGTTGTTGAAGATGATGAACGCTAAGAA

CACCTTGGAATTGGGTGTTTTCACTGGTTACTCTTTGTTAACCACCGCCTTGGCTTTGCCTGAAGACGGTAGAAT

TACTGCTATTGATATCGATAAAGAAGCTTACGAAATGGGTTTGGAATTCATCAAGAACGCCGGTATCGATCACAA

AATTAACTTTATCCAATCCGACGGTTTGCAAGCCTTAGACAAGTTGTTATCTGAAAACCCAAAGCCAGAATTTGA

CTTCGCTTTCGTTGACGCTGATAAGCCAAATTACGTCCACGCTTTGGAAAGATTGATGAAGTTGGTCAAAGTTGG

TGGTATCATTGCTTTCGATAACACCTTATGGTTCGGTTTCGTTGCTGAAGAGGAAGAGACTGTCCCAGTTCACTT

AAGAGTTAACCGTAAGGCTTTGATGGAATTGAACAAAAGATTGGCTTCCGATCCAAGAATTGAAATCTCCCAAGT

TTCCATCGGTGATGGTGTTACCTTGTGTAGAAGATTAGTCTAAATCCCCGCGTGCTTGGCCGGCCGTGAGTATGC

TTCTCTTTTTTTTTGTAGGCCAGTGATAGGAAAGAACAATAGAATATAAATACGTCAGAATATAATAGATATGTT

TTTATATTTAGACCTCGTACATAGGAATAATTGACGTTTTTTTTGGCCAACATTTGAAATTTTTTTTGTTACCT

CGCGCTGAGCCCAAACGGGCTCCACTACCCGAACGCGATCGCCGACGCCGCCGATAACATATTGATGTTTTTCGT

GGGTAACCATAGTTCTTGGAATGTCAACTGAGGGTATTTGCACTTCAAAAAAAAAAATTTATTAAATGAGACTAT

ATACAGTGAGCACAACCTGTCTAATACAACGGCAAAAATTATATACATTGGTAGATTTTCAAAATTGAACTCTTT

GTGCTAAAGAATTGTCACAACAGTTTAAAAAATAGTTTGAATTCTTCAAATTGACCCCATATTAATAAGACCTGA

TGCGATTCCGGTCTCACCCAGATTAGAGAGGGAATTTAATTTTCTTAGGACCGTAGCTACCAAAAATCTTTGTGT

-continued

GGTATTGATTATATGATCGTGCTTGCGAAAAAAATAGAAGACTAAAAGTAGCATTAGTTTACTAACTTTCTCCTC

GTATCTTTCAAATTTGTATTCCCCTCAAAAGTTACTCAGGTTAGGGAAAATTCCAAGTAGCTTATCAAGATCAAT

TGCCATTAGTTGATTCAAGGCTTCATTGTCCGGTGTTTAAACCCCAGCGCCTGGCGGG

SEQ ID NO: 8
Length: 9995
Type:
Organism: artificial sequence
Other information: MS129629 sequence

GACGGCACGGCCACGCGTTTAAACCGCCTCGCAAGTCCTGTTTCTATGCCTTTCTCTTAGTAATTCACGAAATAA

ACCTATGGTTTACGAAATGATCCACGAAAATCATGTTATTATTTACATCAACATATCGCGAAAATTCATGTCATG

TCCACATTAACATCATTGCAGAGCAACAATTCATTTTCATAGAGAAATTTGCTACTATCACCCACTAGTACTACC

ATTGGTACCTACTACTTTGAATTGTACTACCGCTGGGCGTTATTAGGTGTGAAACCACGAAAAGTTCACCATAAC

TTCGAATAAAGTCGCGGAAAAAAGTAAACAGCTATTGCTACTCAAATGAGGTTTGCAGAAGCTTGTTGAAGCATG

ATGAAGCGTTCTAAACGCACTATTCATCATTAAATATTTAAAGCTCATAAAATTGTATTCAATTCCTATTCTAAA

TGGCTTTTATTTCTATTACAACTATTAGCTCTAAATCCATATCCTCATAAGCAGCAATCAATTCTATCTATACTT

TAAACGCTCGTCCAACGCCGGCGGACCTGGTATACAGGATCTATCTTTTCGATAACGTAACTTAGTATCACATGT

ATTAGTATTAATACTGCGATAGGATTGTTAGCTGTTGTTTTTATATTTGCAATTTATTTATGATCTTTTTTGATG

ATCAAACCGTTGAGTTTTTGAACATTAAAAAATAGTGAGAAAGAAGAACTGAAATGGGAATTGAATTGATCAGTA

TCTGTAGTGGTCGGCCTTGAATGGACCTTCTTCTGGGATACCCAAGTATTCAGATTGGACTTTACTCAATTTAGT

CAATCTAACACCCAAGTTGCCCAAGTGGAACTTAGCGACAGCTTCATCCAAGATCTTTGGCAAAACGTGGACACC

AACTTCGAATGGGCCTGTCTTTTGGAATTCAATGTGCTTTTCTCTGAAAGACTTATCGTTAGACTTGAACAAAGC

AATTTGAGCTAAGACTTGGTTAGAGAAGGAACAAGACATAACGAAAGATGAGTGACCAGTAGCACAACCCAAGTT

AACTAATCTACCGTTAGCCAACAAGATGACGTGTCTACCAGAAGACAACAAGTAACGGTCGACTTGTGGTTTGAT

GTTAATACATTCTTTAGCGTTAGCCTTTAACCAGGCGACATCAATTTCGATGTCGAAATGGCCAATGTTACAAAC

AATGGCATCTTCTGGCATGTTGATGAAATGTTCACCGTTGATAATATCTCTACAACCAGTGGTGGTAACGAAAAC

TTGACCAATGTGGGATGCATCTTCCATGGTAACAACTTGGTAGCCTTCCATGGCAGCTTGTAAAGCGTTGATTGG

GTCAATTTCGGTAACCAAGACACGAGCACCCATTCCTCTTAAGGCAGCAGCACAACCCTTACCGACATCACCGTA

ACCAGCAACAACGGCAACCTTACCAGCCAACATGACATCAGTGGCTCTCTTAATACCGTCGACTAAGGATTCTCT

ACAGCCGTACAAGTTGTCAAACTTGGACTTAGTGACGGAGTCGTTAACGTTAATGGCAGGAACCTTTAACTTGCC

TTCTTTGACCATTCTGTATAAGTGGTGAACACCGGTGGTAGTTTCTTCGGAAAGACCAAAGCAGTCTTCCAACAT

TTCAGGGTGCTTTTCATGAACTAAAGTGGTTAAATCACCACCATCATCTAAGATCAAGTTCAATTTCTTGTTGTC

CTTGAAGGCAAACAATTGTTGTTCAATACACCACAAATACTCTTCTTCAGTTTCACCCTTCCAGGCAAAAACTGG

AACACCGGAAGCGGCAATAGCAGCGGCGGCATGATCTTGAGTCGAATAGATGTTACAAGAGGACCAGGTAACTTC

GGCACCCAAAGCAACTAAAGTTTCAATTAAAACAGCAGTTTGAATGGTCATGTGCAAACAACCAGCAATACGGGC

GCCTTTCAAAGGTTGGACGTCACCGTAAGCCTTTCTGATGGCCATCAAACCTGGCATTTCATGTTCAGCCAATTC

GATTTCCTTTCTACCGAAGGCAGCCAAAGAGATATCAGCGATTTTGTAGTTTTGAGCTGGAGCAGACATTGTAAA

GTTAGTTGGTTGCGCGACTTCGGGTGGGGTTACTTTTTTTTTGGATGGACGCAAAGAAGTTTAATAATCATATTA

CATGGCAATACCACCATATACATATCCATATCTAATCTTACTTATATGTTGTGGAAATGTAAAGAGCCCCATTAT

CTTAGCCTAAAAAAACCTTCTCTTTGGAACTTTCAGTAATACGCTTAACTGCTCATTGCTATATTGAAGTACGGA

TTAGAAGCCGCCGAGCGGGCGACAGCCCTCCGACGGAAGACTCTCCTCCGTGCGTCCTGGTCTTCACCGGTCGCG

TTCCTGAAACGCAGATGTGCCTCGCGCCGCACTGCTCCGAACAATAAAGATTCTACAATACTAGCTTTTATGGTT

-continued

ATGAAGAGGAAAAATTGGCAGTAACCTGGCCCCACAAACCTTCAAATCAACGAATCAAATTAACAACCATAGGAT
AATAATGCGATTAGTTTTTAGCCTTATTTCTGGGGTAATTAATCAGCGAAGCGATGATTTTTGATCTATTAACA
GATATATAAATGCAAAAGCTGCATAACCACTTTAACTAATACTTTCAACATTTTCGGTTTGTATTACTTCTTATT
CAAATGTCATAAAAGTATCAACAAAAAATTGTTAATATACCTCTATACTTACCTCCCGCGACCTCCAAAATCGAA
CTACCTTCACAATGGTTCAATCTGCTGTCTTAGGGTTCCCAAGAATCGGTCCAAACAGAGAATTAAAGAAGGCCA
CTGAAGGTTACTGGAACGGTAAAATCACTGTCGATGAATTATTCAAAGTCGGTAAGGATTTGAGAACTCAAAACT
GGAAGTTGCAAAAGGAGGCTGGTGTTGATATCATCCCATCCAATGACTTCTCCTTTTACGACCAAGTTTTGGATT
TGTCTTTGTTGTTCAATGTCATTCCAGACCGTTACACTAAGTACGATCTATCTCCAATCGACACTTTGTTTGCTA
TGGGTAGAGGTTTACAAAGAAAGGCCACTGAAACTGAAAAGGCTGTCGACGTCACTGCTTTGGAAATGGTTAAAT
GGTTCGACTCTAACTACCATTACGTTAGACCAACTTTCTCCAAGACCACTCAATTTAAGTTGAACGGCCAAAAGC
CAGTTGACGAATTTTTGGAAGCCAAGGAGTTAGGTATTCACACTAGACCTGTCTTGTTAGGTCCAGTTTCTTACT
TATTCTTGGGTAAGGCTGACAAGGATTCTCTAGATTTGGAACCATTGTCCCTATTGGAACAATTGTTGCCTCTAT
ACACTGAAATCCTATCTAAATTGGCTTCTGCTGGTGCCACTGAAGTTCAAATTGACGAACCTGTCTTAGTTTTGG
ACTTGCCTGCCAACGCCCAAGCCGCCATTAAGAAGGCTTACACTTACTTCGGTGAACAAAGCAATCTACCAAAGA
TTACTTTGGCTACTTACTTCGGTACCGTTGTCCCTAACTTAGACGCCATCAAGGGCTTGCCAGTTGCTGCCTTAC
ACGTTGACTTTGTTAGAGCTCCAGAACAATTTGATGAAGTCGTTGCCGCCATTGGTAACAAACAAACCTTGTCCG
TTGGTATTGTTGATGGTAGAAACATTTGGAAGAATGATTTCAAGAAGTCTTCCGCTATCGTTAACAAGGCTATTG
AAAAGTTGGGTGCTGACAGAGTCGTTGTTGCCACTTCTTCTTCTCTATTGCACACACCAGTTGACTTGAACAACG
AAACCAAGTTGGACGCTGAAATCAAGGGCTTTTTCTCTTTCGCCACTCAAAAATTGGATGAAGTTGTTGTGATCA
CCAAGAACGTTTCCGGTCAAGACGTTGCTGCTGCCCTAGAAGCTAACGCTAAATCTGTTGAATCCAGAGGTAAAT
CCAAGTTTATCCACGATGCTGCCGTTAAGGCCAGAGTTGCCTCTATCGACGAAAAAATGTCTACTAGAGCAGCTC
CATTTGAACAAAGATTGCCTGAACAACAAAAAGTCTTCAACTTGCCATTGTTCCCAACAACAACTATTGGTTCCT
TCCCTCAAACCAAGGACATCAGAATTAACAGAAACAAATTCAACAAGGGTACCATCTCTGCTGAAGAATATGAAA
AATTCATCAATTCTGAAATTGAAAAGGTCATCAGATTCCAAGAAGAAATTGGTTTGGATGTCTTAGTCCACGGTG
AACCAGAAAGAAACGATATGGTTCAATACTTCGGTGAACAAATCAACGGTTATGCTTTCACTGTTAACGGTTGGG
TTCAATCTTACGGTTCCAGATATGTCAGACCACCAATTATTGTTGGTGACTTGTCCAGACCAAAGGCTATGTCCG
TCAAGGAATCTGTTTACGCTCAATCCATCACTTCTAAGCCAGTAAAGGGTATGTTGACTGGTCCAATTACCTGTT
TGAGATGGTCTTTCCCAAGAGACGATGTCGACCAAAAAACTCAAGCTATGCAATTAGCTTTGGCTTTGAGAGATG
AAGTCAATGATTTGGAAGCTGCCGGTATCAAGGTTATCCAAGTTGATGAACCAGCTTTAAGAGAAGGTTTACCAT
TGAGAGAAGGTGCTGAGAGATCTGCTTACTACACCTGGGCTGCCGAAGCTTTCAGAGTTGCTACTTCTGGTGTTG
CTAACAAGACTCAAATACACTCTCATTTCTGTTACTCTGACTTGGATCCAAACCATATCAAGGCTTTGGATGCTG
ATGTTGTTTCCATCGAATTCTCTAAGAAGGACGATGCTAACTACATTGCTGAATTCAAAAACTATCCAAACCACA
TTGGTCTGGGTTTATTCGATATTCATTCTCCAAGAATTCCATCAAAGGATGAATTTATCGCCAAGATTTCAACCA
TCTTGAAGAGCTACCCAGCTGAAAAGTTCTGGGTTAACCCAGACTGTGGTTTGAAGACTAGAGGCTGGGAAGAAA
CTAGATTGTCTTTGACTCATATGGTCGAAGCCGCCAAGTACTTCCGTGAACAATACAAGAATTAAGGTTTTAAAA
AGGAAGCAAAGTAATGATATTTTCTGAACTTTTTGTTTTTTATTCTGGGATTCAACATCGGTGATTTAATTTTTG
TGTTCACATTTAAAAGTTTATTTGGGTAATTTTTTGATATCAATTTTATTACAAAGCCATAACTCTTGCATTTTT
TTTATTATATTTTTATATACACGTACATTCTGTATTATTTATAACGCATTCAATCCCCGCGTGCTTGGCCGGCCG
TCGTTGGATCTGCCAAAAGAGCTGGCAGAACGTGCTGATTTACCCTTGCTTTCACATAATCTGCCCGCCGATTTT
GCTGCGTTGCGTAAATTGATGATGAATCATCAGTAAAATCTATTCATTATCTCAATCAGGCCGGGTTTGCTTTTA
TGCAGCCCGGCTTTTTTATGAAGAAATTATGGAGAAAAATGACAGGGAAAAAGGAGAAATTCTCAATAAATGCGG

-continued

TAACTTAGAGATTAGGATTGCGGAGAATAACAACCGCCGTTCTCATCGAGTAATCTCCGGATATCGACCCATAAC

GGGCAATGATAAAAGGAGTAACCTGTGAAAAAGATGCAATCTATCGTACTCGCACTTTCCCTGGTTCTGGTCGCT

CCCATGGCAGCACAGGCTGCGGAAATTACGTTAGTCCCGTCAGTAAAATTACAGATAGGCGATCGTGATAATCGT

GGCTATTACTGGGATGGAGGTCACTGGCGCGACCACGGCTGGTGGAAACAACATTATGAATGGCGAGGCAATCGC

TGGCACCTACACGGACCGCCGCCACCGCCGCGCCACCATAAGAAAGCTCCTCATGATCATCACGGCGGTCATGGT

CCAGGCAAACATCACCGCTAAATGACAAATGCCGGGTAACAATCCGGCATTCAGCGCCTGATGCGACGCTGGCGC

GTCTTATCAGGCCTACGTTAATTCTGACGGCCGGCCAAGCACGCGGGGATTAGAAAGGAAAAGGAATCCTGTATA

ATGCAAAATGAAATCGATACAAATTTGATTTGAGAAAAATGAGTCTATATCAAGAATATGATGGTATTGCGTCCC

TGCATCAAATACGGTATAATGTACATGTTGACTTGTGTTGAGCAAATGAAAACATGGGAGGTTGAAGGCAGAAAA

AAGTCCAAAAGGAAAAAAGCTTAGAACTTCAAAGTCTTAGGCTTTTCCCATGGGTATTCTTGGTTTGTGAAATGG

CCATAAGAAGCGGTTGGCAAGTAGATTGGTCTAGCTAAGTCCAACTCCTTGACCAATACACCAGGTCTCAAGTCA

AAGTTCTTGCTGATAATGTCGATAATTTCTTCGTCAGACTTGGTCGCAGTACCATAGGTGTCAACGTGCAAGGAC

AATGGTTCCGCAATACCGATGGCATAAGAAAATTGAACTTGAACTCTCTTACATAAACCAGCGGCAACTAGGGAC

TTGGCAACCCATCTAGCGGCATAAGCGGCAGAACGATCAACCTTAGAGTAGTCCTTACCGGAGAAGGCACCACCA

CCGACGGATGAGGCACCACCGTAAGCGTCGACGATGATCTTTCTACCGGTCAAACCAGCGTCACCTTGAGGACCA

CCGATGACGAATCTACCGGAAGGTTGGATAAAGTATTTGGTGTTTTCGTCCAACATGTCTCTTGGGATGACTTTT

TCAATGATCTCGGACTTTAGTTGCGCTCTTAAGTCCTCGGTCGTGATTTCGTCAGCATGTTGAGCGGAGACGACG

ACGGTGTCGATTCTTTGTGGAACCCATCTACCGTGGTCATCCTTGTATTCGACGGTGACTTGAGTCTTGGTGTCT

GGTCTCAACCACGCTAAAGAGCCATCTCTTCTCGCGTCAGCCATGGCCATGTTTAGTTTATGAGCCAAAAGAATA

GTCAAAGGCAAACCCTCTGGAGTTTCATCTGTGGCGTAACCAAACATGATACCTTGGTCACCGGCACCGATGTCT

TCCAAATCCTTCTCCTCGTGGACACCTTGGGCGATATCTGGAGATTGTTGCTCAATGGCGACAAGGACGTTACAG

GTCTTATAGTCGAAACCCTTGGCGGAATCATCGTAACCAATCTTCTTGATGGTGTCTCTGACGATTTTTTGGTAA

TCCAACTGTGCCTTGGTAGTAATTTCACCAAAGACCATAATCATACCAGTCTTTGCCGCGGTTTCACACGCAACT

TTGGAGTGAGGGTCCTCGGCTAAACAAGCGTCCAAGATGGCGTCGGAAACTTGGTCACAGATCTTATCTGGGTGA

CCTTCACCAACGGATTCAGAAGTGAATAAAAATGTACCGGCCATTGTGAAGGTAGTTCGATTTTGGAGGTCGCGG

GAGGTAAGTATAGAGGTATATTAACAATTTTTTGTTGATACTTTTATGACATTTGAATAAGAAGTAATACAAACC

GAAAATGTTGAAAGTATTAGTTAAAGTGGTTATGCAGCTTTTGCATTTATATATCTGTTAATAGATCAAAAATCA

TCGCTTCGCTGATTAATTACCCCAGAAATAAGGCTAAAAAACTAATCGCATTATTATCCTATGGTTGTTAATTTG

ATTCGTTGATTTGAAGGTTTGTGGGGCCAGGTTACTGCCAATTTTTCCTCTTCATAACCATAAAAGCTAGTATTG

TAGAATCTTTATTGTTCGGAGCAGTGCGGCGCGAGGCACATCTGCGTTTCAGGAACGCGACCGGTGAAGACCAGG

ACGCACGGAGGAGAGTCTTCCGTCGGAGGGCTGTCGCCCGCTCGGCGGCTTCTAATCCGTACTTCAATATAGCAA

TGAGCAGTTAAGCGTATTACTGAAAGTTCCAAAGAGAAGGTTTTTTTAGGCTAAGATAATGGGGCTCTTTACATT

TCCACAACATATAAGTAAGATTAGATATGGATATGTATATGGTGGTATTGCCATGTAATATGATTATTAAACTTC

TTTGCGTCCATCCAAAAAAAAAGTAACCCCACCCGAAGTCGCGCAACCAACTAACTTTACAATGTCCAAGAGCAA

AACTTTCTTATTTACCTCTGAATCCGTCGGTGAAGGTCACCCAGACAAGATTTGTGACCAAGTTTCTGATGCTAT

TTTGGACGCTTGTTTAGAACAAGATCCATTCTCCAAGGTTGCCTGTGAAACAGCTGCCAAAACTGGTATGATTAT

GGTTTTCGGTGAAATTACCACCAAAGCTAGACTTGACTACCAACAAATAGTAAGAGATACCATCAAGAAGATTGG

TTATGACGATTCTGCCAAGGGTTTCGACTACAAGACATGTAATGTTTTAGTAGCTATCGAACAACAATCTCCAGA

TATCGCTCAAGGTCTGCACTATGAAAAGAGCTTAGAAGACTTAGGTGCTGGTGACCAAGGTATAATGTTTGGTTA

CGCTACAGACGAAACTCCAGAAGGGTTACCATTGACCATTCTTTTGGCTCACAAATTGAACATGGCTATGGCAGA

-continued

TGCTAGAAGAGATGGTTCTCTCCCATGGTTGAGACCAGACACAAAGACTCAAGTCACTGTCGAATACGAAGACGA

CAATGGTAGATGGGTTCCAAAGAGGATAGATACCGTTGTTATTTCTGCTCAACATGCTGATGAAATTTCCACCGC

TGACTTGAGAACTCAACTTCAAAAAGATATTGTTGAAAAGGTCATACCAAAGGATATGTTAGACGAAAATACCAA

ATATTTCATCCAACCATCCGGTAGATTCGTCATCGGTGGTCCTCAAGGTGACGCTGGTTTGACCGGTAGAAAGAT

TATTGTCGACGCTTACGGTGGTGCCTCATCCGTCGGTGGTGGTGCCTTCTCCGGTAAGGACTATTCCAAGGTCGA

TCGTTCCGCTGCTTACGCTGCTAGATGGGTTGCCAAGTCTCTAGTTGCCGCTGGTTTGTGTAAGAGAGTCCAAGT

CCAATTTTCATATGCTATTGGTATTGCTGAACCATTGTCTTTACATGTGGACACCTATGGTACAGCTACAAAATC

AGATGACGAAATCATTGAAATTATTAAGAAGAACTTCGACTTGAGACCAGGTGTGTTAGTAAAGGAATTAGATTT

GGCTAGACCAATTTACTTACCAACCGCTTCTTATGGTCACTTCACTAATCAAGAGTACTCATGGGAAAAACCAAA

GAAATTGGAATTTTAAACATTTAGACAATAAATGTTTTATTTTGATTTTTATAATTATTTCAATCCCTTTCTTTA

TGCTAGGCTGGTCCCGATCACCTCCCTATATTGAGAAGACGATGCCTTATCGTTTGATTCGCTCAACTCGAGTCA

TGTAATTACTAGAAAATGATACAATAGAAAAGTTTTAAACATTCTTAAACTTGACAAACACCAATATCGGCGCTC

GCGGCCTGCAGGTTAATGTGTATATTAGTTTAAAAAGTTGTATGTAATAAAAGTAAAATTTAATATTTTGGATGA

AAAAAACCATTTTTAGACTTTTTCTTAACTAGAATGCTGGAGTAGAAATACGCCATCTCAAGATACAAAAAGCGT

TACCGGCACTGATTTGTTTCAACCAGTATATAGATTATTATTGGGTCTTGATCAACTTTCCTCAGACATATCAGT

AACAGTTATCAAGCTAAATATTTACGCGAAAGAAAAACAAATATTTTAATTGTGATACTTGTGAATTTTATTTTA

TTAAGGATACAAAGTTAAGAGAAAACAAAATTTATATACAATATAAGTAATATTCATATATATGTGATGAATGCA

GTCTTAACGAGAAGACATGGCCTTGGTGACAACTCTCTTCAAACCAACTTCAGCCTTTCTCAATTCATCAGCAGA

TGGGTCTTCGATTTGCAAAGCAGCCAAAGCATCGGACAAAGCAGCTTCAATCTTGGACTTGGAACCTGGCGGTTT

AAACGCGTGGCCGTGCCGTC

SEQ ID NO: 9
Length: 5467
Type:
Organism: artificial sequence
Other information: MS 332389 sequence

GACGGCACGGCCACGCGTTTAAACCGCCACCCAGCCAAGGTAGTCTAAAAGCTAATTTCTCTAAAAGGGAGAAAG

TTGGTGATTTTTTATCTCGCATTATTATATATGCAAGAATAGTTAAGGTATAGTTATAAAGTTTTATCTTAATTG

CCACATACGTACATTGACACGTAGAAGGACTCCATTATTTTTTTCATTCTAGCATACTATTATTCCTTGTAACGT

CCCAGAGTATTCCATTTAATTGTCCTCCATTTCTTAACGGTGACGAAGGATCACCATACAACAACTACTAAAGAT

TATAGTACACTCTCACCTTGCAACTATTTATCTGACATTTGCCTTACTTTTATCTCCAGCTTCCCCTCGATTTTA

TTTTTCAATTTGATTTCTAAAGCTTTTTGCTTAGGCATACCAAACCATCCACTCATTTAACACCTTATTTTTTTT

TTCGAAGACAGCATCCAACTTTATACGTTCACTACCTTTTTTTTTACAACAATTTCATTCTTCATCCTATGAACG

CTCGTCCAACGCCGGCGGACCTGTGTCAAAAGTAGGCAGCCAATCTGTTTTGCTGCCATATTTTTCCTAACAGGA

TTTGCTATGTATGAAGTACGATAAGTATGAAATATTAGTGCTTGTACATACGACCAATTTGTAATAAATAGTGAT

GTAGAGAATAAACTTAAAGAAAACTTATGAATAAATAATTATGGAGATATAATTACGAATAATTATGAATAAATA

GTGCTGCCTTAATTGGCACTTGCAATGGACCAAGTCTTGGCATAACCTTCAAGGTCAACAGGTTCCCAAGGAACT

CCCAAGCCTTCTGCAATGACTTTACCCAAATCTTCGTTTAGCAAACCAAAGTATTGCGTAACTCTCTTTTTGACT

TTAGGATCTTTGATCTTACAAGCGTGGCAAACAACGTTATGAACGAATAATTTCTTCTGTTCATCGTTGTATACC

TTTTCATATAGAGCTCTTGGCTGTTCGAAGTCTAGTGGACTAATACCATAAACGTAGTAATATTGATTAATTTTG

GCATCAACAATATGCTCGTTTCTGATTTGGTCTTGTTCCTGTTTTCTCACAGAAACTTCTGTTACTTCGTCAAGA

ACTATCCCTTTGAACTTATCAGATACTTCGTCGTTGTCTTCATTTTTGAATTTCAGAGTTTGATTTGGTAAACTG

-continued

GAAATATAATTTGGCTCAGGACCGAAATTGTAGTAACTCATTGGGCCGTCCCTTTGGAAGTTCACTGCTTTAAAT

GGACACTGTTCGGCAGTGTATTGGGAATCACCTTTGGAGTATGGACATCCCAAGTTTCTTGGTCTGTTGACGGGC

AATTGCTGATAGTTGGCTCCCAATCTATGACGTTGAGTGTCTGGATAGGAGAAAAGTCTGGCTTGTAGAACGGAA

TCATTAGAAGGCTTAATACCTGGGATACAAGTGTTCGTTGGACTGAATGCAACTTGTTCAATTTCTTGGAAATAA

TTGTCAACATTCTCCGTTAGGGTGATGGTACCAAATTTTCTCAAAGGGAATTCCTTGTGTGGCCATATTTTCGTT

AGGTCATTTACCGAATACCTGAACTTAGTTGCTTGTTCGGGTGTCATTGTTTGCACATAACAGTTAAATTTTGGC

TTTTCGCCATTTTGCAATTGAGTGAACAGCTTTGCCTGATTATAATCAGGGTGGGAGCCTGACAGTTCAGCAGCC

TTATCTCCAGTCAAGGTTTCAAAACCAGTATCCGACAAGACGTGGAATTGCACATATGTGTCCTTACCTTCTTTG

TTGACCATGATGAAGGAATGACCAGAGTACGCGTTCATACTAGCCCACGAAGCAGGAGTACCTCTATCACCAAAC

ATGTAAGTTATTTGATGGATTGATTCCGGATTCAATGTTAGATAATCCCAGTATATGGTAGTGTCCTGAAACTGA

TTCAGATGAGACTGAGGGTCTCTCTTTTGCGAATGAATAAATACGGGAAACTTAATAGCGTCTCTGAGGAAGAAG

ACGGGAGTATTGTTGAAGACCCAGTCATGGTTCCCCCACTCGGTATAGAATTTAAAAGAAACACCTCTTGGGTCT

CTTGCAGTGTCTGGTGTACCACTTTCACCACCAACGGTGGAAAAACGAACAAGACCAGGACATTTGTAACCCACA

TTCTGGTATGGAGCGGCGTATGTAATATCACTCAAAGAATCTGTTAGTTCGAACTCCAGTCTACAACCACCACCT

TTGGCATGGACTACACGCTCCGGAACTCTTTCTCTATCGAAACTTGCGATATTTTCCAGCAGATGGAAGTCTTGC

AGTAAGATAGGGCCGTCTGGTCTTGAGTATTGAGAAGCGTATGGGTGATGAGAGTACGGAAAACCGTTTTGTAGA

GAGTAAACTTTTTCTTGCTTTTCTTCTTTTTTACCGAACACGTTCATTGTAAAGTTAGTTGGTTGCGCGACTTCG

GGTGGGGTAAGTATAGAGGTATATTAACAATTTTTTGTTGATACTTTTATGACATTTGAATAAGAAGTAATACAA

ACCGAAAATGTTGAAAGTATTAGTTAAAGTGGTTATGCAGCTTTTGCATTTATATATCTGTTAATAGATCAAAAA

TCATCGCTTCGCTGATTAATTACCCCAGAAATAAGGCTAAAAAACTAATCGCATTATTATCCTATGGTTGTTAAT

TTGATTCGTTGATTTGAAGGTTTGTGGGGCCAGGTTACTGCCAATTTTTCCTCTTCATAACCATAAAAGCTAGTA

TTGTAGAATCTTTATTGTTCGGAGCAGTGCGGCGCGAGGCACATCTGCGTTTCAGGAACGCGACCGGTGAAGACC

AGGACGCACGGAGGAGAGTCTTCCGTCGGAGGGCTGTCGCCCGCTCGGCGGCTTCTAATCCGTACTTCAATATAG

CAATGAGCAGTTAAGCGTATTACTGAAAGTTCCAAAGAGAAGGTTTTTTTAGGCTAAGATAATGGGGCTCTTTAC

ATTTCCACAACATATAAGTAAGATTAGATATGGATATGTATATGGTGGTATTGCCATGTAATATGATTATTAAAC

TTCTTTGCGTCCATCCAAAAAAAAAGTAACCTCCCGCGACCTCCAAAATCGAACTACCTTCACAATGACTAGAAC

CTTACCTCCTGGTGTATCCGATGAAAGATTTGATGCCGCTTTACAAAGATTTAGAGATGTCGTCGGTGATAAGTG

GGTTTTATCTACCGCTGATGAATTGGAGGCCTTCAGAGATCCATACCCTGTTGGTGCTGCTGAAGCCAACTTACC

ATCTGCTGTTGTTTCTCCAGAATCTACTGAACAAGTTCAAGATATCGTCAGAATTGCCAACGAATACGGTATCCC

ATTGTCTCCAGTTTCTACTGGTAAGAATAACGGTTACGGTGGTGCTGCTCCAAGATTGTCCGGTTCCGTCATTGT

TAAAACCGGTGAAAGAATGAACAGAATTTTGGAAGTTAACGAAAAATACGGTTACGCTTTGTTGGAACCAGGTGT

TACCTATTTCGATTTGTACGAATATTTACAATCTCACGATTCTGGTTTGATGTTGGATTGTCCAGACTTGGGTTG

GGGTTCTGTTGTTGGTAACACCTTGGACCGTGGTGTTGGTTACACTCCATATGGTGATCACTTCATGTGGCAAAC

CGGTTTGGAAGTCGTCTTACCACAAGGTGAAGTCATGAGAACCGGTATGGGTGCCTTGCCAGGTTCCGATGCCTG

GCAATTATTCCCATACGGTTTTGGTCCATTCCCAGATGGTATGTTTACTCAATCTAACTTAGGTATTGTTACCAA

GATGGGTATTGCCTTGATGCAAAGACCACCAGCTTCCCAATCCTTTTTGATCACCTTTGACAAGGAGGAAGATTT

AGAACAAATTGTTGACATTATGTTGCCATTGAGAATTAATATGGCTCCATTGCAAAACGTTCCAGTCTTAAGAAA

CATTTTCATGGACGCTGCTGCTGTCTCTAAGAGAACCGAATGGTTTGACGGTGACGGTCCTATGCCAGCTGAAGC

TATTGAAAGAATGAAGAAGGACTTAGATTTGGGTTTCTGGAACTTTTATGGTACTTTGTACGGTCCACCACCATT

GATCGAAATGTATTACGGTATGATTAAGGAAGCCTTCGGTAAGATCCCAGGTGCTAGATTCTTCACTCACGAGGA

AAGAGACGATAGAGGTGGTCACGTCTTGCAAGATAGACACAAGATCAACAATGGTATTCCATCTTTGGATGAATT

-continued

GCAATTGTTGGACTGGGTTCCAAACGGTGGTCACATCGGTTTCTCTCCAGTTTCTGCTCCAGACGGTAGAGAAGC

TATGAAGCAATTTGAAATGGTTCGTAATAGAGCCAATGAATACAACAAAGATTACGCTGCTCAATTCATTATTGG

TTTGAGAGAAATGCACCACGTCTGTTTGTTTATCTATGACACCGCTATTCCAGAAGCTAGAGAAGAGATCTTGCA

AATGACCAAGGTTTTAGTTCGTGAAGCCGCTGAAGCTGGTTATGGTGAATACAGAACCCATAACGCCTTGATGGA

CGACGTTATGGCTACTTTCAACTGGGGTGACGGTGCCTTGTTGAAATTTCACGAAAAGATCAAAGATGCTTTGGA

CCCAAACGGTATTATTGCCCCTGGTAAGTCTGGTATTTGGTCCCAAAGATTCAGAGGTCAAAACTTGTAAAACCT

GCAGGCCGCGAGCGCCGATGAGTATGCTTCTCTTTTTTTTTGTAGGCCAGTGATAGGAAAGAACAATAGAATATA

AATACGTCAGAATATAATAGATATGTTTTTATATTTAGACCTCGTACATAGGAATAATTGACGTTTTTTTTGGCC

AACATTTGAAATTTTTTTTTGTTACCTCGCGCTGAGCCCAAACGGGCTCCACTACCCGATCCCCGCGTGCTTGGC

CGGCCGTCTCCATGCTGGACTTACTCGTCGAAGATTTCCTGCTACTCTCTATATAATTAGACACCCATGTTATAG

ATTTCAGAAAACAATGTAATAATATATGGTAGCCTCCTGAAACTACCAAGGGAAAAATCTCAACACCAAGAGCTC

ATATTCGTTGGAATAGCGATAATATCTCTTTACCTCAATCTTATATGCATGTTATTTGCTCTTATAATTGGTCTC

TATTTAGGGAAAAAAGTCGGTTTGAGAGCTTCTCGCGATGTGAAATCTCAATTTGAACTGCACGCCAAAGCTAGC

CCATTTCACGAACACCAGAAAGAAGAAATCCCCAAGGATCGCATGACAGAGTATGCTCTCTCATATCGTTGAGTA

TGAATGCCAATACACTGATCAGCTTTACAAGAAACGTAAAATCTGGCACGATGGTAGACTGAAATACTTTCAGTT

AAACAACAGATTCATGCTTTATACGGAAAAGGATAACGTCGGTGTTTAAACCCCAGCGCCTGGGGGG

SEQ ID NO: 10
Length: 5117
Type:
Organism: artificial sequence
Other information: MS 137140 sequence

GACGGCACGGCCACGCGTTTAAACCGCCACGAGCCTGAGACAAGCCCGTAACCAGGCGCGTTGCCGCAAATACAG

AGGCGCCCCAGACAACACCGCAGTGTGAAGCACTGTCAATTTAAAACCGTGGCTTGCTGGAGATGCCCAGACCAA

CCCTGTTGGGTTTTTCTCTCGAGCACGCCGTTATAATTTTAGCGTGTTCCGTACCTGTGTGCACATCAATAAGCG

GTGTAACAAACTTGAACTTGCCATCTCATATCGTCATATGAGCAGTTGCAGAGAAAGGCACTTTAAATAAAAAGG

CGTGGATGATAAAAAATGTATATAAGTTGGATGGATTTTTGGGAAAAAGTAATGTTTTTGCAGACGTTTTAAATA

CTCCCTCCCTTTTCTTAGTAATTTTTATTATGTATTGACTAAGTCAAAAATAACTATAGAAAACTAAAGTTTACG

AGAGGACCCAAAAGTTTTGAATAACACGTGCCTTTGATTTTTTGTACCTCCCGCGACCTCCAAAATCGAACTACC

TTCACAATGCACATAACCAAACCTCATGCTGCAATGTTTTCTTCCCCAGGTATGGGTCATGTCATTCCAGTTATC

GAATTGGGTAAGAGATTATCTGCCAACAACGGTTTCCACGTCACCGTCTTCGTCTTGGAAACTGACGCTGCTTCT

GCTCAATCTAAGTTCTTGAACTCTACCGGTGTTGATATTGTCAAATTGCCATCTCCAGACATTTACGGTTTGGTC

GACCCAGACGACCACGTTGTTACTAAGATTGGTGTTATTATGAGAGCTGCTGTTCCTGCTTTGAGATCCAAAATT

GCTGCTATGCACCAAAAGCCAACTGCTTTGATCGTTGATTTGTTTGGTACCGATGCCTTGTGTTTAGCTAAGGAA

TTTAATATGTTGTCTTATGTTTTTATTCCAACCAACGCCCGTTTCTTGGGTGTTTCCATTTACTACCCAAATTTA

GACAAGGACATTAAGGAAGAACATACCGTCCAAAGAAACCCTTTAGCTATCCCAGGTTGTGAGCCAGTCAGATTC

GAAGATACCTTGGATGCTTACTTGGTCCCAGATGAACCAGTCTACAGAGATTTCGTTAGACATGGTTTGGCCTAC

CCAAAGGCCGACGGTATTTTGGTTAACACTTGGGAAGAAATGGAACCAAAGTCTTTAAAGTCTTTGTTAAACCCA

AAATTGTTGGGTAGAGTCGCTAGAGTTCCAGTTTACCCAATCGGTCCATTGTGTAGACCAATCCAATCTTCTGAA

ACCGATCACCCAGTCTTGGATTGGTTGAATGAACAACCTAACGAATCTGTCTTATACATCTCTTTTGGTTCCGGT

GGTTGCTTGTCTGCTAAGCAATTGACTGAATTAGCCTGGGGTTTGGAGCAATCTCAACAAAGATTCGTTTGGGTT

GTCAGACCACCAGTCGATGGTTCTTGTTGTTCCGAATACGTTTCTGCTAACGGTGGTGGTACCGAAGACAACACT

-continued

CCTGAATACTTGCCAGAAGGTTTCGTCTCCAGAACTTCCGACAGAGGTTTCGTTGTTCCATCCTGGGCCCCACAA

GCTGAAATCTTGTCTCACAGAGCTGTTGGTGGTTTCTTGACTCATTGTGGTTGGTCCTCCACCTTAGAATCCGTT

GTCGGTGGTGTTCCTATGATCGCTTGGCCATTGTTCGCCGAGCAAAACATGAACGCCGCTTTGTTATCTGACGAA

TTAGGTATTGCTGTTAGATTGGACGACCCTAAGGAAGACATTTCCAGATGGAAGATCGAAGCCTTAGTTAGAAAG

GTCATGACTGAAAAGGAAGGTGAAGCTATGAGAAGAAAGGTTAAGAAGTTGAGAGACTCTGCCGAAATGTCTTTG

TCTATCGATGGTGGTGGTTTGGCTCATGAATCTTTGTGTAGAGTTACCAAGGAATGTCAAAGATTTTTGGAACGT

GTTGTTGACTTGTCCAGAGGTGCTTAAATCCCCGCGTGCTTGGCCGGCCGTGAGTATGCTTCTCTTTTTTTTTGT

AGGCCAGTGATAGGAAAGAACAATAGAATATAAATACGTCAGAATATAATAGATATGTTTTTATATTTAGACCTC

GTACATAGGAATAATTGACGTTTTTTTTGGCCAACATTTGAAATTTTTTTTTGTTACCTCGCGCTGAGCCCAAAC

GGGCTCCACTACCCGAACGCGATCGCCGACGCCGCCGATGTCGCCCTCAGTCCGCTCATTTTAGCTGAATTTTCT

AATGTTATTTTTCATCAGCAAAACTTAACAGAACGTTAATTTATCTACCCCTTTTAGTTCATTATCTCTTTTTTA

TCCAACATTTTACAGAGATCTCTCACTTAAGTCTAAGTAAAGACATTATTTTATATGGTACACTTATAGAATATA

CGATAATAATAATAAAAACTATGTAACATAACCTTCAGAATTTAATATTAGTTTCCTTTTTACCTCATTGCACTA

ATAAAAAAATTCTACAGAATCTCCGAAAAAGAAAATCCAGCTTACTCTTTTTGTTTTCTTCTTCACACGTGAGCT

TTTCCGCCGGCATACGTTCCGTTCCGTGTCGTCTTGCATAAAATTTCCGAATCACATGTTCGTAAAACAACCGGA

AGTGCCCCGAATATAAAGTCAATTCTCACCGCTGTTGTAACTGGAGCTTTAAGGTGTTATCTAAGGAAGGATAAA

AGAACTTAAACAACCGGTGTTTAAACCCCAGCGCCTGGCGGG

SEQ ID NO: 10
Length: 1912
Type:
Organism: artificial sequence
Other information: R21 sequence SEQ ID NO: 11
Length: 8672
Type:
Organism: artificial sequence
Other information: MS146176 sequence

GACGGCACGGCCACGCGTTTAAACCGCCCGAACAAGCTTATCCCTATTACAGAATTCCAAGGAGGAAATCATTCA

ACTTGAAAGTAAATGGATGTCTATGCAATCTGTTAAAACAACTGCCCTACCCCTTCAAGAGACTACGAATACATC

ATCGACCTTAACTTCTCTGACGTCCAGCATAATTCCCAAGAGTATACCTATAATCACGAAAGGTGAAGTCGCCAC

TAAACCAGCATCTTACTGAATTATTTTCAACAGAACACATCGCATCCAACTGAACAAACTGTTACCGCTGTTGAT

ACCAAGGAACATTCAGTGAACGTAGGGAAGAACGAACATTCTCCATATTTTTGCATACTAGATACAAGGGGGAAG

AATGCAATTATTTCACAAACCGAAAGAAAAAGAATCACAAGCTATGTTTGCTATTATCAATTTTTCTTATGATTA

ATTTAACATAAATTATGGCCTTTTTCATTCCGGCTGCGCTTGTTCTCCAATTTTTTTTTTTTTTTTGAGAAAACT

TTTCGATTACCTGCCTTGATACGCTGCCAGAATACATGTCGGAAAGCTTCCTTCCGGAATGGCTTAAGTAGGTTG

CAATTTCTTTTTCTATTAGTAGCTAAAAATGGGTCACGTGATCTATATTCGAAAGGGGCGGTTGCCTCAGGAAGG

CACCGGCGGTCTTTCGTCCGTGCGGAGATATCTGCGCCGTTCAGGGGTCCATGTGCCTTGGACGATATTAAGGCA

GAAGGCAGTATCGGGGCGGATCACTCCGAACCGAGATTAGTTAAGCCCTTCCCATCTCAAGATGGGGAGCAAATG

GCATTATACTCCTGCTAGAAAGTTAACTGTGCACATATTCTTAAATTATACAATGTTCTGGAGAGCTATTGTTTA

AAAAACAAACATTTCGCAGGCTAAAATGTGGAGATAGGATTAGTTTTGTAGACATATATAAACAATCAGTAATTG

GATTGAAAATTTGGTGTTGTGAATTGCTCTTCATTATGCACCTTATTCAATTATCATCAAGAATAGCAATAGTTA

AGTAAACACAAGATTAACATAATAAAAAAAATAATTCTTTCATAATGCCCAGTAAATTGGCTATAACTTCCATGT

CCTTGGGCAGGTGTTATGCAGGCCATTCTTTCACAACTAAGTTAGACATGGCTAGGAAATATGGTTACCAGGGTT

TGGAGTTGTTTCATGAGGACTTAGCCGATGTCGCATACAGGTTGTCAGGTGAAACACCTAGTCCATGCGGTCCCA

GTCCAGCTGCTCAATTATCAGCCGCTAGACAGATATTGAGGATGTGCCAGGTTAGAAACATCGAAATAGTGTGCT

TGCAACCCTTTTCACAATATGATGGTTTATTGGATAGAGAGGAGCACGAGAGGAGGTTGGAGCAATTAGAGTTTT

-continued

GGATTGAATTGGCCCACGAGTTGGATACTGACATCATTCAAATTCCAGCCAATTTCTTGCCCGCCGAAGAAGTCA

CAGAAGATATTTCATTAATTGTGAGTGACTTACAGGAAGTTGCCGATATGGGTTTACAGGCAAACCCTCCAATAA

GGTTTGTATATGAGGCATTATGCTGGTCCACTAGAGTTGACACTTGGGAGAGGTCTTGGGAAGTTGTCCAAAGAG

TAAATAGACCTAACTTTGGCGTTTGCTTAGACACTTTTAACATCGCAGGTAGAGTTTATGCTGACCCCACAGTTG

CCTCAGGCAGAACACCAAACGCTGAAGAAGCAATTAGAAAGTCAATTGCCAGGTTGGTCGAAAGGGTCGATGTAT

CTAAAGTCTTCTACGTTCAAGTAGTGGACGCCGAAAAGTTAAAGAAACCATTAGTTCCCGGTCATAGATTCTATG

ACCCTGAGCAACCAGCCAGAATGTCATGGTCAAGAAATTGTAGGTTGTTCTACGGCGAAAAAGACAGAGGCGCTT

ACTTACCTGTTAAAGAAATCGCTTGGGCTTTTTTCAATGGATTGGGCTTCGAAGGTTGGGTGTCCTTGGAATTAT

TTAACAGAAGAATGTCAGATACTGGATTTGGAGTTCCAGAGGAGTTAGCTAGGAGAGGCGCCGTATCATGGGCCA

AATTAGTTAGAGATATGAAAATCACAGTGGATTCTCCAACTCAACAACAAGCTACACAGCAGCCTATTAGAATGT

TGTCCTTATCTGCAGCCTTATAAAAAGCTTCGACACATACATAATAACTCGATAAGGTATGGTATCTTATTTCAT

TGTGGGGTAGTTTTTACGAAAAAAATGAAAAGTTGTAAGTATAGTATATATTTTTTTTCTATGTAAGTTTTATAT

CCCCGCGTGCTTGGCCGGCCGTTCACATGTAGGGACCGAATTGTTTACAAGTTCTCTGTACCACCATGGAGACAT

CAAAGATTGAAAATCTATGGAAAGATATGGACGGTAGCAACAAGAATATAGCACGAGCCGCGAAGTTCATTTCGT

TACTTTTGATATCGCTCACAACTATTGCGAAGCGCTTCAGTGAAAAAATCATAAGGAAAAGTTGTAAATATTATT

GGTAGTATTCGTTTGGTAAAGTAGAGGGGGTAATTTTTCCCCTTTATTTTGTTCATACATTCTTAAATTGCTTTG

CCTCTCCTTTTGGAAAGCTATACTTCGGAGCACTGTTGAGCGAAGGCTCATTAGATATATTTTCTGTCATTTTCC

TTAACCCAAAAATAAGGGAAAGGGTCCAAAAAGCGCTCGGACAACTGTTGACCGTGATCCGAAGGACTGGCTATA

CAGTGTTCACAAAATAGCCAAGCTGAAAATAATGTGTAGCTATGTTCAGTTAGTTTGGCTAGCAAAGATATAAAA

GCAGGTCGGAAATATTTATGGGCATTATTATGCAGAGCATCAACATGATAAAAAAAAACAGTTGAATATTCCCTC

AAAAATGGAAAGAATTGTTGTAACATTGGGTGAAAGGTCTTATCCAATCACTATTGCATCTGGTTTATTTAACGA

ACCAGCCAGTTTTTTACCATTGAAATCCGGTGAGCAAGTGATGTTAGTCACTAACGAAACATTAGCTCCCTTGTA

TTTAGACAAGGTAAGGGGTGTTTTGGAACAAGCAGGCGTAAACGTCGATTCTGTGATATTACCAGACGGTGAACA

ATACAAAAGTTTGGCAGTTTTAGATACTGTATTCACTGCCTTATTACAGAAACCACATGGTAGAGATACTACATT

GGTTGCCTTAGGAGGCGGAGTTGTCGGCGATTTAACAGGTTTCGCTGCCGCATCATATCAGAGAGGTGTTAGATT

CATTCAGGTCCCAACTACTTTGTTATCCCAAGTAGACTCATCAGTTGGAGGAAAGACTGCTGTCAATCATCCTTT

AGGAAAGAACATGATTGGTGCCTTCTACCAGCCAGCATCAGTCGTTGTTGATTTAGATTGTTTGAAGACATTACC

TCCAAGAGAGTTGGCAAGTGGTTTGGCAGAAGTAATAAAATATGGTATCATATTGGATGGTGCATTTTTTAATTG

GTTGGAAGAAAATTTAGATGCATTATTGAGGTTAGACGGTCCTGCTATGGCTTATTGTATTAGAAGGTGTTGTGA

ATTAAAGGCTGAGGTTGTAGCAGCCGACGAGAGAGAAACTGGTTTAAGAGCTTTGTTGAACTTAGGTCATACATT

TGGTCATGCTATCGAAGCTGAAATGGGTTACGGTAATTGGTTGCATGGTGAAGCCGTTGCAGCCGGTATGGTTAT

GGCTGCCAGGACATCTGAAAGATTGGGTCAATTCAGTTCTGCAGAAACACAAAGGATAATAACCTTATTGAAAAG

GGCAGGTTTACCTGTGAATGGTCCTAGAGAGATGAGTGCTCAAGCTTATTTGCCCCACATGTTGAGAGATAAGAA

GGTTTTAGCAGGTGAAATGAGGTTAATTTTGCCCTTAGCAATTGGAAAAAGTGAAGTCAGATCCGGTGTTTCACA

TGAATTAGTATTGAACGCCATAGCTGATTGCCAATCAGCCTAAATAAATGACTTAATTTTAACTATATATCGCCA

AACATGTAAATTAAAAAAAGAAGCGAGAAGTATATACATGTGTGTATGAATAAATAATTCGTTTACTATTGATAC

GTATTGCAAGATATGATTAACCTGCAGGCCGCGAGCGCCGATGATCATCTACCCATGCCGAAATTCGGGCCGTTG

GCCGGATTGCGCGTTGTCTTCTCCGGTATCGAAATCGCCGGACCGTTTGCCGGGCAAATGTTCGCAGAATGGGGC

GCGGAAGTTATCTGGATCGAGAACGTCGCCTGGGCCGACACCATTCGCGTTCAACCGAACTACCCGCAACTCTCC

CGCCGCAATTTGCACGCGCTGTCGTTAAATATTTTCAAAGATGAAGGCCGCGAAGCGTTTCTGAAATTAATGGAA

-continued

ACCACCGATATCTTCATCGAAGCCAGTAAAGGTCCGGCCTTTGCCCGTCGTGGCATTACCGATGAAGTACTGTGG

CAGCACAACCCGAAACTGGTTATCGCTCACCTGTCCGGTTTTGGTCAGTACGGCACCGAGGAGTACACCAATCTT

CCGGCCTATAACACTATCGCCCAGGCCTTTAGTGGTTACCTGATTCAGAACGGTGATGTTGACCAGCCAATGCCT

GCCTTCCCGTATACCGCCGATTACTTTTCTGGCCTGACCGCCACCACGGCGGCGCTGGCAGCACTGCATAAAGTG

CGTGAAACCGGTAAAGGCGAAAGTATCGACATCGCCATGTATGAAGTGATGCTGCGTATGGGCCAGTACTTCATG

ATGGATTACTTCAACGGCGGCGAAATGTGCCCGCGCATGAGCAAAGGTAAAGATCCCTACTACGCCGATCGGCGC

TCGCGGCCTGCAGGTTCAATGCTGCTTCGTATAGGCGCTATTTAATTAAGTAGTTATATAAAGAGAACGGTGCAA

TTGAATAGGAAAGGAATGACGGATTTTGCTTCTATGTTTGCTTTTATTTGAAGCGTGGGTTCTTATTTATGCTTG

GTGTAATATGGTCAAAACTGTTCTCAAATCATTTACTGAGATCTGTCCTGGAGCAGAAGCTTTTTTGACAGCACC

AAATGTAGCAGCAGATCCGAACACTTCACCAGCTAATCTAGAAATCACACCGGTTTTTGCCATAGACATAGTTAT

GATAGGTCTATCAGCGTATTGTTCTTGCATTTCCAATGTGGCAGCTAACAATGTTAAGACATCAGAGGTAGACTG

TGGCATTAAAGCAATTTTGGGTATATCAGCATCAAAGGATTGCATTTTTCTTAATCTGGCTATGATTTCCTCTGC

TTCTGGGGTCTTGTGGAAATCATGATTAGACATAACTACCTTAACATCGTGAGCGTGAGCGTAAGCTACAGTTTC

CTTAACCTGGTCATCACCAGTAAACAACTCCAAATCTATCATATCCACTAAACCACTATCAATAGCAGCTCTGTT

CAAAGCAATGTAGGCTTCGGTACTAATTGCTTGTTCACCACCTTCCTTAGCTGATCTGAAAGTGAACAATAATGG

TTTTTCAGGCATAGTCTCTCTTAATATCTTTGCTGCAGCCATTACTGATTCGACATTTGACAAGTCTGCATAGTG

ATCCACTCTCCATTCTAATATGTCAAAATCTGCTTCTCTATAAGCTAAGGCCTCACTCTTTACAGAGGCTATGTC

TTTAGCCATTAAACTAACAATTATTTTAGGGGCTCCTGTTCCAATAACCAAATCTTTCACTGTAACTGTCTTCAT

TTTTGAGGGAATATTCAACTGTTTTTTTTATCATGTTGATGCTCTGCATAATAATGCCCATAAATATTTCCGAC

CTGCTTTTATATCTTTGCTAGCCAAACTAACTGAACATAGCTACACATTATTTTCAGCTTGGCTATTTTGTGAAC

ACTGTATAGCCAGTCCTTCGGATCACGGTCAACAGTTGTCCGAGCGCTTTTTGGACCCTTTCCCTTATTTTTGGG

TTAAGGAAAATGACAGAAAATATATCTAATGAGCCTTCGCTCAACAGTGCTCCGAAGTATAGCTTTCCAAAAGGA

GAGGCAAAGCAATTTAAGAATGTATGAACAAAATAAAGGGGAAAAATTACCCCCTCTACTTTACCAAACGAATAC

TACCAATAATATTTACAACTTTTCCTTATGATTTTTCACTGAAGCGCTTCGCAATAGTTGTGAGCGATATCAAA

AGTAACGAAATGAACTTCGCGGCTCGTGCTATATTCTTGTTGCTACCGTCCATATCTTTCCATAGATTTTCAATC

TTTGATGTCTCCATGGTGGTACAGAGAACTTGTAAACAATTCGGTCCCTACATGTGAACGGCCGGCCAAGCACGC

GGGGATAGGATGGTAAAAAGTCTGAGTGGTTCTTTTAATTAAGGTAGCAAAAGTTGATGAAACTGGAACTTCAAA

ACAGTAATAATATAGTAACAATAAGAAATAAAAGAGATATTAACGACACTAAAATTTTAGGCCACTCTTGCTGTC

AATTGGCCATTCAAATCCTGATGAATTTCTCTCAACAATGCGTCGGTCATTTCCCATGAAATACATGCGTCTGTA

ACAGACACGCCATACTTCATTTCTGATCTTGGCTGTTCGGATGATTGGTTACCCTCATGAATATTTGATTCGATC

ATCAAACCGATGATAGATCTGTTTCCATCTTTTATCTGTGCAACTACAGATTCAGCGACGGCGGGTTGTCTCCTG

TAATCCTTATTAGAGTTACCGTGAGAACAGTCGACCATCAAGGAAGGTCTTAAACCTGCTTGTTCCATTTCCTTT

TCGCACTGTGCCACGTCGGCAGGTGAATAGTTTGGGGCCTTACCACCCCTCAATATTACATGACCATCTGGGTTA

CCCTGAGTTTGTAATAATGCGACCTGACCAGCTTGATTGATACCGACAAATCTATGTGGTTGAGCTGCGGCCCTC

ATGGCATTTATGGCAGTTGCCAATGAACCGTCTGTGCCGTTTTTGAAGCCAACTGGCATACTCAAACCAGATGCC

ATTTCTCTGTGAGTTTGTGATTCGGTGGTTCTAGCACCTATTGCAGACCAGGAGAATAAATCGCCCAAATATTGA

GGACTGTTTAAATCCAAGGCTTCGGTAGCTAAAGGCAAACCCATATTTACTAATTCCAACAACAATTTCCTTGCG

ATTTGCAAACCAGCTTCCACATCAAAAGATCCATCCATATGTGGGTCGTTAATCAATCCCTTCCAACCTACAGTG

GTCCTTGGCTTTTCAAAATAAACCCTCATAACCAAATACAAGGAGTCGGAGACTTCAGCTGCCAAGGCCTTAAAT

CTTCTTGCGTATTCCAATGCTGTTTCAGGATCGTGGATACTACATGGGCCACATACAACCAATAACCTTGGATCT

CTACCGGCTATAATATCAGAAATACTCTTTCTTGAATCGGCTATCTGAGCCTCTTGTTGCAAAGATAAGGGAAAG

-continued

GCAGCTTTTAATTGCTCAGGTGTCATCAAAACCTGTTCATCTGTTATATGTACGTTATTTAAGGCATCTTTCTGC

ATTATGAAAGAATTATTTTTTTATTATGTTAATCTTGTGTTTACTTAACTATTGCTATTCTTGATGATAATTGA

ATAAGGTGCATAATGAAGAGCAATTCACAACACCAAATTTTCAATCCAATTACTGATTGTTTATATATGTCTACA

AAACTAATCCTATCTCCACATTTTAGCCTGCGAAATGTTTGTTTTTTAAACAATAGCTCTCCAGAACATTGTATA

ATTTAAGAATATGTGCACAGTTAACTTTCTAGCAGGAGTATAATGCCATTTGCTCCCCATCTTGAGATGGGAAGG

GCTTAACTAATCTCGGTTCGGAGTGATCCGCCCCGATACTGCCTTCTGCCTTAATATCGTCCAAGGCACATGGAC

CCCTGAACGGCGCAGATATCTCCGCACGGACGAAAGACCGCCGGTGCCTTCCTGAGGCAACCGCCCCTTTCGAAT

ATAGATCACGTGACCCATTTTTAGCTACTAATAGAAAAAGAAATTGCAACCTACTTAAGCCATTCCGGAAGGAAG

CTTTCCGACATGTATTCTGGCAGCGTATCAAGGCAGGTAATCGAGCATAGTAAAAAAATAGATGCAGAATTTACT

CACCTCAAGGAGGGGCAAAGTAATAAGAAAAGTTACCATAGGCTAGTTGAATGTCCAAGATCGTAAAGAATGAAG

AAAAAAGGAGTAAAAAGTATGAATAAGATAAATGAAAATATAAAAATAAAAACCAACTAATACATGAAGAAAAAA

AAGCAGACAAAAACATTTTATGGACCTGATGCAATCTAGTAGTCCATAGAATAATCACCACTAGAAAATTCTTCC

TCTTCATTACTACCGTTTGCCATTATAGGAATATGATTTGCTGCAGGATTCTGCGGAGGTATTATATAGGGCACT

GGCGGCACCTGTGGAATAAACCCAAATGATGGGAACATTGGCATCATCCAGTTAGCGTTATTTTGGTTTGCACTT

ATTAAGTTGTAACTGTTCACGGGCTTTGTGTTGGTATTAGGGTACTGCAGTGGTATGAAATAATTTTCCCTCGAG

ACTTGCTGTTGCGATTGGTGGCGGTTTAAACGCGTGGCCGTGCCGTC

SEQ ID NO: 12
Length: 8123
Type:
Organism: artificial sequence
Other information: MS146277 sequence

GACGGCACGGCCACGCGTTTAAACCGCCAAAAACTCACAAGAAGTTCGGTGTCCTTATTTGCGATGGGAATTGCT

AATATCATATCACCACAAATATGGAGAGAGAAGGACTCTCCTCGCTTTTTACCTGCCTGGATTGTTCAAATCGTT

TTATCATTCTCTCTTGCACCAGCCATTTTGTTACTGATCCATTTCATACTAAAAAGAAGGAATAATCAAAGACTA

AAAAATTATGACGAAAATTTACAAAATTATTTGGACAGAATTCAACTCATTGAAAGCGAAAATCCTTCTTCCATT

GAAGAAGGGAAAGTGGTAACCCACGAGAACAATTTGGCAGTCTTTGATTTGACTGATTTAGAAAACGAAACTTTT

ATATATCCTTTGTAAATATTGATGTTTTGTTGTGTAAATGTTCTATCTGACACTTAATAATTAGAAAATTAATTT

TTTAAACTTTCCGGCTGCAAGAAAGAGGAACTGTGTCTCTTTGAAAGGCACAATTTCCCAAAGAATCATTTACAA

TGTCGATTACCTGCCTTGATACGCTGCCAGAATACATGAGTGAGTTCTATTCACGCAATCGGTAGTATCAAAGAA

GATTATTTGGGTGCTATTTAATCACTTGTTACTCCGCAACGCTTTTCTGAACGCCCGCCTTCGCCTTTCATTATC

ATTCTCATCCCAAAAGAACTGTGCATGTTATTTGCAATACTTCATATACGCTCTGTATTATTAATAGTATCATTA

ATTACGTCAATTGAAATTCAAAATATCATCTTTGACAGTAACATCTATCCTCTTAGACAACTAGGGCCATTGCAG

TGTCTCGAAACCATTAATATCACTGAAAAGATGAAAAGAAAGGCAAATATATATTGATCACTAATTTTCTAAGCT

AAAGAATCTATTCCCCCTCTGTTAAATGGAATTGTGTGAAATAAAATATTATAAAATCAGAACTTTGGGGGGGAA

ACATAAAAAAATGAGAAAAAGAAAACGAACTAACTAATGTTTAAGTAAAAGAACAAAAAGGTAGACCAATGTAGC

GCTCTTACTTTATTAGACTAATCTTCTACACAAGGTAACACCATCACCGATGGAAACTTGGGAGATTTCAATTCT

TGGATCGGAAGCCAATCTTTTGTTCAATTCCATCAAAGCCTTACGGTTAACTCTTAAGTGAACTGGGACAGTCTC

TTCCTCTTCAGCAACGAAACCGAACCATAAGGTGTTATCGAAAGCAATGATACCACCAACTTTGACCAACTTCAT

CAATCTTTCCAAAGCGTGGACGTAATTTGGCTTATCAGCGTCAACGAAAGCGAAGTCAAATTCTGGCTTTGGGTT

TTCAGATAACAACTTGTCTAAGGCTTGCAAACCGTCGGATTGGATAAAGTTAATTTTGTGATCGATACCGGCGTT

CTTGATGAATTCCAAACCCATTTCGTAAGCTTCTTTATCGATATCAATAGCAGTAATTCTACCGTCTTCAGGCAA

-continued

AGCCAAGGCGGTGGTTAACAAAGAGTAACCAGTGAAAACACCCAATTCCAAGGTGTTCTTAGCGTTCATCATCTT

CAACAACATGGACAAGAAATGACCTTCGTCAACAGGGACTTCCATCTCGGACAAGTTACCGTACTTATGAACGGT

AGCTTCTCTTAACTTCTTCAATTCTTCGTGTTCTCTTGGGTAAGCGGAAGTTTCAAAGATGTACTTTTTCAATTC

TTCGTTCTTCAAGATACCCTTAGATGGTATAAGATTTTCCATGTCTGGTTCCATTTATATTGAATTTTCAAAAAT

TCTTACTTTTTTTTTGGATGGACGCAAAGAAGTTTAATAATCATATTACATGGCAATACCACCATATACATATCC

ATATCTAATCTTACTTATATGTTGTGGAAATGTAAAGAGCCCCATTATCTTAGCCTAAAAAAACCTTCTCTTTGG

AACTTTCAGTAATACGCTTAACTGCTCATTGCTATATTGAAGTACGGATTAGAAGCCGCCGAGCGGGCGACAGCC

CTCCGACGGAAGACTCTCCTCCGTGCGTCCTGGTCTTCACCGGTCGCGTTCCTGAAACGCAGATGTGCCTCGCGC

CGCACTGCTCCGAACAATAAAGATTCTACAATACTAGCTTTTATGGTTATGAAGAGGAAAAATTGGCAGTAACCT

GGCCCCACAAACCTTCAAATCAACGAATCAAATTAACAACCATAGGATAATAATGCGATTAGTTTTTTAGCCTTA

TTTCTGGGGTAATTAATCAGCGAAGCGATGATTTTTGATCTATTAACAGATATATAAATGCAAAAGCTGCATAAC

CACTTTAACTAATACTTTCAACATTTTCGGTTTGTATTACTTCTTATTCAAATGTCATAAAAGTATCAACAAAAA

ATTGTTAATATACCTCTATACTTTAACGTCAAGGAGAAAAAACTATAATGGATATGGCAAGTAATGGTTCTGCCG

GTGAGGTTAGAGAAGTTCACTCCTCCGAAACTACCAAGACTTTATTGAAATCCGATGCTTTATACGATTATATGT

TGAAGACTATGGTCTATCCAAGAGAGAACGAATTTATGAGAGAATTGAGACAAATCACTTCCGAACATATCTTCG

GTTTCATGTCTTCTCCACCAGATGAAGGTTTGTTATTGTCCTTGTTGTTAAAGGTTATGGGTGCTAAGAGAACCA

TCGAAGTCGGTGTCTACACTGGTTGTTCCGTCTTGACTACTGCCTTAGCTATCCCAGACGATGGTAGAATCATTG

CTATTGACGTTTCCCGTGAATACTTTGACTTGGGTTTGCCAGTTATTAAGAAGGCCGGTGTTGCCCATAAGGTTG

ATTTCCGTGAAGGTCCTGCTGGTCCAATTTTGGACAAATTGATTGCTGATGAAGACGAAGGTTCTTTTGATTTCG

CTTTCGTTGATGCCGATAAGTACAACTACGGTTCCTACCACGAACAATTGTTGAGATTGGTTAGAGTTGGTGGTG

TTTTGGCTTACGACAATACCTTATGGGGTGGTACCGTCTCCATGCCAGATGACACTCCATTGACCGAAGAAGACA

GAAAGAAGAGAGACTCCATTCGTGGTTTCAATGCCATGATTGCTGCCGACGCCAGAGTCGAACCAGTTCAATTAC

CAATCGCCGACGGTATTACCTTGTGCAGACGTGTCGTCTAAAGTTTCAGGCAGAACAAGACCCTTTTCAAAAATA

TGTAAGCCATTATTAAAAAAAAGGATATTTTGTATAATTGTTTAATAAAATAACATCTTTTTAAACAATCATAAA

TAGCACTTCTTATCATACAACCTCAAATCATATCGGTCCAAATTTGCTCAAATTGTACATGAGATATAACTTTTT

CTTCTAATGCTTTCATTTCAGAGTTTGTTTTTTTTTTTTCTTTTTTTTTTTTTTCCTTACCGGAGTCTGAATCTC

TTACTTCCTTAACTTAGATGTTAGTGACTAAAATCTGATGGACAGTATCAAAATGTAAATATTGTACCTAAAAAG

AAAAAAGTATTAAAGTGGTTTGCCATAAATTTTAAACAAGTGAAAAGTTTCAATATTTATATTTACATGATTGTG

GACAAGCGGCATTGTCTACAGGCTGTGCAAAATTATATAGTACAGATAAATGTAACCAGAACAACGAAGAAAAGG

TCCCTATGTTGCAACGCGATCGCCGACGCCGCCGATGCTGATTATCAGGGTAAAAATGTCGTCATTATCGGCCTG

GGCCTCACCGGGCTTTCCTGCGTGGACTTTTTCCTCGCTCGCGGTGTGACGCCGCGCGTTATGGATACGCGTATG

ACACCGCCTGGCCTGGATAAATTACCCGAAGCCGTAGAACGCCACACGGGCAGTCTGAATGATGAATGGCTGATG

GCGGCAGATCTGATTGTCGCCAGTCCCGGTATTGCACTGGCGCATCCATCCTTAAGCGCTGCCGCTGATGCCGGA

ATCGAAATCGTTGGCGATATCGAGCTGTTCTGTCGCGAAGCACAAGCACCGATTGTGGCGATTACCGGTTCTAAC

GGCAAAAGCACGGTCACCACGCTAGTGGGTGAAATGGCGAAAGCGGCGGGGGTTAACGTTGGTGTGGGTGGCAAT

ATTGGCCTGCCTGCGTTGATGCTACTGGATGATGAGTGTGAACTGTACGTGCTGGAACTGTCGAGCTTCCAGCTG

GAAACCACCTCCAGCTTACAGGCGGTAGCAGCGACCATTCTGAACGTGACTGAAGATCATATGGATCGCTATCCG

TTTGGTTTACAACAGTATCGTGCAGCAAAACTGCGCATTTACGAAAACGCGAAAGTTTGCGTGGTTAATGCTGAT

GATGCCTTAACAATGCCGATTCGCGGTGCGGATGAACGCTGCGTCAGCTTTGGCGTCAACAATCGGCGGCGTCGG

CGATCGCGTTGCAACATAGGGACCTTTTCTTCGTTGTTCTGGTTACATTTATCTGTACTATATAATTTTGCACAG

-continued

CCTGTAGACAATGCCGCTTGTCCACAATCATGTAAATATAAATATTGAAACTTTTCACTTGTTTAAAATTTATGG

CAAACCACTTTAATACTTTTTTCTTTTTAGGTACAATATTTACATTTTGATACTGTCCATCAGATTTTAGTCACT

AACATCTAAGTTAAGGAAGTAAGAGATTCAGACTCCGGTAAGGAAAAAAAAAAAAAAGAAAAAAAAAAAACAAAC

TCTGAAATGAAAGCATTAGAAGAAAAAGTTATATCTCATGTACAATTTGAGCAAATTTGGACCGATATGATTTGA

GGTTGTATGATAAGAAGTGCTATTTATGATTGTTTAAAAGATGTTATTTTATTAAACAATTATACAAAATATCC

TTTTTTTTAATAATGGCTTACATATTTTTGAAAAGGGTCTTGTTCTGCCTGAAACTTTAGACGACACGTCTGCAC

AAGGTAATACCGTCGGCGATTGGTAATTGAACTGGTTCGACTCTGGCGTCGGCAGCAATCATGGCATTGAAACCA

CGAATGGAGTCTCTCTTCTTTCTGTCTTCTTCGGTCAATGGAGTGTCATCTGGCATGGAGACGGTACCACCCCAT

AAGGTATTGTCGTAAGCCAAAACACCACCAACTCTAACCAATCTCAACAATTGTTCGTGGTAGGAACCGTAGTTG

TACTTATCGGCATCAACGAAAGCGAAATCAAAAGAACCTTCGTCTTCATCAGCAATCAATTTGTCCAAAATTGGA

CCAGCAGGACCTTCACGGAAATCAACCTTATGGGCAACACCGGCCTTCTTAATAACTGGCAAACCCAAGTCAAAG

TATTCACGGGAAACGTCAATAGCAATGATTCTACCATCGTCTGGGATAGCTAAGGCAGTAGTCAAGACGGAACAA

CCAGTGTAGACACCGACTTCGATGGTTCTCTTAGCACCCATAACCTTTAACAACAAGGACAATAACAAACCTTCA

TCTGGTGGAGAAGACATGAAACCGAAGATATGTTCGGAAGTGATTTGTCTCAATTCTCTCATAAATTCGTTCTCT

CTTGGATAGACCATAGTCTTCAACATATAATCGTATAAAGCATCGGATTTCAATAAAGTCTTGGTAGTTTCGGAG

GAGTGAACTTCTCTAACCTCACCGGCAGAACCATTACTTGCCATATCCATTATAGTTTTTTCTCCTTGACGTTAA

AGTATAGAGGTATATTAACAATTTTTTGTTGATACTTTTATGACATTTGAATAAGAAGTAATACAAACCGAAAAT

GTTGAAAGTATTAGTTAAAGTGGTTATGCAGCTTTTGCATTTATATATCTGTTAATAGATCAAAAATCATCGCTT

CGCTGATTAATTACCCCAGAAATAAGGCTAAAAAACTAATCGCATTATTATCCTATGGTTGTTAATTTGATTCGT

TGATTTGAAGGTTTGTGGGGCCAGGTTACTGCCAATTTTTCCTCTTCATAACCATAAAAGCTAGTATTGTAGAAT

CTTTATTGTTCGGAGCAGTGCGGCGCGAGGCACATCTGCGTTTCAGGAACGCGACCGGTGAAGACCAGGACGCAC

GGAGGAGAGTCTTCCGTCGGAGGGCTGTCGCCCGCTCGGCGGCTTCTAATCCGTACTTCAATATAGCAATGAGCA

GTTAAGCGTATTACTGAAAGTTCCAAAGAGAAGGTTTTTTTAGGCTAAGATAATGGGGCTCTTTACATTTCCACA

ACATATAAGTAAGATTAGATATGGATATGTATATGGTGGTATTGCCATGTAATATGATTATTAAACTTCTTTGCG

TCCATCCAAAAAAAAAGTAAGAATTTTTGAAAATTCAATATAAATGGAACCAGACATGGAAAATCTTATACCATC

TAAGGGTATCTTGAAGAACGAAGAATTGAAAAAGTACATCTTTGAAACTTCCGCTTACCCAAGAGAACACGAAGA

ATTGAAGAAGTTAAGAGAAGCTACCGTTCATAAGTACGGTAACTTGTCCGAGATGGAAGTCCCTGTTGACGAAGG

TCATTTCTTGTCCATGTTGTTGAAGATGATGAACGCTAAGAACACCTTGGAATTGGGTGTTTTCACTGGTTACTC

TTTGTTAACCACCGCCTTGGCTTTGCCTGAAGACGGTAGAATTACTGCTATTGATATCGATAAAGAAGCTTACGA

AATGGGTTTGGAATTCATCAAGAACGCCGGTATCGATCACAAAATTAACTTTATCCAATCCGACGGTTTGCAAGC

CTTAGACAAGTTGTTATCTGAAAACCCAAAGCCAGAATTTGACTTCGCTTTCGTTGACGCTGATAAGCCAAATTA

CGTCCACGCTTTGGAAAGATTGATGAAGTTGGTCAAAGTTGGTGGTATCATTGCTTTCGATAACACCTTATGGTT

CGGTTTCGTTGCTGAAGAGGAAGAGACTGTCCCAGTTCACTTAAGAGTTAACCGTAAGGCTTTGATGGAATTGAA

CAAAAGATTGGCTTCCGATCCAAGAATTGAAATCTCCCAAGTTTCCATCGGTGATGGTGTTACCTTGTGTAGAAG

ATTAGTCTAATAAAGTAAGAGCGCTACATTGGTCTACCTTTTTGTTCTTTTACTTAAACATTAGTTAGTTCGTTT

TCTTTTTCTCATTTTTTTATGTTTCCCCCCCAAAGTTCTGATTTTATAATATTTTATTTCACACAATTCCATTTA

ACAGAGGGGGAATAGATTCTTTAGCTTAGAAAATTAGTGATCAATATATATTTGCCTTTCTTTTCATCTTTTCAG

TGATATTAATGGTTTCGAGACACTGCAATGGCCCTAGTTGTCTAAGAGGATAGATGTTACTGTCAAAGATGATAT

TTTGAATTTCAATTGACGTAATTAATGATACTATTAATAATACAGAGCGTATATGAAGTATTGCAAATAACATGC

ACAGTTCTTTTGGGATGAGAATGATAATGAAAGGCGAAGGCGGGCGTTCAGAAAAGCGTTGCGGAGTAACAAGTG

ATTAAATAGCACCCAAATAATCTTCTTTGATACTACCGATTGCGTGAATAGAACTCACTCATGTATTCTGGCAGC

-continued

GTATCAAGGCAGGTAATCGAAACATATTGATGTTTTTCGTGGGTAACCATAGTTCTTGGAATGTCAACTGAGGGT

ATTTGCACTTCAAAAAAAAAAATTTATTAAATGAGACTATATACAGTGAGCACAACCTGTCTAATACAACGGCAA

AAATTATATACATTGGTAGATTTTCAAAATTGAACTCTTTGTGCTAAAGAATTGTCACAACAGTTTAAAAAATAG

TTTGAATTCTTCAAATTGACCCCATATTAATAAGACCTGATGCGATTCCGGTCTCACCCAGATTAGAGAGGGAAT

TTAATTTTCTTAGGACCGTAGCTACCAAAAATCTTTGTGTGGTATTGATTATATGATCGTGCTTGCGAAAAAAAT

AGAAGACTAAAAGTAGCATTAGTTTACTAACTTTCTCCTCGTATCTTTCAAATTTGTATTCCCCTCAAAAGTTAC

TCAGGTTAGGGAAAATTCCAAGTAGCTTATCAAGATCAATTGCCATTAGTTGATTCAAGGCTTCATTGTCGGCGG

TTTAAACGCGTGGCCGTGCCGTC

SEQ ID NO: 13
Length: 8216
Type:
Organism: artificial sequence
Other information: MS153767 sequence

GACGGCACGGCCACGCGTTTAAACCGCCTGCATACTTCAAGTTCAGGGTTGGACCTGCCAATGAAAATTTTAGAT

ATGTTTGGCTCAGGTCTTCCTGTTATTGCAATGAACTATCCAGTGCTTGACGAATTAGTACAACACAATGTAAAT

GGGTTAAAATTTGTTGATAGAAGGGAGCTTCATGAATCTCTGATTTTTGCTATGAAAGATGCTGATTTATACCAA

AAATTGAAGAAAAATGTAACGCAGGAAGCTGAGAACAGATGGCAATCAAATTGGGAACGAACAATGAGAGATTTG

AAGCTAATTCATTGAGTCAATGGTAACTCAGCCTTTCTTTTTTGAAAATTACTATTTTCGACTCTTTTTTTATAC

AGTTACATAGTACTACCTCTAATACACATTCATGATTAACAATGTTTCAAACAATATAAAGTCCCGATAACGACC

TTTTGAAGTGGTGACGTTACCGCTCTTCGTTGACAAGATTCAAGAGGGCTGTCAGAATAACAGCTATCATGGTGG

AATCGATTACCTGCCTTGATACGCTGCCAGAATACATGTCACATGTAGGGACCGAATTGTTTACAAGTTCTCTGT

ACCACCATGGAGACATCAAAGATTGAAAATCTATGGAAAGATATGGACGGTAGCAACAAGAATATAGCACGAGCC

GCGAAGTTCATTTCGTTACTTTTGATATCGCTCACAACTATTGCGAAGCGCTTCAGTGAAAAAATCATAAGGAAA

AGTTGTAAATATTATTGGTAGTATTCGTTTGGTAAAGTAGAGGGGGTAATTTTTCCCCTTTATTTTGTTCATACA

TTCTTAAATTGCTTTGCCTCTCCTTTTGGAAAGCTATACTTCGGAGCACTGTTGAGCGAAGGCTCATTAGATATA

TTTTCTGTCATTTTCCTTAACCCAAAAATAAGGGAAAGGGTCCAAAAAGCGCTCGGACAACTGTTGACCGTGATC

CGAAGGACTGGCTATACAGTGTTCACAAAATAGCCAAGCTGAAAATAATGTGTAGCTATGTTCAGTTAGTTTGGC

TAGCAAAGATATAAAAGCAGGTCGGAAATATTTATGGGCATTATTATGCAGAGCATCAACATGATAAAAAAAAAC

AGTTGAATATTCCCTCAAAAATGGATACAAGAGAAGATCAATTAGAAAGACGTATTGCTGCCTTAACTGCTAACG

ACCCTCAATTCGCCGCTGCCAGACCAGACGAAGCCGTTGCCACTGCCGTCCAAAGACCTGGTTTGAGATTACCAG

AAGTCATCGAAACCGTCTTGCAAGGTTACGCTGACCGTCCAGCCTTAGGTCAAAGAGCTGTCGAATTTGTTAAAG

ATCCAAACACTGGTAGAACCTCCGCCCATTTGTTACCAAGATTCGACACCATCACCTACAGAGAATTGGCTGATA

GAGTCGGTGCTTTAGCTTCTGCTTGGGCTAGAGAAGCCGTTTCCCCAGGTGACAGAGTTGCCATTTTGGGTTTCA

CTTCCGTTGACTATACTACCATTGATGTTACTTTGGCTAGAATTGGTGCTGTCTCTGTTCCATTACAAACCTCTG

CTGCCTTGGCTCAATTAAGACCAATTGTTGTCGAAACCGAACCAACTGTTATCGCTGCTTCCGTTGATTACTTGT

CCGACGCTGTTGAATTAATTAGAACTGGTCACGCCCCAGCCAGATTGGTTGTTTTTGATCATCACCCAGAAGTTG

ACGATCACAGAGAAGCTTTGGACGCTGCTAGAGGTCGTTTGGCTGGTCACGCTGTCATTGTTGAAACTTTGGCTG

AAGTCTTGGAGAGAGGTACTTCTTTGCCAGCTCCAACTGTTGCTGCCGAAGATAATGATTTGGCTTTGTTAATCT

ACACCTCTGGTTCCACTGGTGCTCCAAAGGGTGCTATGTACCCACAAAGAAATGTTGCTAAGATGTGGCAAAGAT

CTTCCAGAAACTGGTTCGGTCCTTCTGCCGCTTCTATTACCTTGAACTTTATGCCAATGTCCCATGTTATGGGTA

GAGGTATTTTGTACGGTACCTTAGGTAACGGTGGTACTGCCTACTTCGGTGCTACCTCTGACTTGTCTACTTTGT

-continued

TGGAAGACTTGACTTTGGTCAGACCTACCGAATTGAACTTCGTTCCAAGAGTCTGGGACACTTTGCATGCCGAGT

TCTTGACTAGAGTCGACAGATTGACCGCTGAAGGTGCCGACAGAGCTTCCGCTGAGGCTTTGGTCATGGGTGACT

TGAGAGACAACTTATTGGGTGGTCGTGCCATTTTCGCCATGACTGGTTCCGCTCCAATCTCTTCTCAATTGAAAA

CTTGGGTTGAGTCCTTGTTGGGTATCCATTTATTGGACGGTTATGGTTCTACTGAAGCTGGTATGGTTTTGTACG

ATGGTGTCGTCCAAAGACCTCCAGTCATTGACTACAAGTTAGCTGATGTCCCAGATTTGGGTTACTTTTCTACTG

ATAGACCATTCCCAAGAGGTGAATTATTATTGAAAACTGAAAACATGTTCCCTGGTTACTACAAAAGACCAGAAA

TCACCGCTGGTGTCTTCGATGATGACGGTTACTACCGTACTGGTGATGTTGTTGCTGAAGTCGGTCCAGATCGTT

TGGTTTACGTCGATAGAAGAAACAATGTTTTAAAATTAGCTCAAGGTGAGTTCGTTACTGTTGCCAAGTTGGAAG

CTGGTTTCAACAACTCCCCATTGGTCAGACAAATCTACATTTACGGTAACTCTGCTCATCCATACTTATTGGCTG

TTGTTGTTCCTACTGATGTCAATGCCTCCAAGTCCGCTATTGCTGAATCCTTGCAAAGAGTCGCTAAGGACGCTG

GTTTACAATCCTATGAAGTTCCTAGAGACTTCTTGATTGAACCAGAACCATTTACCTTGGAAAACGGTTTGTTAA

CTGGTATTAGAAAGTTGGCTTGGCCTAAGTTGAAGGAGAGATACGGTGAACGTTTGGAACAATTGTACGCTGAAT

TGGACAGATCCCAAGCTGACGAATTGTCTGAATTAAGAAGATCTGGTGCCCAAAGACCAGTTTTGGAAACTGTCA

CCAGAGCTGCCGGTGCTTTGTTAGGTGCTGCTGCTTCTGAATTACAACCAGATGCTCACTTCACTGACTTGGGTG

GTGACTCCTTGTCCGCTTTGACTTTCGGTAACTTGTTGAGAGAAATCTTTGACGTCGACGTCCCAGTCGGTGTTA

TCGTTTCTCCAGCTTCTGACTTGCAAGCCATTGCTGGTTACATTGAAGCCGAAAGACAAGGTTCTAAAAGACCAA

CCTTCGCCTCCGTTCATGGTAGAGCTGAGGAAGGTGAAGCTGTTGAGGTTAGAGCTAGAGATTTGCGTTTGGATA

AGTTCTTGGACGCCAGAACCTTGGAGTACGTTCCAGCCTTGCCAGGTCCATCCACCGAATTGCGTACTGTTTTGT

TGACTGGTGCTACTGGTTTCTTGGGTAGATATTTGGCTTTGGAATGGTTGGAGAGAATGGACGCTGTTGACGGTA

CCGTTATCGCTTTAGTCAGAGCTAAGGACGACGCCGCTGCTAGAGAGAGATTGGACAGAACTTTCGACTCTGACC

CTAAGTTGAGAGCCCACTACAGAGCTTTGGCCGCTGACCATTTGGAAGTTGTTGCTGGTGACAAGGGTGAAGCTA

ACTTAGGTTTGTCTCAACAAGTTTGGCAAAGATTAGCCGACACTGTTGACGTTATCGTTGACCCAGCCGCTTTGG

TCAACCACGTTTTACCATACTCTGAATTGTTTGGTCCAAATGTTTTGGGTACTGCCGAATTGATCAGATTGGCTT

TGACTACCAAGATCAAGCCATACACTTACGTTTCCACCATCGGTGTTGGTGACCAAATCGAGCCAGGTAAGTTTA

CTGAAGATGCTGACATCAGAGTTATTTCTCCAACTAGAAGAATTTCTGACTCTTACGCTAACGGTTACGGTAACT

CCAAGTGGGCTGGTGAAGTCTTGTTGAGAGAAGCTCATGACAGATGTGGTTTGCCAGTCGCTGTTTTCAGATGTG

ATATGATCTTGGCCGACACCACCTACGCCGGTCAATTAAACTTGCCAGATATGTTCACTCGTTTAATGTTGTCCT

TGGCCGCTACTGGTATTGCCCCAAGATCTTTCTACGAATTGGATGCTGAAGGTAACAGACAACGTGCTCATTACG

ACGGTTTGCCAGTCGAATTCATTGCTAAGGCTGTCTCTACTTTGGGTGCTCAAACTGTTGAGGGTTATCAAACCT

ACCACGTCATGAACCCTCATGACGACGGTATTGGTTTGGACGAATACGTTGACTGGTTGATTGAAGCTGGTTACC

CTATTCGTAGAGTTGACGACTACGCTGATTGGTTACAAAGATTTGAAACCGCTATGAGAGCTTTGCCAGACAGAC

AAAGAAGATACTCCTTGTTGCCTTTGTTACATAACTACCAAAAGCCAGAAAAGCCAATGAGAGGTTCTATGGCTC

CAACTGATAGATTTAGAGCTGCTGTTCAAGAAGCCAAAATTGGTCCAGACAAGGATATTCCACACGTCACCAGAG

AAGTTATCGTCAAGTATGCTACTGATTTGCAATTGTTGGGTTTATTGGATGAAAAAAGAGTCTAAAAGGCTTTTT

TATAAACTTTTTATAATTAACATTAAAGCAAAAACAACATTGTAAAGATTAACAAATAAATGAAAAAAACAACGA

AATAACTTAGGTTTTAGGCTAAAAAAAACAGAAGGAATTTTGAACGATAAACTTTTCGACTGCACACGAAACATT

ATTACTAATTTGTGTAACCACTATATAAGGAATCGTGTTTATTAATTGAATTTATTCCGGGAATATTCAAGTTAT

GTATATCTCTTTTCATATTCTTAAATACACATACTCATAATATCTTGTCGAAAATACGCGGTGTAGGGAGTTATG

GTGGATAACTTTTTCACGATTAGAAGAAAAGGAAAATTTCATTATTCGTAGCTTAACATGGCAAAAACGAGAAAG

ACATATAATCAAAACGTGAGTTTCCTGTGGAAAAAAAAAAAAAGGGAACCTCTGGTTACGATGATATACCTGCGTG

-continued

AAAAAGGACAGTTATTACCAATACATACAAAGGCAACCTGCAGGCCGCGAGCGCCGATAAGATTATTACTTGCTA

TAAGTGCGTGCCTGATGAACAGGATATTGCGGTCAATAATGCTGATGGTTCATTAGACTTCAGCAAAGCCGATGC

CAAAATAAGCCAATACGATCTCAACGCTATTGAAGCGGCTTGCCAGCTAAAGCAACAGGCAGCAGAGGCGCAGGT

GACAGCCTTAAGTGTGGGCGGTAAAGCCCTGACCAACGCCAAAGGGCGTAAAGATGTGCTATCGCGCGGCCCGGA

TGAACTGATTGTGGTGATTGATGACCAGTTCGAGCAGGCACTGCCGCAACAAACGGCGAGCGCACTGGCTGCAGC

CGCCCAGAAAGCAGGCTTTGATCTGATCCTCTGTGGCGATGGTTCTTCCGACCTTTATGCCCAGCAGGTTGGTCT

GCTGGTGGGCGAAATCCTCAATATTCCGGCAGTTAACGGCGTCAGCAAAATTATCTCCCTGACGGCAGATACCCT

CACCGTTGAGCGCGAACTGGAAGATGAAACCGAAACCTTAAGCATTCCGCTGCCTGCGGTTGTTGCTGTTTCCAC

TGATATCAACTCCCCACAAATTCCTTCGATGAAAGCCATTCTCGGCGCGGCGAAAAAGCCCGTCCAGGTATGGTC

GGCGGCGGATATTGGTTTTAACGCAGAGGCAGCCTGGTCAGAACAACAGGTTGCCGCGCCGAAACAGCGCGAACG

TCAGCGCAATCGGCGCTCGCGGCCTGCAGGTTCCGTTACAGGAATGGATGATCCACCAATTATATCGACGGGGGC

TAGAATCTTAGATCTCAGTACTCGCATTCTAGCGTATGTTTCTTGAAACTTGTAAGGGACTTTCGTCGAGGCCGG

AGTGACAAGGATCGAGGGGTCCAATGGTGTGGCCCACCTGTTGGGCACATTGCCGTTTCTAACCACAATCCATTC

GAAGTACTGCTTATTTGGCAGCGATTTAACCCAGTCGATATCCACGGGTTGAGGGACAACCTCTTCTTGTTTGAT

TTTGGTCCTTTTCTCCGGTAGGAGTTCTGATTCTGGCCCAGTTTCAGTCTTTACCAGCGGTCTTTTCCTCAGAAT

TGCCATAGATGAGTATTTACTGATCTTTTGCATATTTTTTTTTTTTTTTTAAGTATATATAGATACAAATATATG

ATGAATCATTAAAGAGGAGGTTATTACTAAGTGAAAGAAAAAGAAAAAAAAAAAGATCAAAACCAAACTTCGTAT

TCGAGCCTAAAAAACAGAATATAATGTTAAGCGTAAGCGATAGCAGTCAAGATGAAACCGTCAGCAATCAACCAT

CTACCATCAAAAGACAACAATGGGGTACCACCATCGTTAGTTTGACCAGGAACCAATAATTCGGAGTGGAAAGTA

CCGTTACCAGAATCAGCAGAACCATCTTCAATTTCGAAAGTAATGTGAGCTTCCTCGAAACCTAACCATCTGGCA

GTCAATGGCCACCAAGCCTTGTAAGTAGCTTCTTTGGCACAAAATAACAATCTGTCTAAATGTAAAGCAGAATCG

GTAGTCTTCAACCATTCTCTTTCTGGTGGCAAGGAAACGGAATCCAAGACACCTTCTGGCAAGGTAGCGTGTGGT

TCGGCGTCGATACCGATGGATCTGAATCTCATCTTATGAGCAACAGCAGCGGCTCTGTAACCGTCACAGTGAGTC

AAAGAACCGACAACACCTCTTGGCCAAATAGGAGCACCACGTTCACCTTTACCGATAGCGACTGGTGGTTCACCC

AATTCAGCCAAAGCTAATCTAGCACAATGTCTGGCACCAATAAAGTCTCTTCTTCTCTTTTCGACAGATTTGGCG

ATTAAATGTTCCTCGGCTGGGTGAGCTTTTAAGTCTTCAGGGTACTCTAACAATTCAGCAGACTCAACTCCAGCA

GGAAGAATGGTTTCAATCATTTTTGAGGGAATATTCAACTGTTTTTTTTTATCATGTTGATGCTCTGCATAATAA

TGCCCATAAATATTTCCGACCTGCTTTTATATCTTTGCTAGCCAAACTAACTGAACATAGCTACACATTATTTTC

AGCTTGGCTATTTTGTGAACACTGTATAGCCAGTCCTTCGGATCACGGTCAACAGTTGTCCGAGCGCTTTTTGGA

CCCTTTCCCTTATTTTTGGGTTAAGGAAAATGACAGAAAATATATCTAATGAGCCTTCGCTCAACAGTGCTCCGA

AGTATAGCTTTCCAAAAGGAGAGGCAAAGCAATTTAAGAATGTATGAACAAAATAAAGGGGAAAAATTACCCCCT

CTACTTTACCAAACGAATACTACCAATAATATTTACAACTTTTCCTTATGATTTTTTCACTGAAGCGCTTCGCAA

TAGTTGTGAGCGATATCAAAAGTAACGAAATGAACTTCGCGGCTCGTGCTATATTCTTGTTGCTACCGTCCATAT

CTTTCCATAGATTTTCAATCTTTGATGTCTCCATGGTGGTACAGAGAACTTGTAAACAATTCGGTCCCTACATGT

GACATGTATTCTGGCAGCGTATCAAGGCAGGTAATCGAAAGATGGCAAATAGCCTTGTCAAATTTCCTACGGAAT

GTTATTTTCATTACGTCCTTCTTTTTCAATGTACTTATTCATAAATGGGACACTATCTTGTTGCAAAAGGTACTT

TGTATTTTGGTATTAACATCTCGCCTATTTTTCATACAGAAACACTACTTATCGCTATCTATTTGATGTGGTATT

GCTTGGCCATGAGGATACCTTGAGCTACGTTTTGAACACGTGCATCCAACTTGTAGCCTTGTTGATCCAACTTAA

-continued

CCATTTCATCAGGAAACTTGTGCAACTCAACGCTAAAGCATTCGATAAATTCATTATCTTCCAATTGAGTAACTG

GTTTTTGGTTTTCAGGTAAACTCATATCAACTTCGACAGTAACCAGACAGAGGTTGGTGTTTGTGAAACCAGGAT

CGTTAAAAACTGTTGGGCTTTTAGAAATTATTTTACCACTGTAACCAGTCTCTTCTTTTAATTCTCTTAAGGCAG

CAGTGTCAATATCGGCGGTTTAAACGCGTGGCCGTGCCGTC

SEQ ID NO: 14
Length: 11527
Type:
Organism: artificial sequence
Other information: MS141850 sequence

GACGGCACGGCCACGCGTTTAAACCGCCGAAATCACCTCCAAAGTTATGTTGCCGATTAGGCAAATACTCTAAAA

GTATAGTACTAAAGAACTACGTAAAGGTAAAATAAAACACCTGAATTTCATTTCTGAAATGAAGTACCATCATGA

AATATGATGAAAGTCAAGACTCGTTGGGTCAATATACACCACAAAAAAAGGTACACACGAATGGTTTAACCCTTT

CGGTTCCTTCTGTAAATCGAAAAATGCCCTTTATACAGCGGGTTGGTCTCCCATCAAAGTTGAGAAGCGATTAGA

AATTAGGTTACCTAATGAATCCATAAATAAATGGAAAACGCTATTTTGTTCGAACGATGGAATAAAAATATGAAC

GGGTGTCATTGAAATTCGGTGTATTTTTTGATCGGGCCTGATCTGGCTCGGGTTTGGCACAATTTGGCTTGGTTA

GTTCGGCAAAGCTTATTTAAAGAACCTTTTTGGATAGCCAATTGAGAGACTTGAAATAGAAAGATCGTAAGTATT

TTTACGCTCGTCCAACGCCGGCGGACCTGGGTGTTAACCAAACACATGTTGAAATGCTAGTTAAAAAAGAATGGT

AAAACAATGGAAAAGGAAGGAGCAAAATCTGGTAAAAAAGAAGAACCATAATAATAGTGAATAAAAAAAAAAAAA

TGCAATGTAATGTTGAATGTAATGCAAAGAGGGGGGGTTGACAATTCTGTTAAAGAACTGTTATCGTTGTCTGTG

TTATTATAGGCTTAGTAGGATGGAATGGATTTGATCATCTGGAGAAATGTAGTCATTGTCAACAATATTGACCAA

GCAGTAATCGTCAATCAAGGACTGAATGAATTGGGCACTATGCGGTTTATCGTATTTATTCATGTTTAGTTTCCA

TTCATTCAAGATATGATAGAACTCCTCCTTCCACGCTAAGAACGAAATTTTCTCGACAATGGTAGGTTGAAGAAT

TTCTCTGCCGGGGAAAATACCCCAAGTCACAGCGTTGGACTTGGAGTTGTCTGGATGATTACTTAGCAGGTCACC

TTGAGAGTCGATGGCGAAGTAGGTCAAGAACTCATTGTTTTTCAAGGTGTCAATCAACTTGGGCAACTTAGTCTT

GGGCAACATAAATTCCAAATATTGCTTCTGGTAAACGTAACCATCCTTGGGTCCCCAACCATGAATTTTGTCATT

GGACCTAATGCCGTTGACTTGAGGTTGAGAGTTTATAGTGATGATAGAATGCTGGTTCAGCTCAATCAAGTGTGC

TTTGATTGGATTTATTTCATCATTGATGGGGATATCACTCCAAGGTAAACACTTCAAGTTTCCATTCAAGTAGTT

GATGACCAAGAAGGCGACGTCGTTGATGGAAGTAGGGGTGGACCATAATTCGAGACATTTGTTCGCTGATTGCCT

GATCAAGTCTGAACCACACAGATCCAAGTCACCGAACGCAGGAGAAGACGAATCACCGAATCTACCGTTGGGGAA

TTCGTCCACGGCCCATTGAGAGGTTCTTGCGACATAGGAGTAAGGTCTTCTCTTCCAGAAGATAGGTCTGACTTC

CTCGTTTTTACGCTTTGGATTCAAAGATTTTCTCCATGGCAACACGGCCAATGGATGTGCATTGAACTCTGATTC

CGTAGGTAGAATGTTCAATCTTTCCAGAATCATGAGAGGCGCTTTTTCCAAGTTCATGGTGTAGATGTGCAAGTG

AGAAACGTAACCACTGTCGAGCAATTTTTGACACATTTCCACGATCAAGTTAGTTCCGATATCACGGACCAACTC

GTCATCGTCCTTGATAGGATCCAATCGGGACGAGAAATGTTGAGGGATGGAGATTTGGCCCCATTGGGCCCTTCT

CAAGAAGGCCGCGTAGGTAGTGATCGGCATGATCCCGGGAATAATGGGCACGTCCATGCCCGCAGCTCTAACTTG

GGAACACCAGTTGATGAAATTATCAACATCGTAAAACATCTGAGTGATGATGAAGTCGCCGCCGGCGTCGATCTT

CTGCTTCAAATACTCGAGATCAAGCTTCACGTCTTTGTTAGGCAACTCCGGATGGCACTCCGGGTAGCCGGCAAC

GCCGATAGCGAAATGGTCACCGTACTTGGACTTGATATACTTAATCAAGTCCTTGGCATACTGGAAGCCACCTTC

AACGGGAGTCCAGTTTTCTGCGTCCCTAGGAGGATCTCCTCTCAGCGCTAGGATGTTCTGGCAACCGGAGTGATA

AGCGTTTTCTAAAGCGTCGTCAATCATCGAAATGGGCATATTGGTGCAGGTAAGGTGCATGCACGTTTCCAAACC

AAGCACAGACTGCGCTGTCGCAACCAAGTCCGTGGACAGATGTGACAACCGTCCACCGCCTGCATTCCAGGTGAT

-continued

GTCAATAAATTGGGGCAAAGAAGCCTCGTACATCCGGTCCATCCGGTCATACAGGTTCTGTACACCTTGTGTAGT

CTTCGGGACGAAGTACTCGAATGAGTAAGTGGGCTTGCCAGAGGTCTGTCTATGTTGCTCTAATTTTTCTGTGAT

CTTCATTGTAAAGTTAGTTGGTTGCGCGACTTCGGGTGGGGTTACTTTTTTTTGGATGGACGCAAAGAAGTTTA

ATAATCATATTACATGGCAATACCACCATATACATATCCATATCTAATCTTACTTATATGTTGTGGAAATGTAAA

GAGCCCCATTATCTTAGCCTAAAAAAACCTTCTCTTTGGAACTTTCAGTAATACGCTTAACTGCTCATTGCTATA

TTGAAGTACGGATTAGAAGCCGCCGAGCGGGCGACAGCCCTCCGACGGAAGACTCTCCTCCGTGCGTCCTGGTCT

TCACCGGTCGCGTTCCTGAAACGCAGATGTGCCTCGCGCCGCACTGCTCCGAACAATAAAGATTCTACAATACTA

GCTTTTATGGTTATGAAGAGGAAAAATTGGCAGTAACCTGGCCCCACAAACCTTCAAATCAACGAATCAAATTAA

CAACCATAGGATAATAATGCGATTAGTTTTTAGCCTTATTTCTGGGGTAATTAATCAGCGAAGCGATGATTTTT

GATCTATTAACAGATATATAAATGCAAAAGCTGCATAACCACTTTAACTAATACTTTCAACATTTTCGGTTTGTA

TTACTTCTTATTCAAATGTCATAAAAGTATCAACAAAAAATTGTTAATATACCTCTATACTTACCTCCCGCGACC

TCCAAAATCGAACTACCTTCACAATGGTTCAATCTGCTGTCTTAGGGTTCCCAAGAATCGGTCCAAACAGAGAAT

TAAAGAAGGCCACTGAAGGTTACTGGAACGGTAAAATCACTGTCGATGAATTATTCAAAGTCGGTAAGGATTTGA

GAACTCAAAACTGGAAGTTGCAAAAGGAGGCTGGTGTTGATATCATCCCATCCAATGACTTCTCCTTTTACGACC

AAGTTTTGGATTTGTCTTTGTTGTTCAATGTCATTCCAGACCGTTACACTAAGTACGATCTATCTCCAATCGACA

CTTTGTTTGCTATGGGTAGAGGTTTACAAAGAAAGGCCACTGAAACTGAAAAGGCTGTCGACGTCACTGCTTTGG

AAATGGTTAAATGGTTCGACTCTAACTACCATTACGTTAGACCAACTTTCTCCAAGACCACTCAATTTAAGTTGA

ACGGCCAAAAGCCAGTTGACGAATTTTTGGAAGCCAAGGAGTTAGGTATTCACACTAGACCTGTCTTGTTAGGTC

CAGTTTCTTACTTATTCTTGGGTAAGGCTGACAAGGATTCTCTAGATTTGGAACCATTGTCCCTATTGGAACAAT

TGTTGCCTCTATACACTGAAATCCTATCTAAATTGGCTTCTGCTGGTGCCACTGAAGTTCAAATTGACGAACCTG

TCTTAGTTTTGGACTTGCCTGCCAACGCCCAAGCCGCCATTAAGAAGGCTTACACTTACTTCGGTGAACAAAGCA

ATCTACCAAAGATTACTTTGGCTACTTACTTCGGTACCGTTGTCCCTAACTTAGACGCCATCAAGGGCTTGCCAG

TTGCTGCCTTACACGTTGACTTTGTTAGAGCTCCAGAACAATTTGATGAAGTCGTTGCCGCCATTGGTAACAAAC

AAACCTTGTCCGTTGGTATTGTTGATGGTAGAAACATTTGGAAGAATGATTTCAAGAAGTCTTCCGCTATCGTTA

ACAAGGCTATTGAAAAGTTGGGTGCTGACAGAGTCGTTGTTGCCACTTCTTCTTCTCTATTGCACACACCAGTTG

ACTTGAACAACGAAACCAAGTTGGACGCTGAAATCAAGGGCTTTTTCTCTTTCGCCACTCAAAAATTGGATGAAG

TTGTTGTGATCACCAAGAACGTTTCCGGTCAAGACGTTGCTGCTGCCCTAGAAGCTAACGCTAAATCTGTTGAAT

CCAGAGGTAAATCCAAGTTTATCCACGATGCTGCCGTTAAGGCCAGAGTTGCCTCTATCGACGAAAAAATGTCTA

CTAGAGCAGCTCCATTTGAACAAAGATTGCCTGAACAACAAAAAGTCTTCAACTTGCCATTGTTCCCAACAACAA

CTATTGGTTCCTTCCCTCAAACCAAGGACATCAGAATTAACAGAAACAAATTCAACAAGGGTACCATCTCTGCTG

AAGAATATGAAAAATTCATCAATTCTGAAATTGAAAAGGTCATCAGATTCCAAGAAGAAATTGGTTTGGATGTCT

TAGTCCACGGTGAACCAGAAAGAAACGATATGGTTCAATACTTCGGTGAACAAATCAACGGTTATGCTTTCACTG

TTAACGGTTGGGTTCAATCTTACGGTTCCAGATATGTCAGACCACCAATTATTGTTGGTGACTTGTCCAGACCAA

AGGCTATGTCCGTCAAGGAATCTGTTTACGCTCAATCCATCACTTCTAAGCCAGTAAAGGGTATGTTGACTGGTC

CAATTACCTGTTTGAGATGGTCTTTCCCAAGAGACGATGTCGACCAAAAAACTCAAGCTATGCAATTAGCTTTGG

CTTTGAGAGATGAAGTCAATGATTTGGAAGCTGCCGGTATCAAGGTTATCCAAGTTGATGAACCAGCTTTAAGAG

AAGGTTTACCATTGAGAGAAGGTGCTGAGAGATCTGCTTACTACACCTGGGCTGCCGAAGCTTTCAGAGTTGCTA

CTTCTGGTGTTGCTAACAAGACTCAAATACACTCTCATTTCTGTTACTCTGACTTGGATCCAAACCATATCAAGG

CTTTGGATGCTGATGTTGTTTCCATCGAATTCTCTAAGAAGGACGATGCTAACTACATTGCTGAATTCAAAAACT

ATCCAAACCACATTGGTCTGGGTTTATTCGATATTCATTCTCCAAGAATTCCATCAAAGGATGAATTTATCGCCA

AGATTTCAACCATCTTGAAGAGCTACCCAGCTGAAAAGTTCTGGGTTAACCCAGACTGTGGTTTGAAGACTAGAG

-continued

GCTGGGAAGAAACTAGATTGTCTTTGACTCATATGGTCGAAGCCGCCAAGTACTTCCGTGAACAATACAAGAATT

AAGGTTTTAAAAAGGAAGCAAAGTAATGATATTTTCTGAACTTTTTGTTTTTTATTCTGGGATTCAACATCGGTG

ATTTAATTTTTGTGTTCACATTTAAAAGTTTATTTGGGTAATTTTTTGATATCAATTTTATTACAAAGCCATAAC

TCTTGCATTTTTTTTATTATATTTTTATATACACGTACATTCTGTATTATTTATAACGCATTCAAACGCGATCGC

CGACGCCGCCGATGATCATCTACCCATGCCGAAATTCGGGCCGTTGGCCGGATTGCGCGTTGTCTTCTCCGGTAT

CGAAATCGCCGGACCGTTTGCCGGGCAAATGTTCGCAGAATGGGGCGCGGAAGTTATCTGGATCGAGAACGTCGC

CTGGGCCGACACCATTCGCGTTCAACCGAACTACCCGCAACTCTCCCGCCGCAATTTGCACGCGCTGTCGTTAAA

TATTTTCAAAGATGAAGGCCGCGAAGCGTTTCTGAAATTAATGGAAACCACCGATATCTTCATCGAAGCCAGTAA

AGGTCCGGCCTTTGCCCGTCGTGGCATTACCGATGAAGTACTGTGGCAGCACAACCCGAAACTGGTTATCGCTCA

CCTGTCCGGTTTTGGTCAGTACGGCACCGAGGAGTACACCAATCTTCCGGCCTATAACACTATCGCCCAGGCCTT

TAGTGGTTACCTGATTCAGAACGGTGATGTTGACCAGCCAATGCCTGCCTTCCCGTATACCGCCGATTACTTTTC

TGGCCTGACCGCCACCACGGCGGCGCTGGCAGCACTGCATAAAGTGCGTGAAACCGGTAAAGGCGAAAGTATCGA

CATCGCCATGTATGAAGTGATGCTGCGTATGGGCCAGTACTTCATGATGGATTACTTCAACGGCGGCGAAATGTG

CCCGCGCATGAGCAAAGGTAAAGATCCCTACTACGCCGATCGGCGGCGTCGGCGATCGCGTTGAATGAAAATAGA

GATCAGAAATTTTGTGATTATTTGGAATCTAAATTACAACGTGACAAACAACTTGTAAATGGCGGCTCCAAGAAA

AGGAAAGCCAATGATTAGCATATGCCTCTTCTTCTTAGAAGGGCGTTCTGCCCGTTATGTATACGTTAAATATTA

CATTATTTTCGCATTTTTGTATTTATATTCAGTGAAATATTAGGCTTGGTCGAGTAACATTTCCCATAGCTCGTC

GGTTTCTTTGAAGTCGTGATGAACAATTGAGACAAGACAGTAGTCTTTATGCACTAGTCTTAGAAGAATATTGGC

TGGGGTGTTCCTTGGAAATAACTTGGCCCACTCGGACCAGATACTAAACGCTTCATCTCTCCATGCCTTGAATGA

CTCTTCTTCAATGATTGTAGTCTGTTTGACCGGACTGTTGGGAAAAACACCCCATGTTACAACGCTAGAGCTGTG

CGGGTCTAGGTTCGTTTCAAATGAACCAGATGAATCGCCCGCGTAATAACTGAATTTCCGACGCCCGTAATGGTC

TAGCTTGGGTTTCAAAGTTGTTTCCCATTGCTGTCTATGAATAAACATTTCTACGAATGCCTTCTGATACAACCT

CCCTTTCGCGGGCCCCCAGCCGAATATTTTATCACTACTCAATGTAGCATTTGTGGCAGGTTGCGATGCCAAAGT

CAAATATCCGCGATAGTTTAGTTGGATTAGTTCTTCTTGTATTAACGCCGTTTCAGCTGATAAACCCAGGTCAGA

CCAGGGAATCGCATCCGTTGAACCTTCCAAATATTTTATAAAAATATCTTTTAAATCGCCAATTGTCTTTGGTAT

ACCCCATAGTTCAAGCGCTTTGCTTTTGCTTACCTTGATGGATGGCCCATAACCGTCTATTTCACCATATGCGGG

AGACCTGGAGTCACCAAATCTACCATTGGGGAACTCATCCCAAGTGGCATCACGACCCAAAGTTCCGTGACCTTT

AGAAATAGATATTAAAGCCTTTTTAGATGGCATGGAACCATTCTCATTATTATAGCGTAAGCCTTTTTCAGTGAC

GATAGCCCTATTGAAAATCAACTTGGCCGAATCAAGACTTGAATGCCTTCTCCTTTTCCGGTTTGCTACAGTTTC

TTCATTCGAATCATCCAACACAATATCCCCGTCAGCATCTTCTATTGGCACATTTTCTATGCTTCCTATTTCGCC

ACTGGTTTCATCTTCTCCCTCTTCTTCGCTAGATTCATTTACGATATGGGATAAGACGGGAGATTGCGAGACAAT

TTGAGCAATAGCCTTTTCCAAATTTAATGTATAGAAATGAAACCCTTTAATTCTACCAGATGTTCTTTGATATAT

TTCCTGAATCAATTCGATAAGAATGTCCACACCAATGGACTTCACGGCATTATCATCCGATTGGATTTCTGGGGG

GAACCTACTCAGTATTGCAGGTGGAATAGATGCATGTGATAACTTTGCTGCTCTGTGGAAAAGCAGATAGGAGTT

AATAGGCATCAACCCAGGGAAAAGGGGCAAATCTTGCGAAATCCGTTCCCGAAATAGCATTTCAAAAGTTAAGAA

TTTTTCAACGTCGTAAAACAGTTGTGTTATCACAAAATCGGCCCCAGCTTCAACTTTTTCTTTTAAATATACCAA

ATCCTTCAATGGGTCTTGCTCGTGACCTTCTGCTTCACCTTCACAATGACCTTCTGGATATGCTGCAACACCGAC

GCAGAACTTGTCTCCGTAGCTTTGCTTGATATAACGAACTAAATCAACCGCATATTTAAAAGGTGATTCGTTCGA

TTGAGAATCTAGCCAATCTTCCCCAATAGGTGGGTCACCTCGAAGAGCCAAAATATTCCTGATTCCTGCATTATA

ACATCTATCCAGCGCATCATCAATGATGGCTTTTTCTGTGTTTGTACAGGTCAAATGCATACAAACTGGTATATT

-continued

TAGTGTCTGCTGTGCCAAGGAAGCTAATGTCAGAGTCTTTTCCGCAGTAGTACCACCTGCTCCCCAAGTAACCGT

GATAAACAGTGGATCTAAAGCAGTCATACGATGCATACGTTCCATCAAATTTCTCGTCCCTAATTCAGTCTTTGG

AGGGAAGAATTCTAACGATATAAAAGGGGAAGCCCTCGCATGATATAAATCTCTGATGGACATTGTGAAGGTAGT

TCGATTTTGGAGGTCGCGGGAGGTAAGTATAGAGGTATATTAACAATTTTTTGTTGATACTTTTATGACATTTGA

ATAAGAAGTAATACAAACCGAAAATGTTGAAAGTATTAGTTAAAGTGGTTATGCAGCTTTTGCATTTATATATCT

GTTAATAGATCAAAAATCATCGCTTCGCTGATTAATTACCCCAGAAATAAGGCTAAAAAACTAATCGCATTATTA

TCCTATGGTTGTTAATTTGATTCGTTGATTTGAAGGTTTGTGGGGCCAGGTTACTGCCAATTTTTCCTCTTCATA

ACCATAAAAGCTAGTATTGTAGAATCTTTATTGTTCGGAGCAGTGCGGCGCGAGGCACATCTGCGTTTCAGGAAC

GCGACCGGTGAAGACCAGGACGCACGGAGGAGAGTCTTCCGTCGGAGGGCTGTCGCCCGCTCGGCGGCTTCTAAT

CCGTACTTCAATATAGCAATGAGCAGTTAAGCGTATTACTGAAAGTTCCAAAGAGAAGGTTTTTTTAGGCTAAGA

TAATGGGGCTCTTTACATTTCCACAACATATAAGTAAGATTAGATATGGATATGTATATGGTGGTATTGCCATGT

AATATGATTATTAAACTTCTTTGCGTCCATCCAAAAAAAAAGTAACCCCACCCGAAGTCGCGCAACCAACTAACT

TTACAATGCCTTACACTCTATCCGACGCTCATCATAAGTTGATCACCTCTCATTTGGTGGACACCGACCCTGAAG

TGGACTCCATTATCAAGGATGAAATTGAAAGACAAAAGCACTCCATCGATTTGATTGCTTCTGAAAATTTCACCT

CAACCTCCGTTTTCGATGCCCTTGGAACTCCATTGTCCAACAAATATTCTGAAGGTTATCCAGGTGCTCGTTACT

ACGGTGGTAATGAACACATTGACAGAATGGAAATTCTATGTCAACAAAGAGCTTTAAAAGCTTTCCATGTTACTC

CAGACAAATGGGGTGTTAACGTCCAAACTTTATCTGGTTCTCCTGCTAACTTGCAAGTTTATCAAGCTATTATGA

AGCCTCATGAAAGATTGATGGGTCTATACCTACCAGATGGTGGTCATTTGTCTCACGGTTACGCTACTGAAAACA

GAAAAATTTCTGCTGTTTCCACATACTTCGAATCTTTCCCATACAGAGTTAACCCAGAAACCGGTATTATCGACT

ACGATACTTTAGAAAAGAACGCCATCCTATATAGACCAAAGGTTCTTGTTGCTGGTACTTCAGCATACTGTCGTT

TAATTGACTACAAGAGAATGAGAGAAATCGCCGACAAATGTGGTGCTTACTTGATGGTAGACATGGCCCACATTT

CAGGTTTGATCGCCGCAGGTGTCATCCCATCTCCTTTCGAATACGCTGATATCGTTACCACCACCACTCACAAGT

CTTTGAGAGGTCCACGTGGTGCTATGATTTTCTTCAGAAGAGGTGTGAGATCTATCAACCCTAAGACCGGTAAGG

AAGTCCTATACGACTTGGAAAACCCAATTAACTTCTCTGTTTTCCCAGGTCACCAAGGTGGTCCACACAACCATA

CCATTGCTGCTTTGGCCACTGCTTTGAAGCAAGCTGCCACTCCAGAATTCAAGGAATACCAAACTCAAGTCTTGA

AGAATGCTAAGGCTTTGGAAAGTGAATTTAAGAACTTGGGCTACAGATTAGTTTCCAACGGTACCGATTCTCACA

TGGTTCTGGTATCCTTGAGAGAAAAGGGTGTTGATGGTGCTCGTGTTGAATACATTTGTGAAAAGATTAACATTG

CTTTGAACAAAAACTCTATTCCAGGTGACAAATCTGCTTTGGTTCCAGGTGGTGTCCGTATTGGGGCTCCAGCCA

TGACCACTAGAGGAATGGGTGAAGAAGATTTCCACAGAATTGTTCAATACATTAACAAGGCTGTAGAATTCGCTC

AACAAGTTCAACAAAGCTTGCCAAAGGATGCTTGTAGATTAAAGGACTTCAAAGCCAAGGTCGACGAAGGCTCTG

ATGTTTTGAACACCTGGAAAAAGGAAATTTACGACTGGGCTGGCGAATACCCATTGGCTGTGTAAAGAAATCACC

ACAACGACACTTAATCCCAAAAAAATAAACATTACTGTATAAGTATTCATTTTCTCCTCTTCTCATTATGTATAT

ATGTACCTATATGTATGTATGTATGTGCGTACGATTTTTCTAACGTTAACTTCATTTCTTTTTGATTATGTGCCC

TCCTTGAGTTAAGATGTGCTTGTCCAGGTCCGCCGGCGTTGGACGAGCGAATTAAGCTTTCGAGAAAAACTTTCT

TTTAACCCCTCTAATCTAAATATAAACATATAGCTTATAGAAATGAATGAATATTTTAAATAGTTACGGATACAA

AGAGTTCATTATAGTGCGGGCAGTTAGTACGGTATCGATTTATCATTGGAGATCTGCAGTGTTACAGAAGCACTG

CTCACCAGTTGTCTACGGAAGGACGTTGAGATAGTTTTACCACGTTTGAGCTAAAAGTTTCTACCACAAGAGCCT

TTATTTGCACATGGCAGTGAATGCATGATTAAGGATATGAAGAAGAAAGGAATAACTAGGAATAAATTTTATTA

-continued

GAGAGGGTATGATGAAAGGAGAGCCTCGTTATTTATGACCTGCATTTTTATCAGCATCTTCTTTCCAGCTCCCGC

TAAACATGTGCTTTACAAAAGCCATTTTGTCGTCACTAGACTGGGCGCCCATCTGCCCCACATCTGGTGAAAAAC

TTGTTATTGGTAGAACCATCACATGGCGGTTTAAACGCGTGGCCGTGCCGTC

SEQ ID NO: 15
Length: 1912
Type:
Organism: artificial sequence
Other information: R21 sequence

TCGACACTAGTAATACACATCATCGTCCTACAAGTTCATCAAAGTGTTGGACAGACAACTATACCAGCATGGATC

TCTTGTATCGGTTCTTTTCTCCCGCTCTCTCGCAATAACAATGAACACTGGGTCAATCATAGCCTACACAGGTGA

ACAGAGTAGCGTTTATACAGGGTTTATACGGTGATTCCTACGGCAAAAATTTTTCATTTCTAAAAAAAAAAAGAA

AAATTTTTCTTTCCAACGCTAGAAGGAAAAGAAAAATCTAATTAAATTGATTTGGTGATTTTCTGAGAGTTCCCT

TTTTCATATATCGAATTTTGAATATAAAAGGAGATCGAAAAAATTTTTCTATTCAATCTGTTTTCTGGTTTTATT

TGATAGTTTTTTTGTGTATTATTATTATGGATTAGTACTGGTTTATATGGGTTTTTCTGTATAACTTCTTTTTAT

TTTAGTTTGTTTAATCTTATTTTGAGTTACATTATAGTTCCCTAACTGCAAGAGAAGTAACATTAAAAATGAAAA

AGCCTGAACTCACCGCGACGTCTGTCGAGAAGTTTCTGATCGAAAAGTTCGACAGCGTCTCCGACCTGATGCAGC

TCTCGGAGGGCGAAGAATCTCGTGCTTTCAGCTTCGATGTAGGAGGGCGTGGATATGTCCTGCGGGTAAATAGCT

GCGCCGATGGTTTCTACAAAGATCGTTATGTTTATCGGCACTTTGCATCGGCCGCGCTCCCGATTCCGGAAGTGC

TTGACATTGGGGAATTCAGCGAGAGCCTGACCTATTGCATCTCCCGCCGTGCACAGGGTGTCACGTTGCAAGACC

TGCCTGAAACCGAACTGCCCGCTGTTCTGCAGCCGGTCGCGGAGGCCATGGATGCGATCGCTGCGGCCGATCTTA

GCCAGACGAGCGGGTTCGGCCCATTCGGACCGCAAGGAATCGGTCAATACACTACATGGCGTGATTTCATATGCG

CGATTGCTGATCCCCATGTGTATCACTGGCAAACTGTGATGGACGACACCGTCAGTGCGTCCGTCGCGCAGGCTC

TCGATGAGCTGATGCTTTGGGCCGAGGACTGCCCCGAAGTCCGGCACCTCGTGCACGCGGATTTCGGCTCCAACA

ATGTCCTGACGGACAATGGCCGCATAACAGCGGTCATTGACTGGAGCGAGGCGATGTTCGGGGATTCCCAATACG

AGGTCGCCAACATCTTCTTCTGGAGGCCGTGGTTGGCTTGTATGGAGCAGCAGACGCGCTACTTCGAGCGGAGGC

ATCCGGAGCTTGCAGGATCGCCGCGGCTCCGGGCGTATATGCTCCGCATTGGTCTTGACCAACTCTATCAGAGCT

TGGTTGACGGCAATTTCGATGATGCAGCTTGGGCGCAGGGTCGATGCGACGCAATCGTCCGATCCGGAGCCGGGA

CTGTCGGGCGTACACAAATCGCCCGCAGAAGCGCGGCCGTCTGGACCGATGGCTGTGTAGAAGTACTCGCCGATA

GTGGAAACCGACGCCCCAGCACTCGTCCGAGGGCAAAGGAATAGGTTTAACTTGATACTACTAGATTTTTTCTCT

TCATTTATAAAATTTTTGGTTATAATTGAAGCTTTAGAAGTATGAAAAAATCCTTTTTTTTCATTCTTTGCAACC

AAAATAAGAAGCTTCTTTTATTCATTGAAATGATGAATATAAACCTAACAAAAGAAAAAGACTCGAATATCAAAC

ATTAAAAAAAAATAAAAGAGGTTATCTGTTTTCCCATTTAGTTGGAGTTTGCATTTTCTAATAGATAGAACTCTC

AATTAATGTGGATTTAGTTTCTCTGTTCGTTTTTTTTTGTTTTGTTCTCACTGTATTTACATTTCTATTTAGTAT

TTAGTTATTCATATAATCTTAACTTCTCGAGGAGCTC

SEQ ID NO: 16
Length: 4761
Type:
Organism: artificial sequence
Other information: MS150540 sequence

GACGGCACGGCCACGCGTTTAAACCGCCCCATGGCAAAGAATGCTTTCCATGACGATCATCGTAGTGCCCAATTG

GGTGCCTCTATGATGGGTATGGCTTGGGCAAGTGTCTTTTTATGTATCGTGGAATTTATCCTGCTGGTCTTCTGG

TCTGTTAGGGCAAGGTTGGCCTCTACTTACTCCATCGACAATTCAAGATACAGAACCTCCTCCAGATGGAATCCC

-continued

TTCCATAGAGAGAAGGAGCAAGCAACTGACCCAATATTGACTGCCACTGGACCTGAAGACATGCAACAAAGTGCA

AGCATAGTGGGGCCTTCTTCCAATGCTAATCCGGTCACTGCCACTGCTGCTACGGAAAACCAACCTAAAGGTATT

AACTTCTTCACTATAAGAAAATCACACGAGCGCCCGGACGATGTCTCTGTTTAAATGGCGCAAGTTTTCCGCTTT

GTAATATATATTTATACCCCTTTCTTCTCTCCCCTGCAATATAATAGTTTCAAATCAGATTCAAGTTTGAGGGTA

GTTAATTAATAGTCTTGGATGTAATTCTTATTGTTATACTGAATACGCTAAAACCACTCACAACAAGTATGGAGT

ATATTGTGTCTCTTTATATACTGAGTACTTATGCAATATGCGCTCACTCAGGATGAAATGTACACAGCCGAAAGT

ATATTGAAAGCTGCCTCTGTGGAAACTTCTATCTAATGTTGTCTCCAGATGTAGACTATGAGGCCTGAAGAAGTC

TTTAAACACCTGTTGGAGAGTATAAGGAGACTGCTACAACAACGTCTTCCCCACAAAAATTATGTGGAGGCCGGT

ATGATACCTGCACAAACGTTAAGTTACACATGAAAAAGAGACTGACATAACTTTGATCTCTGAAAATATGTTTTC

CCCTGAGTAGCTTCACTGCTTGGATACCAATACGAATAGACCTTGGCTATAGTAAGTTGCATCTGTACCGTAGAG

ATTCTTGCAACCTCGCTTAAACTCTCGCTTTTATATAATATTTCTCCTTATTGCGCGCTTCGTTGAAAATTTCGC

TAAACACGGGGTTTAAGTTTAAGTTTACAGGATTTATCCGGAAGTTTTCGCGGACCCCACACAATTAAGAATTGG

CTCGAAGAGTGATAACGCATACTTTTCTTTTCTTTTTTCAGTTCCTAGCGTACCTAACGTAGGTAACATGATTTG

GATCGTGGGATGATACAAACAACGTAAGATGAGTAGTTCCTTCCTCAATTCTTCTTTCAGCATCATTTTCTTGAG

GCGCTCTGGGCAAGGTATAAAAAGTTCCATTAATACGTCTCTAAAAAATTAAACCATCTATCTCTTAAGCAGTTT

TTTTGATAATCTCAAATGTACATCAACCTCCCGCGACCTCCAAAATCGAACTACCTTCACAATGGACTACAACAA

GAGATCTTCGGTCTCAACCGTGCCTAATGCAGCTCCCATAAGAGTCGGATTCGTCGGTCTCAACGCAGCCAAAGG

ATGGGCAATCAAGACACATTACCCCGCCATACTGCAACTATCGTCACAATTTCAAATCACTGCCTTATACAGTCC

AAAAATTGAGACTTCTATTGCCACCATCCAGCGTCTAAAATTGAGTAATGCCACTGCTTTTCCCACTTTAGAGTC

ATTTGCATCATCTTCCACTATAGATATGATAGTGATAGCTATCCAAGTGGCCAGTCATTATGACGTTGTTATGCC

TCTCTTGGAATTCTCCAAAAATAATCCGAACCTCAAGTATCTTTTCGTAGAATGGGCCCTTGCATGTTCACTAGA

TCAAGCCGAATCCATTTATAAGGCTGCTGCTGAACGTGGGGTTCAAACCATCATCTCTTTACAAGGTCGTAAATC

ACCATATATTTTGAGAGCAAAAGAATTAATATCTCAAGGCTATATCGGCGACATTAATTCTATCGAGATTGCTGG

AAATGGCGGTTGGTACGGCTACGAAAGGCCTGTTAAATCACCAAAATACATCTATGAAATCGGGAACGGTGTAGA

TCTGGTAACCACAACATTTGGTCACACAATCGATATTTTACAATACATGACAAGTTCGTACTTTTCCAGGATAAA

TGCAATGGTTTTCAATAATATTCCAGAGCAAGAGCTGATAGATGAGCGTGGTAACCGATTGGGCCAGCGAGTCCC

AAAGACAGTACCGGATCATCTTTTATTCCAAGGCACATTGTTAAATGGCAATGTTCCAGTGTCATGCAGTTTCAA

AGGTGGCAAACCTACCAAAAAATTTACCAAAAATTTGGTCATTGATATTCACGGTACCAAGGGAGATTTGAAACT

TGAAGGCGATGCCGGATTCGCAGAAATTTCAAATCTGGTCCTTTACTACAGTGGAACTAGAGCAAACGACTTCCC

GCTAGCTAATGGACAACAAGCTCCTTTAGACCCGGGGTATGATGCAGGTAAAGAAATCATGGAAGTATATCATTT

ACGAAATTATAATGCCATTGTCGGTAATATTCATCGACTGTATCAATCTATCTCTGACTTCCACTTCAATACAAA

GAAAATTCCTGAATTACCCTCACAATTTGTAATGCAAGGTTTCGATTTCGAAGGCTTTCCCACCTTGATGGATGC

TCTGATATTACACAGGTTAATCGAGAGCGTTTATAAAAGTAACATGATGGGCTCCACATTAAACGTTAGCAATAT

CTCGCATTATAGTTTAATGAAAATCGAAGAAGGTAAGTTAGTCACTTGGATCAACGGTGACAAGGGTTACAATGG

TTTGGCTGAAGCTGGTAAGAAGTTTGAAAAAGACACTGGTATCAAGGTTACCGTCGAACATCCAGTTGAGTTGGA

AGAAAAGTTCCCACAAGTCGCCGCTACTGGTGATGGTCCAGATATTATCTTCTGGGCTCACGACAGATTCGGTGG

TTACGCTCAATCTGGTTTGTTAGCCGAAATTACTCCTGGCAAGGCTTTCCAAGACAAATTATACCCATTCACCTG

GGATGCTGTCAGATATAACGGTAAATTGATCGCTTACCCAATCGCTGTCGAAGCTTTGTCCTTGATCTACAACAA

GGATTTGTTACCTAACCCACCAAAAACTTGGGAAGAAATCCCAGCTTTGGACAAGGAATTGAAAGCTAAAGGTAA

ATCCGCTTTGATCTTCAACTTACAAGAACCATATTTCACTTGGCCTTTGATTGCTGCTGATGGTGGTAATGCCTT

-continued

TAAGTACGAAAACGGTAAGTACGATATTAAGGACGTCGGTGTTGACAGCGCCGGTGCTAAGGCTGGTTTAACTTT

CTTGGTCGATTTGATCAAGAACAAGCATATGAACGCCGACACTGACTACTCTATCGCTGAAGTCGCTTTCAATAA

GGGTGAGACTGCTATGACTATTAACGGTCCTTGGGCTTGGTCTAATATCGATACTTCTAAGGTCAACTACGGTGT

TACCGTTTTGCCAACCTTCAAAGGTCAACCATCCAAGCCATTTGTTGGTGTTTTGTCCGCTGGTATCAACGCTGC

TTCTCCTAACAAGGAATTGGCTAAGGAATTCTTGGAAAACTATTTGTTGACTGATGAAGGTTTAGAAGCTGTTAA

CAAGGACAAGCCATTGGGTGCCGTTGCCTTGAAGTCTTACGAAGAAGAATTGGCCAAGGACCCTAGAATTGCTGC

TACTATGGAAAATGCCCAAAAAGGTGAGATCATGCCAAACATTCCACAAATGTCTGCTTTCTGGTATGCTGTTAG

AACTGCCGTCATTAACGCTGCTTCCGGTAGACAAACTGTTGATGAAGCCTTGAAAGATGCCTAAACTAACTCCTC

TTCCAACAACAATAATAACAACAACAACAACAACTTGGGTATCGAAGGTAGATAAAAGCATCTTGCCCTGTGCTT

GGCCCCCAGTGCAGCGAACGTTATAAAAACGAATACTGAGTATATATCTATGTAAAACAACCATATCATTTCTTG

TTCTGAACTTTGTTTACCTAACTAGTTTTAAATTTCCCTTTTTCGTGCATGCGGGTGTTCTTATTTATTAGCATA

CTACATTTGAAATATCAAATTTCCTTAGTAGAAAAGTGAGAGAAGGTGGCACTGACACACTTAACCTTCATACAG

ATCTGGGTAAGATTATTACTTGCTATAAGTGCGTGCCTGATGAACAGGATATTGCGGTCAATAATGCTGATGGTT

CATTAGACTTCAGCAAAGCCGATGCCAAAATAAGCCAATACGATCTCAACGCTATTGAAGCGGCTTGCCAGCTAA

AGCAACAGGCAGCAGAGGCGCAGGTGACAGCCTTAAGTGTGGGCGGTAAAGCCCTGACCAACGCCAAAGGGCGTA

AAGATGTGCTATCGCGCGGCCCGGATGAACTGATTGTGGTGATTGATGACCAGTTCGAGCAGGCACTGCCGCAAC

AAACGGCGAGCGCACTGGCTGCAGCCGCCCAGAAAGCAGGCTTTGATCTGATCCTCTGTGGCGATGGTTCTTCCG

ACCTTTATGCCCAGCAGGTTGGTCTGCTGGTGGGCGAAATCCTCAATATTCCGGCAGTTAACGGCGTCAGCAAAA

TTATCTCCCTGACGGCAGATACCCTCACCGTTGAGCGCGAACTGGAAGATGAAACCGAAACCTTAAGCATTCCGC

TGCCTGCGGTTGTTGCTGTTTCCACTGATATCAACTCCCCACAAATTCCTTCGATGAAAGCCATTCTCGGCGCGG

CGAAAAAGCGGTGTTTAAACCCCAGCGCCTGGCGGG

SEQ ID NO: 17
Length: 8624
Type:
Organism: artificial sequence
Other information: MS159820 sequence

GACGGCACGGCCACGCGTTTAAACCGCCCGAACAAGCTTATCCCTATTACAGAATTCCAAGGAGGAAATCATTCA

ACTTGAAAGTAAATGGATGTCTATGCAATCTGTTAAAACAACTGCCCTACCCCTTCAAGAGACTACGAATACATC

ATCGACCTTAACTTCTCTGACGTCCAGCATAATTCCCAAGAGTATACCTATAATCACGAAAGGTGAAGTCGCCAC

TAAACCAGCATCTTACTGAATTATTTTCAACAGAACACATCGCATCCAACTGAACAAACTGTTACCGCTGTTGAT

ACCAAGGAACATTCAGTGAACGTAGGGAAGAACGAACATTCTCCATATTTTTGCATACTAGATACAAGGGGGAAG

AATGCAATTATTTCACAAACCGAAAGAAAAAGAATCACAAGCTATGTTTGCTATTATCAATTTTTCTTATGATTA

ATTTAACATAAATTATGGCCTTTTTCATTCCGGCTGCGCTTGTTCTCCAATTTTTTTTTTTTTTTTGAGAAAACT

TTCATACTAGGTAACTAGAGGGGGGTATAAAACTTACATAGAAAAAAAATATATACTATACTTACAACTTTTCAT

TTTTTTCGTAAAAACTACCCCACAATGAAATAAGATACCATACCTTATCGAGTTATTATGTATGTGTCGAAGCTT

TTTATAAGGCTGCAGATAAGGACAACATTCTAATAGGCTGCTGTGTAGCTTGTTGTTGAGTTGGAGAATCCACTG

TGATTTTCATATCTCTAACTAATTTGGCCCATGATACGGCGCCTCTCCTAGCTAACTCCTCTGGAACTCCAAATC

CAGTATCTGACATTCTTCTGTTAAATAATTCCAAGGACACCCAACCTTCGAAGCCCAATCCATTGAAAAAAGCCC

AAGCGATTTCTTTAACAGGTAAGTAAGCGCCTCTGTCTTTTTCGCCGTAGAACAACCTACAATTTCTTGACCATG

ACATTCTGGCTGGTTGCTCAGGGTCATAGAATCTATGACCGGGAACTAATGGTTTCTTTAACTTTTCGGCGTCCA

CTACTTGAACGTAGAAGACTTTAGATACATCGACCCTTTCGACCAACCTGGCAATTGACTTTCTAATTGCTTCTT

-continued

CAGCGTTTGGTGTTCTGCCTGAGGCAACTGTGGGGTCAGCATAAACTCTACCTGCGATGTTAAAAGTGTCTAAGC

AAACGCCAAAGTTAGGTCTATTTACTCTTTGGACAACTTCCCAAGACCTCTCCCAAGTGTCAACTCTAGTGGACC

AGCATAATGCCTCATATACAAACCTTATTGGAGGGTTTGCCTGTAAACCCATATCGGCAACTTCCTGTAAGTCAC

TCACAATTAATGAAATATCTTCTGTGACTTCTTCGGGGGGCAAGAAATTGGCTGGAATTTGAATGATGTCAGTAT

CCAACTCGTGGGCCAATTCAATCCAAAACTCTAATTGCTCCAACCTCCTCTCGTGCTCCTCTCTATCCAATAAAC

CATCATATTGTGAAAAGGGTTGCAAGCACACTATTTCGATGTTTCTAACCTGGCACATCCTCAATATCTGTCTAG

CGGCTGATAATTGAGCAGCTGGACTGGGACCGCATGGACTAGGTGTTTCACCTGACAACCTGTATGCGACATCGG

CTAAGTCCTCATGAAACAACTCCAAACCCTGGTAACCATATTTCCTAGCCATGTCTAACTTAGTTGTGAAAGAAT

GGCCTGCATAACACCTGCCCAAGGACATGGAAGTTATAGCCAATTTACTGGGCATTGTAAAGTTAGTTGGTTGCG

CGACTTCGGGGGGGTATGTTAATCTTGTGTTTACTTAACTATTGCTATTCTTGATGATAATTGAATAAGGTGCA

TAATGAAGAGCAATTCACAACACCAAATTTTCAATCCAATTACTGATTGTTTATATATGTCTACAAAACTAATCC

TATCTCCACATTTTAGCCTGCGAAATGTTTGTTTTTTAAACAATAGCTCTCCAGAACATTGTATAATTTAAGAAT

ATGTGCACAGTTAACTTTCTAGCAGGAGTATAATGCCATTTGCTCCCCATCTTGAGATGGGAAGGGCTTAACTAA

TCTCGGTTCGGAGTGATCCGCCCCGATACTGCCTTCTGCCTTAATATCGTCCAAGGCACATGGACCCCTGAACGG

CGCAGATATCTCCGCACGGACGAAAGACCGCCGGTGCCTTCCTGAGGCAACCGCCCCTTTCGAATATAGATCACG

TGACCCATTTTTAGCTACTAATAGAAAAAGAAATTGCAACCTACTTAAGCCATTCCGGAAGGAAGCTTTCCGATC

ACATGTAGGGACCGAATTGTTTACAAGTTCTCTGTACCACCATGGAGACATCAAAGATTGAAAATCTATGGAAAG

ATATGGACGGTAGCAACAAGAATATAGCACGAGCCGCGAAGTTCATTTCGTTACTTTTGATATCGCTCACAACTA

TTGCGAAGCGCTTCAGTGAAAAAATCATAAGGAAAAGTTGTAAATATTATTGGTAGTATTCGTTTGGTAAAGTAG

AGGGGGTAATTTTTCCCCTTTATTTTGTTCATACATTCTTAAATTGCTTTGCCTCTCCTTTTGGAAAGCTATACT

TCGGAGCACTGTTGAGCGAAGGCTCATTAGATATATTTTCTGTCATTTTCCTTAACCCAAAAATAAGGGAAAGGG

TCCAAAAAGCGCTCGGACAACTGTTGACCGTGATCCGAAGGACTGGCTATACAGTGTTCACAAAATAGCCAAGCT

GAAAATAATGTGTAGCTATGTTCAGTTAGTTTGGCTAGCAAAGATATAAAAGCAGGTCGGAAATATTTATGGGCA

TTATTATGCAGAGCATCAACATGATAAAAAAAAACAGTTGAATATTCCCTCAAAAATGGAAAGAATTGTTGTAAC

ATTGGGTGAAAGGTCTTATCCAATCACTATTGCATCTGGTTTATTTAACGAACCAGCCAGTTTTTTACCATTGAA

ATCCGGTGAGCAAGTGATGTTAGTCACTAACGAAACATTAGCTCCCTTGTATTTAGACAAGGTAAGGGGTGTTTT

GGAACAAGCAGGCGTAAACGTCGATTCTGTGATATTACCAGACGGTGAACAATACAAAAGTTTGGCAGTTTTAGA

TACTGTATTCACTGCCTTATTACAGAAACCACATGGTAGAGATACTACATTGGTTGCCTTAGGAGGCGGAGTTGT

CGGCGATTTAACAGGTTTCGCTGCCGCATCATATCAGAGAGGTGTTAGATTCATTCAGGTCCCAACTACTTTGTT

ATCCCAAGTAGACTCATCAGTTGGAGGAAAGACTGCTGTCAATCATCCTTTAGGAAAGAACATGATTGGTGCCTT

CTACCAGCCAGCATCAGTCGTTGTTGATTTAGATTGTTTGAAGACATTACCTCCAAGAGAGTTGGCAAGTGGTTT

GGCAGAAGTAATAAAATATGGTATCATATTGGATGGTGCATTTTTTAATTGGTTGGAAGAAAATTTAGATGCATT

ATTGAGGTTAGACGGTCCTGCTATGGCTTATTGTATTAGAAGGTGTTGTGAATTAAAGGCTGAGGTTGTAGCAGC

CGACGAGAGAGAAACTGGTTTAAGAGCTTTGTTGAACTTAGGTCATACATTTGGTCATGCTATCGAAGCTGAAAT

GGGTTACGGTAATTGGTTGCATGGTGAAGCCGTTGCAGCCGGTATGGTTATGGCTGCCAGGACATCTGAAAGATT

GGGTCAATTCAGTTCTGCAGAAACACAAAGGATAATAACCTTATTGAAAAGGGCAGGTTTACCTGTGAATGGTCC

TAGAGAGATGAGTGCTCAAGCTTATTTGCCCCACATGTTGAGAGATAAGAAGGTTTTAGCAGGTGAAATGAGGTT

AATTTTGCCCTTAGCAATTGGAAAAAGTGAAGTCAGATCCGGTGTTTCACATGAATTAGTATTGAACGCCATAGC

TGATTGCCAATCAGCCTAAATAAATGACTTAATTTTAACTATATATCGCCAAACATGTAAATTAAAAAAAGAAGC

GAGAAGTATATACATGTGTGTATGAATAAATAATTCGTTTACTATTGATACGTATTGCAAGATATGATTAACCTG

CAGGCCGCGAGCGCCGATgATCATCTACCCATGCCGAAATTCGGGCCGTTGGCCGGATTGCGCGTTGTCTTCTCC

-continued

```
GGTATCGAAATCGCCGGACCGTTTGCCGGGCAAATGTTCGCAGAATGGGGCGCGGAAGTTATCTGGATCGAGAAC
GTCGCCTGGGCCGACACCATTCGCGTTCAACCGAACTACCCGCAACTCTCCCGCCGCAATTTGCACGCGCTGTCG
TTAAATATTTTCAAAGATGAAGGCCGCGAAGCGTTTCTGAAATTAATGGAAACCACCGATATCTTCATCGAAGCC
AGTAAAGGTCCGGCCTTTGCCCGTCGTGGCATTACCGATGAAGTACTGTGGCAGCACAACCCGAAACTGGTTATC
GCTCACCTGTCCGGTTTTGGTCAGTACGGCACCGAGGAGTACACCAATCTTCCGGCCTATAACACTATCGCCCAG
GCCTTTAGTGGTTACCTGATTCAGAACGGTGATGTTGACCAGCCAATGCCTGCCTTCCCGTATACCGCCGATTAC
TTTTCTGGCCTGACCGCCACCACGGCGGCGCTGGCAGCACTGCATAAAGTGCGTGAAACCGGTAAAGGCGAAAGT
ATCGACATCGCCATGTATGAAGTGATGCTGCGTATGGGCCAGTACTTCATGATGGATTACTTCAACGGCGGCGAA
ATGTGCCCGCGCATGAGCAAAGGTAAAGATCCCTACTACGCCGACGGCCGGCCAAGCACGCGGGGATCAATGCTG
CTTCGTATAGGCGCTATTTAATTAAGTAGTTATATAAAGAGAACGGTGCAATTGAATAGGAAAGGAATGACGGAT
TTTGCTTCTATGTTTGCTTTTATTTGAAGCGTGGGTTCTTATTTATGCTTGGTGTAATATGGTCAAAACTGTTCT
CAAATCATTTACTGAGATCTGTCCTGGAGCAGAAGCTTTTTTGACAGCACCAAATGTAGCAGCAGATCCGAACAC
TTCACCAGCTAATCTAGAAATCACACCGGTTTTTGCCATAGACATAGTTATGATAGGTCTATCAGCGTATTGTTC
TTGCATTTCCAATGTGGCAGCTAACAATGTTAAGACATCAGAGGTAGACTGTGGCATTAAAGCAATTTTGGGTAT
ATCAGCATCAAAGGATTGCATTTTTCTTAATCTGGCTATGATTTCCTCTGCTTCTGGGGTCTTGTGGAAATCATG
ATTAGACATAACTACCTTAACATCGTGAGCGTGAGCGTAAGCTACAGTTTCCTTAACCTGGTCATCACCAGTAAA
CAACTCCAAATCTATCATATCCACTAAACCACTATCAATAGCAGCTCTGTTCAAAGCAATGTAGGCTTCGGTACT
AATTGCTTGTTCACCACCTTCCTTAGCTGATCTGAAAGTGAACAATAATGGTTTTTCAGGCATAGTCTCTCTTAA
TATCTTTGCTGCAGCCATTACTGATTCGACATTTGACAAGTCTGCATAGTGATCCACTCTCCATTCTAATATGTC
AAAATCTGCTTCTCTATAAGCTAAGGCCTCACTCTTTACAGAGGCTATGTCTTTAGCCATTAAACTAACAATTAT
TTTAGGGGCTCCTGTTCCAATAACCAAATCTTTCACTGTAACTGTCTTCATTTTTGAGGGAATATTCAACTGTTT
TTTTTTATCATGTTGATGCTCTGCATAATAATGCCCATAAATATTTCCGACCTGCTTTTATATCTTTGCTAGCCA
AACTAACTGAACATAGCTACACATTATTTTCAGCTTGGCTATTTTGTGAACACTGTATAGCCAGTCCTTCGGATC
ACGGTCAACAGTTGTCCGAGCGCTTTTTGGACCCTTTCCCTTATTTTTGGGTTAAGGAAAATGACAGAAAATATA
TCTAATGAGCCTTCGCTCAACAGTGCTCCGAAGTATAGCTTTCCAAAAGGAGAGGCAAAGCAATTTAAGAATGTA
TGAACAAAATAAAGGGGAAAAATTACCCCCTCTACTTTACCAAACGAATACTACCAATAATATTTACAACTTTTC
CTTATGATTTTTTCACTGAAGCGCTTCGCAATAGTTGTGAGCGATATCAAAAGTAACGAAATGAACTTCGCGGCT
CGTGCTATATTCTTGTTGCTACCGTCCATATCTTTCCATAGATTTTCAATCTTTGATGTCTCCATGGTGGTACAG
AGAACTTGTAAACAATTCGGTCCCTACATGTGATCGGAAAGCTTCCTTCCGGAATGGCTTAAGTAGGTTGCAATT
TCTTTTTCTATTAGTAGCTAAAAATGGGTCACGTGATCTATATTCGAAAGGGGCGGTTGCCTCAGGAAGGCACCG
GCGGTCTTTCGTCCGTGCGGAGATATCTGCGCCGTTCAGGGGTCCATGTGCCTTGGACGATATTAAGGCAGAAGG
CAGTATCGGGGCGGATCACTCCGAACCGAGATTAGTTAAGCCCTTCCCATCTCAAGATGGGGAGCAAATGGCATT
ATACTCCTGCTAGAAAGTTAACTGTGCACATATTCTTAAATTATACAATGTTCTGGAGAGCTATTGTTTAAAAAA
CAAACATTTCGCAGGCTAAAATGTGGAGATAGGATTAGTTTTGTAGACATATATAAACAATCAGTAATTGGATTG
AAAATTTGGTGTTGTGAATTGCTCTTCATTATGCACCTTATTCAATTATCATCAAGAATAGCAATAGTTAAGTAA
ACACAAGATTAACATACCCCACCCGAAGTCGCGCAACCAACTAACTTTACAATGCAGAAAGATGCCTTAAATAAC
GTACATATAACAGATGAACAGGTTTTGATGACACCTGAGCAATTAAAAGCTGCCTTTCCCTTATCTTTGCAACAA
GAGGCTCAGATAGCCGATTCAAGAAAGAGTATTTCTGATATTATAGCCGGTAGAGATCCAAGGTTATTGGTTGTA
TGTGGCCCATGTAGTATCCACGATCCTGAAACAGCATTGGAATACGCAAGAAGATTTAAGGCCTTGGCAGCTGAA
GTCTCCGACTCCTTGTATTTGGTTATGAGGGTTTATTTTGAAAAGCCAAGGACCACTGTAGGTTGGAAGGGATTG
```

-continued

ATTAACGACCCACATATGGATGGATCTTTTGATGTGGAAGCTGGTTTGCAAATCGCAAGGAAATTGTTGTTGGAA

TTAGTAAATATGGGTTTGCCTTTAGCTACCGAAGCCTTGGATTTAAACAGTCCTCAATATTTGGGCGATTTATTC

TCCTGGTCTGCAATAGGTGCTAGAACCACCGAATCACAAACTCACAGAGAAATGGCATCTGGTTTGAGTATGCCA

GTTGGCTTCAAAAACGGCACAGACGGTTCATTGGCAACTGCCATAAATGCCATGAGGGCCGCAGCTCAACCACAT

AGATTTGTCGGTATCAATCAAGCTGGTCAGGTCGCATTATTACAAACTCAGGGTAACCCAGATGGTCATGTAATA

TTGAGGGGTGGTAAGGCCCCAAACTATTCACCTGCCGACGTGGCACAGTGCGAAAAGGAAATGGAACAAGCAGGT

TTAAGACCTTCCTTGATGGTCGACTGTTCTCACGGTAACTCTAATAAGGATTACAGGAGACAACCCGCCGTCGCT

GAATCTGTAGTTGCACAGATAAAAGATGGAAACAGATCTATCATCGGTTTGATGATCGAATCAAATATTCATGAG

GGTAACCAATCATCCGAACAGCCAAGATCAGAAATGAAGTATGGCGTGTCTGTTACAGACGCATGTATTTCATGG

GAAATGACCGACGCATTGTTGAGAGAAATTCATCAGGATTTGAATGGCCAATTGACAGCAAGAGTGGCCTAAAAT

TTTAGTGTCGTTAATATCTCTTTTATTTCTTATTGTTACTATATTATTACTGTTTTGAAGTTCCAGTTTCATCAA

CTTTTGCTACCTTAATTAAAAGAACCACTCAGACTTTTTACCATCCTACCCCCCTCTAGTTACCTAGTATGGCAT

AGTAAAAAAATAGATGCAGAATTTACTCACCTCAAGGAGGGGCAAAGTAATAAGAAAAGTTACCATAGGCTAGTT

GAATGTCCAAGATCGTAAAGAATGAAGAAAAAAGGAGTAAAAAGTATGAATAAGATAAATGAAAATATAAAAATA

AAAACCAACTAATACATGAAGAAAAAAAAGCAGACAAAAACATTTTATGGACCTGATGCAATCTAGTAGTCCATA

GAATAATCACCACTAGAAAATTCTTCCTCTTCATTACTACCGTTTGCCATTATAGGAATATGATTTGCTGCAGGA

TTCTGCGGAGGTATTATATAGGGCACTGGCGGCACCTGTGGAATAAACCCAAATGATGGGAACATTGGCATCATC

CAGTTAGCGTTATTTTGGTTTGCACTTATTAAGTTGTAACTGTTCACGGGCTTTGTGTTGGTATTAGGGTACTGC

AGTGGTATGAAATAATTTTCCCTCGAGACTTGCTGTTGCGATTGGTGGCGGTTTAAACGCGTGGCCGTGCCGTC

SEQ ID NO: 18
Length: 9013
Type:
Organism: artificial sequence
Other information: MS156217 sequence

GACGGCACGGCCACGCGTTTAAACCGCCAAAAACTCACAAGAAGTTCGGTGTCCTTATTTGCGATGGGAATTGCT

AATATCATATCACCACAAATATGGAGAGAGAAGGACTCTCCTCGCTTTTTACCTGCCTGGATTGTTCAAATCGTT

TTATCATTCTCTCTTGCACCAGCCATTTTGTTACTGATCCATTTCATACTAAAAAGAAGGAATAATCAAAGACTA

AAAAATTATGACGAAAATTTACAAAATTATTTGGACAGAATTCAACTCATTGAAAGCGAAAATCCTTCTTCCATT

GAAGAAGGGAAAGTGGTAACCCACGAGAACAATTTGGCAGTCTTTGATTTGACTGATTTAGAAAACGAAACTTTT

ATATATCCTTTGTAAATATTGATGTTTTGTTGTGTAAATGTTCTATCTGACACTTAATAATTAGAAAATTAATTT

TTTAAACTTTCCGGCTGCAAGAAAGAGGAACTGTGTCTCTTTGAAAGGCACAATTTCCCAAAGAATCATTTACAA

TGCGAAAAAAAGATATCAGGAGGGGTAGTGAGTTCTATTCACGCAATCGGTAGTATCAAAGAAGATTATTTGGGT

GCTATTTAATCACTTGTTACTCCGCAACGCTTTTCTGAACGCCCGCCTTCGCCTTTCATTATCATTCTCATCCCA

AAAGAACTGTGCATGTTATTTGCAATACTTCATATACGCTCTGTATTATTAATAGTATCATTAATTACGTCAATT

GAAATTCAAAATATCATCTTTGACAGTAACATCTATCCTCTTAGACAACTAGGGCCATTGCAGTGTCTCGAAACC

ATTAATATCACTGAAAAGATGAAAAGAAAGGCAAATATATATTGATCACTAATTTTCTAAGCTAAAGAATCTATT

CCCCCTCTGTTAAATGGAATTGTGTGAAATAAAATATTATAAAATCAGAACTTTGGGGGGGAAACATAAAAAAAT

GAGAAAAAGAAAACGAACTAACTAATGTTTAAGTAAAAGAACAAAAAGGTAGACCAATGTAGCGCTCTTACTTTA

TTAGACTAATCTTCTACACAAGGTAACACCATCACCGATGGAAACTTGGGAGATTTCAATTCTTGGATCGGAAGC

CAATCTTTTGTTCAATTCCATCAAAGCCTTACGGTTAACTCTTAAGTGAACTGGGACAGTCTCTTCCTCTTCAGC

AACGAAACCGAACCATAAGGTGTTATCGAAAGCAATGATACCACCAACTTTGACCAACTTCATCAATCTTTCCAA

-continued
AGCGTGGACGTAATTTGGCTTATCAGCGTCAACGAAAGCGAAGTCAAATTCTGGCTTTGGGTTTTCAGATAACAA
CTTGTCTAAGGCTTGCAAACCGTCGGATTGGATAAAGTTAATTTTGTGATCGATACCGGCGTTCTTGATGAATTC
CAAACCCATTTCGTAAGCTTCTTTATCGATATCAATAGCAGTAATTCTACCGTCTTCAGGCAAAGCCAAGGCGGT
GGTTAACAAAGAGTAACCAGTGAAAACACCCAATTCCAAGGTGTTCTTAGCGTTCATCATCTTCAACAACATGGA
CAAGAAATGACCTTCGTCAACAGGGACTTCCATCTCGGACAAGTTACCGTACTTATGAACGGTAGCTTCTCTTAA
CTTCTTCAATTCTTCGTGTTCTCTTGGGTAAGCGGAAGTTTCAAAGATGTACTTTTTCAATTCTTCGTTCTTCAA
GATACCCTTAGATGGTATAAGATTTTCCATGTCTGGTTCCATTGTAAAGTTAGTTGGTTGCGCGACTTCGGGTGG
GGTATGTTAATCTTGTGTTTACTTAACTATTGCTATTCTTGATGATAATTGAATAAGGTGCATAATGAAGAGCAA
TTCACAACACCAAATTTTCAATCCAATTACTGATTGTTTATATATGTCTACAAAACTAATCCTATCTCCACATTT
TAGCCTGCGAAATGTTTGTTTTTTAAACAATAGCTCTCCAGAACATTGTATAATTTAAGAATATGTGCACAGTTA
ACTTTCTAGCAGGAGTATAATGCCATTTGCTCCCCATCTTGAGATGGGAAGGGCTTAACTAATCTCGGTTCGGAG
TGATCCGCCCCGATACTGCCTTCTGCCTTAATATCGTCCAAGGCACATGGACCCCTGAACGGCGCAGATATCTCC
GCACGGACGAAAGACCGCCGGTGCCTTCCTGAGGCAACCGCCCCTTTCGAATATAGATCACGTGACCCATTTTTA
GCTACTAATAGAAAAAGAAATTGCAACCTACTTAAGCCATTCCGGAAGGAAGCTTTCCGATCACATGTAGGGACC
GAATTGTTTACAAGTTCTCTGTACCACCATGGAGACATCAAAGATTGAAAATCTATGGAAAGATATGGACGGTAG
CAACAAGAATATAGCACGAGCCGCGAAGTTCATTTCGTTACTTTTGATATCGCTCACAACTATTGCGAAGCGCTT
CAGTGAAAAAATCATAAGGAAAAGTTGTAAATATTATTGGTAGTATTCGTTTGGTAAAGTAGAGGGGGTAATTTT
TCCCCTTTATTTTGTTCATACATTCTTAAATTGCTTTGCCTCTCCTTTTGGAAAGCTATACTTCGGAGCACTGTT
GAGCGAAGGCTCATTAGATATATTTTCTGTCATTTTCCTTAACCCAAAAATAAGGGAAAGGGTCCAAAAAGCGCT
CGGACAACTGTTGACCGTGATCCGAAGGACTGGCTATACAGTGTTCACAAAATAGCCAAGCTGAAAATAATGTGT
AGCTATGTTCAGTTAGTTTGGCTAGCAAAGATATAAAAGCAGGTCGGAAATATTTATGGGCATTATTATGCAGAG
CATCAACATGATAAAAAAAAACAGTTGAATATTCCCTCAAAAATGGATATGGCAAGTAATGGTTCTGCCGGTGAG
GTTAGAGAAGTTCACTCCTCCGAAACTACCAAGACTTTATTGAAATCCGATGCTTTATACGATTATATGTTGAAG
ACTATGGTCTATCCAAGAGAGAACGAATTTATGAGAGAATTGAGACAAATCACTTCCGAACATATCTTCGGTTTC
ATGTCTTCTCCACCAGATGAAGGTTTGTTATTGTCCTTGTTGTTAAAGGTTATGGGTGCTAAGAGAACCATCGAA
GTCGGTGTCTACACTGGTTGTTCCGTCTTGACTACTGCCTTAGCTATCCCAGACGATGGTAGAATCATTGCTATT
GACGTTTCCCGTGAATACTTTGACTTGGGTTTGCCAGTTATTAAGAAGGCCGGTGTTGCCCATAAGGTTGATTTC
CGTGAAGGTCCTGCTGGTCCAATTTTGGACAAATTGATTGCTGATGAAGACGAAGGTTCTTTTGATTTCGCTTTC
GTTGATGCCGATAAGTACAACTACGGTTCCTACCACGAACAATTGTTGAGATTGGTTAGAGTTGGTGGTGTTTTG
GCTTACGACAATACCTTATGGGGTGGTACCGTCTCCATGCCAGATGACACTCCATTGACCGAAGAAGACAGAAAG
AAGAGAGACTCCATTCGTGGTTTCAATGCCATGATTGCTGCCGACGCCAGAGTCGAACCAGTTCAATTACCAATC
GCCGACGGTATTACCTTGTGCAGACGTGTCGTCTAAAGTTTCAGGCAGAACAAGACCCTTTTCAAAAATATGTAA
GCCATTATTAAAAAAAAGGATATTTTGTATAATTGTTTAATAAAATAACATCTTTTTAAACAATCATAAATAGCA
CTTCTTATCATACAACCTCAAATCATATCGGTCCAAATTTGCTCAAATTGTACATGAGATATAACTTTTTCTTCT
AATGCTTTCATTTCAGAGTTTGTTTTTTTTTTTTCTTTTTTTTTTTTTTCCTTACCGGAGTCTGAATCTCTTACT
TCCTTAACTTAGATGTTAGTGACTAAAATCTGATGGACAGTATCAAAATGTAAATATTGTACCTAAAAAGAAAAA
AGTATTAAAGTGGTTTGCCATAAATTTTAAACAAGTGAAAAGTTTCAATATTTATATTTACATGATTGTGGACAA
GCGGCATTGTCTACAGGCTGTGCAAAATTATATAGTACAGATAAATGTAACCAGAACAACGAAGAAAAGGTCCCT
ATGTTGCAACGCGATCGCCGACGCCGCCGATGCTGATTATCAGGGTAAAAATGTCGTCATTATCGGCCTGGGCCT
CACCGGGCTTTCCTGCGTGGACTTTTTCCTCGCTCGCGGTGTGACGCCGCGCGTTATGGATACGCGTATGACACC
GCCTGGCCTGGATAAATTACCCGAAGCCGTAGAACGCCACACGGGCAGTCTGAATGATGAATGGCTGATGGCGGC -continued

AGATCTGATTGTCGCCAGTCCCGGTATTGCACTGGCGCATCCATCCTTAAGCGCTGCCGCTGATGCCGGAATCGA

AATCGTTGGCGATATCGAGCTGTTCTGTCGCGAAGCACAAGCACCGATTGTGGCGATTACCGGTTCTAACGGCAA

AAGCACGGTCACCACGCTAGTGGGTGAAATGGCGAAAGCGGCGGGGGTTAACGTTGGTGTGGGTGGCAATATTGG

CCTGCCTGCGTTGATGCTACTGGATGATGAGTGTGAACTGTACGTGCTGGAACTGTCGAGCTTCCAGCTGGAAAC

CACCTCCAGCTTACAGGCGGTAGCAGCGACCATTCTGAACGTGACTGAAGATCATATGGATCGCTATCCGTTTGG

TTTACAACAGTATCGTGCAGCAAAACTGCGCATTTACGAAAACGCGAAAGTTTGCGTGGTTAATGCTGATGATGC

CTTAACAATGCCGATTCGCGGTGCGGATGAACGCTGCGTCAGCTTTGGCGTCAACAATCGGGGGCGTCGGCGATC

GCGTTGCAACATAGGGACCTTTTCTTCGTTGTTCTGGTTACATTTATCTGTACTATATAATTTTGCACAGCCTGT

AGACAATGCCGCTTGTCCACAATCATGTAAATATAAATATTGAAACTTTTCACTTGTTTAAAATTTATGGCAAAC

CACTTTAATACTTTTTTCTTTTTAGGTACAATATTTACATTTTGATACTGTCCATCAGATTTTAGTCACTAACAT

CTAAGTTAAGGAAGTAAGAGATTCAGACTCCGGTAAGGAAAAAAAAAAAAAAGAAAAAAAAAAAACAAACTCTGA

AATGAAAGCATTAGAAGAAAAAGTTATATCTCATGTACAATTTGAGCAAATTTGGACCGATATGATTTGAGGTTG

TATGATAAGAAGTGCTATTTATGATTGTTTAAAAAGATGTTATTTTATTAAACAATTATACAAAATATCCTTTTT

TTTAATAATGGCTTACATATTTTTGAAAAGGGTCTTGTTCTGCCTGAAACTTTAGACGACACGTCTGCACAAGGT

AATACCGTCGGCGATTGGTAATTGAACTGGTTCGACTCTGGCGTCGGCAGCAATCATGGCATTGAAACCACGAAT

GGAGTCTCTCTTCTTTCTGTCTTCTTCGGTCAATGGAGTGTCATCTGGCATGGAGACGGTACCACCCCATAAGGT

ATTGTCGTAAGCCAAAACACCACCAACTCTAACCAATCTCAACAATTGTTCGTGGTAGGAACCGTAGTTGTACTT

ATCGGCATCAACGAAAGCGAAATCAAAAGAACCTTCGTCTTCATCAGCAATCAATTTGTCCAAAATTGGACCAGC

AGGACCTTCACGGAAATCAACCTTATGGGCAACACCGGCCTTCTTAATAACTGGCAAACCCAAGTCAAAGTATTC

ACGGGAAACGTCAATAGCAATGATTCTACCATCGTCTGGGATAGCTAAGGCAGTAGTCAAGACGGAACAACCAGT

GTAGACACCGACTTCGATGGTTCTCTTAGCACCCATAACCTTTAACAACAAGGACAATAACAAACCTTCATCTGG

TGGAGAAGACATGAAACCGAAGATATGTTCGGAAGTGATTTGTCTCAATTCTCTCATAAATTCGTTCTCTCTTGG

ATAGACCATAGTCTTCAACATATAATCGTATAAAGCATCGGATTTCAATAAAGTCTTGGTAGTTTCGGAGGAGTG

AACTTCTCTAACCTCACCGGCAGAACCATTACTTGCCATATCCATTTTTGAGGGAATATTCAACTGTTTTTTTTT

ATCATGTTGATGCTCTGCATAATAATGCCCATAAATATTTCCGACCTGCTTTTATATCTTTGCTAGCCAAACTAA

CTGAACATAGCTACACATTATTTTCAGCTTGGCTATTTTGTGAACACTGTATAGCCAGTCCTTCGGATCACGGTC

AACAGTTGTCCGAGCGCTTTTTGGACCCTTTCCCTTATTTTTGGGTTAAGGAAAATGACAGAAAATATATCTAAT

GAGCCTTCGCTCAACAGTGCTCCGAAGTATAGCTTTCCAAAAGGAGAGGCAAAGCAATTTAAGAATGTATGAACA

AAATAAAGGGGAAAAATTACCCCCTCTACTTTACCAAACGAATACTACCAATAATATTTACAACTTTTCCTTATG

ATTTTTTCACTGAAGCGCTTCGCAATAGTTGTGAGCGATATCAAAAGTAACGAAATGAACTTCGCGGCTCGTGCT

ATATTCTTGTTGCTACCGTCCATATCTTTCCATAGATTTTCAATCTTTGATGTCTCCATGGTGGTACAGAGAACT

TGTAAACAATTCGGTCCCTACATGTGATCGGAAAGCTTCCTTCCGGAATGGCTTAAGTAGGTTGCAATTTCTTTT

TCTATTAGTAGCTAAAAATGGGTCACGTGATCTATATTCGAAAGGGGCGGTTGCCTCAGGAAGGCACCGGCGGTC

TTTCGTCCGTGCGGAGATATCTGCGCCGTTCAGGGGTCCATGTGCCTTGGACGATATTAAGGCAGAAGGCAGTAT

CGGGGCGGATCACTCCGAACCGAGATTAGTTAAGCCCTTCCCATCTCAAGATGGGGAGCAAATGGCATTATACTC

CTGCTAGAAAGTTAACTGTGCACATATTCTTAAATTATACAATGTTCTGGAGAGCTATTGTTTAAAAAACAAACA

TTTCGCAGGCTAAAATGTGGAGATAGGATTAGTTTTGTAGACATATATAAACAATCAGTAATTGGATTGAAAATT

TGGTGTTGTGAATTGCTCTTCATTATGCACCTTATTCAATTATCATCAAGAATAGCAATAGTTAAGTAAACACAA

GATTAACATACCCCACCCGAAGTCGCGCAACCAACTAACTTTACAATGGAACCAGACATGGAAAATCTTATACCA

TCTAAGGGTATCTTGAAGAACGAAGAATTGAAAAAGTACATCTTTGAAACTTCCGCTTACCCAAGAGAACACGAA

-continued

GAATTGAAGAAGTTAAGAGAAGCTACCGTTCATAAGTACGGTAACTTGTCCGAGATGGAAGTCCCTGTTGACGAA

GGTCATTTCTTGTCCATGTTGTTGAAGATGATGAACGCTAAGAACACCTTGGAATTGGGTGTTTTCACTGGTTAC

TCTTTGTTAACCACCGCCTTGGCTTTGCCTGAAGACGGTAGAATTACTGCTATTGATATCGATAAAGAAGCTTAC

GAAATGGGTTTGGAATTCATCAAGAACGCCGGTATCGATCACAAAATTAACTTTATCCAATCCGACGGTTTGCAA

GCCTTAGACAAGTTGTTATCTGAAAACCCAAAGCCAGAATTTGACTTCGCTTTCGTTGACGCTGATAAGCCAAAT

TACGTCCACGCTTTGGAAAGATTGATGAAGTTGGTCAAAGTTGGTGGTATCATTGCTTTCGATAACACCTTATGG

TTCGGTTTCGTTGCTGAAGAGGAAGAGACTGTCCCAGTTCACTTAAGAGTTAACCGTAAGGCTTTGATGGAATTG

AACAAAAGATTGGCTTCCGATCCAAGAATTGAAATCTCCCAAGTTTCCATCGGTGATGGTGTTACCTTGTGTAGA

AGATTAGTCTAATAAAGTAAGAGCGCTACATTGGTCTACCTTTTTGTTCTTTTACTTAAACATTAGTTAGTTCGT

TTTCTTTTTCTCATTTTTTTATGTTTCCCCCCCAAAGTTCTGATTTTATAATATTTTATTTCACACAATTCCATT

TAACAGAGGGGGAATAGATTCTTTAGCTTAGAAAATTAGTGATCAATATATATTTGCCTTTCTTTTCATCTTTTC

AGTGATATTAATGGTTTCGAGACACTGCAATGGCCCTAGTTGTCTAAGAGGATAGATGTTACTGTCAAAGATGAT

ATTTTGAATTTCAATTGACGTAATTAATGATACTATTAATAATACAGAGCGTATATGAAGTATTGCAAATAACAT

GCACAGTTCTTTTGGGATGAGAATGATAATGAAAGGCGAAGGCGGGCGTTCAGAAAAGCGTTGCGGAGTAACAAG

TGATTAAATAGCACCCAAATAATCTTCTTTGATACTACCGATTGCGTGAATAGAACTCACTACCCCTCCTGATAT

CTTTTTTTCGAACATATTGATGTTTTTCGTGGGTAACCATAGTTCTTGGAATGTCAACTGAGGGTATTTGCACTT

CAAAAAAAAAAATTTATTAAATGAGACTATATACAGTGAGCACAACCTGTCTAATACAACGGCAAAAATTATATA

CATTGGTAGATTTTCAAAATTGAACTCTTTGTGCTAAAGAATTGTCACAACAGTTTAAAAAATAGTTTGAATTCT

TCAAATTGACCCCATATTAATAAGACCTGATGCGATTCCGGTCTCACCCAGATTAGAGAGGGAATTTAATTTTCT

TAGGACCGTAGCTACCAAAAATCTTTGTGTGGTATTGATTATATGATCGTGCTTGCGAAAAAAATAGAAGACTAA

AAGTAGCATTAGTTTACTAACTTTCTCCTCGTATCTTTCAAATTTGTATTCCCCTCAAAAGTTACTCAGGTTAGG

GAAAATTCCAAGTAGCTTATCAAGATCAATTGCCATTAGTTGATTCAAGGCTTCATTGTCGGCGGTTTAAACGCG

TGGCCGTGCCGTC

SEQ ID NO: 19
Length: 8216
Type:
Organism: artificial sequence
Other information: MS153767 sequence

GACGGCACGGCCACGCGTTTAAACCGCCTGCATACTTCAAGTTCAGGGTTGGACCTGCCAATGAAAATTTTAGAT

ATGTTTGGCTCAGGTCTTCCTGTTATTGCAATGAACTATCCAGTGCTTGACGAATTAGTACAACACAATGTAAAT

GGGTTAAAATTTGTTGATAGAAGGGAGCTTCATGAATCTCTGATTTTTGCTATGAAAGATGCTGATTTATACCAA

AAATTGAAGAAAAATGTAACGCAGGAAGCTGAGAACAGATGGCAATCAAATTGGGAACGAACAATGAGAGATTTG

AAGCTAATTCATTGAGTCAATGGTAACTCAGCCTTTCTTTTTTGAAAATTACTATTTTCGACTCTTTTTTTATAC

AGTTACATAGTACTACCTCTAATACACATTCATGATTAACAATGTTTCAAACAATATAAAGTCCCGATAACGACC

TTTTGAAGTGGTGACGTTACCGCTCTTCGTTGACAAGATTCAAGAGGGCTGTCAGAATAACAGCTATCATGGTGG

AATCGATTACCTGCCTTGATACGCTGCCAGAATACATGTCACATGTAGGGACCGAATTGTTTACAAGTTCTCTGT

ACCACCATGGAGACATCAAAGATTGAAAATCTATGGAAAGATATGGACGGTAGCAACAAGAATATAGCACGAGCC

GCGAAGTTCATTTCGTTACTTTTGATATCGCTCACAACTATTGCGAAGCGCTTCAGTGAAAAAATCATAAGGAAA

AGTTGTAAATATTATTGGTAGTATTCGTTTGGTAAAGTAGAGGGGGTAATTTTTCCCCTTTATTTTGTTCATACA

TTCTTAAATTGCTTTGCCTCTCCTTTTGGAAAGCTATACTTCGGAGCACTGTTGAGCGAAGGCTCATTAGATATA

TTTTCTGTCATTTTCCTTAACCCAAAAATAAGGGAAAGGGTCCAAAAAGCGCTCGGACAACTGTTGACCGTGATC

-continued

CGAAGGACTGGCTATACAGTGTTCACAAAATAGCCAAGCTGAAAATAATGTGTAGCTATGTTCAGTTAGTTTGGC

TAGCAAAGATATAAAAGCAGGTCGGAAATATTTATGGGCATTATTATGCAGAGCATCAACATGATAAAAAAAAAC

AGTTGAATATTCCCTCAAAAATGGATACAAGAGAAGATCAATTAGAAAGACGTATTGCTGCCTTAACTGCTAACG

ACCCTCAATTCGCCGCTGCCAGACCAGACGAAGCCGTTGCCACTGCCGTCCAAAGACCTGGTTTGAGATTACCAG

AAGTCATCGAAACCGTCTTGCAAGGTTACGCTGACCGTCCAGCCTTAGGTCAAAGAGCTGTCGAATTTGTTAAAG

ATCCAAACACTGGTAGAACCTCCGCCCATTTGTTACCAAGATTCGACACCATCACCTACAGAGAATTGGCTGATA

GAGTCGGTGCTTTAGCTTCTGCTTGGGCTAGAGAAGCCGTTTCCCCAGGTGACAGAGTTGCCATTTTGGGTTTCA

CTTCCGTTGACTATACTACCATTGATGTTACTTTGGCTAGAATTGGTGCTGTCTCTGTTCCATTACAAACCTCTG

CTGCCTTGGCTCAATTAAGACCAATTGTTGTCGAAACCGAACCAACTGTTATCGCTGCTTCCGTTGATTACTTGT

CCGACGCTGTTGAATTAATTAGAACTGGTCACGCCCCAGCCAGATTGGTTGTTTTTGATCATCACCCAGAAGTTG

ACGATCACAGAGAAGCTTTGGACGCTGCTAGAGGTCGTTTGGCTGGTCACGCTGTCATTGTTGAAACTTTGGCTG

AAGTCTTGGAGAGAGGTACTTCTTTGCCAGCTCCAACTGTTGCTGCCGAAGATAATGATTTGGCTTTGTTAATCT

ACACCTCTGGTTCCACTGGTGCTCCAAAGGGTGCTATGTACCCACAAAGAAATGTTGCTAAGATGTGGCAAAGAT

CTTCCAGAAACTGGTTCGGTCCTTCTGCCGCTTCTATTACCTTGAACTTTATGCCAATGTCCCATGTTATGGGTA

GAGGTATTTTGTACGGTACCTTAGGTAACGGTGGTACTGCCTACTTCGGTGCTACCTCTGACTTGTCTACTTTGT

TGGAAGACTTGACTTTGGTCAGACCTACCGAATTGAACTTCGTTCCAAGAGTCTGGGACACTTTGCATGCCGAGT

TCTTGACTAGAGTCGACAGATTGACCGCTGAAGGTGCCGACAGAGCTTCCGCTGAGGCTTTGGTCATGGGTGACT

TGAGAGACAACTTATTGGGTGGTCGTGCCATTTTCGCCATGACTGGTTCCGCTCCAATCTCTTCTCAATTGAAAA

CTTGGGTTGAGTCCTTGTTGGGTATCCATTTATTGGACGGTTATGGTTCTACTGAAGCTGGTATGGTTTTGTACG

ATGGTGTCGTCCAAAGACCTCCAGTCATTGACTACAAGTTAGCTGATGTCCCAGATTTGGGTTACTTTTCTACTG

ATAGACCATTCCCAAGAGGTGAATTATTATTGAAAACTGAAAACATGTTCCCTGGTTACTACAAAAGACCAGAAA

TCACCGCTGGTGTCTTCGATGATGACGGTTACTACCGTACTGGTGATGTTGTTGCTGAAGTCGGTCCAGATCGTT

TGGTTTACGTCGATAGAAGAAACAATGTTTTAAAATTAGCTCAAGGTGAGTTCGTTACTGTTGCCAAGTTGGAAG

CTGGTTTCAACAACTCCCCATTGGTCAGACAAATCTACATTTACGGTAACTCTGCTCATCCATACTTATTGGCTG

TTGTTGTTCCTACTGATGTCAATGCCTCCAAGTCCGCTATTGCTGAATCCTTGCAAAGAGTCGCTAAGGACGCTG

GTTTACAATCCTATGAAGTTCCTAGAGACTTCTTGATTGAACCAGAACCATTTACCTTGGAAAACGGTTTGTTAA

CTGGTATTAGAAAGTTGGCTTGGCCTAAGTTGAAGGAGAGATACGGTGAACGTTTGGAACAATTGTACGCTGAAT

TGGACAGATCCCAAGCTGACGAATTGTCTGAATTAAGAAGATCTGGTGCCCAAAGACCAGTTTTGGAAACTGTCA

CCAGAGCTGCCGGTGCTTTGTTAGGTGCTGCTGCTTCTGAATTACAACCAGATGCTCACTTCACTGACTTGGGTG

GTGACTCCTTGTCCGCTTTGACTTTCGGTAACTTGTTGAGAGAAATCTTTGACGTCGACGTCCCAGTCGGTGTTA

TCGTTTCTCCAGCTTCTGACTTGCAAGCCATTGCTGGTTACATTGAAGCCGAAAGACAAGGTTCTAAAAGACCAA

CCTTCGCCTCCGTTCATGGTAGAGCTGAGGAAGGTGAAGCTGTTGAGGTTAGAGCTAGAGATTTGCGTTTGGATA

AGTTCTTGGACGCCAGAACCTTGGAGTACGTTCCAGCCTTGCCAGGTCCATCCACCGAATTGCGTACTGTTTTGT

TGACTGGTGCTACTGGTTTCTTGGGTAGATATTTGGCTTTGGAATGGTTGGAGAGAATGGACGCTGTTGACGGTA

CCGTTATCGCTTTAGTCAGAGCTAAGGACGACGCCGCTGCTAGAGAGAGATTGGACAGAACTTTCGACTCTGACC

CTAAGTTGAGAGCCCACTACAGAGCTTTGGCCGCTGACCATTTGGAAGTTGTTGCTGGTGACAAGGGTGAAGCTA

ACTTAGGTTTGTCTCAACAAGTTTGGCAAAGATTAGCCGACACTGTTGACGTTATCGTTGACCCAGCCGCTTTGG

TCAACCACGTTTTACCATACTCTGAATTGTTTGGTCCAAATGTTTTGGGTACTGCCGAATTGATCAGATTGGCTT

TGACTACCAAGATCAAGCCATACACTTACGTTTCCACCATCGGTGTTGGTGACCAAATCGAGCCAGGTAAGTTTA

CTGAAGATGCTGACATCAGAGTTATTTCTCCAACTAGAAGAATTTCTGACTCTTACGCTAACGGTTACGGTAACT

CCAAGTGGGCTGGTGAAGTCTTGTTGAGAGAAGCTCATGACAGATGTGGTTTGCCAGTCGCTGTTTTCAGATGTG

-continued

ATATGATCTTGGCCGACACCACCTACGCCGGTCAATTAAACTTGCCAGATATGTTCACTCGTTTAATGTTGTCCT

TGGCCGCTACTGGTATTGCCCCAAGATCTTTCTACGAATTGGATGCTGAAGGTAACAGACAACGTGCTCATTACG

ACGGTTTGCCAGTCGAATTCATTGCTAAGGCTGTCTCTACTTTGGGTGCTCAAACTGTTGAGGGTTATCAAACCT

ACCACGTCATGAACCCTCATGACGACGGTATTGGTTTGGACGAATACGTTGACTGGTTGATTGAAGCTGGTTACC

CTATTCGTAGAGTTGACGACTACGCTGATTGGTTACAAAGATTTGAAACCGCTATGAGAGCTTTGCCAGACAGAC

AAAGAAGATACTCCTTGTTGCCTTTGTTACATAACTACCAAAAGCCAGAAAAGCCAATGAGAGGTTCTATGGCTC

CAACTGATAGATTTAGAGCTGCTGTTCAAGAAGCCAAAATTGGTCCAGACAAGGATATTCCACACGTCACCAGAG

AAGTTATCGTCAAGTATGCTACTGATTTGCAATTGTTGGGTTTATTGGATGAAAAAAGAGTCTAAAAGGCTTTTT

TATAAACTTTTTATAATTAACATTAAAGCAAAAACAACATTGTAAAGATTAACAAATAAATGAAAAAAACAACGA

AATAACTTAGGTTTTAGGCTAAAAAAAACAGAAGGAATTTTGAACGATAAACTTTTCGACTGCACACGAAACATT

ATTACTAATTTGTGTAACCACTATATAAGGAATCGTGTTTATTAATTGAATTTATTCCGGGAATATTCAAGTTAT

GTATATCTCTTTTCATATTCTTAAATACACATACTCATAATATCTTGTCGAAAATACGCGGTGTAGGGAGTTATG

GTGGATAACTTTTTCACGATTAGAAGAAAAGGAAAATTTCATTATTCGTAGCTTAACATGGCAAAAACGAGAAAG

ACATATAATCAAAACGTGAGTTTCCTGTGGAAAAAAAAAAAAGGGAACCTCTGGTTACGATGATATACCTGCGTG

AAAAAGGACAGTTATTACCAATACATACAAAGGCAACCTGCAGGCCGCGAGCGCCGATAAGATTATTACTTGCTA

TAAGTGCGTGCCTGATGAACAGGATATTGCGGTCAATAATGCTGATGGTTCATTAGACTTCAGCAAAGCCGATGC

CAAAATAAGCCAATACGATCTCAACGCTATTGAAGCGGCTTGCCAGCTAAAGCAACAGGCAGCAGAGGCGCAGGT

GACAGCCTTAAGTGTGGGCGGTAAAGCCCTGACCAACGCCAAAGGGCGTAAAGATGTGCTATCGCGCGGCCCGGA

TGAACTGATTGTGGTGATTGATGACCAGTTCGAGCAGGCACTGCCGCAACAAACGGCGAGCGCACTGGCTGCAGC

CGCCCAGAAAGCAGGCTTTGATCTGATCCTCTGTGGCGATGGTTCTTCCGACCTTTATGCCCAGCAGGTTGGTCT

GCTGGTGGGCGAAATCCTCAATATTCCGGCAGTTAACGGCGTCAGCAAAATTATCTCCCTGACGGCAGATACCCT

CACCGTTGAGCGCGAACTGGAAGATGAAACCGAAACCTTAAGCATTCCGCTGCCTGCGGTTGTTGCTGTTTCCAC

TGATATCAACTCCCCACAAATTCCTTCGATGAAAGCCATTCTCGGCGCGGCGAAAAAGCCCGTCCAGGTATGGTC

GGCGGCGGATATTGGTTTTAACGCAGAGGCAGCCTGGTCAGAACAACAGGTTGCCGCGCCGAAACAGCGCGAACG

TCAGCGCAATCGGCGCTCGCGGCCTGCAGGTTCCGTTACAGGAATGGATGATCCACCAATTATATCGACGGGGGC

TAGAATCTTAGATCTCAGTACTCGCATTCTAGCGTATGTTTCTTGAAACTTGTAAGGGACTTTCGTCGAGGCCGG

AGTGACAAGGATCGAGGGGTCCAATGGTGTGGCCCACCTGTTGGGCACATTGCCGTTTCTAACCACAATCCATTC

GAAGTACTGCTTATTTGGCAGCGATTTAACCCAGTCGATATCCACGGGTTGAGGGACAACCTCTTCTTGTTTGAT

TTTGGTCCTTTTCTCCGGTAGGAGTTCTGATTCTGGCCCAGTTTCAGTCTTTACCAGCGGTCTTTTCCTCAGAAT

TGCCATAGATGAGTATTTACTGATCTTTTGCATATTTTTTTTTTTTTTTTAAGTATATATAGATACAAATATATG

ATGAATCATTAAAGAGGAGGTTATTACTAAGTGAAAGAAAAAGAAAAAAAAAAAGATCAAAACCAAACTTCGTAT

TCGAGCCTAAAAAACAGAATATAATGTTAAGCGTAAGCGATAGCAGTCAAGATGAAACCGTCAGCAATCAACCAT

CTACCATCAAAAGACAACAATGGGGTACCACCATCGTTAGTTTGACCAGGAACCAATAATTCGGAGTGGAAAGTA

CCGTTACCAGAATCAGCAGAACCATCTTCAATTTCGAAAGTAATGTGAGCTTCCTCGAAACCTAACCATCTGGCA

GTCAATGGCCACCAAGCCTTGTAAGTAGCTTCTTTGGCACAAAATAACAATCTGTCTAAATGTAAAGCAGAATCG

GTAGTCTTCAACCATTCTCTTTCTGGTGGCAAGGAAACGGAATCCAAGACACCTTCTGGCAAGGTAGCGTGTGGT

TCGGCGTCGATACCGATGGATCTGAATCTCATCTTATGAGCAACAGCAGCGGCTCTGTAACCGTCACAGTGAGTC

AAAGAACCGACAACACCTCTTGGCCAAATAGGAGCACCACGTTCACCTTTACCGATAGCGACTGGTGGTTCACCC

AATTCAGCCAAAGCTAATCTAGCACAATGTCTGGCACCAATAAAGTCTCTTCTTCTCTTTTCGACAGATTTGGCG

ATTAAATGTTCCTCGGCTGGGTGAGCTTTTAAGTCTTCAGGGTACTCTAACAATTCAGCAGACTCAACTCCAGCA

-continued

GGAAGAATGGTTTCAATCATTTTTGAGGGAATATTCAACTGTTTTTTTTTATCATGTTGATGCTCTGCATAATAA

TGCCCATAAATATTTCCGACCTGCTTTTATATCTTTGCTAGCCAAACTAACTGAACATAGCTACACATTATTTTC

AGCTTGGCTATTTTGTGAACACTGTATAGCCAGTCCTTCGGATCACGGTCAACAGTTGTCCGAGCGCTTTTTGGA

CCCTTTCCCTTATTTTTGGGTTAAGGAAAATGACAGAAAATATATCTAATGAGCCTTCGCTCAACAGTGCTCCGA

AGTATAGCTTTCCAAAAGGAGAGGCAAAGCAATTTAAGAATGTATGAACAAAATAAAGGGGAAAAATTACCCCCT

CTACTTTACCAAACGAATACTACCAATAATATTTACAACTTTTCCTTATGATTTTTTCACTGAAGCGCTTCGCAA

TAGTTGTGAGCGATATCAAAAGTAACGAAATGAACTTCGCGGCTCGTGCTATATTCTTGTTGCTACCGTCCATAT

CTTTCCATAGATTTTCAATCTTTGATGTCTCCATGGTGGTACAGAGAACTTGTAAACAATTCGGTCCCTACATGT

GACATGTATTCTGGCAGCGTATCAAGGCAGGTAATCGAAAGATGGCAAATAGCCTTGTCAAATTTCCTACGGAAT

GTTATTTTCATTACGTCCTTCTTTTTCAATGTACTTATTCATAAATGGGACACTATCTTGTTGCAAAAGGTACTT

TGTATTTTGGTATTAACATCTCGCCTATTTTTCATACAGAAACACTACTTATCGCTATCTATTTGATGTGGTATT

GCTTGGCCATGAGGATACCTTGAGCTACGTTTTGAACACGTGCATCCAACTTGTAGCCTTGTTGATCCAACTTAA

CCATTTCATCAGGAAACTTGTGCAACTCAACGCTAAAGCATTCGATAAATTCATTATCTTCCAATTGAGTAACTG

GTTTTTGGTTTTCAGGTAAACTCATATCAACTTCGACAGTAACCAGACAGAGGTTGGTGTTTGTGAAACCAGGAT

CGTTAAAAACTGTTGGGCTTTTAGAAATTATTTTACCACTGTAACCAGTCTCTTCTTTTAATTCTCTTAAGGCAG

CAGTGTCAATATCGGCGGTTTAAACGCGTGGCCGTGCCGTC

SEQ ID NO: 20
Length: 2942
Type:
Organism; artificial sequence
Other information: MS172561 sequence

GACGGCACGGCCACGCGTTTAAACCGCCATAATAAAATGGAAGCCGCGAGTACGAACAATGATGTGTTCTGGGAA

TACCTCGTCAAAACAAGACAATGGCAAGGATTTTCTTTCATCAGGCAGAAAGATCTGGATCTGAATGGCATCATT

TTGTGATGTGTAAAAGCGGGACCTTGTTATTTCGACTTTTTGCATCATGTTGATGCAATTTGCTACTTTTCCGAC

GGTGCGCTCCAACGGATGGGTATTTCCTTAATAACAAGGCATTTCTCTGGAAGTTGGCTTACTGTTTGAAATCAC

AGCCGGTCACAAAATAAAGTAAAAAAACTATCTCTCTCCACAAGAAGTAATTACAGGTTGTATACTACATATGAT

CGTATTTCTTTATGAACACTAAGGAGTTTCCCGCTGTGTACCGCAATATCCACACAAAAGGAAGGAAGAAACTTC

TGTGGCTTGACAGATAAATAACTGCAGTAGTCGGTGCGTACTAATTGTTTGGTCGTGTCTGAAAAATCTTGAATT

TTCCTCCCGCGTGCGAGATAAAAGGGTTGGCAATACCACCATATACATATCCATATCTAATCTTACTTATATGTT

GTGGAAATGTAAAGAGCCCCATTATCTTAGCCTAAAAAAACCTTCTCTTTGGAACTTTCAGTAATACGCTTAACT

GCTCATTGCTATATTGAAGTACGGATTAGAAGCCGCCGAGCGGGCGACAGCCCTCCGACGGAAGACTCTCCTCCG

TGCGTCCTGGTCTTCACCGGTCGCGTTCCTGAAACGCAGATGTGCCTCGCGCCGCACTGCTCCGAACAATAAAGA

TTCTACAATACTAGCTTTTATGGTTATGAAGAGGAAAAATTGGCAGTAACCTGGCCCCACAAACCTTCAAATCAA

CGAATCAAATTAACAACCATAGGATAATAATGCGATTAGTTTTTTAGCCTTATTTCTGGGGTAATTAATCAGCGA

AGCGATGATTTTTGATCTATTAACAGATATATAAATGCAAAAGCTGCATAACCACTTTAACTAATACTTTCAACA

TTTTCGGTTTGTATTACTTCTTATTCAAATGTCATAAAAGTATCAACAAAAAATTGTTAATATACCTCTATACTT

ACCTCCCGCGACCTCCAAAATCGAACTACCTTCACAATGCCCAGTAAATTGGCTATAACTTCCATGTCCTTGGGC

AGGTGTTATGCAGGCCATTCTTTCACAACTAAGTTAGACATGGCTAGGAAATATGGTTACCAGGGTTTGGAGTTG

TTTCATGAGGACTTAGCCGATGTCGCATACAGGTTGTCAGGTGAAACACCTAGTCCATGCGGTCCCAGTCCAGCT

GCTCAATTATCAGCCGCTAGACAGATATTGAGGATGTGCCAGGTTAGAAACATCGAAATAGTGTGCTTGCAACCC

TTTTCACAATATGATGGTTTATTGGATAGAGAGGAGCACGAGAGGAGGTTGGAGCAATTAGAGTTTTGGATTGAA

-continued

TTGGCCCACGAGTTGGATACTGACATCATTCAAATTCCAGCCAATTTCTTGCCCGCCGAAGAAGTCACAGAAGAT

ATTTCATTAATTGTGAGTGACTTACAGGAAGTTGCCGATATGGGTTTACAGGCAAACCCTCCAATAAGGTTTGTA

TATGAGGCATTATGCTGGTCCACTAGAGTTGACACTTGGGAGAGGTCTTGGGAAGTTGTCCAAAGAGTAAATAGA

CCTAACTTTGGCGTTTGCTTAGACACTTTTAACATCGCAGGTAGAGTTTATGCTGACCCCACAGTTGCCTCAGGC

AGAACACCAAACGCTGAAGAAGCAATTAGAAAGTCAATTGCCAGGTTGGTCGAAAGGGTCGATGTATCTAAAGTC

TTCTACGTTCAAGTAGTGGACGCCGAAAAGTTAAAGAAACCATTAGTTCCCGGTCATAGATTCTATGACCCTGAG

CAACCAGCCAGAATGTCATGGTCAAGAAATTGTAGGTTGTTCTACGGCGAAAAAGACAGAGGCGCTTACTTACCT

GTTAAAGAAATCGCTTGGGCTTTTTTCAATGGATTGGGCTTCGAAGGTTGGGTGTCCTTGGAATTATTTAACAGA

AGAATGTCAGATACTGGATTTGGAGTTCCAGAGGAGTTAGCTAGGAGAGGCGCCGTATCATGGGCCAAATTAGTT

AGAGATATGAAAATCACAGTGGATTCTCCAACTCAACAACAAGCTACACAGCAGCCTATTAGAATGTTGTCCTTA

TCTGCAGCCTTATAAAAAGCTTCGACACATACATAATAACTCGATAAGGTATGGTATCTTATTTCATTGTGGGGT

AGTTTTTACGAAAAAAATGAAAAGTTGTAAGTATAGTATATATTTTTTTTCTATGTAAGTTTTATAACCTGCAGG

CCGCGAGCGCCGATAGTACTCCCCTACGATTTTAGATACTTTAGAGAGCCCACCTTCAGAATCGGAAGGAGGATA

ATTTTGTAAAGCCCTTCTGTTTTTTCTCTTGCATAACTTATATTTCCACATCAAAAAGTAGTGTGCTAAGAAAAA

GGAGACGAGAAAAAGGATTACGGCACTCTCTGCATCTAGACATATACCAAAAGTTGGGTTTGCTCACGAAAATAC

CATAATTGTGGTGTCAAAAAAATCCTGCCTCATAATACCACTGCAGCAATTGTGGATGACTAAAAAATAACTTGC

ATTCCACGATGTTATTTTACTTTATAAAGCACCTGCAATTTTTTTTTTTGTATTAACTCATCGAGTATGTCTGAT

GTGTAAACTGAACCAGGCTTAATATCGTTTCTAATTCTTGTTGTGAGAAAACTTTCCTGCCTAGTGTATTTCGTC

AGGGCGAACCTTCGGATAGGCACCGAACTCCGAGATTCTTGCTCCAATTTAAGAAATAAGCTTTCGGTGTTTAAA

CCCCAGCGCCTGGCGGG

SEQ ID NO: 21
Length: 8441
Type:
Organism: artificial sequence
Other information: MS167660 sequence

GACGGCACGGCCACGCGTTTAAACCGCCAAAAACTCACAAGAAGTTCGGTGTCCTTATTTGCGATGGGAATTGCT

AATATCATATCACCACAAATATGGAGAGAGAAGGACTCTCCTCGCTTTTTACCTGCCTGGATTGTTCAAATCGTT

TTATCATTCTCTCTTGCACCAGCCATTTTGTTACTGATCCATTTCATACTAAAAAGAAGGAATAATCAAAGACTA

AAAAATTATGACGAAAATTTACAAAATTATTTGGACAGAATTCAACTCATTGAAAGCGAAAATCCTTCTTCCATT

GAAGAAGGGAAAGTGGTAACCCACGAGAACAATTTGGCAGTCTTTGATTTGACTGATTTAGAAAACGAAACTTTT

ATATATCCTTTGTAAATATTGATGTTTTGTTGTGTAAATGTTCTATCTGACACTTAATAATTAGAAAATTAATTT

TTTAAACTTTCCGGCTGCAAGAAAGAGGAACTGTGTCTCTTTGAAAGGCACAATTTCCCAAAGAATCATTTACAA

TGCGGAGATTACCGAGCATTCTGGGTAGTGAGTTCTATTCACGCAATCGGTAGTATCAAAGAAGATTATTTGGGT

GCTATTTAATCACTTGTTACTCCGCAACGCTTTTCTGAACGCCCGCCTTCGCCTTTCATTATCATTCTCATCCCA

AAAGAACTGTGCATGTTATTTGCAATACTTCATATACGCTCTGTATTATTAATAGTATCATTAATTACGTCAATT

GAAATTCAAAATATCATCTTTGACAGTAACATCTATCCTCTTAGACAACTAGGGCCATTGCAGTGTCTCGAAACC

ATTAATATCACTGAAAAGATGAAAAGAAAGGCAAATATATATTGATCACTAATTTTCTAAGCTAAAGAATCTATT

CCCCCTCTGTTAAATGGAATTGTGTGAAATAAAATATTATAAAATCAGAACTTTGGGGGGGAAACATAAAAAAAT

GAGAAAAAGAAAACGAACTAACTAATGTTTAAGTAAAAGAACAAAAAGGTAGACCAATGTAGCGCTCTTACTTTA

TTAGACTAATCTTCTACACAAGGTAACACCATCACCGATGGAAACTTGGGAGATTTCAATTCTTGGATCGGAAGC

CAATCTTTTGTTCAATTCCATCAAAGCCTTACGGTTAACTCTTAAGTGAACTGGGACAGTCTCTTCCTCTTCAGC

-continued

AACGAAACCGAACCATAAGGTGTTATCGAAAGCAATGATACCACCAACTTTGACCAACTTCATCAATCTTTCCAA

AGCGTGGACGTAATTTGGCTTATCAGCGTCAACGAAAGCGAAGTCAAATTCTGGCTTTGGGTTTTCAGATAACAA

CTTGTCTAAGGCTTGCAAACCGTCGGATTGGATAAAGTTAATTTTGTGATCGATACCGGCGTTCTTGATGAATTC

CAAACCCATTTCGTAAGCTTCTTTATCGATATCAATAGCAGTAATTCTACCGTCTTCAGGCAAAGCCAAGGCGGT

GGTTAACAAAGAGTAACCAGTGAAAACACCCAATTCCAAGGTGTTCTTAGCGTTCATCATCTTCAACAACATGGA

CAAGAAATGACCTTCGTCAACAGGGACTTCCATCTCGGACAAGTTACCGTACTTATGAACGGTAGCTTCTCTTAA

CTTCTTCAATTCTTCGTGTTCTCTTGGGTAAGCGGAAGTTTCAAAGATGTACTTTTTCAATTCTTCGTTCTTCAA

GATACCCTTAGATGGTATAAGATTTTCCATGTCTGGTTCCATTGTAAAGTTAGTTGGTTGCGCGACTTCGGGTGG

GGTATGTTAATCTTGTGTTTACTTAACTATTGCTATTCTTGATGATAATTGAATAAGGTGCATAATGAAGAGCAA

TTCACAACACCAAATTTTCAATCCAATTACTGATTGTTTATATATGTCTACAAAACTAATCCTATCTCCACATTT

TAGCCTGCGAAATGTTTGTTTTTTAAACAATAGCTCTCCAGAACATTGTATAATTTAAGAATATGTGCACAGTTA

ACTTTCTAGCAGGAGTATAATGCCATTTGCTCCCCATCTTGAGATGGGAAGGGCTTAACTAATCTCGGTTCGGAG

TGATCCGCCCCGATACTGCCTTCTGCCTTAATATCGTCCAAGGCACATGGACCCCTGAACGGCGCAGATATCTCC

GCACGGACGAAAGACCGCCGGTGCCTTCCTGAGGCAACCGCCCCTTTCGAATATAGATCACGTGACCCATTTTTTA

GCTACTAATAGAAAAAGAAATTGCAACCTACTTAAGCCATTCCGGAAGGAAGCTTTCCGATCACATGTAGGGACC

GAATTGTTTACAAGTTCTCTGTACCACCATGGAGACATCAAAGATTGAAAATCTATGGAAAGATATGGACGGTAG

CAACAAGAATATAGCACGAGCCGCGAAGTTCATTTCGTTACTTTTGATATCGCTCACAACTATTGCGAAGCGCTT

CAGTGAAAAAATCATAAGGAAAAGTTGTAAATATTATTGGTAGTATTCGTTTGGTAAAGTAGAGGGGGTAATTTT

TCCCCTTTATTTTGTTCATACATTCTTAAATTGCTTTGCCTCTCCTTTTGGAAAGCTATACTTCGGAGCACTGTT

GAGCGAAGGCTCATTAGATATATTTTCTGTCATTTTCCTTAACCCAAAAATAAGGGAAAGGGTCCAAAAAGCGCT

CGGACAACTGTTGACCGTGATCCGAAGGACTGGCTATACAGTGTTCACAAAATAGCCAAGCTGAAAATAATGTGT

AGCTATGTTCAGTTAGTTTGGCTAGCAAAGATATAAAAGCAGGTCGGAAATATTTATGGGCATTATTATGCAGAG

CATCAACATGATAAAAAAAAACAGTTGAATATTCCCTCAAAAATGGCTATAAACAACGAAGGCCAACAACAAAAC

CAAAACCAACAATTGATCGGTCACAAAGATTTGGCTCATAAGACCTTGTTACAATCTGACGCCTTATACCAATAC

ATTTTGGATACCTCTGTTCACCCAAGAGAACACCCATGTTTGAAGGAATTGCGTGAAATGACTGAAAAGCACCCA

AGAAACTTGATGGCCACCCCTGCTGATGAAGGTCAATTGTTGTCTATGTTAATCAAATTGATCAATGCTAAGAAC

ACCTTAGAAATTGGTGTTTTTACCGGTTACTCTTTGTTGTCTACTGCTTTAGCTTTGCCATCTGACGGTAAGATT

TTGGCTTTGGACGTTTCTCGTGAATACTACGAATTGGGTTTACCAATTATCGAAAAGGCTGGTGTCGCTCACAAG

ATCGACTTTCGTGAAGGTCCTGCTTTGCCATTATTGGACCAATTATTGCAAGATGTCACCAAGGAAAACAACAAG

GGTATTTTTGATTTTGTTTTCGTCGATGCCGATAAGGACAACTATTTAAACTACCACAAGAGAGTTATCGATTTG

GTCAAGATTGGTGGTTTGATCGGTTACGACAACACCTTATGGTCCGGTTCCGTTGTCGCTCCACCAGACGCTCCA

TTAATGGATTATGTTAAGCATTACAGACCACATGTTATTGCCTTGAACAAGTACTTGGCTCAAGACTCCCGTATT

GAAATTTGTCAATTGCCAGTCGGTGATGGTATCACCTTGTGTAGAAGAACCACTTAAGAGTATGCTTCTCTTTTT

TTTTGTAGGCCAGTGATAGGAAAGAACAATAGAATATAAATACGTCAGAATATAATAGATATGTTTTTATATTTA

GACCTCGTACATAGGAATAATTGACGTTTTTTTTGGCCAACATTTGAAATTTTTTTTTGTTACCTCGCGCTGAGC

CCAAACGGGCTCCACTACCCGAACGCGATCGCCGACGCCGCCGATGCTGATTATCAGGGTAAAAATGTCGTCATT

ATCGGCCTGGGCCTCACCGGGCTTTCCTGCGTGGACTTTTTCCTCGCTCGCGGTGTGACGCCGCGCGTTATGGAT

ACGCGTATGACACCGCCTGGCCTGGATAAATTACCCGAAGCCGTAGAACGCCACACGGGCAGTCTGAATGATGAA

TGGCTGATGGCGGCAGATCTGATTGTCGCCAGTCCCGGTATTGCACTGGCGCATCCATCCTTAAGCGCTGCCGCT

GATGCCGGAATCGAAATCGTTGGCGATATCGAGCTGTTCTGTCGCGAAGCACAAGCACCGATTGTGGCGATTACC

GGTTCTAACGGCAAAAGCACGGTCACCACGCTAGTGGGTGAAATGGCGAAAGCGGCGGGGGTTAACGTTGGTGTG

-continued

GGTGGCAATATTGGCCTGCCTGCGTTGATGCTACTGGATGATGAGTGTGAACTGTACGTGCTGGAACTGTCGAGC

TTCCAGCTGGAAACCACCTCCAGCTTACAGGCGGTAGCAGCGACCATTCTGAACGTGACTGAAGATCATATGGAT

CGCTATCCGTTTGGTTTACAACAGTATCGTGCAGCAAAACTGCGCATTTACGAAAACGCGAAAGTTTGCGTGGTT

AATGCTGATGATGCCTTAACAATGCCGATTCGCGGTGCGGATGAACGCTGCGTCAGCTTTGGCGTCAACAATCGG

CGGCGTCGGCGATCGCGTTCGGGTAGTGGAGCCCGTTTGGGCTCAGCGCGAGGTAACAAAAAAAAATTTCAAATG

TTGGCCAAAAAAAACGTCAATTATTCCTATGTACGAGGTCTAAATATAAAAACATATCTATTATATTCTGACGTA

TTTATATTCTATTGTTCTTTCCTATCACTGGCCTACAAAAAAAAAGAGAAGCATACTCTTAAGTGGTTCTTCTAC

ACAAGGTGATACCATCACCGACTGGCAATTGACAAATTTCAATACGGGAGTCTTGAGCCAAGTACTTGTTCAAGG

CAATAACATGTGGTCTGTAATGCTTAACATAATCCATTAATGGAGCGTCTGGTGGAGCGACAACGGAACCGGACC

ATAAGGTGTTGTCGTAACCGATCAAACCACCAATCTTGACCAAATCGATAACTCTCTTGTGGTAGTTTAAATAGT

TGTCCTTATCGGCATCGACGAAAACAAAATCAAAAATACCCTTGTTGTTTTCCTTGGTGACATCTTGCAATAATT

GGTCCAATAATGGCAAAGCAGGACCTTCACGAAAGTCGATCTTGTGAGCGACACCAGCCTTTTCGATAATTGGTA

AACCCAATTCGTAGTATTCACGAGAAACGTCCAAAGCCAAAATCTTACCGTCAGATGGCAAAGCTAAAGCAGTAG

ACAACAAAGAGTAACCGGTAAAAACACCAATTTCTAAGGTGTTCTTAGCATTGATCAATTTGATTAACATAGACA

ACAATTGACCTTCATCAGCAGGGGTGGCCATCAAGTTTCTTGGGTGCTTTTCAGTCATTTCACGCAATTCCTTCA

AACATGGGTGTTCTCTTGGGTGAACAGAGGTATCCAAAATGTATTGGTATAAGGCGTCAGATTGTAACAAGGTCT

TATGAGCCAAATCTTTGTGACCGATCAATTGTTGGTTTTGGTTTTGTTGTTGGCCTTCGTTGTTTATAGCCATTT

TTGAGGGAATATTCAACTGTTTTTTTTTATCATGTTGATGCTCTGCATAATAATGCCCATAAATATTTCCGACCT

GCTTTTATATCTTTGCTAGCCAAACTAACTGAACATAGCTACACATTATTTTCAGCTTGGCTATTTTGTGAACAC

TGTATAGCCAGTCCTTCGGATCACGGTCAACAGTTGTCCGAGCGCTTTTTGGACCCTTTCCCTTATTTTTGGGTT

AAGGAAAATGACAGAAAATATATCTAATGAGCCTTCGCTCAACAGTGCTCCGAAGTATAGCTTTCCAAAAGGAGA

GGCAAAGCAATTTAAGAATGTATGAACAAAATAAAGGGGAAAAATTACCCCCTCTACTTTACCAAACGAATACTA

CCAATAATATTTACAACTTTTCCTTATGATTTTTTCACTGAAGCGCTTCGCAATAGTTGTGAGCGATATCAAAAG

TAACGAAATGAACTTCGCGGCTCGTGCTATATTCTTGTTGCTACCGTCCATATCTTTCCATAGATTTTCAATCTT

TGATGTCTCCATGGTGGTACAGAGAACTTGTAAACAATTCGGTCCCTACATGTGATCGGAAAGCTTCCTTCCGGA

ATGGCTTAAGTAGGTTGCAATTTCTTTTTCTATTAGTAGCTAAAAATGGGTCACGTGATCTATATTCGAAAGGGG

CGGTTGCCTCAGGAAGGCACCGGCGGTCTTTCGTCCGTGCGGAGATATCTGCGCCGTTCAGGGGTCCATGTGCCT

TGGACGATATTAAGGCAGAAGGCAGTATCGGGGCGGATCACTCCGAACCGAGATTAGTTAAGCCCTTCCCATCTC

AAGATGGGGAGCAAATGGCATTATACTCCTGCTAGAAAGTTAACTGTGCACATATTCTTAAATTATACAATGTTC

TGGAGAGCTATTGTTTAAAAAACAAACATTTCGCAGGCTAAAATGTGGAGATAGGATTAGTTTTGTAGACATATA

TAAACAATCAGTAATTGGATTGAAAATTTGGTGTTGTGAATTGCTCTTCATTATGCACCTTATTCAATTATCATC

AAGAATAGCAATAGTTAAGTAAACACAAGATTAACATACCCCACCCGAAGTCGCGCAACCAACTAACTTTACAAT

GGAACCAGACATGGAAAATCTTATACCATCTAAGGGTATCTTGAAGAACGAAGAATTGAAAAAGTACATCTTTGA

AACTTCCGCTTACCCAAGAGAACACGAAGAATTGAAGAAGTTAAGAGAAGCTACCGTTCATAAGTACGGTAACTT

GTCCGAGATGGAAGTCCCTGTTGACGAAGGTCATTTCTTGTCCATGTTGTTGAAGATGATGAACGCTAAGAACAC

CTTGGAATTGGGTGTTTTCACTGGTTACTCTTTGTTAACCACCGCCTTGGCTTTGCCTGAAGACGGTAGAATTAC

TGCTATTGATATCGATAAAGAAGCTTACGAAATGGGTTTGGAATTCATCAAGAACGCCGGTATCGATCACAAAAT

TAACTTTATCCAATCCGACGGTTTGCAAGCCTTAGACAAGTTGTTATCTGAAAACCCAAAGCCAGAATTTGACTT

CGCTTTCGTTGACGCTGATAAGCCAAATTACGTCCACGCTTTGGAAAGATTGATGAAGTTGGTCAAAGTTGGTGG

TATCATTGCTTTCGATAACACCTTATGGTTCGGTTTCGTTGCTGAAGAGGAAGAGACTGTCCCAGTTCACTTAAG

-continued

AGTTAACCGTAAGGCTTTGATGGAATTGAACAAAAGATTGGCTTCCGATCCAAGAATTGAAATCTCCCAAGTTTC

CATCGGTGATGGTGTTACCTTGTGTAGAAGATTAGTCTAATAAAGTAAGAGCGCTACATTGGTCTACCTTTTTGT

TCTTTTACTTAAACATTAGTTAGTTCGTTTTCTTTTTCTCATTTTTTTATGTTTCCCCCCCAAAGTTCTGATTTT

ATAATATTTTATTTCACACAATTCCATTTAACAGAGGGGGAATAGATTCTTTAGCTTAGAAAATTAGTGATCAAT

ATATATTTGCCTTTCTTTTCATCTTTTCAGTGATATTAATGGTTTCGAGACACTGCAATGGCCCTAGTTGTCTAA

GAGGATAGATGTTACTGTCAAAGATGATATTTTGAATTTCAATTGACGTAATTAATGATACTATTAATAATACAG

AGCGTATATGAAGTATTGCAAATAACATGCACAGTTCTTTTGGGATGAGAATGATAATGAAAGGCGAAGGCGGGC

GTTCAGAAAAGCGTTGCGGAGTAACAAGTGATTAAATAGCACCCAAATAATCTTCTTTGATACTACCGATTGCGT

GAATAGAACTCACTACCCAGAATGCTCGGTAATCTCCGAACATATTGATGTTTTTCGTGGGTAACCATAGTTCTT

GGAATGTCAACTGAGGGTATTTGCACTTCAAAAAAAAAAATTTATTAAATGAGACTATATACAGTGAGCACAACC

TGTCTAATACAACGGCAAAAATTATATACATTGGTAGATTTTCAAAATTGAACTCTTTGTGCTAAAGAATTGTCA

CAACAGTTTAAAAAATAGTTTGAATTCTTCAAATTGACCCCATATTAATAAGACCTGATGCGATTCCGGTCTCAC

CCAGATTAGAGAGGGAATTTAATTTTCTTAGGACCGTAGCTACCAAAAATCTTTGTGTGGTATTGATTATATGAT

CGTGCTTGCGAAAAAAATAGAAGACTAAAAGTAGCATTAGTTTACTAACTTTCTCCTCGTATCTTTCAAATTTGT

ATTCCCCTCAAAAGTTACTCAGGTTAGGGAAAATTCCAAGTAGCTTATCAAGATCAATTGCCATTAGTTGATTCA

AGGCTTCATTGTCGGCGGTTTAAACGCGTGGCCGTGCCGTC

SEQ ID NO: 22
Length: 2855
Type
Organism: artificial sequence
Other information: MS188586 sequence

GACGGCACGGCCACGCGTTTAAACCGCCTTATGGCAGCTGCTGTTGACTGCGGTGGCGTCCCGTTTCCACACCGT

ACGTGAGCACATGTCTGGATTGCTAGCTGCGTACATAGTGACAGGCCTTGTCTACGCTCGCGACGCAGCCGCGCT

ACGTCCAGTATGACTCAGGAAAAGTTGGCGATAGACCACGAGCGACTGAAAAAATAACAGCGACTTTTCTCCCGG

TAGCGGGCCGTCGTTTAGTCATTCTATCCCTCGGATTATAGACTGTGAATATTGCATATGCAACTTTGACTCAAA

TTTTTCCAAAATTTGATATATATATATATATATATATGTTTGTATGTATATATATATATACGTATATATATCATA

TATACGAAAAGTAGAAAAAAAAAGGTGATATTTCGCTCGTGGAAAAGCTAATGCCACAGCTTGTGTTTCGTGTAG

TTTGCCTTGCTCCCCTTGATTGAAATAGTCTCCCTAAACTAAAGTTATCAGCAAACAGAACCACCACAGTTACTA

CTACAACCACATCGCAATATGAAGATCACAGAAAAATTAGAGCAACATAGACAGACCTCTGGCAAGCCCACTTAC

TCATTCGAGTACTTCGTCCCGAAGACTACACAAGGTGTACAGAACCTGTATGACCGGATGGACCGGATGTACGAG

GCTTCTTTGCCCCAATTTATTGACATCACCTGGAATGCAGGCGGTGGACGGTTGTCACATCTGTCCACGGACTTG

GTTGCGACAGCGCAGTCTGTGCTTGGTTTGGAAACGTGCATGCACCTTACCTGCACCAATATGCCCATTTCGATG

ATTGACGACGCTTTAGAAAACGCTTATCACTCCGGTTGCCAGAACATCCTAGCGCTGAGAGGAGATCCTCCTAGG

GACGCAGAAAACTGGACTCCCGTTGAAGGTGGCTTCCAGTATGCCAAGGACTTGATTAAGTATATCAAGTCCAAG

TACGGTGACCATTTCGCTATCGGCGTTGCCGGCTACCCGGAGTGCCATCCGGAGTTGCCTAACAAAGACGTGAAG

CTTGATCTCGAGTATTTGAAGCAGAAGATCGACGCCGGCGGCGACTTCATCATCACTCAGATGTTTTACGATGTT

GATAATTTCATCAACTGGTGTTCCCAAGTTAGAGCTGCGGGCATGGACGTGCCCATTATTCCCGGGATCATGCCG

ATCACTACCTACGCGGCCTTCTTGAGAAGGGCCCAATGGGGCCAAATCTCCATCCCTCAACATTTCTCGTCCCGA

TTGGATCCTATCAAGGACGATGACGAGTTGGTCCGTGATATCGGAACTAACTTGATCGTGGAAATGTGTCAAAAA

TTGCTCGACAGTGGTTACGTTTCTCACTTGCACATCTACACCATGAACTTGGAAAAAGCGCCTCTCATGATTCTG

GAAAGATTGAACATTCTACCTACGGAATCAGAGTTCAATGCACATCCATTGGCCGTGTTGCCATGGAGAAAATCT

-continued

TTGAATCCAAAGCGTAAAAACGAGGAAGTCAGACCTATCTTCTGGGCGAATAGACCCAAATCTTATATTTCACGT

ACTAAGGGTTGGAATGACTTTCCACACGGTAGATGGGGTGATTCTCACTCCGCCGCTTACTCTACTTTATCCGAC

TACCAATTCGCTCGTCCAAAGGGTAGAGACAAGAAGTTGCAACAAGAATGGGTCGTTCCTTTGAAATCTATCGAA

GACGTCCAAGAAAAGTTCAAGGAATTGTGTATTGGTAACTTAAAGTCTTCTCCATGGTCTGAATTGGATGGTTTG

CAACCAGAAACCAAGATTATCAACGAGCAATTGGGTAAGATTAACTCTAACGGTTTCTTGACCATTAACTCTCAA

CCATCTGTTAACGCTGCTAAGTCCGATTCTCCAGCTATTGGTTGGGGTGGTCCAGGTGGTTACGTTTACCAAAAA

GCTTACTTGGAATTCTTCTGTTCCAAGGATAAGTTGGACACCTTGGTCGAAAAGTCCAAGGCCTTCCCTTCTATC

ACTTACATGGCTGTTAACAAGTCTGAAAACTGGGTTTCTAACACTGGTGAATCTGATGTTAACGCCGTTACTTGG

GGTGTCTTCCCAGCTAAGGAAGTCATCCAACCAACCATTGTCGACCCAGCTTCCTTCAAAGTTTGGAAGGATGAA

GCTTTCGAAATCTGGTCTAGATCTTGGGCTAACTTGTATCCAGAAGATGACCCATCTCGTAAGTTGTTAGAAGAG

GTTAAGAACTCTTACTACTTGGTTTCTTTAGTCGATAACAACTACATTAACGGTGATATCTTCTCTGTTTTTGCC

TAATAACACAGACAACGATAACAGTTCTTTAACAGAATTGTCAACCCCCCCTCTTTGCATTACATTCAACATTAC

ATTGCATTTTTTTTTTTTTATTCACTATTATTATGGTTCTTCTTTTTTACCAGATTTTGCTCCTTCCTTTTCCAT

TGTTTTACCATTCTTTTTTAACTAGCATTTCAACATGTGTTTGGTTAACACCCCTTCTTTTTTTTCAGGAAAATC

CTTTCATTTCTTCTCATACTTTCAACAAAGTTTTTTAAAGGTACTTTAAAATAGTTCAACACCCTCTTCCTTCAT

TTATTTATTCTCTTCATATTCAACATACTCGAAAAGGAAGAACACTAAAAGTACTTACATTTTCACATGTATGTA

TACCTATATATATATATATATATACTCTTATAGATATATTTACAAATTAAAGGAAAAAATAATAAAATAACCTCC

CTGTCACAAGTTAAAACACGGCCCCATCACTTATAAATAGTCTCGACTCGTGCGGTGTTTAAACCCCAGCGCCTG

GCGGG

SEQ ID NO: 23
Length: 11309
Type;
Organism: artificial sequence
Other information: MS173680 sequence

GACGGCACGGCCACGCGTTTAAACCGCCGAAATCACCTCCAAAGTTATGTTGCCGATTAGGCAAATACTCTAAAA

GTATAGTACTAAAGAACTACGTAAAGGTAAAATAAAACACCTGAATTTCATTTCTGAAATGAAGTACCATCATGA

AATATGATGAAAGTCAAGACTCGTTGGGTCAATATACACCACAAAAAAAGGTACACACGAATGGTTTAACCCTTT

CGGTTCCTTCTGTAAATCGAAAAATGCCCTTTATACAGCGGGTTGGTCTCCCATCAAAGTTGAGAAGCGATTAGA

AATTAGGTTACCTAATGAATCCATAAATAAATGGAAAACGCTATTTTGTTCGAACGATGGAATAAAAATATGAAC

GGGTGTCATTGAAATTCGGTGTATTTTTTGATCGGGCCTGATCTGGCTCGGGTTTGGCACAATTTGGCTTGGTTA

GTTCGGCAAAGCTTATTTAAAGAACCTTTTTGGATAGCCAATTGAGAGACTTGAAATAGAAAGATCGTAAGTATT

TTTACGCTCGTCCAACGCCGGCGGACCTATGAAGATCACAGAAAAATTAGAGCAACATAGACAGACCTCTGGCAA

GCCCACTTACTCATTCGAGTACTTCGTCCCGAAGACTACACAAGGTGTACAGAACCTGTATGACCGGATGGACCG

GATGTACGAGGCTTCTTTGCCCCAATTTATTGACATCACCTGGAATGCAGGCGGTGGACGGTTGTCACATCTGTC

CACGGACTTGGTTGCGACAGCGCAGTCTGTGCTTGGTTTGGAAACGTGCATGCACCTTACCTGCACCAATATGCC

CATTTCGATGATTGACGACGCTTTAGAAAACGCTTATCACTCCGGTTGCCAGAACATCCTAGCGCTGAGAGGAGA

TCCTCCTAGGGACGCAGAAAACTGGACTCCCGTTGAAGGTGGCTTCCAGTATGCCAAGGACTTGATTAAGTATAT

CAAGTCCAAGTACGGTGACCATTTCGCTATCGGCGTTGCCGGCTACCCGGAGTGCCATCCGGAGTTGCCTAACAA

AGACGTGAAGCTTGATCTCGAGTATTTGAAGCAGAAGATCGACGCCGGCGGCGACTTCATCATCACTCAGATGTT

TTACGATGTTGATAATTTCATCAACTGGTGTTCCCAAGTTAGAGCTGCGGGCATGGACGTGCCCATTATTCCCGG

GATCATGCCGATCACTACCTACGCGGCCTTCTTGAGAAGGGCCCAATGGGGCCAAATCTCCATCCCTCAACATTT

-continued

CTCGTCCCGATTGGATCCTATCAAGGACGATGACGAGTTGGTCCGTGATATCGGAACTAACTTGATCGTGGAAAT

GTGTCAAAAATTGCTCGACAGTGGTTACGTTTCTCACTTGCACATCTACACCATGAACTTGGAAAAAGCGCCTCT

CATGATTCTGGAAAGATTGAACATTCTACCTACGGAATCAGAGTTCAATGCACATCCATTGGCCGTGTTGCCATG

GAGAAAATCTTTGAATCCAAAGCGTAAAAACGAGGAAGTCAGACCTATCTTCTGGGCGAATAGACCCAAATCTTA

TATTTCACGTACTAAGGGTTGGAATGACTTTCCACACGGTAGATGGGGTGATTCTCACTCCGCCGCTTACTCTAC

TTTATCCGACTACCAATTCGCTCGTCCAAAGGGTAGAGACAAGAAGTTGCAACAAGAATGGGTCGTTCCTTTGAA

ATCTATCGAAGACGTCCAAGAAAAGTTCAAGGAATTGTGTATTGGTAACTTAAAGTCTTCTCCATGGTCTGAATT

GGATGGTTTGCAACCAGAAACCAAGATTATCAACGAGCAATTGGGTAAGATTAACTCTAACGGTTTCTTGACCAT

TAACTCTCAACCATCTGTTAACGCTGCTAAGTCCGATTCTCCAGCTATTGGTTGGGGTGGTCCAGGTGGTTACGT

TTACCAAAAAGCTTACTTGGAATTCTTCTGTTCCAAGGATAAGTTGGACACCTTGGTCGAAAAGTCCAAGGCCTT

CCCTTCTATCACTTACATGGCTGTTAACAAGTCTGAAAACTGGGTTTCTAACACTGGTGAATCTGATGTTAACGC

CGTTACTTGGGGTGTCTTCCCAGCTAAGGAAGTCATCCAACCAACCATTGTCGACCCAGCTTCCTTCAAAGTTTG

GAAGGATGAAGCTTTCGAAATCTGGTCTAGATCTTGGGCTAACTTGTATCCAGAAGATGACCCATCTCGTAAGTT

GTTAGAAGAGGTTAAGAACTCTTACTACTTGGTTTCTTTAGTCGATAACAACTACATTAACGGTGATATCTTCTC

TGTTTTTGCCTAATGTAAAGTTAGTTGGTTGCGCGACTTCGGGTGGGGTTACTTTTTTTTTGGATGGACGCAAAG

AAGTTTAATAATCATATTACATGGCAATACCACCATATACATATCCATATCTAATCTTACTTATATGTTGTGGAA

ATGTAAAGAGCCCCATTATCTTAGCCTAAAAAAACCTTCTCTTTGGAACTTTCAGTAATACGCTTAACTGCTCAT

TGCTATATTGAAGTACGGATTAGAAGCCGCCGAGCGGGCGACAGCCCTCCGACGGAAGACTCTCCTCCGTGCGTC

CTGGTCTTCACCGGTCGCGTTCCTGAAACGCAGATGTGCCTCGCGCCGCACTGCTCCGAACAATAAAGATTCTAC

AATACTAGCTTTTATGGTTATGAAGAGGAAAAATTGGCAGTAACCTGGCCCCACAAACCTTCAAATCAACGAATC

AAATTAACAACCATAGGATAATAATGCGATTAGTTTTTTAGCCTTATTTCTGGGGTAATTAATCAGCGAAGCGAT

GATTTTTGATCTATTAACAGATATATAAATGCAAAAGCTGCATAACCACTTTAACTAATACTTTCAACATTTTCG

GTTTGTATTACTTCTTATTCAAATGTCATAAAAGTATCAACAAAAAATTGTTAATATACCTCTATACTTACCTCC

CGCGACCTCCAAAATCGAACTACCTTCACAATGGTTCAATCTGCTGTCTTAGGGTTCCCAAGAATCGGTCCAAAC

AGAGAATTAAAGAAGGCCACTGAAGGTTACTGGAACGGTAAAATCACTGTCGATGAATTATTCAAAGTCGGTAAG

GATTTGAGAACTCAAAACTGGAAGTTGCAAAAGGAGGCTGGTGTTGATATCATCCCATCCAATGACTTCTCCTTT

TACGACCAAGTTTTGGATTTGTCTTTGTTGTTCAATGTCATTCCAGACCGTTACACTAAGTACGATCTATCTCCA

ATCGACACTTTGTTTGCTATGGGTAGAGGTTTACAAAGAAAGGCCACTGAAACTGAAAAGGCTGTCGACGTCACT

GCTTTGGAAATGGTTAAATGGTTCGACTCTAACTACCATTACGTTAGACCAACTTTCTCCAAGACCACTCAATTT

AAGTTGAACGGCCAAAAGCCAGTTGACGAATTTTTGGAAGCCAAGGAGTTAGGTATTCACACTAGACCTGTCTTG

TTAGGTCCAGTTTCTTACTTATTCTTGGGTAAGGCTGACAAGGATTCTCTAGATTTGGAACCATTGTCCCTATTG

GAACAATTGTTGCCTCTATACACTGAAATCCTATCTAAATTGGCTTCTGCTGGTGCCACTGAAGTTCAAATTGAC

GAACCTGTCTTAGTTTTGGACTTGCCTGCCAACGCCCAAGCCGCCATTAAGAAGGCTTACACTTACTTCGGTGAA

CAAAGCAATCTACCAAAGATTACTTTGGCTACTTACTTCGGTACCGTTGTCCCTAACTTAGACGCCATCAAGGGC

TTGCCAGTTGCTGCCTTACACGTTGACTTTGTTAGAGCTCCAGAACAATTTGATGAAGTCGTTGCCGCCATTGGT

AACAAACAAACCTTGTCCGTTGGTATTGTTGATGGTAGAAACATTTGGAAGAATGATTTCAAGAAGTCTTCCGCT

ATCGTTAACAAGGCTATTGAAAAGTTGGGTGCTGACAGAGTCGTTGTTGCCACTTCTTCTTCTCTATTGCACACA

CCAGTTGACTTGAACAACGAAACCAAGTTGGACGCTGAAATCAAGGGCTTTTTCTCTTTCGCCACTCAAAAATTG

GATGAAGTTGTTGTGATCACCAAGAACGTTTCCGGTCAAGACGTTGCTGCTGCCCTAGAAGCTAACGCTAAATCT

GTTGAATCCAGAGGTAAATCCAAGTTTATCCACGATGCTGCCGTTAAGGCCAGAGTTGCCTCTATCGACGAAAAA

ATGTCTACTAGAGCAGCTCCATTTGAACAAAGATTGCCTGAACAACAAAAAGTCTTCAACTTGCCATTGTTCCCA

-continued

ACAACAACTATTGGTTCCTTCCCTCAAACCAAGGACATCAGAATTAACAGAAACAAATTCAACAAGGGTACCATC

TCTGCTGAAGAATATGAAAAATTCATCAATTCTGAAATTGAAAAGGTCATCAGATTCCAAGAAGAAATTGGTTTG

GATGTCTTAGTCCACGGTGAACCAGAAAGAAACGATATGGTTCAATACTTCGGTGAACAAATCAACGGTTATGCT

TTCACTGTTAACGGTTGGGTTCAATCTTACGGTTCCAGATATGTCAGACCACCAATTATTGTTGGTGACTTGTCC

AGACCAAAGGCTATGTCCGTCAAGGAATCTGTTTACGCTCAATCCATCACTTCTAAGCCAGTAAAGGGTATGTTG

ACTGGTCCAATTACCTGTTTGAGATGGTCTTTCCCAAGAGACGATGTCGACCAAAAAACTCAAGCTATGCAATTA

GCTTTGGCTTTGAGAGATGAAGTCAATGATTTGGAAGCTGCCGGTATCAAGGTTATCCAAGTTGATGAACCAGCT

TTAAGAGAAGGTTTACCATTGAGAGAAGGTGCTGAGAGATCTGCTTACTACACCTGGGCTGCCGAAGCTTTCAGA

GTTGCTACTTCTGGTGTTGCTAACAAGACTCAAATACACTCTCATTTCTGTTACTCTGACTTGGATCCAAACCAT

ATCAAGGCTTTGGATGCTGATGTTGTTTCCATCGAATTCTCTAAGAAGGACGATGCTAACTACATTGCTGAATTC

AAAAACTATCCAAACCACATTGGTCTGGGTTTATTCGATATTCATTCTCCAAGAATTCCATCAAAGGATGAATTT

ATCGCCAAGATTTCAACCATCTTGAAGAGCTACCCAGCTGAAAAGTTCTGGGTTAACCCAGACTGTGGTTTGAAG

ACTAGAGGCTGGGAAGAAACTAGATTGTCTTTGACTCATATGGTCGAAGCCGCCAAGTACTTCCGTGAACAATAC

AAGAATTAAGGTTTTAAAAAGGAAGCAAAGTAATGATATTTTCTGAACTTTTTGTTTTTTATTCTGGGATTCAAC

ATCGGTGATTTAATTTTTGTGTTCACATTTAAAAGTTTATTTGGGTAATTTTTTGATATCAATTTTATTACAAAG

CCATAACTCTTGCATTTTTTTTATTATATTTTTATATACACGTACATTCTGTATTATTTATAACGCATTCAAACG

CGATCGCCGACGCCGCCGATgatcatctacccatgccgaaattcgggccgttggccggattgcgcgttgtcttct ccggtatcgaaatcgccggaccgtttgccgggcaaatgttcgcagaatggggcgcggaagttatctggatcgaga acgtcgcctgggccgacaccattcgcgttcaaccgaactacccgcaactctcccgccgcaatttgcacgcgctgt cgttaaatattttcaaagatgaaggccgcgaagcgtttctgaaattaatggaaaccaccgatatcttcatcgaag ccagtaaaggtccggcctttgcccgtcgtggcattaccgatgaagtactgtggcagcacaacccgaaactggtta tcgctcacctgtccggttttggtcagtacggcaccgaggagtacaccaatcttccggcctataacactatcgccc aggcctttagtggttacctgattcagaacggtgatgttgaccagccaatgcctgccttcccgtataccgccgatt acttttctggcctgaccgccaccacggcggcgctggcagcactgcataaagtgcgtgaaaccggtaaaggcgaaa gtatcgacatcgccatgtatgaagtgatgctgcgtatgggccagtacttcatgatggattacttcaacggcggcg aaatgtgcccgcgcatgagcaaaggtaaagatccctactacgccgATCGGCGGCGTCGGCGATCGCGTTGAATGA

AAATAGAGATCAGAAATTTTGTGATTATTTGGAATCTAAATTACAACGTGACAAACAACTTGTAAATGGCGGCTC

CAAGAAAAGGAAAGCCAATGATTAGCATATGCCTCTTCTTCTTAGAAGGGCGTTCTGCCCGTTATGTATACGTTA

AATATTACATTATTTTCGCATTTTTGTATTTATATTCAGTGAAATATTAGGCTTGGTCGAGTAACATTTCCCATA

GCTCGTCGGTTTCTTTGAAGTCGTGATGAACAATTGAGACAAGACAGTAGTCTTTATGCACTAGTCTTAGAAGAA

TATTGGCTGGGGTGTTCCTTGGAAATAACTTGGCCCACTCGGACCAGATACTAAACGCTTCATCTCTCCATGCCT

TGAATGACTCTTCTTCAATGATTGTAGTCTGTTTGACCGGACTGTTGGGAAAAACACCCCATGTTACAACGCTAG

AGCTGTGCGGGTCTAGGTTCGTTTCAAATGAACCAGATGAATCGCCCGCGTAATAACTGAATTTCCGACGCCCGT

AATGGTCTAGCTTGGGTTTCAAAGTTGTTTCCCATTGCTGTCTATGAATAAACATTTCTACGAATGCCTTCTGAT

ACAACCTCCCTTTCGCGGGCCCCCAGCCGAATATTTTATCACTACTCAATGTAGCATTTGTGGCAGGTTGCGATG

CCAAAGTCAAATATCCGCGATAGTTTAGTTGGATTAGTTCTTCTTGTATTAACGCCGTTTCAGCTGATAAACCCA

GGTCAGACCAGGGAATCGCATCCGTTGAACCTTCCAAATATTTTATAAAAATATCTTTTAAATCGCCAATTGTCT

TTGGTATACCCCATAGTTCAAGCGCTTTGCTTTTGCTTACCTTGATGGATGGCCCATAACCGTCTATTTCACCAT

ATGCGGGAGACCTGGAGTCACCAAATCTACCATTGGGGAACTCATCCCAAGTGGCATCACGACCCAAAGTTCCGT

GACCTTTAGAAATAGATATTAAAGCCTTTTTAGATGGCATGGAACCATTCTCATTATTATAGCGTAAGCCTTTTT

-continued

CAGTGACGATAGCCCTATTGAAAATCAACTTGGCCGAATCAAGACTTGAATGCCTTCTCCTTTTCCGGTTTGCTA

CAGTTTCTTCATTCGAATCATCCAACACAATATCCCCGTCAGCATCTTCTATTGGCACATTTTCTATGCTTCCTA

TTTCGCCACTGGTTTCATCTTCTCCCTCTTCTTCGCTAGATTCATTTACGATATGGGATAAGACGGGAGATTGCG

AGACAATTTGAGCAATAGCCTTTTCCAAATTTAATGTATAGAAATGAAACCCTTTAATTCTACCAGATGTTCTTT

GATATATTTCCTGAATCAATTCGATAAGAATGTCCACACCAATGGACTTCACGGCATTATCATCCGATTGGATTT

CTGGGGGGAACCTACTCAGTATTGCAGGTGGAATAGATGCATGTGATAACTTTGCTGCTCTGTGGAAAAGCAGAT

AGGAGTTAATAGGCATCAACCCAGGGAAAAGGGGCAAATCTTGCGAAATCCGTTCCCGAAATAGCATTTCAAAAG

TTAAGAATTTTTCAACGTCGTAAAACAGTTGTGTTATCACAAAATCGGCCCCAGCTTCAACTTTTTCTTTTAAAT

ATACCAAATCCTTCAATGGGTCTTGCTCGTGACCTTCTGCTTCACCTTCACAATGACCTTCTGGATATGCTGCAA

CACCGACGCAGAACTTGTCTCCGTAGCTTTGCTTGATATAACGAACTAAATCAACCGCATATTTAAAAGGTGATT

CGTTCGATTGAGAATCTAGCCAATCTTCCCCAATAGGTGGGTCACCTCGAAGAGCCAAAATATTCCTGATTCCTG

CATTATAACATCTATCCAGCGCATCATCAATGATGGCTTTTTCTGTGTTTGTACAGGTCAAATGCATACAAACTG

GTATATTTAGTGTCTGCTGTGCCAAGGAAGCTAATGTCAGAGTCTTTTCCGCAGTAGTACCACCTGCTCCCCAAG

TAACCGTGATAAACAGTGGATCTAAAGCAGTCATACGATGCATACGTTCCATCAAATTTCTCGTCCCTAATTCAG

TCTTTGGAGGGAAGAATTCTAACGATATAAAAGGGGAAGCCCTCGCATGATATAAATCTCTGATGGACATTGTGA

AGGTAGTTCGATTTTGGAGGTCGCGGGAGGTAAGTATAGAGGTATATTAACAATTTTTTGTTGATACTTTTATGA

CATTTGAATAAGAAGTAATACAAACCGAAAATGTTGAAAGTATTAGTTAAAGTGGTTATGCAGCTTTTGCATTTA

TATATCTGTTAATAGATCAAAAATCATCGCTTCGCTGATTAATTACCCCAGAAATAAGGCTAAAAAACTAATCGC

ATTATTATCCTATGGTTGTTAATTTGATTCGTTGATTTGAAGGTTTGTGGGGCCAGGTTACTGCCAATTTTTCCT

CTTCATAACCATAAAAGCTAGTATTGTAGAATCTTTATTGTTCGGAGCAGTGCGGCGCGAGGCACATCTGCGTTT

CAGGAACGCGACCGGTGAAGACCAGGACGCACGGAGGAGAGTCTTCCGTCGGAGGGCTGTCGCCCGCTCGGCGGC

TTCTAATCCGTACTTCAATATAGCAATGAGCAGTTAAGCGTATTACTGAAAGTTCCAAAGAGAAGGTTTTTTTAG

GCTAAGATAATGGGGCTCTTTACATTTCCACAACATATAAGTAAGATTAGATATGGATATGTATATGGTGGTATT

GCCATGTAATATGATTATTAAACTTCTTTGCGTCCATCCAAAAAAAAAGTAACCCCACCCGAAGTCGCGCAACCA

ACTAACTTTACAATGCCTTACACTCTATCCGACGCTCATCATAAGTTGATCACCTCTCATTTGGTGGACACCGAC

CCTGAAGTGGACTCCATTATCAAGGATGAAATTGAAAGACAAAAGCACTCCATCGATTTGATTGCTTCTGAAAAT

TTCACCTCAACCTCCGTTTTCGATGCCCTTGGAACTCCATTGTCCAACAAATATTCTGAAGGTTATCCAGGTGCT

CGTTACTACGGTGGTAATGAACACATTGACAGAATGGAAATTCTATGTCAACAAAGAGCTTTAAAAGCTTTCCAT

GTTACTCCAGACAAATGGGGTGTTAACGTCCAAACTTTATCTGGTTCTCCTGCTAACTTGCAAGTTTATCAAGCT

ATTATGAAGCCTCATGAAAGATTGATGGGTCTATACCTACCAGATGGTGGTCATTTGTCTCACGGTTACGCTACT

GAAAACAGAAAAATTTCTGCTGTTTCCACATACTTCGAATCTTTCCCATACAGAGTTAACCCAGAAACCGGTATT

ATCGACTACGATACTTTAGAAAAGAACGCCATCCTATATAGACCAAAGGTTCTTGTTGCTGGTACTTCAGCATAC

TGTCGTTTAATTGACTACAAGAGAATGAGAGAAATCGCCGACAAATGTGGTGCTTACTTGATGGTAGACATGGCC

CACATTTCAGGTTTGATCGCCGCAGGTGTCATCCCATCTCCTTTCGAATACGCTGATATCGTTACCACCACCACT

CACAAGTCTTTGAGAGGTCCACGTGGTGCTATGATTTTCTTCAGAAGAGGTGTGAGATCTATCAACCCTAAGACC

GGTAAGGAAGTCCTATACGACTTGGAAAACCCAATTAACTTCTCTGTTTTCCCAGGTCACCAAGGTGGTCCACAC

AACCATACCATTGCTGCTTTGGCCACTGCTTTGAAGCAAGCTGCCACTCCAGAATTCAAGGAATACCAAACTCAA

GTCTTGAAGAATGCTAAGGCTTTGGAAAGTGAATTTAAGAACTTGGGCTACAGATTAGTTTCCAACGGTACCGAT

TCTCACATGGTTCTGGTATCCTTGAGAGAAAAGGGTGTTGATGGTGCTCGTGTTGAATACATTTGTGAAAAGATT

AACATTGCTTTGAACAAAAACTCTATTCCAGGTGACAAATCTGCTTTGGTTCCAGGTGGTGTCCGTATTGGGGCT

CCAGCCATGACCACTAGAGGAATGGGTGAAGAAGATTTCCACAGAATTGTTCAATACATTAACAAGGCTGTAGAA

-continued

TTCGCTCAACAAGTTCAACAAAGCTTGCCAAAGGATGCTTGTAGATTAAAGGACTTCAAAGCCAAGGTCGACGAA

GGCTCTGATGTTTTGAACACCTGGAAAAAGGAAATTTACGACTGGGCTGGCGAATACCCATTGGCTGTGTAAAGA

AATCACCACAACGACACTTAATCCCAAAAAAATAAACATTACTGTATAAGTATTCATTTTCTCCTCTTCTCATTA

TGTATATATGTACCTATATGTATGTATGTATGTGCGTACGATTTTTCTAACGTTAACTTCATTTCTTTTTGATTA

TGTGCCCTCCTTGAGTTAAGATGTGCTTGTCCAGGTCCGCCGGCGTTGGACGAGCGAATTAAGCTTTCGAGAAAA

ACTTTCTTTTAACCCCTCTAATCTAAATATAAACATATAGCTTATAGAAATGAATGAATATTTTAAATAGTTACG

GATACAAAGAGTTCATTATAGTGCGGGCAGTTAGTACGGTATCGATTTATCATTGGAGATCTGCAGTGTTACAGA

AGCACTGCTCACCAGTTGTCTACGGAAGGACGTTGAGATAGTTTTACCACGTTTGAGCTAAAAGTTTCTACCACA

AGAGCCTTTATTTGCACATGGCAGTGAATGCATGATTAAGGATATGAAGAAGAAAGGAATAACTAGGAATAAATT

TTATTTAGAGAGGGTATGATGAAAGGAGAGCCTCGTTATTTATGACCTGCATTTTTATCAGCATCTTCTTTCCAG

CTCCCGCTAAACATGTGCTTTACAAAAGCCATTTTGTCGTCACTAGACTGGGCGCCCATCTGCCCCACATCTGGT

GAAAAACTTGTTATTGGTAGAACCATCACATGGCGGTTTAAACGCGTGGCCGTGCCGTC

SEQ ID NO: 24
Length: 2128
Type:
Organism: artificial sequence
Other information: MS 116593 sequence

GACGGCACGGCCACGCGTTTAAACCGCCCTAATACCCAGCCAAGGTAGTCTAAAAGCTAATTTCTCTAAAAGGGA

GAAAGTTGGTGATTTTTTATCTCGCATTATTATATATGCAAGAATAGTTAAGGTATAGTTATAAAGTTTTATCTT

AATTGCCACATACGTACATTGACACGTAGAAGGACTCCATTATTTTTTTCATTCTAGCATACTATTATTCCTTGT

AACGTCCCAGAGTATTCCATTTAATTGTCCTCCATTTCTTAACGGTGACGAAGGATCACCATACAACAACTACTA

AAGATTATAGTACACTCTCACCTTGCAACTATTTATCTGACATTTGCCTTACTTTTATCTCCAGCTTCCCCTCGA

TTTTATTTTTCAATTTGATTTCTAAAGCTTTTTGCTTAGGCATACCAAACCATCCACTCATTTAACACCTTATTT

TTTTTTTCGAAGACAGCATCCAACTTTATACGTTCACTACCTTTTTTTTTACAACAATTTCATTCTTCATCCTAT

GAACGCTCGTCCAACGCCGGCGGACCTTGGAACTTTCAGTAATACGCTTAACTGCTCATTGCTATATTGAAGTAC

GGATTAGAAGCCGCCGAGCGGGCGACAGCCCTCCGACGGAAGACTCTCCTCCGTGCGTCCTGGTCTTCACCGGTC

GCGTTCCTGAAACGCAGATGTGCCTCGCGCCGCACTGCTCCGAACAATAAAGATTCTACAATACTAGCTTTTATG

GTTATGAAGAGGAAAAATTGGCAGTAACCTGGCCCCACAAACCTTCAAATCAACGAATCAAATTAACAACCATAG

GATAATAATGCGATTAGTTTTTTAGCCTTATTTCTGGGGTAATTAATCAGCGAAGCGATGATTTTTGATCTATTA

ACAGATATATAAATGCAAAAGCTGCATAACCACTTTAACTAATACTTTCAACATTTTCGGTTTGTATTACTTCTT

ATTCAAATGTCATAAAAGTATCAACAAAAAATTGTTAATATACCTCTATACTTTAACGTCAAGGAGAAAAAACTA

TAGATGCACGAGCGCAACGCTCACAAACAGGCCCCTTTTCCTTTGTCGATATCATGTAATTAGTTATGTCACGCT

TACATTCACGCCCTCCCCCCACATCCGCTCTAACCGAAAAGGAAGGAGTTAGACAACCTGAAGTCTAGGTCCCTA

TTTATTTTTTTATAGTTATGTTAGTATTAAGAACGTTATTTATATTTCAAATTTTTCTTTTTTTTCTGTACAAAC

GCGTGTACGCATGTAACATTATACTGAAAACCTTGCTTGAGAAGGTTTTGGGACGCTCGAAGGCTTTAATTTGCA

AGCTTCGCAGTTTACACTCTCATCGTCGCTCTCATCATCGCTTCCGTTGTTGTTTTCCTTAGTAGCGTCTGCTTC

CAGAGAGTATTTATCTCTTATTACCTCTAAAGGTTCTGCTTGATTTCTGACTTTGTTCGCCTCATGTGCATATTT

TTCTTGGTTCTTTTGGGACAAAATATGCGTAAAGGACTTTTGTTGTTCCCTCACATTCCAGTTTAGTTGTCGACT

GATCCCCGCGTGCTTGGCCGGCCGTCTCCATGCTGGACTTACTCGTCGAAGATTTCCTGCTACTCTCTATATAAT

TAGACACCCATGTTATAGATTTCAGAAAACAATGTAATAATATATGGTAGCCTCCTGAAACTACCAAGGGAAAAA

TCTCAACACCAAGAGCTCATATTCGTTGGAATAGCGATAATATCTCTTTACCTCAATCTTATATGCATGTTATTT

-continued

GCTCTTATAATTGGTCTCTATTTAGGGAAAAAAGTCGGTTTGAGAGCTTCTCGCGATGTGAAATCTCAATTTGAA

CTGCACGCCAAAGCTAGCCCATTTCACGAACACCAGAAAGAAGAAATCCCCAAGGATCGCATGACAGAGTATGCT

CTCTCATATCGTTGAGTATGAATGCCAATACACTGATCAGCTTTACAAGAAACGTAAAATCTGGCACGATGGTAG

ACTGAAATACTTTCAGTTAAACAACAGATTCATGCTTTATACGGAAAAGGATAACGTTTTGTTAGCTAGTGAATT

CGGTGTTTAAACCCCAGCGCCTGGCGGG

What is claimed is:

1. A genetically modified yeast host cell capable of producing vanillin or glucovanillin comprising:

(a) one or more nucleic acids comprising nucleic acids capable of overexpressing SHM2, SAH1, MET6, and MET13; or SHM2, SAH1, MET6, and a chimeric MET13; and (b) deletion of ADH6.

2. The genetically modified host cell of claim 1, wherein the one or more nucleic acids further comprise nucleic acids capable of overexpressing SAM1.

3. The genetically modified host cell of claim 2, wherein SAM1 encodes an amino acid sequence at least 80, 85, 90, 95, 99, or 100% identical to the Sam1 amino acid sequence encoded by nucleotides 7394-6051 of SEQ ID NO:8.

4. The genetically modified host cell of claim 1, wherein the one or more nucleic acids further comprise nucleic acids capable of overexpressing SAM2.

5. The genetically modified host cell of claim 4, wherein SAM2 encodes an amino acid sequence at least 80, 85, 90, 95, 99, or 100% identical to the Sam2 amino acid sequence encoded by nucleotides 8087-9440 of SEQ ID NO:8.

6. The genetically modified host cell of claim 1, wherein the one or more nucleic acids further comprise nucleic acids capable of overexpressing SAM1 and SAM2.

7. The genetically modified host cell of claim 1 that is capable of overexpressing SHM2, SAH1, MET6 under one or more inducible promoters.

8. The genetically modified host cell of claim 1, wherein the one or more nucleic acids further comprise nucleic acids capable of overexpressing MET12.

9. The genetically modified host cell of claim 1, wherein the chimeric MET13 comprises a *S. cerevisiae* MET13 N-terminal domain and an *Arabadopsis* MTHFR C-terminal domain.

10. The genetically modified host cell of claim 1, wherein the nucleic acids capable of overexpressing MET6 comprise two copies of MET6.

11. The genetically modified host cell of claim 1, wherein the one or more nucleic acids further comprise nucleic acids capable of overexpressing MET12; and wherein the one or more nucleic acids capable of overexpressing MET6 comprise two or more copies of MET6.

12. The genetically modified host cell of claim 11 wherein MET12 and the two or more copies of MET6 are overexpressed under one inducible promoter.

13. The genetically modified host cell of claim 12 wherein, SAM1 and SAM2 are overexpressed under one inducible promoter.

14. The genetically modified host cell of claim 1 wherein, SHM2, SAH1, MET6, and MET13 or chimeric MET13 are overexpressed under one or more inducible promoters.

15. The genetically modified host cell of claim 1 wherein, SHM2, SAH1, MET6, and MET13 or chimeric MET13 are overexpressed under one inducible promoter.

16. The genetically modified host cell of claim 1 further comprising deletion of GRE2.

17. The genetically modified host cell of claim 1 further comprising deletion of YGL039W.

18. The genetically modified host cell of claim 1 further comprising one or more nucleic acids expressing AroB, AroD, and AroZ.

19. The genetically modified host cell of claim 18, wherein the AroB gene product comprises an amino acid sequence at least 80, 85, 90, 95, 99, or 100% identical to the AroB amino acid sequence encoded by nucleotides 5596-6684 of SEQ ID NO:5, nucleotides 2930-4143 of SEQ ID NO:11, or nucleotides 2906-4119 of SEQ ID NO:17.

20. The genetically modified host cell of claim 18, wherein the AroD gene product comprises an amino acid sequence at least 80, 85, 90, 95, 99, or 100% identical to the AroD amino acid sequence encoded by nucleotides 7951-7193 of SEQ ID NO:5, nucleotides 5775-4892 of SEQ ID NO:11, or nucleotides 5751-4868 of SEQ ID NO:17.

21. The genetically modified host cell of claim 18, wherein the AroZ gene product comprises an amino acid sequence at least 80, 85, 90, 95, 99, or 100% identical to the AroZ amino acid sequence encoded by nucleotides 1134-2237 of SEQ ID NO:5, nucleotides 1095-2323 of SEQ ID NO:11, or nucleotides 1780-55218.

22. The genetically modified host cell of claim 1 further comprising one or more nucleic acids expressing AroB, AroD, AroF, and AroZ.

23. The genetically modified host cell of claim 22, wherein the AroF gene product comprises an amino acid sequence at least 80, 85, 90, 95, 99, or 100% identical to the AroF amino acid sequence encoded by nucleotides 3761-2961 of SEQ ID NO:5, nucleotides 7577-6382 of SEQ ID NO:11, or nucleotides 6877-8072 of SEQ ID NO:17.

24. The genetically modified host cell of claim 1 further comprising one or more nucleic acids expressing *E. coli* AroB, *E. coli* AroD, *E. coli* AroF, and *Podospora pauciseta* AroZ.

25. The genetically modified host cell of claim 1 further comprising one or more nucleic acids expressing PPTASE and ACAR.

26. The genetically modified host cell of claim 25, wherein the PPTASE gene product comprises an amino acid sequence at least 80, 85, 90, 95, 99, or 100% identical to the PPTASE amino acid sequence encoded by nucleotides 1618-825 of SEQ ID NO: 6, nucleotides 7070-5883 of SEQ ID NO: 14, or nucleotides 5883-7070 of SEQ ID NO: 19.

27. The genetically modified host cell of claim 1 further comprising one or more nucleic acids expressing UDP-glycosyltransferase (UGT).

28. The genetically modified host cell of claim 27, wherein the UGT gene product comprises an amino acid sequence at least 80, 85, 90, 95, 99, or 100% identical to the UGT amino acid sequence encoded by nucleotides 2214-769 and 2907-4352 of SEQ ID NO:10.

29. The genetically modified host cell of claim 1 further comprising one or more nucleic acids expressing *Arabidopsis thaliana* UGT.

30. The genetically modified host cell of claim 1, wherein SHM2, SAH1, MET6, and MET13 or the chimeric MET13 are each expressed from a GAL promoter, and wherein a GAL80 gene is expressed from a MAL promoter.

31. The genetically modified host cell of claim 1, wherein the yeast host cell is *Saccharomyces cerevisiae.*

32. The genetically modified host cell of claim 1, wherein SAH1 encodes an amino acid sequence at least 80, 85, 90, 95, 99, or 100% identical to the Sah1 amino acid sequence encoded by nucleotides 2094-554 of SEQ ID NO:8.

33. The genetically modified host cell of claim 1, wherein MET6 encodes an amino acid sequence at least 80, 85, 90, 95, 99, or 100% identical to the Met6 amino acid sequence encoded by nucleotides 2787-5302 of SEQ ID NO:8 or nucleotides 3249-5764 of SEQ ID NO:14.

34. The genetically modified host cell of claim 1, wherein SHM2 encodes an amino acid sequence at least 80, 85, 90, 95, 99, or 100% identical to the Shm2 amino acid sequence encoded by nucleotides 9381-10975 of SEQ ID NO:14.

35. The genetically modified host cell of claim 1, wherein MET12 encodes an amino acid sequence at least 80, 85, 90, 95, 99, or 100% identical to the Met12 amino acid sequence encoded by nucleotides 8688-6513 of SEQ ID NO:14.

36. The genetically modified host cell of claim 1, wherein MET13 encodes an amino acid sequence at least 80, 85, 90, 95, 99, or 100% identical to the Met13 amino acid sequence encoded by nucleotides 2556-554 of SEQ ID NO: 14, and the chimeric MET13 encodes an amino acid sequence at least 80, 85, 90, 95, 99, or 100% identical to the chimeric Met13 amino acid sequence encoded by nucleotides 554-2338 of SEQ ID NO:23.

37. The genetically modified host cell of claim 1 that produces at least a 5, 10, 15, or 20% increase in peak cumulative yield or productivity, or both, compared to a parent strain.

38. The genetically modified host cell of claim 37 that produces up to 7% increase in peak cumulative yield and up to 17% productivity, compared to a parent strain.

39. A method for producing vanillin or one or more glucovanillins comprising the steps:

(a) culturing a population of the host cells of claim 1 in a medium with a carbon source under conditions suitable for making vanillin or one or more glucovanillins to yield a culture broth; and (b) recovering said vanillin or one or more glucovanillins from the culture broth.

* * * * *